(12) United States Patent
Thompson et al.

(10) Patent No.: US 9,278,019 B2
(45) Date of Patent: Mar. 8, 2016

(54) ANCHORS AND METHODS FOR INTESTINAL BYPASS SLEEVES

(75) Inventors: Paul J. Thompson, Minnetonka, MN (US); Kedar R. Belhe, Minnetonka, MN (US); Alexander D. Grafov, Eden Prairie, MN (US)

(73) Assignee: METAMODIX, INC, Plymouth, MN (US)

(*) Notice: Subject to any disclaimer, the term of this patent is extended or adjusted under 35 U.S.C. 154(b) by 970 days.

(21) Appl. No.: 13/360,689

(22) Filed: Jan. 28, 2012

(65) Prior Publication Data

US 2012/0184893 A1     Jul. 19, 2012

Related U.S. Application Data

(63) Continuation-in-part of application No. 12/752,697, filed on Apr. 1, 2010, now Pat. No. 8,211,186, and a continuation-in-part of application No. 12/833,605, filed on Jul. 9, 2010, now Pat. No. 8,282,598, and a (Continued)

(51) Int. Cl.
*A61M 5/00*     (2006.01)
*A61F 5/00*     (2006.01)

(Continued)

(52) U.S. Cl.
CPC ............... *A61F 5/0076* (2013.01); *A61F 2/04* (2013.01); *A61F 2/24* (2013.01); *A61F 5/0079* (2013.01); *A61F 2002/044* (2013.01); *A61F 2002/045* (2013.01); *A61F 2220/0008* (2013.01)

(58) Field of Classification Search
CPC ... A61F 5/0076; A61F 5/0083; A61F 5/0079; A61F 2/04; A61F 5/0036; A61F 5/0089; A61M 27/002; A61B 17/1114; A61B 17/221

USPC ............. 604/8–10, 154, 192; 623/23.64–23.7
See application file for complete search history.

(56) References Cited

U.S. PATENT DOCUMENTS

| | | |
|---|---|---|
| 4,134,405 A | 1/1979 | Smit |
| 4,204,530 A | 5/1980 | Finney |

(Continued)

FOREIGN PATENT DOCUMENTS

| | | |
|---|---|---|
| AU | 2006227471 B2 | 9/2006 |
| CN | 1618411 A | 5/2005 |

(Continued)

OTHER PUBLICATIONS

International Search Report and Written Opinion issued in PCT/US12/58202, mailed Jan. 23, 2013, 14 pages.

(Continued)

*Primary Examiner* — Philip R Wiest
(74) *Attorney, Agent, or Firm* — Faegre Baker Daniels LLP

(57) ABSTRACT

A gastrointestinal device for implanting within a pylorus, a duodenal bulb, and a duodenum of a patient's gastrointestinal tract includes an expandable structure including a proximal portion having a plurality of spring arms and a distal portion having a plurality of spring arms, the proximal and distal portions coupled by a rigid central cylinder having a diameter capable of fitting within the pylorus and having a length greater than a width of the pylorus. An intestinal bypass sleeve is coupled to at least one of the proximal and distal portions of the expandable structure and having a length sufficient to extend at least partially into the duodenum. In the expanded configuration, the proximal portion has a diameter larger than a maximum opening diameter of the pylorus and further wherein, in the expanded configuration, the distal portion has a diameter larger than a maximum opening diameter of the pylorus.

17 Claims, 96 Drawing Sheets

Related U.S. Application Data continuation-in-part of application No. 12/986,268, filed on Jan. 7, 2011, now Pat. No. 8,702,641, and a continuation-in-part of application No. 13/298,867, filed on Nov. 17, 2011.

(60) Provisional application No. 61/462,156, filed on Jan. 28, 2011, provisional application No. 61/519,507, filed on May 24, 2011, provisional application No. 61/211,853, filed on Apr. 3, 2009, provisional application No. 61/270,588, filed on Jul. 10, 2009, provisional application No. 61/335,472, filed on Jan. 7, 2010, provisional application No. 61/458,060, filed on Nov. 17, 2010.

(51) Int. Cl.
*A61F 2/04* (2013.01)
*A61F 2/24* (2006.01)

(56) References Cited

U.S. PATENT DOCUMENTS

| | | |
|---|---|---|
| 4,246,893 A | 1/1981 | Berson |
| 4,314,405 A | 2/1982 | Park |
| 4,315,509 A | 2/1982 | Smit |
| 4,416,267 A | 11/1983 | Garren et al. |
| 4,501,264 A | 2/1985 | Rockey |
| 4,641,653 A | 2/1987 | Rockey |
| 4,716,900 A | 1/1988 | Ravo et al. |
| 4,719,916 A | 1/1988 | Ravo |
| 4,763,653 A | 8/1988 | Rockey |
| 4,899,747 A | 2/1990 | Garren et al. |
| 4,905,693 A | 3/1990 | Ravo |
| 5,234,454 A | 8/1993 | Bangs |
| 5,246,456 A | 9/1993 | Wilkinson |
| 5,306,300 A | 4/1994 | Berry |
| 5,322,697 A | 6/1994 | Meyer |
| 5,423,872 A | 6/1995 | Cigaina |
| 5,474,563 A | 12/1995 | Myler et al. |
| 5,480,423 A | 1/1996 | Ravenscroft et al. |
| 5,749,921 A | 5/1998 | Lenker et al. |
| 5,753,253 A | 5/1998 | Meyer |
| 5,820,584 A | 10/1998 | Crabb |
| 6,017,563 A | 1/2000 | Knight et al. |
| 6,224,627 B1 | 5/2001 | Armstrong et al. |
| 6,267,988 B1 | 7/2001 | Meyer |
| 6,454,699 B1 | 9/2002 | Forsell |
| 6,540,789 B1 | 4/2003 | Silverman et al. |
| 6,558,400 B2 | 5/2003 | Deem et al. |
| 6,675,809 B2 | 1/2004 | Stack et al. |
| 6,740,121 B2 | 5/2004 | Geitz |
| 6,755,869 B2 | 6/2004 | Geitz |
| 6,802,868 B2 | 10/2004 | Silverman et al. |
| 6,845,776 B2 | 1/2005 | Stack et al. |
| 6,946,002 B2 | 9/2005 | Geitz |
| 6,994,095 B2 | 2/2006 | Burnett |
| 7,025,791 B2 | 4/2006 | Levine et al. |
| 7,037,343 B2 | 5/2006 | Imran |
| 7,037,344 B2 | 5/2006 | Kagan et al. |
| 7,044,979 B2 | 5/2006 | Silverman et al. |
| 7,090,699 B2 | 8/2006 | Geitz |
| 7,111,627 B2 | 9/2006 | Stack et al. |
| 7,121,283 B2 | 10/2006 | Stack et al. |
| 7,122,058 B2 | 10/2006 | Levine et al. |
| 7,146,984 B2 | 12/2006 | Stack et al. |
| 7,152,607 B2 | 12/2006 | Stack et al. |
| 7,160,312 B2 | 1/2007 | Saadat |
| 7,163,554 B2 | 1/2007 | Williams et al. |
| 7,175,638 B2 | 2/2007 | Gannoe et al. |
| 7,175,669 B2 | 2/2007 | Geitz |
| 7,211,094 B2 | 5/2007 | Gannoe et al. |
| 7,211,114 B2 | 5/2007 | Bessler et al. |
| 7,214,233 B2 | 5/2007 | Gannoe et al. |
| 7,220,237 B2 | 5/2007 | Gannoe et al. |
| 7,220,284 B2 | 5/2007 | Kagan et al. |
| 7,223,277 B2 | 5/2007 | DeLegge |
| 7,229,428 B2 | 6/2007 | Gannoe et al. |
| 7,261,725 B2 | 8/2007 | Binmoeller |
| 7,267,694 B2 | 9/2007 | Levine et al. |
| 7,288,099 B2 | 10/2007 | Deem et al. |
| 7,288,101 B2 | 10/2007 | Deem et al. |
| 7,291,160 B2 | 11/2007 | DeLegge |
| 7,306,614 B2 | 12/2007 | Weller et al. |
| 7,314,489 B2 | 1/2008 | McKenna et al. |
| 7,316,716 B2 | 1/2008 | Egan |
| 7,329,285 B2 | 2/2008 | Levine et al. |
| 7,335,210 B2 | 2/2008 | Smit |
| 7,347,875 B2 | 3/2008 | Levine et al. |
| 7,354,454 B2 | 4/2008 | Stack et al. |
| 7,364,542 B2 | 4/2008 | Jambor et al. |
| 7,364,591 B2 | 4/2008 | Silverman et al. |
| 7,367,937 B2 | 5/2008 | Jambor et al. |
| 7,431,725 B2 | 10/2008 | Stack et al. |
| 7,476,256 B2 | 1/2009 | Meade et al. |
| 7,503,922 B2 | 3/2009 | Deem et al. |
| 7,507,218 B2 | 3/2009 | Aliski et al. |
| 7,510,559 B2 | 3/2009 | Deem et al. |
| 7,513,914 B2 | 4/2009 | Schurr |
| 7,569,056 B2 | 8/2009 | Cragg et al. |
| 7,601,178 B2 | 10/2009 | Imran |
| 7,608,114 B2 | 10/2009 | Levine et al. |
| 7,608,578 B2 | 10/2009 | Miller |
| 7,618,435 B2 | 11/2009 | Opolski |
| 7,628,821 B2 | 12/2009 | Stack et al. |
| 7,678,068 B2 | 3/2010 | Levine et al. |
| 7,682,330 B2 | 3/2010 | Meade et al. |
| 7,695,446 B2 | 4/2010 | Levine et al. |
| 7,758,535 B2 | 7/2010 | Levine et al. |
| 7,766,861 B2 | 8/2010 | Levine et al. |
| 7,766,973 B2 | 8/2010 | Levine et al. |
| 7,815,589 B2 | 10/2010 | Levine et al. |
| 7,837,643 B2 | 11/2010 | Levine et al. |
| 7,837,669 B2 | 11/2010 | Dann et al. |
| 7,935,073 B2 | 5/2011 | Levine et al. |
| 7,976,488 B2 | 7/2011 | Levine et al. |
| 7,981,163 B2 | 7/2011 | Levine et al. |
| 8,114,045 B2 | 2/2012 | Surti |
| 8,211,186 B2 | 7/2012 | Belhe et al. |
| 8,282,598 B2 | 10/2012 | Belhe et al. |
| 8,702,641 B2 | 4/2014 | Belhe et al. |
| 8,702,642 B2 | 4/2014 | Belhe et al. |
| 2002/0183768 A1 | 12/2002 | Deem et al. |
| 2002/0188354 A1 | 12/2002 | Peghini |
| 2003/0040804 A1 | 2/2003 | Stack et al. |
| 2003/0040808 A1 | 2/2003 | Stack et al. |
| 2003/0060894 A1 | 3/2003 | Dua et al. |
| 2003/0109892 A1 | 6/2003 | Deem et al. |
| 2003/0109931 A1 | 6/2003 | Geitz |
| 2003/0109935 A1 | 6/2003 | Geitz |
| 2003/0120265 A1 | 6/2003 | Deem et al. |
| 2003/0158601 A1 | 8/2003 | Silverman et al. |
| 2003/0191476 A1 | 10/2003 | Smit |
| 2003/0199989 A1 | 10/2003 | Stack et al. |
| 2003/0199990 A1 | 10/2003 | Stack et al. |
| 2003/0199991 A1* | 10/2003 | Stack et al. ............... 623/23.65 |
| 2004/0019388 A1 | 1/2004 | Starkebaum |
| 2004/0024386 A1 | 1/2004 | Deem et al. |
| 2004/0039452 A1 | 2/2004 | Bessler |
| 2004/0088022 A1 | 5/2004 | Chen |
| 2004/0092892 A1 | 5/2004 | Kagan et al. |
| 2004/0093091 A1 | 5/2004 | Gannoe et al. |
| 2004/0107004 A1 | 6/2004 | Levine et al. |
| 2004/0117031 A1 | 6/2004 | Stack et al. |
| 2004/0122452 A1 | 6/2004 | Deem et al. |
| 2004/0122453 A1 | 6/2004 | Deem et al. |
| 2004/0122526 A1 | 6/2004 | Imran |
| 2004/0133147 A1 | 7/2004 | Woo |
| 2004/0138760 A1 | 7/2004 | Schurr |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0158331 A1 | 8/2004 | Stack et al. |
| 2004/0172141 A1 | 9/2004 | Stack et al. |

(56) References Cited

U.S. PATENT DOCUMENTS

| | | |
|---|---|---|
| 2004/0172142 A1 | 9/2004 | Stack et al. |
| 2004/0172143 A1 | 9/2004 | Geitz |
| 2004/0199262 A1 | 10/2004 | Dua et al. |
| 2004/0204768 A1 | 10/2004 | Geitz |
| 2004/0220682 A1 | 11/2004 | Levine et al. |
| 2004/0249362 A1 | 12/2004 | Levine et al. |
| 2005/0004681 A1 | 1/2005 | Stack et al. |
| 2005/0022827 A1 | 2/2005 | Woo et al. |
| 2005/0033331 A1* | 2/2005 | Burnett et al. .................. 606/154 |
| 2005/0043817 A1 | 2/2005 | McKenna et al. |
| 2005/0049718 A1 | 3/2005 | Dann et al. |
| 2005/0055039 A1 | 3/2005 | Burnett et al. |
| 2005/0070934 A1 | 3/2005 | Tanaka et al. |
| 2005/0075622 A1 | 4/2005 | Levine et al. |
| 2005/0080395 A1 | 4/2005 | Levine et al. |
| 2005/0080431 A1 | 4/2005 | Levine et al. |
| 2005/0080444 A1 | 4/2005 | Kraemer et al. |
| 2005/0080480 A1 | 4/2005 | Bolea et al. |
| 2005/0080491 A1 | 4/2005 | Levine et al. |
| 2005/0085923 A1 | 4/2005 | Levine et al. |
| 2005/0096673 A1 | 5/2005 | Stack et al. |
| 2005/0096750 A1 | 5/2005 | Kagan et al. |
| 2005/0125020 A1 | 6/2005 | Meade et al. |
| 2005/0125075 A1 | 6/2005 | Meade et al. |
| 2005/0149200 A1 | 7/2005 | Silverman et al. |
| 2005/0177181 A1 | 8/2005 | Kagan et al. |
| 2005/0183730 A1 | 8/2005 | Byrum |
| 2005/0192614 A1 | 9/2005 | Binmoeller |
| 2005/0197714 A1 | 9/2005 | Sayet |
| 2005/0228413 A1 | 10/2005 | Binmoeller et al. |
| 2005/0228504 A1 | 10/2005 | Demarais |
| 2005/0240279 A1 | 10/2005 | Kagan et al. |
| 2005/0246037 A1 | 11/2005 | Starkebaum |
| 2005/0247320 A1 | 11/2005 | Stack et al. |
| 2005/0250980 A1 | 11/2005 | Swanstrom et al. |
| 2005/0251157 A1 | 11/2005 | Saadat et al. |
| 2005/0251206 A1 | 11/2005 | Maahs et al. |
| 2005/0256587 A1 | 11/2005 | Egan |
| 2005/0267499 A1 | 12/2005 | Stack et al. |
| 2005/0273060 A1* | 12/2005 | Levy et al. .................. 604/192 |
| 2005/0277963 A1 | 12/2005 | Fields |
| 2005/0283107 A1 | 12/2005 | Kalanovic et al. |
| 2005/0288555 A1 | 12/2005 | Binmoeller |
| 2006/0009858 A1 | 1/2006 | Levine et al. |
| 2006/0020247 A1 | 1/2006 | Kagan et al. |
| 2006/0020277 A1 | 1/2006 | Gostout et al. |
| 2006/0030949 A1 | 2/2006 | Geitz |
| 2006/0036267 A1 | 2/2006 | Saadat et al. |
| 2006/0064120 A1 | 3/2006 | Levine et al. |
| 2006/0155310 A1 | 7/2006 | Binmoeller |
| 2006/0155312 A1 | 7/2006 | Levine et al. |
| 2006/0155375 A1 | 7/2006 | Kagan et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0178691 A1 | 8/2006 | Binmoeller |
| 2006/0206063 A1 | 9/2006 | Kagan et al. |
| 2006/0206064 A1 | 9/2006 | Kagan et al. |
| 2006/0249165 A1 | 11/2006 | Silverman et al. |
| 2006/0258906 A1 | 11/2006 | Binmoeller |
| 2006/0265082 A1 | 11/2006 | Meade et al. |
| 2006/0282087 A1 | 12/2006 | Binmoeller |
| 2006/0293742 A1 | 12/2006 | Dann et al. |
| 2007/0004963 A1 | 1/2007 | Benchetrit |
| 2007/0005147 A1 | 1/2007 | Levine et al. |
| 2007/0010794 A1 | 1/2007 | Dann et al. |
| 2007/0010864 A1 | 1/2007 | Dann et al. |
| 2007/0010865 A1 | 1/2007 | Dann et al. |
| 2007/0010866 A1 | 1/2007 | Dann et al. |
| 2007/0021761 A1 | 1/2007 | Phillips |
| 2007/0027548 A1 | 2/2007 | Levine et al. |
| 2007/0032702 A1 | 2/2007 | Ortiz |
| 2007/0032879 A1 | 2/2007 | Levine et al. |
| 2007/0038308 A1 | 2/2007 | Geitz |
| 2007/0060932 A1 | 3/2007 | Stack et al. |
| 2007/0078302 A1 | 4/2007 | Ortiz et al. |
| 2007/0083271 A1 | 4/2007 | Levine et al. |
| 2007/0100367 A1 | 5/2007 | Quijano et al. |
| 2007/0118158 A1 | 5/2007 | Deem et al. |
| 2007/0118159 A1 | 5/2007 | Deem et al. |
| 2007/0135825 A1 | 6/2007 | Binmoeller |
| 2007/0167963 A1 | 7/2007 | Deem et al. |
| 2007/0198074 A1 | 8/2007 | Dann et al. |
| 2007/0203517 A1 | 8/2007 | Williams et al. |
| 2007/0213740 A1 | 9/2007 | Deem et al. |
| 2007/0213748 A1 | 9/2007 | Deem et al. |
| 2007/0213751 A1 | 9/2007 | Scirica et al. |
| 2007/0213837 A1 | 9/2007 | Ferreri et al. |
| 2007/0219570 A1 | 9/2007 | Deem et al. |
| 2007/0239284 A1 | 10/2007 | Skerven et al. |
| 2007/0250083 A1 | 10/2007 | Deem et al. |
| 2007/0250132 A1 | 10/2007 | Burnett |
| 2007/0265709 A1 | 11/2007 | Rajan et al. |
| 2007/0276432 A1 | 11/2007 | Stack et al. |
| 2007/0282349 A1 | 12/2007 | Deem et al. |
| 2007/0282418 A1 | 12/2007 | Weitzner |
| 2007/0282452 A1 | 12/2007 | Weitzner et al. |
| 2007/0282453 A1 | 12/2007 | Weitzner et al. |
| 2007/0282454 A1 | 12/2007 | Krueger et al. |
| 2007/0293885 A1 | 12/2007 | Binmoeller |
| 2008/0033574 A1 | 2/2008 | Bessler et al. |
| 2008/0045803 A1 | 2/2008 | Williams et al. |
| 2008/0065122 A1 | 3/2008 | Stack et al. |
| 2008/0065136 A1 | 3/2008 | Young |
| 2008/0071383 A1 | 3/2008 | Levine et al. |
| 2008/0086214 A1 | 4/2008 | Hardin et al. |
| 2008/0092910 A1 | 4/2008 | Brooks |
| 2008/0097466 A1 | 4/2008 | Levine et al. |
| 2008/0103604 A1 | 5/2008 | Levine et al. |
| 2008/0109086 A1 | 5/2008 | Voegele et al. |
| 2008/0109087 A1* | 5/2008 | Durgin .................. 623/23.65 |
| 2008/0140172 A1 | 6/2008 | Carpenter et al. |
| 2008/0161935 A1 | 7/2008 | Albrecht et al. |
| 2008/0167606 A1 | 7/2008 | Dann et al. |
| 2008/0167610 A1 | 7/2008 | Dann et al. |
| 2008/0167629 A1 | 7/2008 | Dann et al. |
| 2008/0167724 A1 | 7/2008 | Ruane et al. |
| 2008/0183238 A1 | 7/2008 | Chen |
| 2008/0195225 A1 | 8/2008 | Silverman et al. |
| 2008/0195226 A1 | 8/2008 | Williams et al. |
| 2008/0208135 A1 | 8/2008 | Annunziata |
| 2008/0208161 A1 | 8/2008 | Kaji et al. |
| 2008/0208224 A1 | 8/2008 | Surti et al. |
| 2008/0208239 A1 | 8/2008 | Annunziata |
| 2008/0208355 A1 | 8/2008 | Stack et al. |
| 2008/0208356 A1 | 8/2008 | Stack et al. |
| 2008/0208357 A1 | 8/2008 | Melanson et al. |
| 2008/0221597 A1 | 9/2008 | Wallace et al. |
| 2008/0221702 A1 | 9/2008 | Wallace et al. |
| 2008/0234834 A1 | 9/2008 | Meade et al. |
| 2008/0243151 A1 | 10/2008 | Binmoeller et al. |
| 2008/0249533 A1 | 10/2008 | Godin |
| 2008/0249566 A1 | 10/2008 | Harris et al. |
| 2008/0249635 A1 | 10/2008 | Weitzner et al. |
| 2008/0255476 A1 | 10/2008 | Boyajian et al. |
| 2008/0255587 A1 | 10/2008 | Cully et al. |
| 2008/0255594 A1 | 10/2008 | Cully et al. |
| 2008/0255678 A1 | 10/2008 | Cully et al. |
| 2008/0262529 A1 | 10/2008 | Jacques |
| 2008/0269715 A1 | 10/2008 | Faller et al. |
| 2008/0269797 A1 | 10/2008 | Stack et al. |
| 2008/0287969 A1 | 11/2008 | Tsonton et al. |
| 2008/0312559 A1 | 12/2008 | Santilli et al. |
| 2008/0319455 A1 | 12/2008 | Harris et al. |
| 2009/0005637 A1 | 1/2009 | Chin et al. |
| 2009/0012541 A1 | 1/2009 | Dahl et al. |
| 2009/0012542 A1 | 1/2009 | N'diaye et al. |
| 2009/0012544 A1 | 1/2009 | Thompson et al. |
| 2009/0012553 A1 | 1/2009 | Swain et al. |
| 2009/0076588 A1 | 3/2009 | Weber |
| 2009/0093767 A1 | 4/2009 | Kelleher |
| 2009/0093839 A1 | 4/2009 | Kelleher |
| 2009/0118749 A1 | 5/2009 | Shalon et al. |

(56) References Cited

U.S. PATENT DOCUMENTS

| | | |
|---|---|---|
| 2009/0125119 A1 | 5/2009 | Obermiller et al. |
| 2009/0138094 A1 | 5/2009 | Schurr |
| 2009/0149871 A9 | 6/2009 | Kagan et al. |
| 2009/0164028 A1 | 6/2009 | Chen |
| 2009/0177215 A1 | 7/2009 | Stack et al. |
| 2009/0182355 A1 | 7/2009 | Levine et al. |
| 2009/0187206 A1 | 7/2009 | Binmoeller et al. |
| 2009/0198210 A1 | 8/2009 | Burnett et al. |
| 2009/0216262 A1 | 8/2009 | Burnett et al. |
| 2009/0240105 A1 | 9/2009 | Smit et al. |
| 2009/0240340 A1 | 9/2009 | Levine et al. |
| 2009/0248171 A1 | 10/2009 | Levine et al. |
| 2009/0276055 A1 | 11/2009 | Harris et al. |
| 2009/0281379 A1 | 11/2009 | Binmoeller et al. |
| 2009/0299486 A1 | 12/2009 | Shohat et al. |
| 2009/0299487 A1 | 12/2009 | Stack et al. |
| 2009/0326433 A1 | 12/2009 | Albrecht et al. |
| 2009/0326675 A1 | 12/2009 | Albrecht et al. |
| 2010/0004755 A1 | 1/2010 | Imran |
| 2010/0016988 A1 | 1/2010 | Stack et al. |
| 2010/0030017 A1 | 2/2010 | Baker et al. |
| 2010/0135971 A1 | 6/2010 | Schiffrin |
| 2010/0256775 A1 | 10/2010 | Belhe et al. |
| 2010/0305590 A1 | 12/2010 | Holmes et al. |
| 2011/0009690 A1 | 1/2011 | Belhe et al. |
| 2011/0106273 A1 | 5/2011 | Belhe et al. |
| 2012/0065571 A1 | 3/2012 | Thompson et al. |
| 2012/0253259 A1 | 10/2012 | Belhe et al. |
| 2012/0253260 A1 | 10/2012 | Belhe et al. |
| 2012/0302936 A1 | 11/2012 | Belhe et al. |
| 2013/0030351 A1 | 1/2013 | Belhe et al. |
| 2014/0194806 A1 | 7/2014 | Belhe et al. |

FOREIGN PATENT DOCUMENTS

| | | |
|---|---|---|
| EP | 0137878 A1 | 4/1985 |
| EP | 1420730 A2 | 5/2004 |
| EP | 1492477 A1 | 1/2005 |
| EP | 1492478 A1 | 1/2005 |
| EP | 1555970 A1 | 7/2005 |
| EP | 1569582 A2 | 9/2005 |
| EP | 1585458 A1 | 10/2005 |
| EP | 1680054 A1 | 7/2006 |
| EP | 1708641 A1 | 10/2006 |
| EP | 1708655 A1 | 10/2006 |
| EP | 1709508 A2 | 10/2006 |
| EP | 1749482 A2 | 2/2007 |
| EP | 1750595 A2 | 2/2007 |
| EP | 1778069 A1 | 5/2007 |
| EP | 1786310 A2 | 5/2007 |
| EP | 1799145 A1 | 6/2007 |
| EP | 1817072 A2 | 8/2007 |
| EP | 1832250 A1 | 9/2007 |
| EP | 1850811 A1 | 11/2007 |
| EP | 1850812 A1 | 11/2007 |
| EP | 1881781 A2 | 1/2008 |
| EP | 1887995 A2 | 2/2008 |
| EP | 1895887 A2 | 3/2008 |
| EP | 1937164 A1 | 7/2008 |
| EP | 1992314 A1 | 11/2008 |
| EP | 1416861 B1 | 12/2008 |
| EP | 1749480 B1 | 12/2008 |
| EP | 2010270 A2 | 1/2009 |
| EP | 1610720 B1 | 2/2009 |
| EP | 2023828 A2 | 2/2009 |
| EP | 2026713 A2 | 2/2009 |
| EP | 2061397 A1 | 5/2009 |
| EP | 2066243 A1 | 6/2009 |
| EP | 2068719 A2 | 6/2009 |
| EP | 2080242 A2 | 7/2009 |
| EP | 1520528 B1 | 9/2009 |
| EP | 1610719 B1 | 1/2010 |
| EP | 1603488 B1 | 4/2010 |
| EP | 1585460 B1 | 5/2010 |
| EP | 1933721 B1 | 5/2010 |
| EP | 1768618 B1 | 4/2011 |
| EP | 1883370 B1 | 8/2011 |
| WO | WO9849943 A2 | 11/1998 |
| WO | WO02096327 A2 | 12/2002 |
| WO | WO03017882 A2 | 3/2003 |
| WO | WO03086246 A1 | 10/2003 |
| WO | WO03086247 A1 | 10/2003 |
| WO | WO03094785 A1 | 11/2003 |
| WO | WO2004011085 A1 | 2/2004 |
| WO | WO2004017863 A2 | 3/2004 |
| WO | WO2004041133 A1 | 5/2004 |
| WO | WO2004064680 A1 | 8/2004 |
| WO | WO2004064685 A1 | 8/2004 |
| WO | WO2004087014 A2 | 10/2004 |
| WO | WO2004087233 A2 | 10/2004 |
| WO | WO2004049982 B1 | 12/2004 |
| WO | WO2005037152 A1 | 4/2005 |
| WO | WO2005058415 A2 | 6/2005 |
| WO | WO2005060869 A2 | 7/2005 |
| WO | WO2005060882 A1 | 7/2005 |
| WO | WO2005065412 A2 | 7/2005 |
| WO | WO2005097012 A2 | 10/2005 |
| WO | WO2005099591 A2 | 10/2005 |
| WO | WO2005110244 A1 | 11/2005 |
| WO | WO2005110280 A2 | 11/2005 |
| WO | WO2005112822 A1 | 12/2005 |
| WO | WO2005120363 A1 | 12/2005 |
| WO | WO2006014496 A2 | 2/2006 |
| WO | WO2006016894 A1 | 2/2006 |
| WO | WO2006020370 A2 | 2/2006 |
| WO | WO2006028898 A2 | 3/2006 |
| WO | WO2006034062 A1 | 3/2006 |
| WO | WO2006060049 A2 | 6/2006 |
| WO | WO2006062996 A2 | 6/2006 |
| WO | WO2006078781 A1 | 7/2006 |
| WO | WO2006078927 A1 | 7/2006 |
| WO | WO2006102012 A1 | 9/2006 |
| WO | WO2006102240 A2 | 9/2006 |
| WO | WO2006124880 A2 | 11/2006 |
| WO | WO2006127593 A2 | 11/2006 |
| WO | WO2006133311 A2 | 12/2006 |
| WO | WO2007019117 A1 | 2/2007 |
| WO | WO2007030829 A2 | 3/2007 |
| WO | WO2007038715 A1 | 4/2007 |
| WO | WO2007041598 A1 | 4/2007 |
| WO | WO2007075396 A2 | 7/2007 |
| WO | WO2007092390 A2 | 8/2007 |
| WO | WO2007107990 A2 | 9/2007 |
| WO | WO2007127209 A2 | 11/2007 |
| WO | WO2007136468 A2 | 11/2007 |
| WO | WO2007139920 A2 | 12/2007 |
| WO | WO2007142829 A1 | 12/2007 |
| WO | WO2007142832 A1 | 12/2007 |
| WO | WO2007142833 A1 | 12/2007 |
| WO | WO2007142834 A1 | 12/2007 |
| WO | WO2007145684 A1 | 12/2007 |
| WO | WO2008005510 A2 | 1/2008 |
| WO | WO2008030403 A1 | 3/2008 |
| WO | WO2008033409 A1 | 3/2008 |
| WO | WO2008033474 A2 | 3/2008 |
| WO | WO2008039800 A2 | 4/2008 |
| WO | WO2008101048 A2 | 8/2008 |
| WO | WO2008106041 A1 | 9/2008 |
| WO | WO2008106279 A1 | 9/2008 |
| WO | WO2008112942 A2 | 9/2008 |
| WO | WO2008127552 A2 | 10/2008 |
| WO | WO2008141288 A1 | 11/2008 |
| WO | WO2008148047 A2 | 12/2008 |
| WO | WO2008150905 A1 | 12/2008 |
| WO | WO2008154450 A1 | 12/2008 |
| WO | WO2008154594 A2 | 12/2008 |
| WO | WO2009011881 A1 | 1/2009 |
| WO | WO2009011882 A2 | 1/2009 |
| WO | WO2009012335 A1 | 1/2009 |
| WO | WO2009036244 A1 | 3/2009 |
| WO | WO2009046126 A1 | 4/2009 |
| WO | WO2009082710 A1 | 7/2009 |
| WO | WO2009085107 A1 | 7/2009 |

(56) References Cited

FOREIGN PATENT DOCUMENTS

| WO | WO2009086549 A1 | 7/2009 |
|---|---|---|
| WO | WO2009097582 A1 | 8/2009 |
| WO | WO2009097585 A1 | 8/2009 |
| WO | WO2010115011 A1 | 10/2010 |
| WO | WO2011062882 A1 | 5/2011 |
| WO | WO2011073970 A1 | 6/2011 |
| WO | WO2011099940 A8 | 8/2011 |
| WO | WO2012103531 A2 | 8/2012 |

OTHER PUBLICATIONS

Buchwald, Henry et al., "Bariatric Surgery: A Systematic Review and Meta-Analysis", JAMA, Oct. 13, 2004, 292 (14), pp. 1724-1737.

Cummings, David E. et al., "Role of the bypassed proximal intestine in the anti-diabetic effects of bariatric surgery", Surgery for Obesity and Related Diseases Mar. 2007, pp. 109-115.

International Search Report and Written Opinion issued in PCT/US2010/029648, mailed Aug. 24, 2010.

International Search Report and Written Opinion issued in PCT/US2010/041574, mailed Jan. 25, 2011.

International Search Report and Written Opinion issued in PCT/US2011/020560, mailed Mar. 28, 2011, 10 pages.

Invitation to Pay Additional Fees issued in PCT/US2010/029648, mailed Jun. 1, 2010.

Pories, Walter J. et al., "Surgical Treatment of Obesity and its Effect on Diabetes: 10-6 Follow-up", Am J Clin Nutr 1992, 55, 582S-585S.

Pories, Walter J. et al., "Who Would Have Thought It? An Operation Proves to be the Most Effective Therapy for Adult-Onset Diabetes Mellitus", Annals of Survery, Sep. 1995, 222(3), pp. 339-352.

Rodriguez-Grunert, Leonardo et al., "First Human Experience With endoscopically Delivered and retrieved duodenal-jejunal bypass sleeve", Surgery for Obesity and Related diseases 4 (2008) 55-59.

Rubino, Francesco et al.,, "Effect of Duodenal-Jejunal Exclusion in a Non-Obese Animal Model of Type 2 Diabetes", Annals of Surgery, vol. 239, No. 1, Jan. 2004, pp. 1-11.

Rubino, Francesco et al., "Potential of Surgery for Curing Type 2 Diabetes Mellitus", Annals of Surgery, Nov. 2002, 236(5), 554-559.

Rubino, Francesco et al., "The Mechanism of Diabetes Control After Gastrointestinal Bypass Surgery Reveals a Role of the Proximal Small Intestine in the pathophysiology of Type 2 Diabetes", Annals of Surgery, 244(5), Nov. 2006, pp. 741-749.

Strader, April et al., "Weight Loss Through Ileal transposition is accompanied by increased ileal hormone secretion and synthesis in rats", Am J Physiol Endocrinol Metab 288: E447-E453, 2005.

Troy, Stephanie et al., "Intestinal Gluconeogenesis is a key factor for early metabolic changes after gastric bypass but not after gastric lap-band in mice", Cell metabolism 8, 201-211, Sep. 3, 2008.

Vetter, Marion et al., "Narrative Review: Effect of bariatric Surgery on Type 2 Diabetes Mellitus", Annals of Internal Medicine, Jan. 20, 2009, 150(2), pp. 94-104.

International Search Report and Written Opinion issued in PCT/US2011/061193.

International Search Report and Written Opinion issued in PCT/US2014/011702, mailed Mar. 21, 2014, 9 pages.

Schouten, Ruben et al., "A Multicenter, Randomized Efficacy Study of the endoBarrier Gastrointestinal Liner for Presurgical Weight Loss Prior to Bariatric Surgery", Annals of Surgery, vol. 251, No. 2, Feb. 2010, pp. 236-243.

International Search Report and Written Opinion issued in PCT/US2012/023048, mailed Jun. 22, 2012.

\* cited by examiner

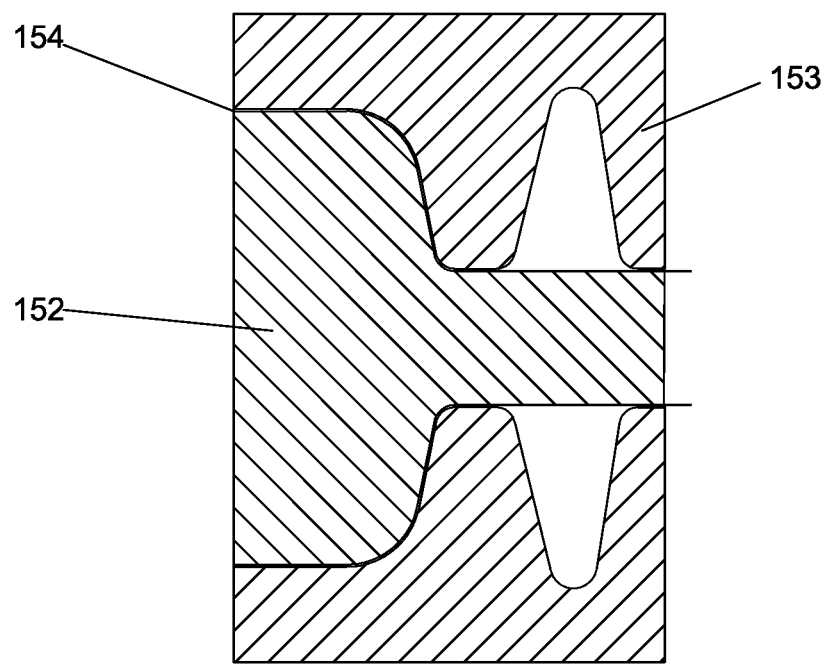
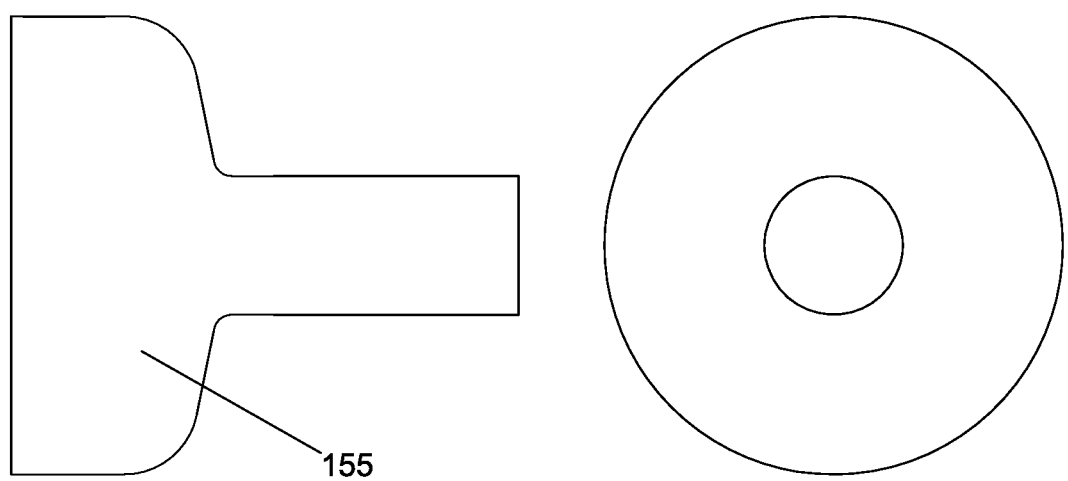
FIG 9

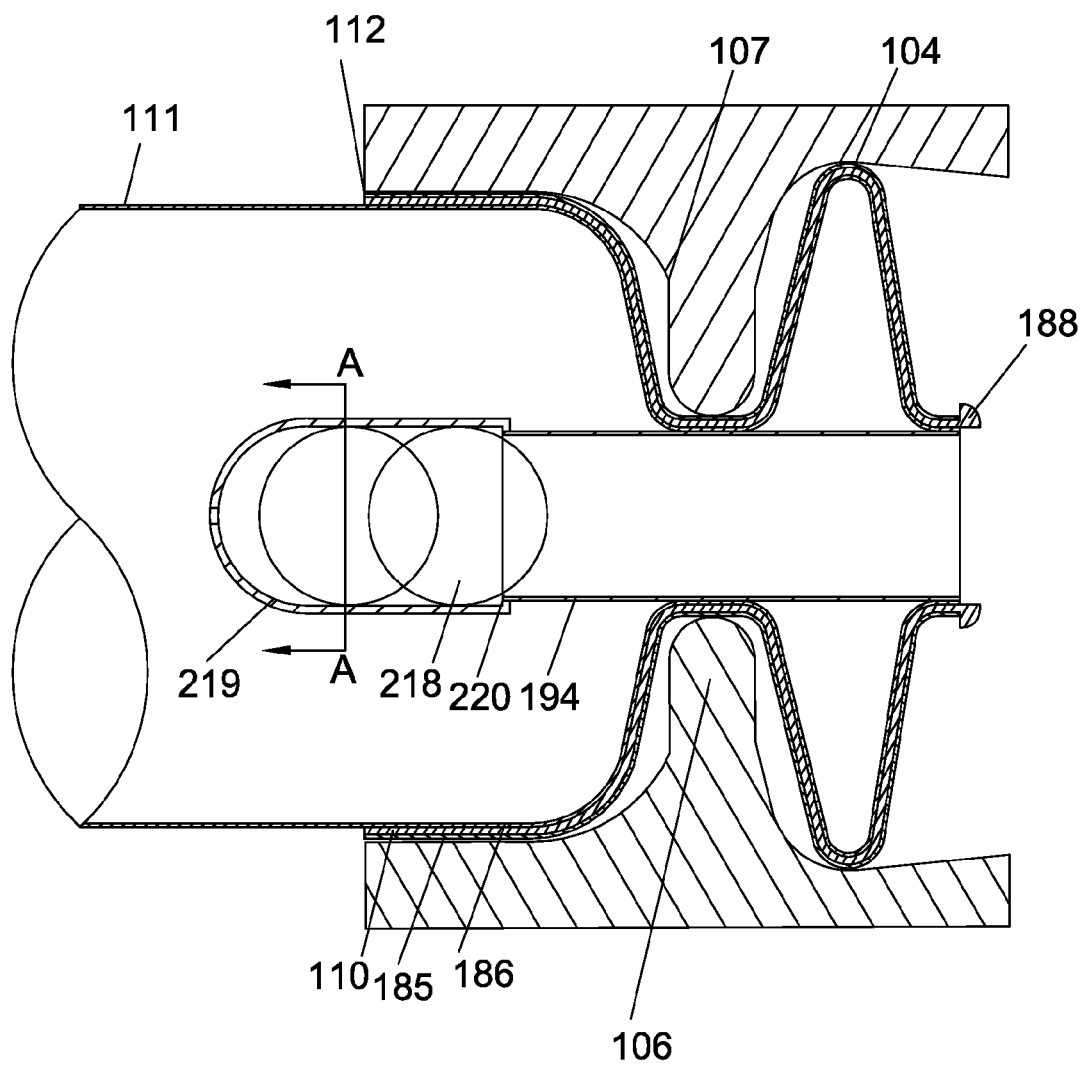
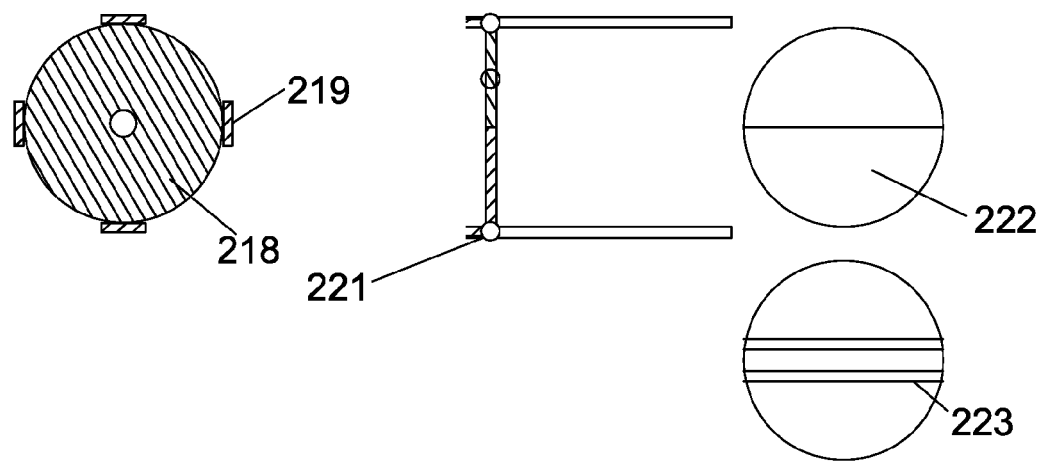
FIG 17

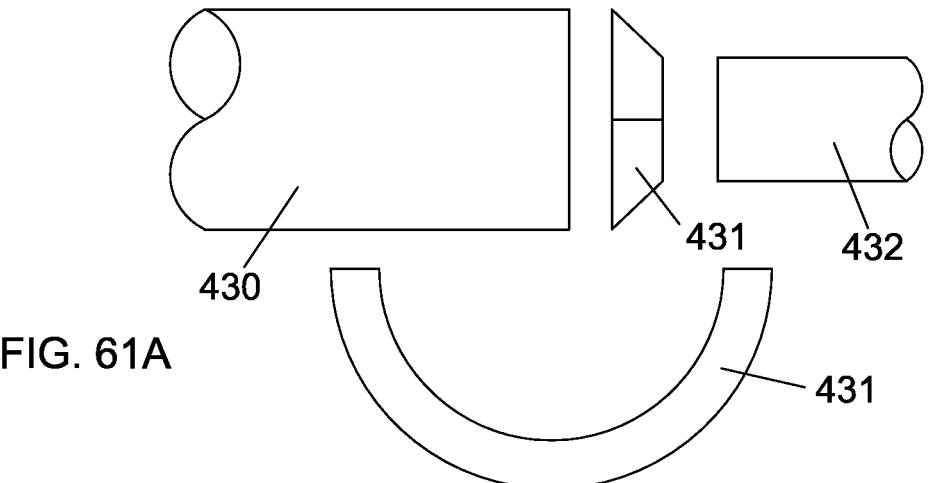
FIG. 61A
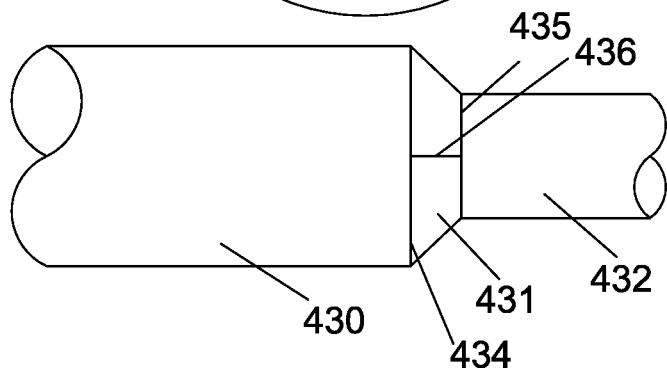
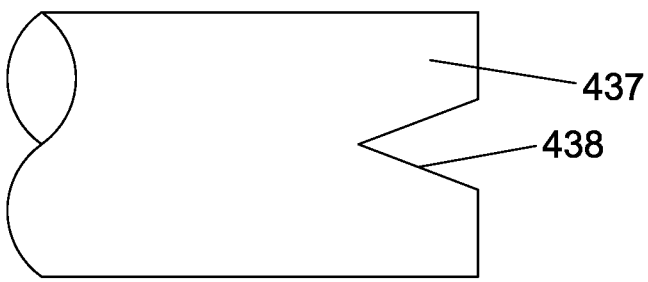
FIG. 61B
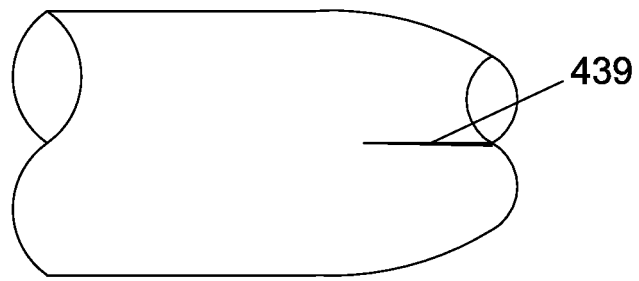

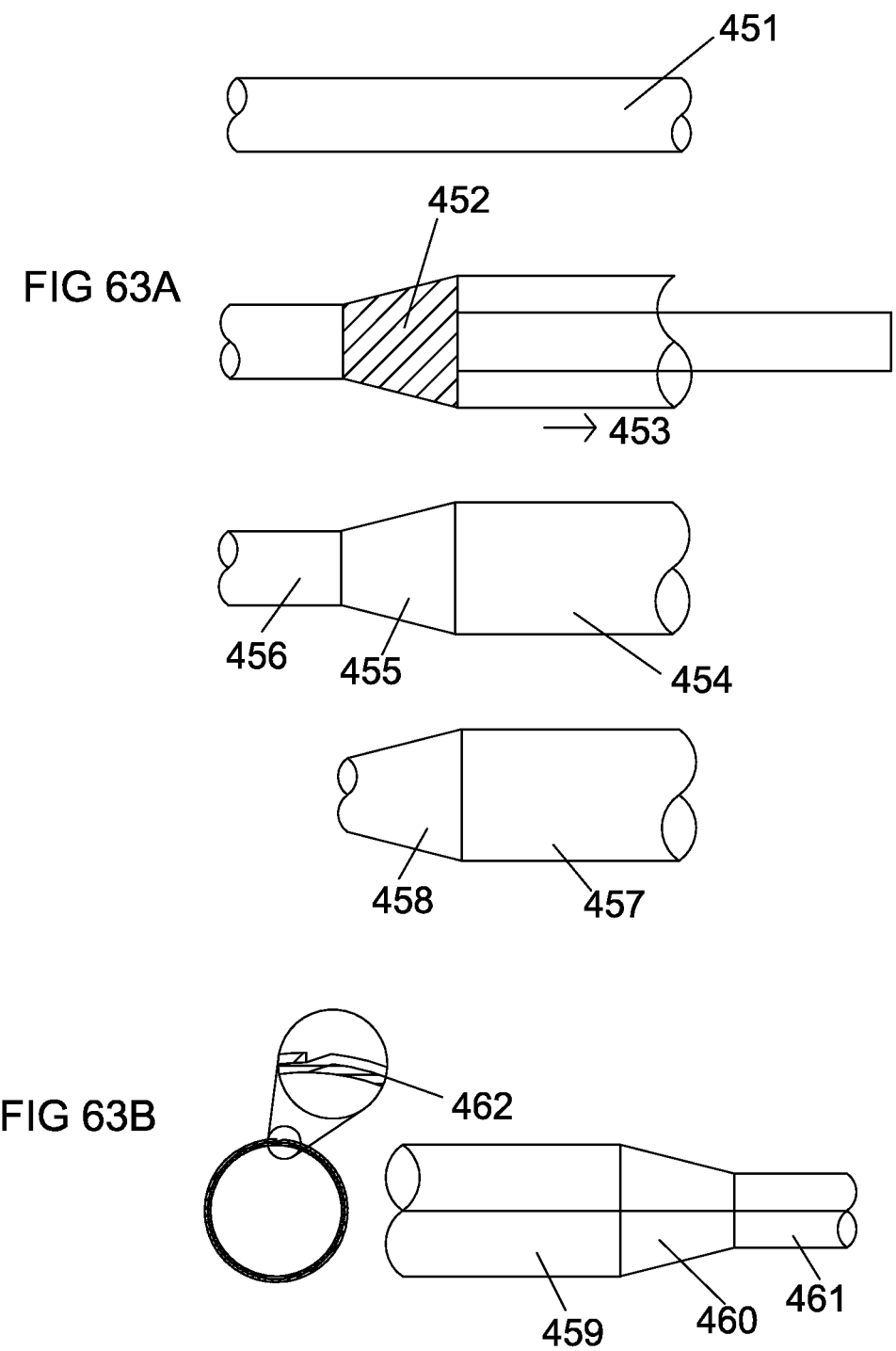

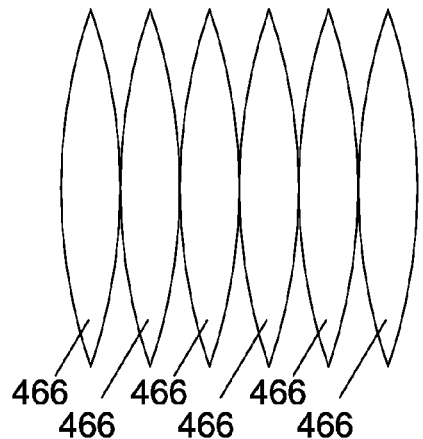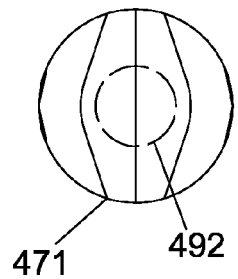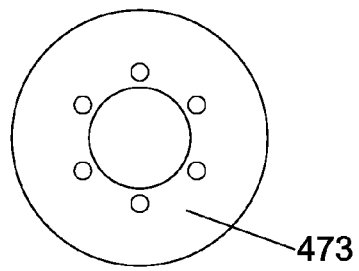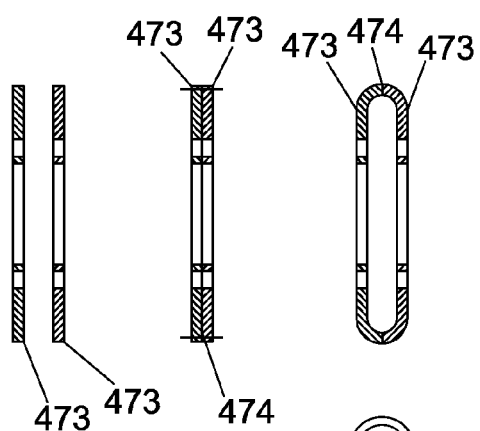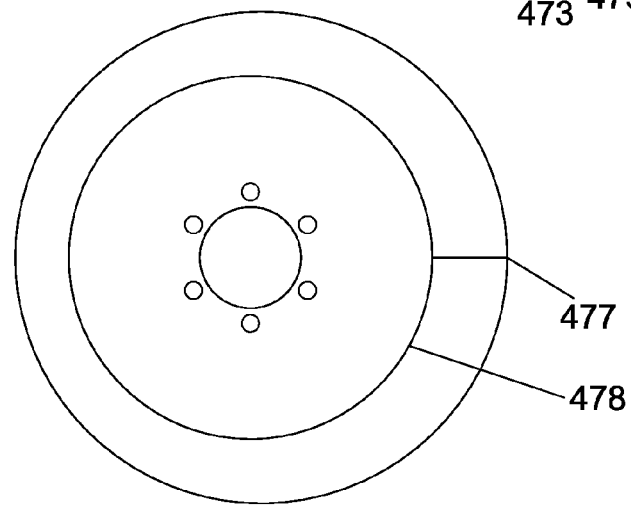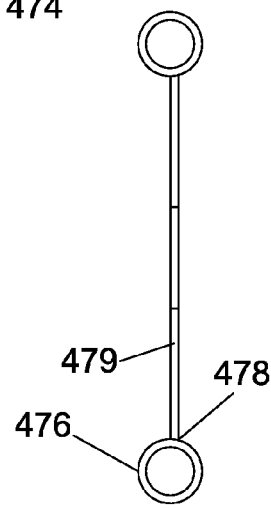
FIG 65A
FIG 65B
FIG 65C FIG. 77A 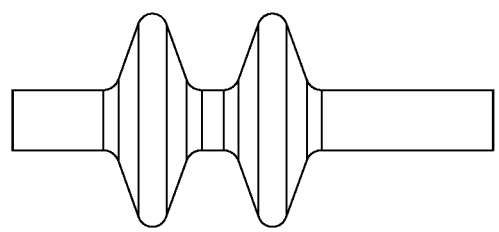 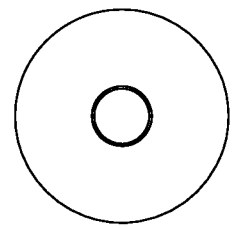
FIG. 77B 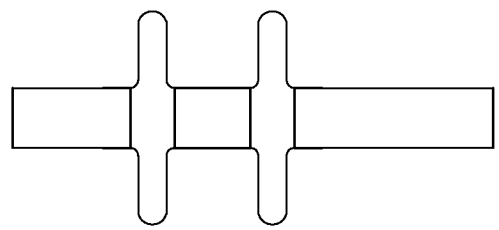 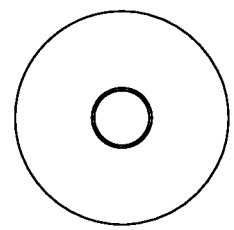
FIG. 77C 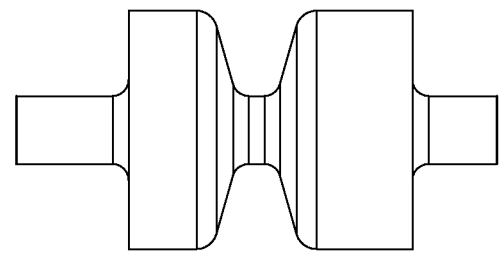 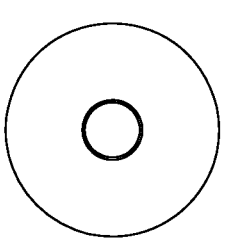
FIG. 77D 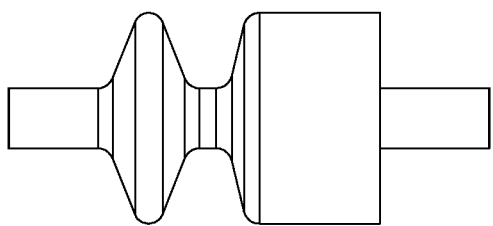 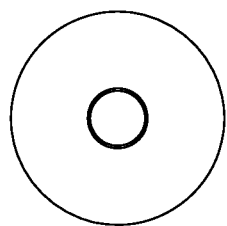
FIG. 77E 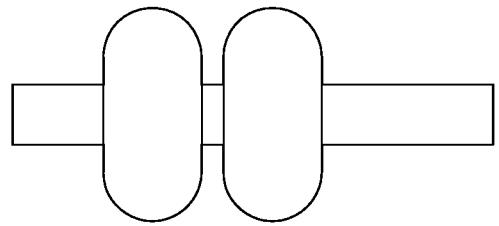 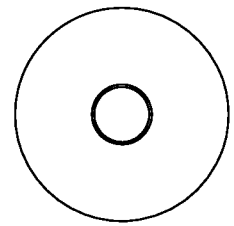

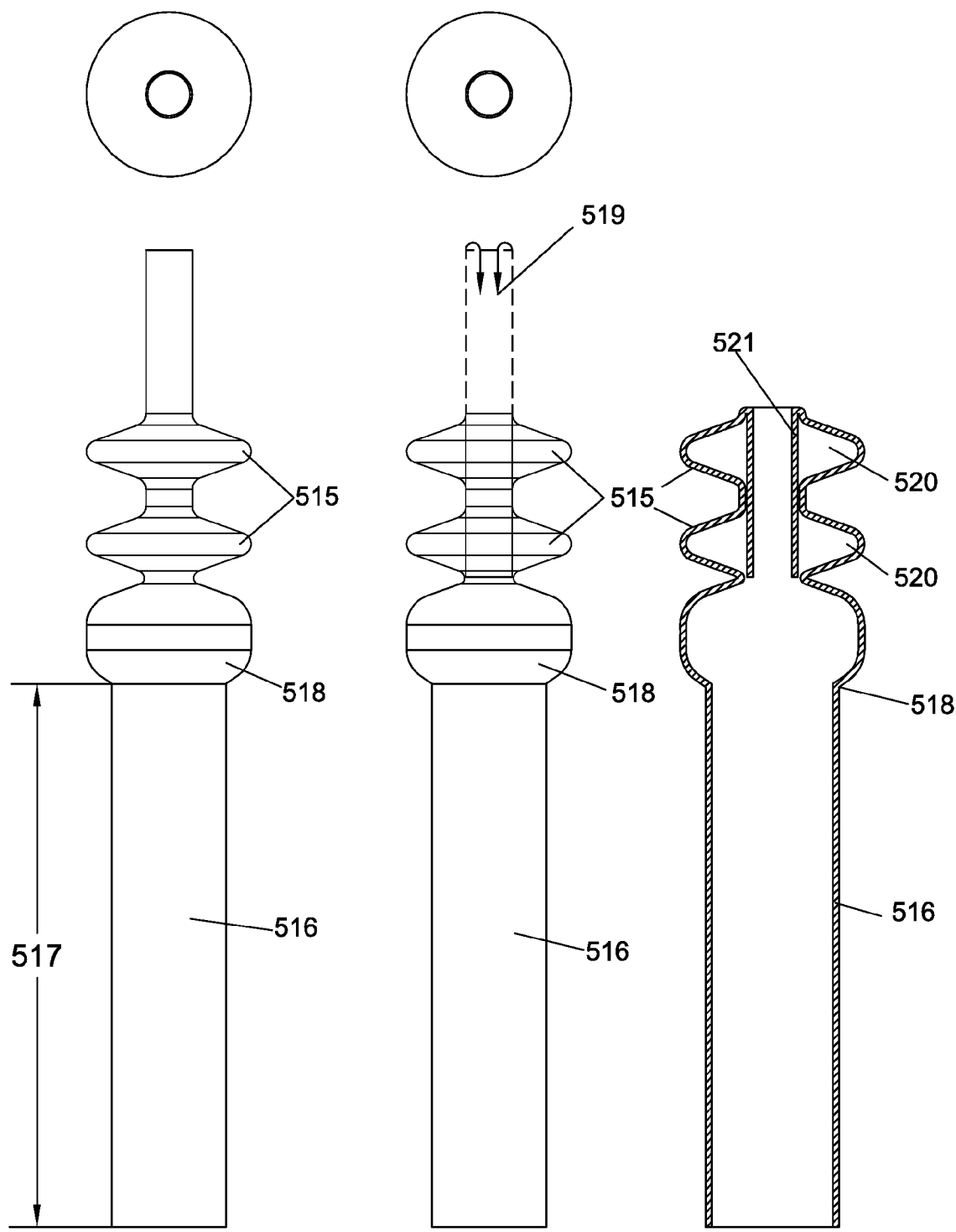

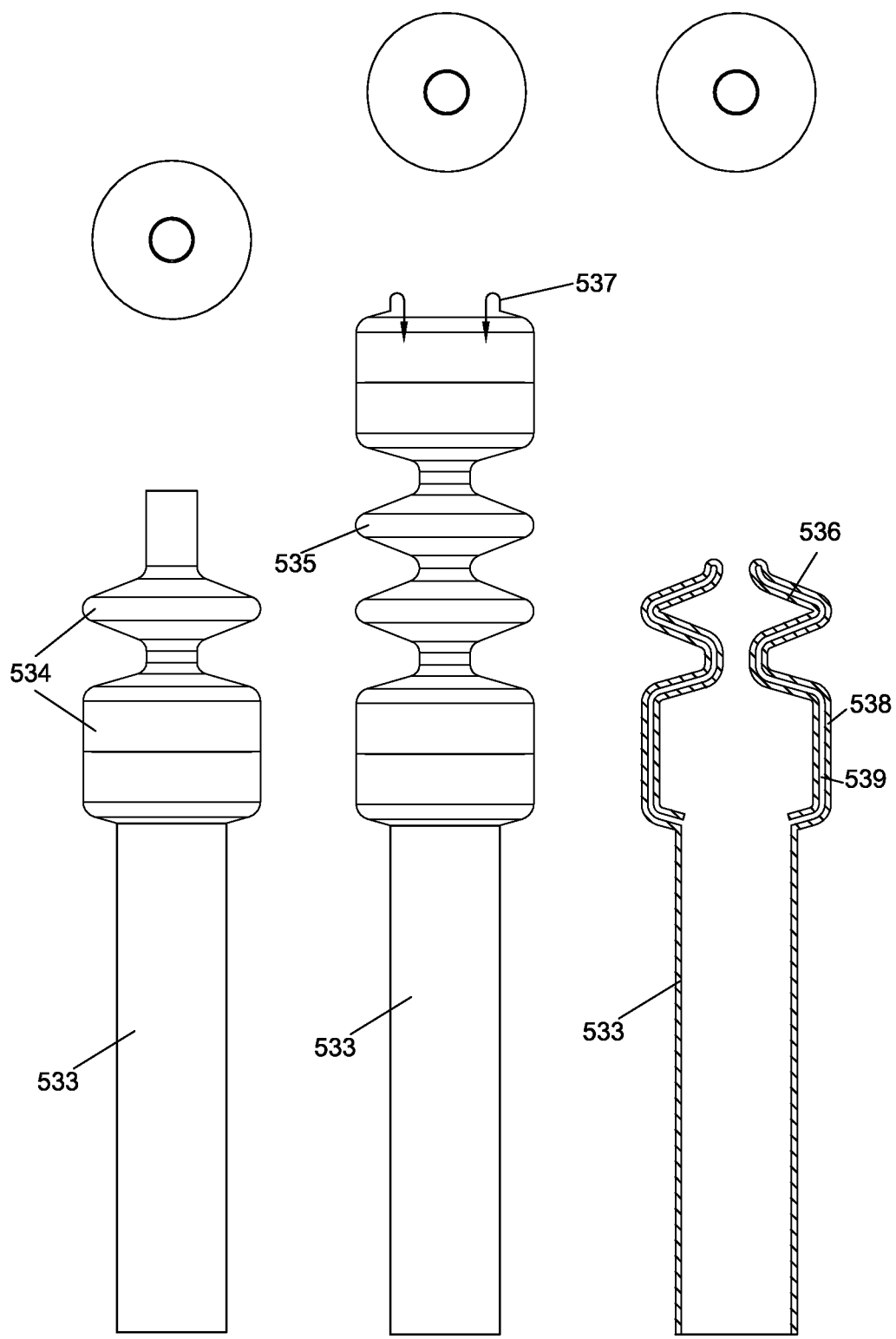

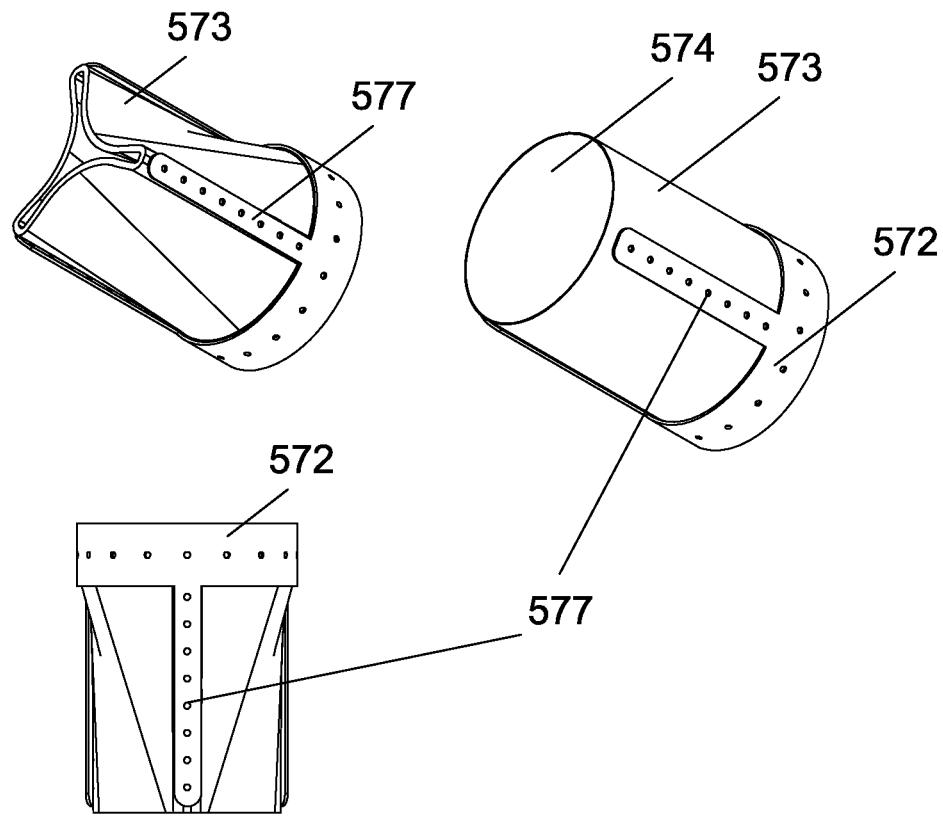
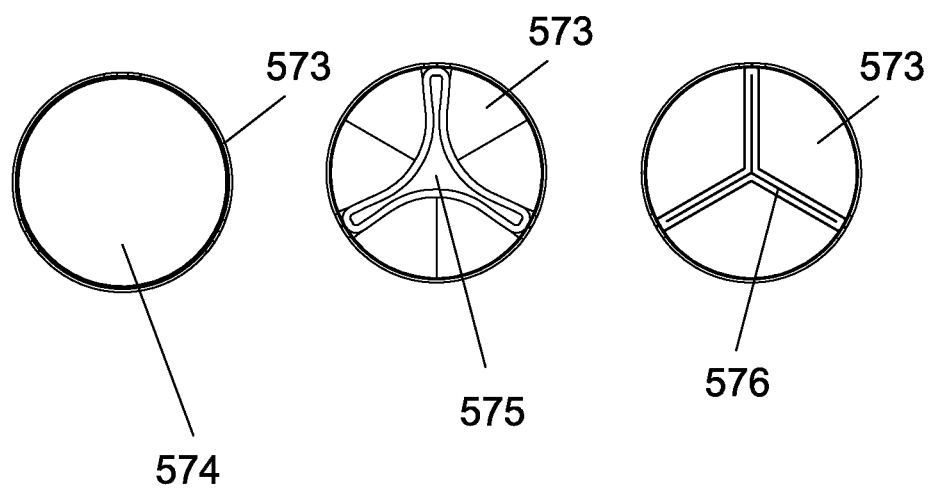
FIG. 93

ANCHORS AND METHODS FOR INTESTINAL BYPASS SLEEVES

CROSS-REFERENCE TO RELATED APPLICATIONS

This application claims the benefit under 35 U.S.C. section 119(e) of U.S. provisional patent application 61/462,156, filed Jan. 28, 2011, and U.S. provisional patent application 61/519,507, filed May 24, 2011, both of which are herein incorporated by reference in their entirety. This application is a continuation-in-part of each of the following applications, each of which are herein incorporated by reference in their entirety: (1) U.S. patent application Ser. No. 12/752,697, filed Apr. 1, 2010, which claims the benefit of U.S. provisional patent application 61/211,853, filed Apr. 3, 2009; (2) U.S. patent application Ser. No. 12/833,605, filed Jul. 9, 2010, which claims the benefit of U.S. provisional patent application 61/270,588, filed Jul. 10, 2009; (3) U.S. patent application Ser. No. 12/986,268, filed Jan. 7, 2011, which claims the benefit of U.S. provisional patent application 61/335,472, filed Jan. 7, 2010; and (4) U.S. patent application Ser. No. 13/298,867, filed Nov. 17, 2011, which claims the benefit of U.S. provisional patent application 61/458,060, filed Nov. 17, 2010.

TECHNICAL FIELD

This invention generally relates to implants placed within gastrointestinal systems, including the esophagus, the stomach and the intestines. In particular it relates to implant systems having components implantable and removable using endoscopic techniques for treatment of obesity, diabetes, reflux, gastroparesis and other gastrointestinal conditions.

BACKGROUND

Bariatric surgery procedures, such a sleeve gastrectomy, the Rouen-Y gastric bypass (RYGB) and the bileo-pancreatic diversion (BPD), modify food intake and/or absorption within the gastrointestinal system to effect weight loss in obese patients. These procedures affect metabolic processes within the gastrointestinal system, by either short circuiting certain natural pathways or creating different interaction between the consumed food, the digestive tract, its secretions and the neuro-hormonal system regulating food intake and metabolism. In the last few years there has been a growing clinical consensus that obese patients who undergo bariatric surgery see a remarkable resolution of their type-2 Diabetes Mellitus (T2DM) soon after the procedure. The remarkable resolution of diabetes after RYGB and BPD typically occurs too fast to be accounted for by weight loss alone, suggesting there may be a direct impact on glucose homeostasis. The mechanism of this resolution of T2DM is not well understood, and it is quite likely that multiple mechanisms are involved.

One of the drawbacks of bariatric surgical procedures is that they require fairly invasive surgery with potentially serious complications and long patient recovery periods. In recent years, there is an increasing amount of ongoing effort to develop minimally invasive procedures to mimic the effects of bariatric surgery using minimally invasive procedures. One such procedure involves the use of gastrointestinal implants that modify transport and absorption of food and organ secretions. For example, U.S. Pat. No. 7,476,256 describes an implant having a tubular sleeve with anchoring barbs, which offer the physician limited flexibility and are not readily removable or replaceable. Moreover, stents with active fixation means, such as barbs that deeply penetrate into surrounding tissue, may potentially cause tissue necrosis and erosion of the implants through the tissue, which can lead to complications, such as bacterial infection of the mucosal tissue or systemic infection. Also, due to the intermittent peristaltic motion within the digestive tract, implants such as stents have a tendency to migrate.

Gastroparesis is a chronic, symptomatic disorder of the stomach that is characterized by delayed gastric emptying in the absence of mechanical obstruction. The cause of gastroparesis is unknown, but it may be caused by a disruption of nerve signals to the intestine. The three most common etiologies are diabetes mellitus, idiopathic, and postsurgical. Other causes include medication, Parkinson's disease, collagen vascular disorders, thyroid dysfunction, liver disease, chronic renal insufficiency, and intestinal pseudo-obstruction. The prevalence of diabetic gastroparesis (DGP) appears to be higher in women than in men, for unknown reasons.

Diabetic gastroparesis affects about 40% of patients with type 1 diabetes and up to 30% of patients with type 2 diabetes and especially impacts those with long-standing disease. Both symptomatic and asymptomatic DGP seem to be associated with poor glycemic control by causing a mismatch between the action of insulin (or an oral hypoglycemic drug) and the absorption of nutrients. Treatment of gastroparesis depends on the severity of the symptoms.

SUMMARY

According to various embodiments, the present invention provides for an apparatus and method to place and anchor an intestinal bypass sleeve within the pyloric antrum, pylorus, duodenum and jejunum. The gastrointestinal implant herein disclosed can be inserted endoscopically (when the device is loaded into a delivery catheter) through the mouth, throat, stomach and intestines. The gastrointestinal implant device includes a flexible thin-walled sleeve and an expandable anchor attached to the proximal end of the sleeve; secondary anchors may also anchor other portions of the thin-walled sleeve.

The present invention herein disclosed (with a short bypass sleeve or no bypass sleeve) can also be used to hold open the pylorus and may help to reduce the symptoms of gastroparesis, by allowing the stomach contents to exit the stomach easier through the pylorus into the duodenum. An active pumping means may also be attached to the expandable anchor to actively pump the stomach contents from the pyloric antrum into the duodenum.

BRIEF DESCRIPTION OF THE DRAWINGS

FIG. 9 is a drawing of exemplary heat set mandrels for forming the shape of the anchor from the laser cut shape of FIG. 7 and FIG. 8 to the final shape of the anchor in FIG. 4.

FIG. 17 is a sectional view of an alternative embodiment of the invention herein disclosed implanted into the pylorus and duodenal bulb and duodenum. The through lumen of the expandable anchor contains a ball and cage anti-reflux valve and alternatively a bi-leaflet anti-reflux valve.

FIG. 61A is a drawing of an intestinal bypass sleeve.

FIG. 61B is a drawing of an alternative embodiment of an intestinal bypass sleeve.

FIG. 63A is a drawing of an alternative embodiment of an intestinal bypass sleeve.

FIG. 63B is a drawing of an alternative embodiment of an intestinal bypass sleeve.

FIG. 65A is drawing of a hemispherical- or disk-shaped covering for an expandable anchor that is assembled from sheet material into a spherical or disk shape.

FIG. 65B is drawing of a disk-shaped covering for an expandable anchor that is assembled from sheet material into a disk shape.

FIG. 65C is a drawing of a hemispherical- or disk-shaped covering for an expandable anchor that is assembled from tube and sheet material into a disk shape.

FIG. 77A is a drawing of the final formed shape of the ePTFE tube after blow-molding/radial stretching of the original cylindrical tube of ePTFE.

FIG. 77B is a drawing of an alternative embodiment the final formed shape of the ePTFE tube after blow-molding/radial stretching of the original cylindrical tube of ePTFE.

FIG. 77C is a drawing of an alternative embodiment the final formed shape of the ePTFE tube after blow-molding/radial stretching of the original cylindrical tube of ePTFE.

FIG. 77D is a drawing of an alternative embodiment the final formed shape of the ePTFE tube after blow-molding/radial stretching of the original cylindrical tube of ePTFE.

FIG. 77E is a drawing of an alternative embodiment the final formed shape of the ePTFE tube after blow-molding/radial stretching of the original cylindrical tube of ePTFE.

FIG. 78A is a drawing of the final formed shape of the ePTFE tube after blow-molding/radial stretching of the original cylindrical tube of ePTFE. The anchor covering portion of the sleeve and the intestinal bypass sleeve are formed integrally into one sleeve.

FIG. 78B is a drawing of the final formed shape of the ePTFE tube after blow-molding/radial stretching of the original cylindrical tube of ePTFE. The anchor covering portion of the sleeve and the intestinal bypass sleeve are formed integrally into one sleeve. The small-diameter end of the tube is started to be inverted inside to pull it inside to form an interior tube layer for the expandable anchor.

FIG. 78C is a drawing of the final formed shape of the ePTFE tube after blow-molding/radial stretching of the original cylindrical tube of ePTFE. The anchor covering portion of the sleeve and the intestinal bypass sleeve are formed integrally into one sleeve. The small-diameter end of the tube is fully inverted inside forming an interior layer for the expandable anchor.

FIG. 80C is a drawing of an alternative embodiment of the final formed shape of the ePTFE tube after blow-molding/radial stretching of the original cylindrical tube of ePTFE. The anchor covering portion of the sleeve and the intestinal bypass sleeve are formed integrally into one sleeve. The small-diameter end of the tube is fully inverted inside forming an interior layer for the expandable anchor.

FIG. 81A is a drawing of an alternative embodiment of the final formed shape of the ePTFE tube after blow-molding/radial stretching of the original cylindrical tube of ePTFE. The anchor covering portion of the sleeve and the intestinal bypass sleeve are formed integrally into one sleeve.

FIG. 81B is a drawing of an alternative embodiment of the final formed shape of the ePTFE tube after blow-molding/radial stretching of the original cylindrical tube of ePTFE. The anchor covering portion of the sleeve and the intestinal bypass sleeve are formed integrally into one sleeve. The one end of the tube is started to be inverted inside to pull it inside to form an interior tube layer for the expandable anchor.

FIG. 81C is a drawing of an alternative embodiment of the final formed shape of the ePTFE tube after blow-molding/radial stretching of the original cylindrical tube of ePTFE. The anchor covering portion of the sleeve and the intestinal bypass sleeve are formed integrally into one sleeve. The one end of the tube is fully inverted inside forming an interior layer for the expandable anchor.

FIG. 82A is a drawing of an alternative embodiment of the final formed shape of the ePTFE tube after blow-molding/radial stretching of the original cylindrical tube of ePTFE. The anchor covering portion of the sleeve and the intestinal bypass sleeve are formed integrally into one sleeve. The small-diameter end of the tube is inverted inside to pull it inside to form an interior tube layer for the expandable anchor. The interior tube is formed into the shape of a restrictive stoma and then an anti-reflux valve in series.

FIG. 85 is a drawing of an expandable anchor. The expandable anchor incorporates optional barbs and/or hooks have been incorporated into the anchor to provide for tissue penetration and additional anchoring.

FIG. 86 is a drawing of an expandable anchor. The expandable anchor incorporates optional barbs and/or hooks have been incorporated into the anchor to provide for tissue penetration and additional anchoring.

FIG. 87 is a drawing of an expandable anchor. The expandable anchor incorporates optional barbs and/or hooks have been incorporated into the anchor to provide for tissue penetration and additional anchoring.

FIG. 88 is a drawing of an expandable anchor. The expandable anchor incorporates optional barbs and/or hooks have been incorporated into the anchor to provide for tissue penetration and additional anchoring.

FIG. 89 is a drawing of an expandable anchor in which the anchors antral disk is larger in diameter than the duodenal bulb disk.

FIG. 90 is a drawing of an expandable anchor.

FIGS. 91-94 show various embodiments of anti-reflux valves for use in conjunction with an expandable anchor.

FIGS. 95-96 show various embodiments of anti-reflux valve frames having flexing posts for use in conjunction with an expandable anchor.

DETAILED DESCRIPTION OF THE DRAWINGS

Figure 1:
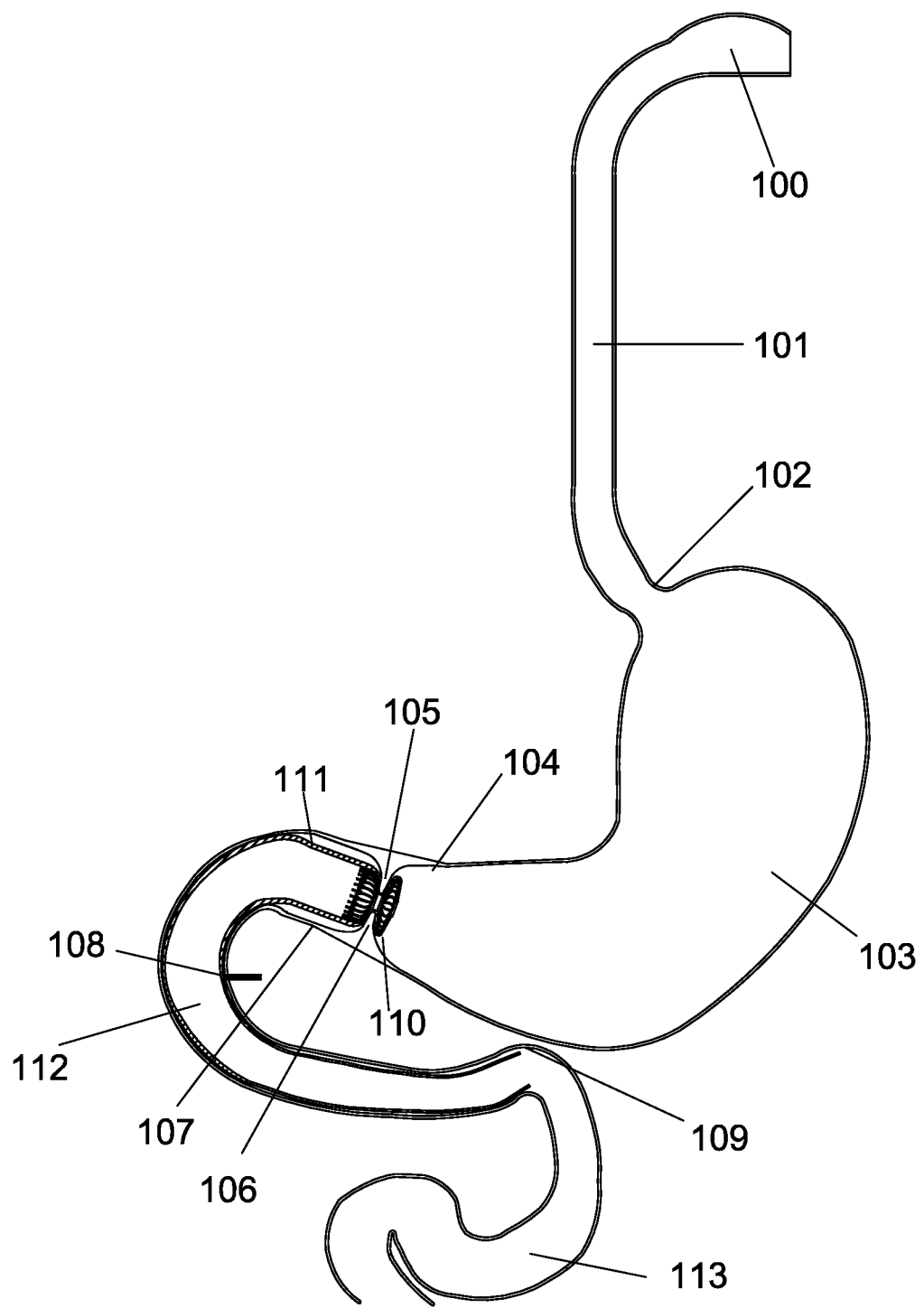
FIG. 1 is a cross-sectional view of a portion of the digestive tract in a human body with an intestinal bypass sleeve implanted in the duodenum from the pylorus to the ligament of treitz. The sleeve is held in place at the pylorus by an expandable anchor that anchors on the pylorus.

FIG. 1 is a sectional view of an embodiment of the invention implanted in a portion of a human digestive tract. As a person ingests food, the food enters the mouth 100, is chewed, and then proceeds down the esophagus 101 to the lower esophageal sphincter at the gastro-esophageal junction 102 and into the stomach 103. The food mixes with enzymes in the mouth 100 and in the stomach 103. The stomach 103 converts the food to a semi-fluid substance called chyme. The chyme enters the pyloric antrum 104 and exits the stomach 103 through the pylorus 106 and pyloric orifice 105. The pylorus (or pyloric sphincter) is a band of muscle that functions to adjust the diameter of the pyloric orifice, which in turn effects the rate at which chyme exits the stomach. The pylorus (or phyloric sphincter) also has a width (or thickness), which is the distance that the pylorus extends between the stomach and the duodenum. The small intestine is about 21 feet long in adults. The small intestine is comprised of three sections: the duodenum 112, jejunum 113 and ileum (not shown). The duodenum 112 is the first portion of the small intestine and is typically 10-12 inches long. The duodenum 112 is comprised of four sections: the superior, descending, horizontal and ascending. The duodenum 112 ends at the ligament of treitz 109. The papilla of vater 108 is the duct that delivers bile and pancreatic enzymes to the duodenum 112. The duodenal bulb 107 is the portion of the duodenum which is closest to the stomach 103. As shown, an intestinal bypass sleeve 111 is implanted in the duodenum from the pyloric antrum 104 and pylorus 106 to the ligament of treitz 109. The intestinal bypass sleeve 111 is held in place at the pylorus 106 by an expandable anchor 110 that anchors on the pylorus 106.

In various exemplary embodiments, the sleeve 111 is integrally formed with or coupled to the expandable anchor 110. According to other exemplary embodiments, the sleeve 111 is removably or releasably coupled to the expandable anchor 110. According to various embodiments, the bypass sleeve has a diameter of between about 10 mm and about 35 mm. According to various embodiments, the bypass sleeve has a thickness of between about 0.001 and about 0.015 inches. Exemplary structures for removably or releasably coupling or attaching the sleeve 111 to the expandable anchor 110 are disclosed for example in U.S. patent application Ser. No. 12/752,697, filed Apr. 1, 2010, entitled "Modular Gastrointestinal Prostheses," which is incorporated herein by reference. According to various embodiments, the sleeve 111 or the expandable anchor 110 (or both) are further coupled at the pylorus 106 using one or more of the techniques described in either of U.S. patent application Ser. No. 12/752,697 or U.S. patent application Ser. No. 12/833,605, filed Jul. 9, 2010, entitled "External Anchoring Configuration for Modular Gastrointestinal Prostheses," both of which are incorporated herein by reference. According to various embodiments of the invention, the sleeve 111 may be configured and coupled to the expandable anchor 110, using one or more of the configurations disclosed in U.S. patent application Ser. No. 12/986,268, filed Jan. 7, 2011, entitled "Gastrointestinal Prostheses Having Partial Bypass Configurations," which is incorporated herein by reference.

Figure 2:
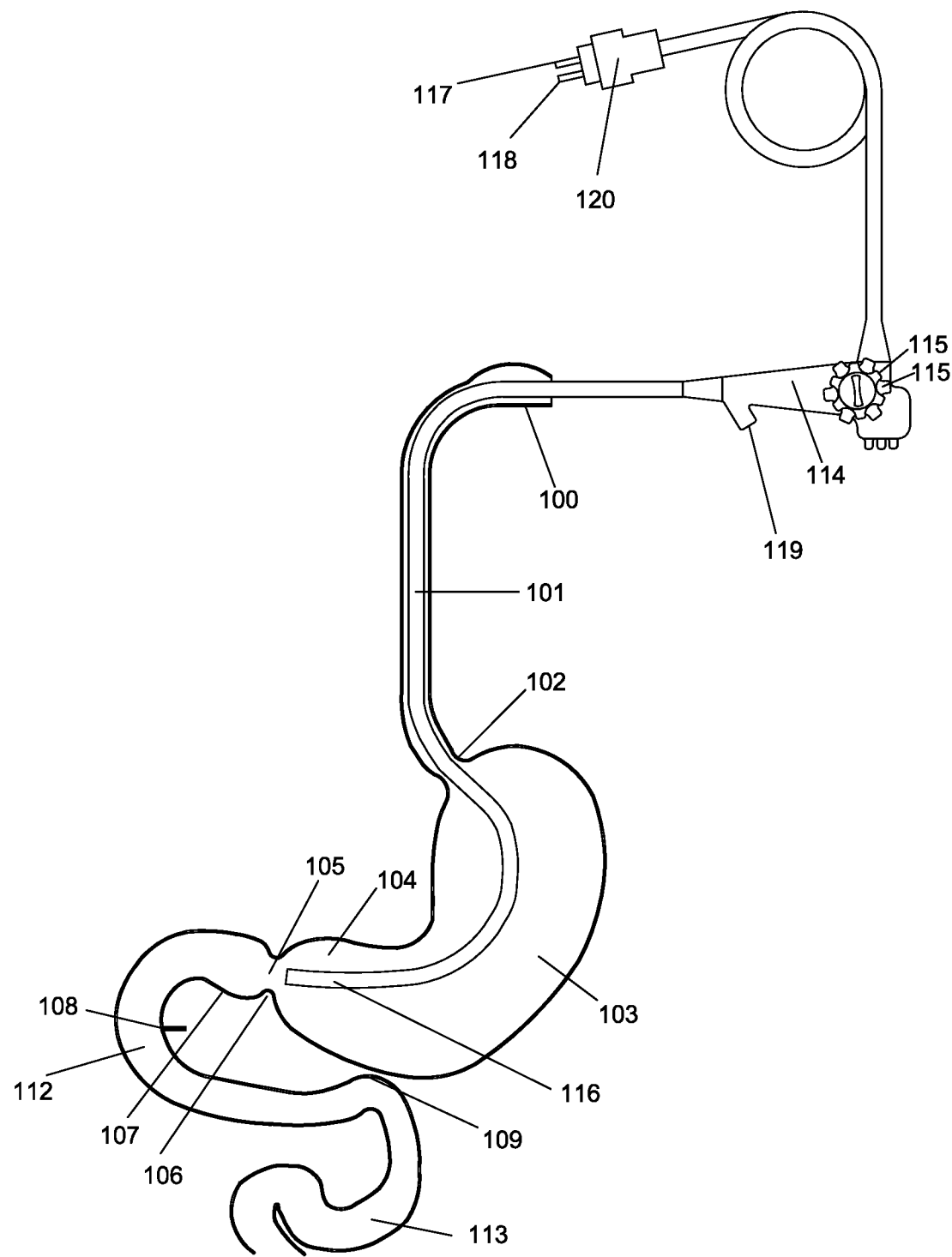
FIG. 2 is a cross-sectional view of a portion of the digestive tract in a human body with an endoscope inserted through the mouth, esophagus and stomach to the pylorus.

FIG. 2 is a sectional view of a portion of the digestive tract in a human body. As shown, an endoscope 114 has been inserted through: the mouth 100, esophagus 101, stomach 103 and pyloric antrum 104 to allow visualization of the pylorus 106. Endoscopes 114 are used for diagnostic and therapeutic procedures in the gastrointestinal tract. The typical endoscope 114 is steerable by turning two rotary dials 115 to cause deflection of the working end 116 of the endoscope. The working end of the endoscope or distal end 116, typically contains two fiber bundles for lighting 117, a fiber bundle for imaging 118 (viewing) and a working channel 119. The working channel 119 can also be accessed on the proximal end of the endoscope. The light fiber bundles and the image fiber bundles are plugged into a console at the plug in connector 120. The typical endoscope has a working channel in the 2.6 to 3.2 mm diameter range. The outside diameter is typically in the 8 to 12 mm diameter range depending on whether the endoscope is for diagnostic or therapeutic purposes.

Figure 3A:
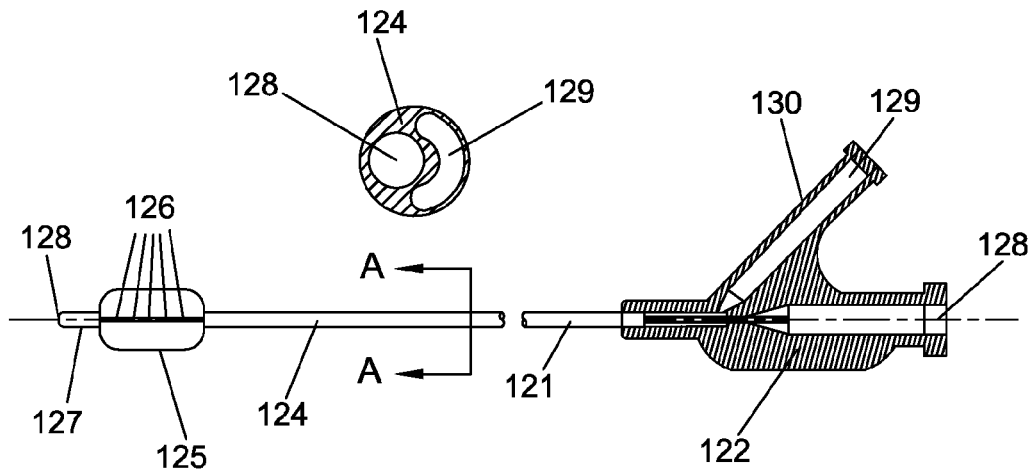
FIG. 3A is a drawing of an over-the-wire sizing balloon that may be used to dilate and measure (size) the intestinal tract and pylorus anatomy.

FIG. 3A is a drawing of an over-the-wire sizing balloon 121 that is used to measure the diameter of the pylorus 106, duodenal bulb 107, esophagus 102, pyloric antrum 104 or other lumen in the GI tract. The sizing balloon is composed of the following elements: proximal hub 122, catheter shaft 124, distal balloon component 125, radiopaque marker bands 126, distal tip 127, guidewire lumen 128, inflation lumen 129. Distal balloon component 125 can be made from silicone, silicone polyurethane copolymers, latex, nylon 12, PET (Polyethylene terephthalate) Pebax (polyether block amide), polyurethane, polyethylene, polyester elastomer or other suitable polymer. The distal balloon component 125 can be molded into a cylindrical shape, into a dogbone or a conical shape. The distal balloon component 125 can be made compliant or non-compliant. The distal balloon component 125 can be bonded to the catheter shaft 124 with glue, heat bonding, solvent bonding, laser welding or suitable means. The catheter shaft can be made from silicone, silicone polyurethane copolymers, latex, nylon 12, PET (Polyethylene terephthalate) Pebax (polyether block amide), polyurethane, polyethylene, polyester elastomer or other suitable polymer. Section A-A in FIG. 3A is a cross-section of the catheter shaft 124. The catheter shaft 124 if shown as a dual lumen extrusion with a guidewire lumen 128 and an inflation lumen 129. The catheter shaft 124 can also be formed from two coaxial single lumen round tubes in place of the dual lumen tubing. The balloon is inflated by attaching a syringe (not shown) to a luer fitting side port 130. The sizing balloon accommodates a guidewire through the guidewire lumen from the distal tip 127 through the proximal hub 122. The sizing balloon can be filled with saline or a radiopaque dye to allow visualization and measurement of the size of the anatomy with a fluoroscope. The sizing balloon 121 has two or more radiopaque marker bands 126 located on the catheter shaft to allow visualization of the catheter shaft and balloon position. The marker bands 126 also serve as fixed known distance reference points that can be measured to provide a means to calibrate and determine the balloon diameter with the use of the fluoroscope. The marker bands can be made from tantalum, gold, platinum, platinum iridium alloys or other suitable material.

Figure 3B:
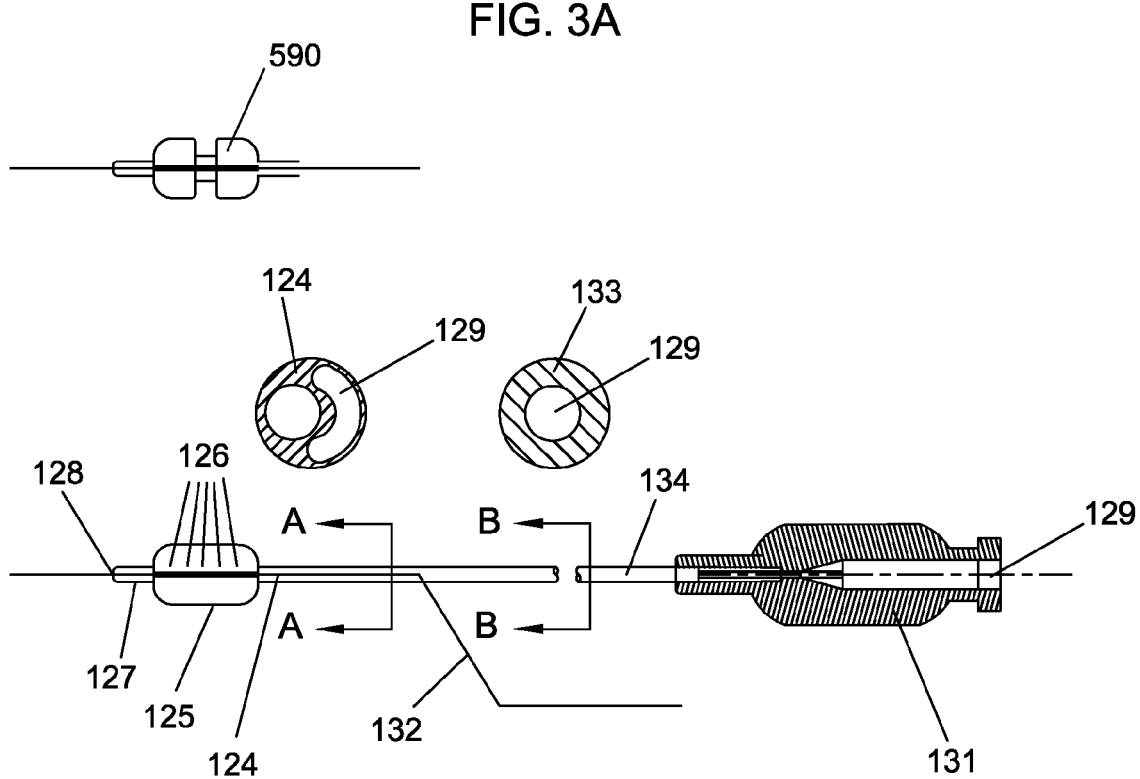
FIG. 3B is a drawing of a rapid exchange or monorail sizing balloon that may be used to dilate and measure (size) the intestinal tract and pylorus anatomy.

FIG. 3B shows a rapid exchange sizing balloon 134 that is used to measure the diameter of the pylorus 106, duodenal bulb 107, esophagus 101, pyloric antrum 104 or other lumen in the GI tract. The sizing balloon is composed of the following elements: proximal luer 131, catheter shaft 124, distal balloon component 125, radiopaque marker bands 126, distal tip 127, guidewire lumen 128, inflation lumen 129. The materials of construction will be similar to that of FIG. 4A. The guidewire lumen 128 does not travel the full length of the catheter. It starts at the distal tip 127 and exits out the side of the catheter at distance shorter than the overall catheter length. The guidewire 132 is inserted into the balloon catheter to illustrate the guidewire path through the sizing balloon. The sizing balloon catheter shaft changes section along its length from a single lumen at section B-B 133 to a dual lumen at section A-A at 124. An alternative hourglass-shaped balloon 590 can be used for sizing the pylorus anatomy without dilating the pylorus aperture.

Figure 4:
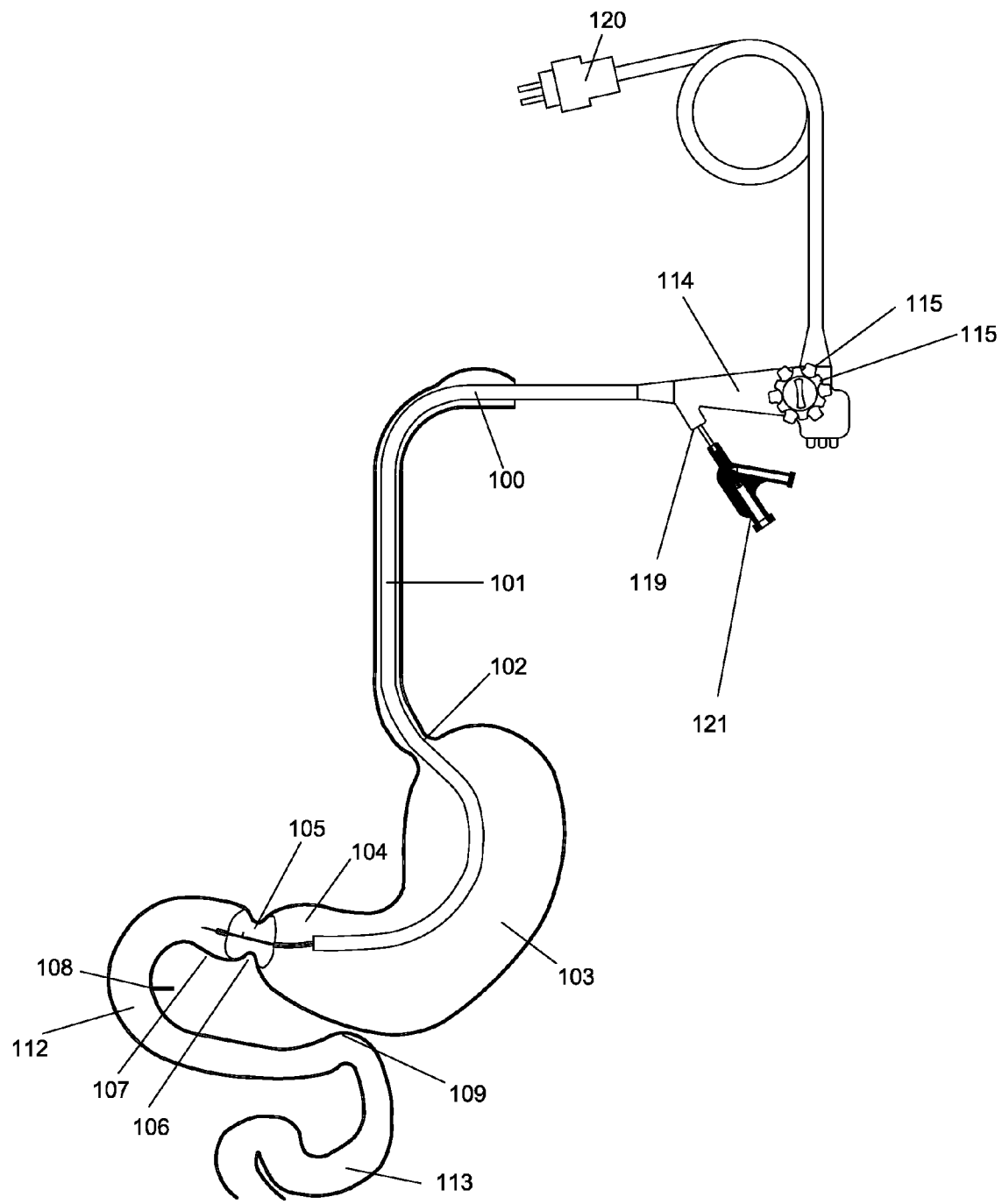
FIG. 4 is a cross-sectional view of a portion of the digestive tract in a human body. An endoscope is inserted through the mouth, esophagus and stomach to the pylorus. An over-the-wire sizing balloon is inserted through the working channel of the endoscope over a guidewire and is advanced across the pyloric opening. The balloon is inflated with saline or contrast media to a low pressure to open the pylorus and duodenum and allow measurement of the lumen diameter of the pyloric antrum, pylorus and duodenal bulb.

FIG. 4 is a sectional view of a portion of the digestive tract in a human body. As shown, an endoscope 114 is inserted through the mouth 100, esophagus 101 and stomach 103 up to the pylorus 106. An over the wire sizing balloon 121 is inserted through the working channel 119 of the endoscope 114 over a guidewire and is advanced across the pyloric opening 105. The balloon is inflated with saline or contrast media to a low pressure to open the pylorus 106, pyloric antrum 104 and duodenal bulb 107 and to allow measurements to be taken.

Figure 5:
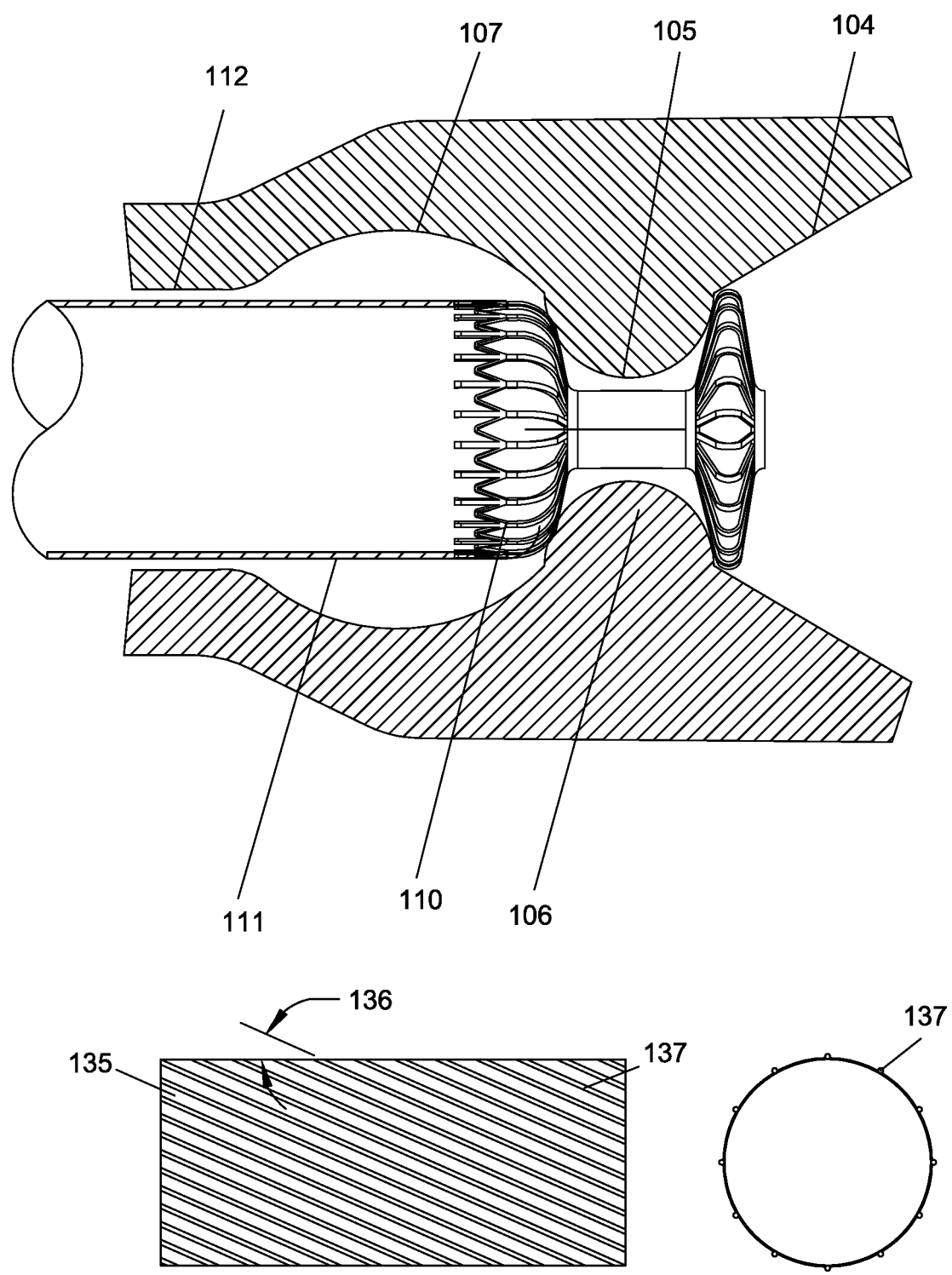
FIG. 5 is a cross-sectional drawing of the pyloric antrum, pylorus, duodenal bulb and duodenum. An expandable anchor and intestinal bypass sleeve is implanted into the pylorus.
Figure 11:
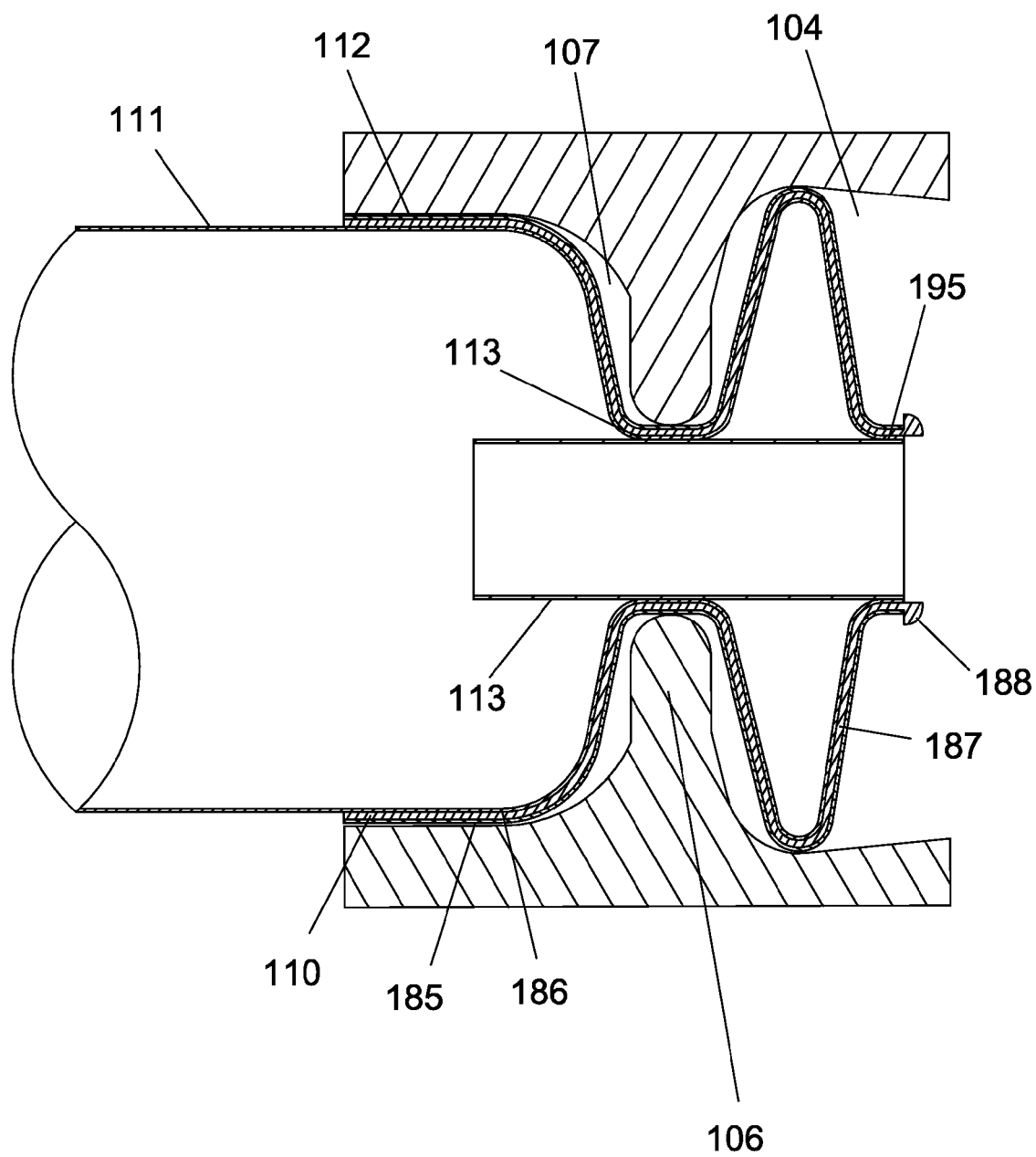
FIG. 11 is a sectional view of an anchor and sleeve implanted into a pylorus and duodenal bulb and duodenum. The expandable anchor is covered with a membrane on both the inside and outside surfaces of the anchor to close the openings in between the spring arm elements. An intestinal bypass sleeve is attached to the expandable anchor.

FIG. 5 is a sectional view of the pyloric antrum 104, pylorus 106, duodenal bulb 107 and duodenum 112. An expandable anchor 110 and intestinal bypass sleeve 111 is implanted into the pylorus 106. The expandable anchor 110 is shown here without a covering material to allow for better visualization of the expandable anchor 110. In various exemplary embodiments, the expandable anchor 110 is not covered, while in other exemplary embodiments, it is covered with a polymer membrane made from a material such as silicone, polyurethane, polytetrafluoroethylene, fluorinated ethylene propylene, polyethylene, expanded polytetrafluoroethylene or other suitable material. FIG. 11, for example, shows an embodiment of the expandable anchor 110 covered with a polymer film. The expandable anchor 110 can be made from metal or plastic. The intestinal bypass sleeve 111 can vary in length from 1-2 inches in length up to several feet. In some embodiments, the sleeve bypasses the length of the duodenum up to the ligament of treitz. While various embodiments disclosed herein describe the intestinal bypass sleeve as extending into the duodenum, in all such embodiments, it is also contemplated that the intestinal bypass sleeve has a length sufficient to allow it to extend partially or fully into the jejunum. The intestinal bypass sleeve 111 may be made from a thin-walled polymer material such as silicone, polyurethane, polytetrafluoroethylene, fluorinated ethylene propylene, polyethylene, expanded polytetrafluoroethylene (ePTFE) or other suitable material. In exemplary embodiments, the wall thickness of the intestinal bypass sleeve 111 may be in the range of 0.001 inch to 0.010 inch thick. The intestinal bypass sleeve 111 may be made by extrusion, into a tubular form or a lay flat tubing, dip coated from a liquid solution, powder coated from fine particles of polymer or paste extruded and then stretched as is the case with ePTFE. As shown in FIG. 5, the intestinal bypass sleeve 111 may have optional helical reinforcements 135 made from a polymer or metal applied to the outer, inner or within the wall thickness of the sleeve. The helical reinforcement can provide for additional kink resistance and prolapse resistance. The wind angle 136 of the helical reinforcement, in exemplary embodiments, has a high pitch angle (for example, 45 degrees) to allow the diameter of the intestinal bypass sleeve to compress easily. According to various embodiments, the wind angle 136 is in the 10 to 85 degrees range. The helical reinforcement may be made integral with the intestinal bypass sleeve or it may be added in a secondary process by bonding on a monofilament(s) 137 of polymer or wire to the surface of the sleeve.

Figure 6:
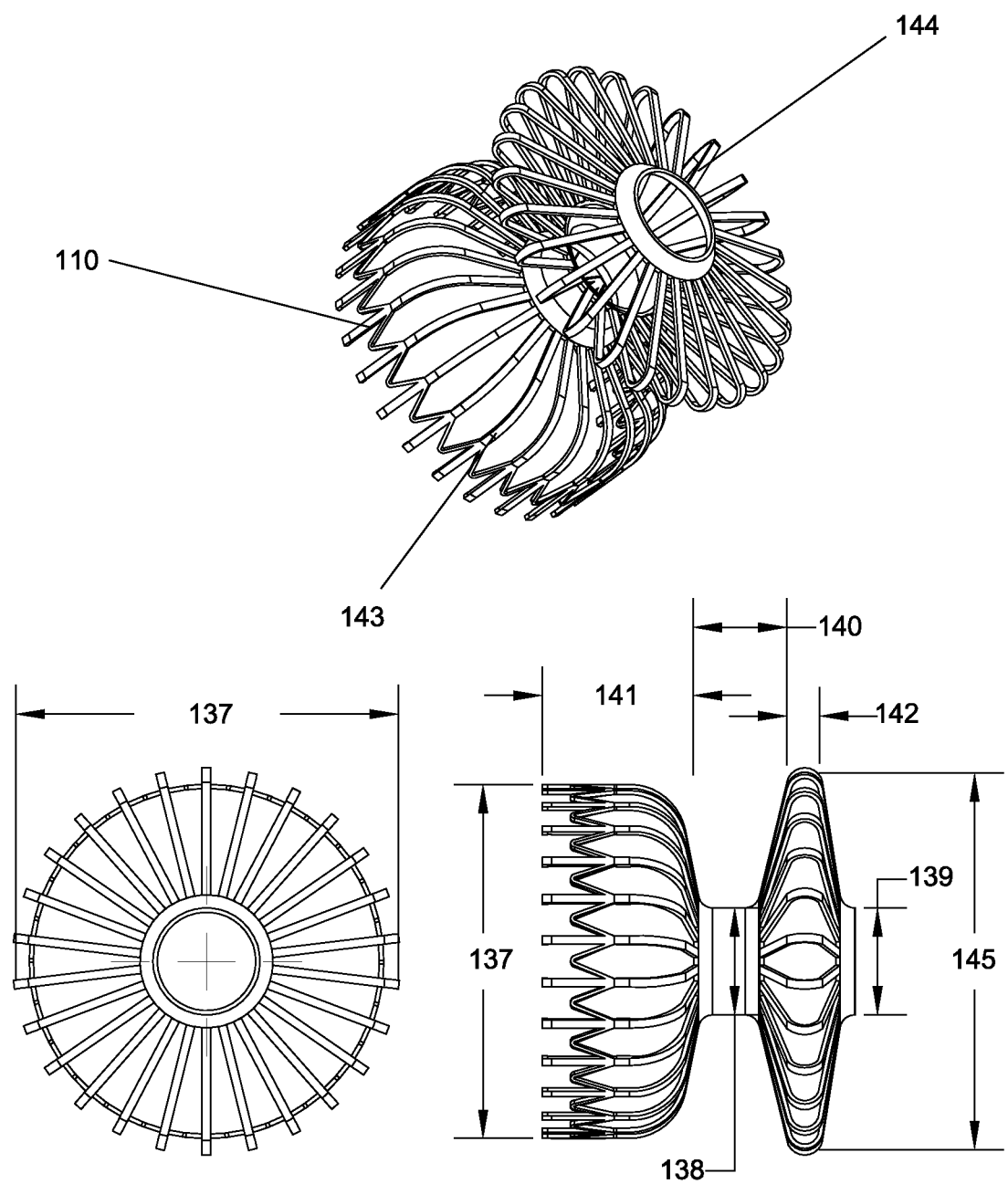
FIG. 6 is a drawing of an expandable anchor according to exemplary embodiments of the invention.

FIG. 6 is a drawing of an expandable anchor 110. The expandable anchor 110 provides for an anchoring means to hold an intestinal bypass sleeve 111 within the small intestine. In exemplary embodiments, the expandable anchor 110 is designed to allow the anchor to be of a self expanding design. A self expanding anchor design can be compressed in diameter to allow the device to be compressed in diameter to be loaded onto a delivery catheter. The anchor 110 can then recover elastically to the original starting diameter, with the anchor diameter decreasing only a small amount due to non elastic recovery. The anchor 110 can also be made of a plastically deformable design and require a mechanical force applied to it in the radial or longitudinal direction to accomplish the expansion of the anchor. The mechanical force can be accomplished with an inflatable balloon type device, radially expanding the anchor 110, or it may also be accomplished by a longitudinal compression of the anchor 110 by a screw type mechanism or cable tensioning means. As shown, the anchor 110 has a proximal portion or proximal disk 144 that is comprised of 26 spring arms.

As shown, the anchor 110 has a distal portion (e.g., open-ended cylindrical portion) 143 that is comprised of 26 spring arms. According to various embodiments, the anchor 110 could have from 3 to 72 spring arms for the proximal disk and the open ended cylinder.

According to exemplary embodiments, the expandable anchor 110 is made from a nickel titanium alloys (Nitinol). Other alternative suitable alloys for manufacturing the anchor 110 are stainless steel alloys: 304, 316L, BioDur® 108 Alloy, Pyromet Alloy® CTX-909, Pyromet® Alloy CTX-3, Pyromet® Alloy 31, Pyromet® Alloy CTX-1, 21Cr-6Ni-9Mn Stainless, 21Cr-6Ni-9Mn stainless, Pyromet Alloy 350, 18Cr-2Ni-12Mn Stainless, Custom 630 (17Cr-4Ni) Stainless, Custom 465® Stainless, Custom 455® Stainless Custom 450® Stainless, Carpenter 13-8 Stainless, Type 440C Stainless, cobalt chromium alloys—MP35N, Elgiloy, L605, Biodur® Carpenter CCM alloy, Titanium and titanium alloys, Ti-6Al-4V/ELI and Ti-6Al-7Nb, Ti-15Mo, Tantalum, Tungsten and tungsten alloys, pure platinum, platinum-iridium alloys, platinum-nickel alloys, niobium, iridium, conichrome, gold and gold alloys. The anchor 110 may also be comprised of the following absorbable metals: Pure Iron and magnesium alloys. The anchor 110 may also be comprised of the following plastics: Polyetheretherketone (PEEK), polycarbonate, polyolefins, polyethylenes, polyether block amides (PEBAX), nylon 6, 6-6, 12, Polypropylene, polyesters, polyurethanes, polytetrafluoroethylene (PTFE) Poly (phenylene sulfide) (PPS), poly(butylene terephthalate) PBT, polysulfone, polyamide, polyimide, poly(p-phenylene oxide) PPO, acrylonitrile butadiene styrene (ABS), Polystyrene, Poly(methyl methacrylate) (PMMA), Polyoxymethylene (POM), Ethylene vinyl acetate, Styrene acrylonitrile resin, Polybutylene. The anchor 110 may also be comprised of the following absorbable polymeres: Polyglycolic acid (PGA), Polylactide (PLA), Poly(ε-caprolactone), Poly(dioxanone) Poly(lactide-co-glycolide).

Figure 7:
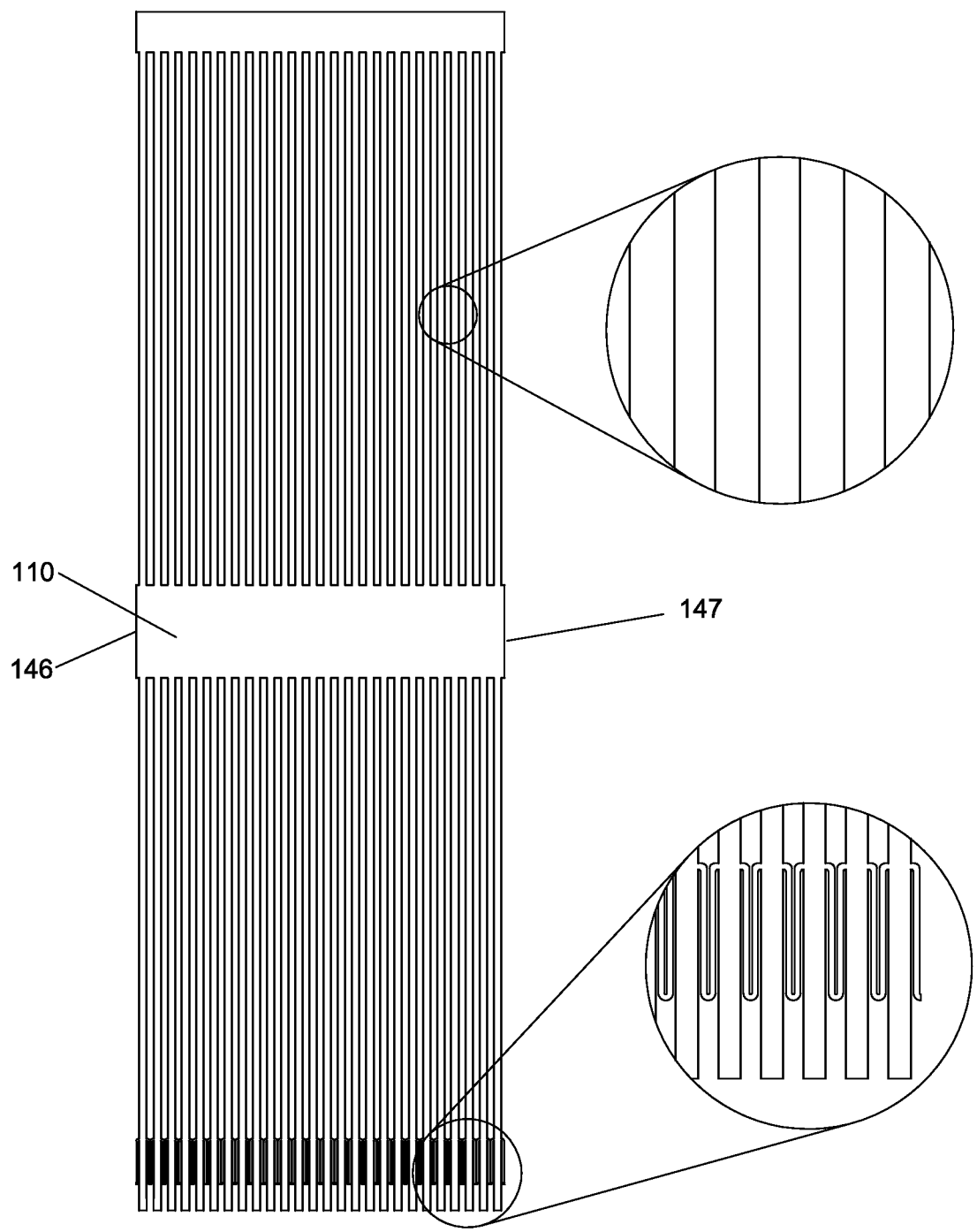
FIG. 7 is a drawing of a flat representation of the circumference of the expandable anchor disclosed in FIG. 2. The anchor can be laser cut from round tubing or a flat sheet of Nitinol.

The anchor 110, according to exemplary embodiments, is laser cut from a round tubing or from a flat sheet of Nitinol and then is rolled into a cylindrical shape after laser cutting. The flat representation of the anchor 110 is shown in FIG. 7. The anchor 110, according to exemplary embodiments, is made from a Nitinol tube of about 9 mm outside diameter by a wall thickness of 0.006 inch thick. Alternatively a starting tube outside diameter can range from about 2 mm to 16 mm. An alternative construction method is to laser cut or chemical etch the pattern form a flat sheet of Nitinol with a thickness of 0.002 inch to 0.020 inch.

According to various embodiment, anchor 110 has an inside diameter 139 in the range of about 2 mm to 20 mm, Anchor 110 has an expanded open end 137 in the range of about 12 mm to 60 mm. Anchor 110 has a disk-shaped feature 144 that has a diameter 145 in the range of about 12 to 60 mm. Anchor 110 has a central cylinder 138 that has an outside diameter in the range of 4 to 20 mm. Anchor 110 has a flange 141 adjacent to large diameter open end that has a length of about 8 mm in length. According to various embodiments, this length 141 could range from a length of about 1 mm to 30 mm in length. Central cylinder section 138 can have a length 140 of about 1 mm to 30 mm. In various embodiments, the length of the cylinder section 138 is about equal to a width of the pylorus 106 (e.g., the phyloric sphincter). The proximal disk can have a length of 1 mm to 20 mm. The proximal disk 144 can alternatively be formed in the shape of a sphere. The central cylinder 138, in various embodiments, is made from a material having a stiffness sufficient to resist compressive forces applied by the pylorus.

FIG. 7 is a drawing of a flat representation of the circumference of the expandable anchor 110 disclosed in FIG. 6. The anchor 110 can be laser cut from a round tubing or flat sheet of Nitinol. In some embodiments of the anchor 110, the edge 146 connects with edge 147 to form a round tubing.

Figure 8:
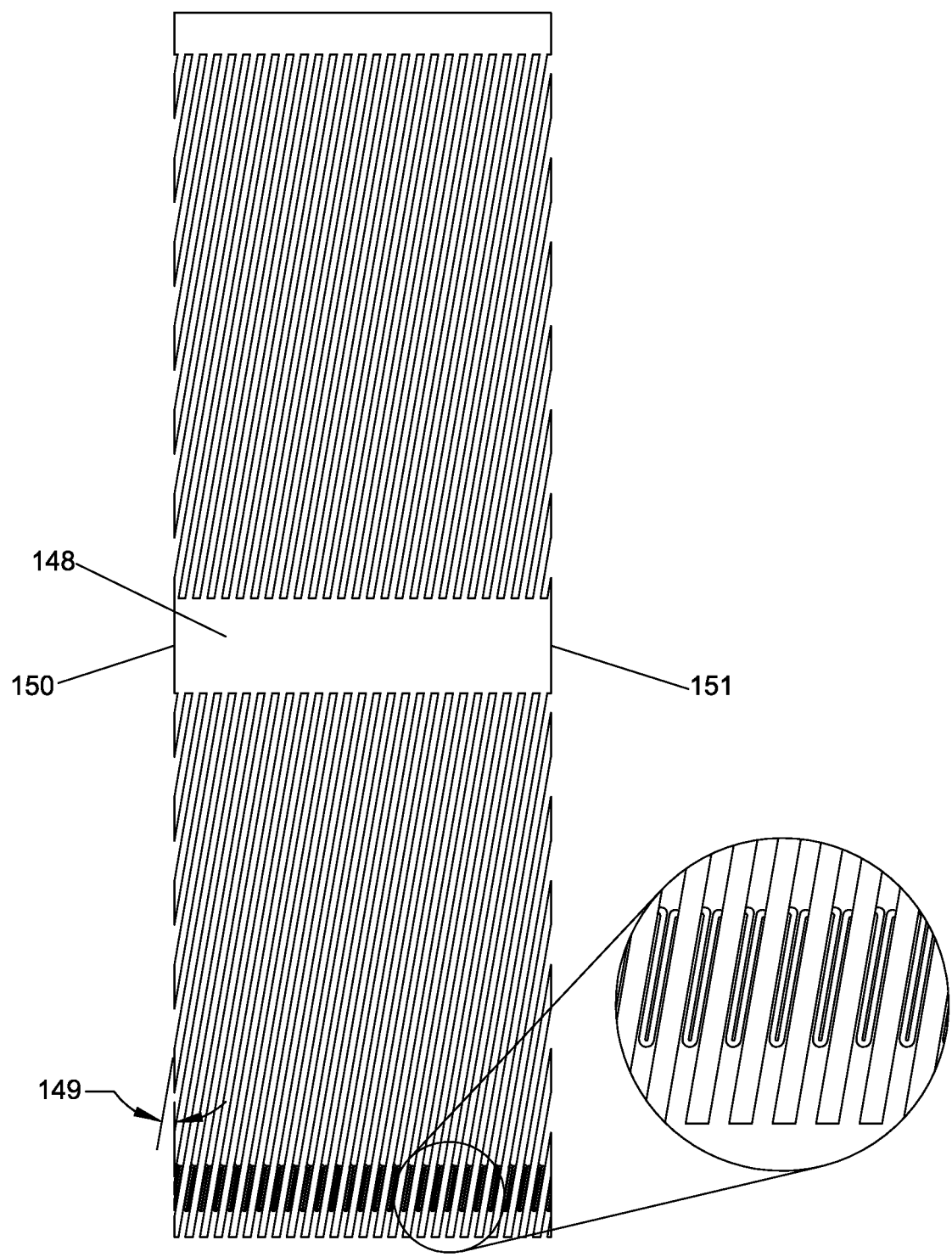
FIG. 8 is a drawing of a flat representation of the circumference of the expandable anchor disclosed in FIG. 2. The expandable anchor can be laser cut from round tubing or flat sheet of Nitinol. The individual spring arm elements of the anchor are cut at a bias angle to the longitudinal axis.

FIG. 8 is a drawing of a flat representation of the circumference of an alternative embodiment of an anchor 148 as disclosed in item 110 of FIG. 6. The expandable 148 anchor can be laser cut from round tubing or a flat sheet of Nitinol. The individual spring arm elements of the anchor are cut at a bias angle 149 to the longitudinal axis. The bias angle 149 can range from about 1 degree to about 45 degrees. In some embodiments of the anchor 148, the edge 150 connects with edge 151 to form a tubing having a round cross-section.

FIG. 9 is a drawing of heat set mandrels for heat setting (i.e., form the shape of) the anchor from the laser cut shape of FIG. 7 and FIG. 8 to the final shape of the anchor in FIG. 6. Female external mandrel 153 is made in two pieces in a clamshell arrangement. Internal mandrel 152 is placed within the external mandrel 153 and forms a cavity 154 in between the two mandrels and provides a means to shape set the Nitinol laser cut parts as in FIG. 7 and FIG. 8 into formed shape of anchor in FIG. 6. Laser cut part of FIG. 7 or FIG. 8 is placed into mold made of items 153 and 152. Mold and anchor is placed in an oven or salt bath at a temperature in the range of 400 to 500 degrees centigrade and held for 10 minutes. The mold and anchor is then rapidly cooled by air or a water bath. An alternative method to heat set the anchor uses a male only mandrel 155. The laser cut part is longitudinally compressed and clamped on the mandrel 155 to form the shape of the proximal disk.

Figure 10:
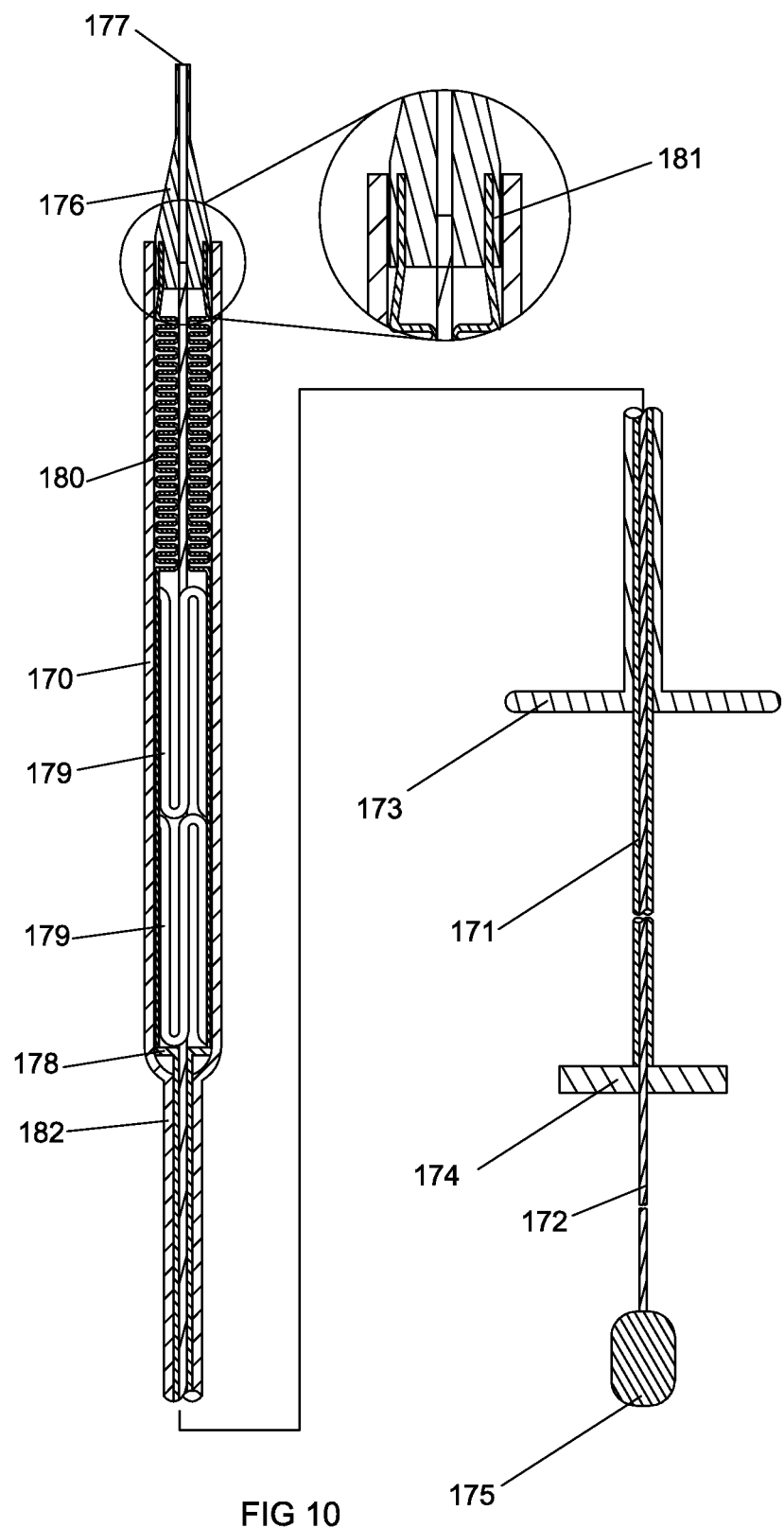
FIG. 10 is a sectional view of a delivery catheter for the expandable anchor and intestinal bypass sleeve implanted.

FIG. 10 is a cross-sectional drawing of a delivery catheter for the invention herein disclosed. The delivery catheter is composed of the three coaxial components: distal outer sheath 170, which transitions down to a smaller diameter at the proximal outer sheath 182, proximal pusher catheter 171, and sleeve advancement pusher 172. There are three handles on the catheter: outer sheath handle 173, proximal pusher handle 174, and sleeve advancement pusher handle 175. The implant pusher 178 serves as a mechanical stop or means to hold stationery or push out the anchor rings 179 or implant from the inside of the distal outer sheath 170. The distal tip 176 provides for a flexible tip that will track over a guidewire. The guidewire may be inserted through the central lumen 177. The proximal shoulder of the tip 181 is rolled back over the end of the intestinal bypass sleeve 180 to constrain the intestinal bypass sleeve 180 to distal tip 176 and the sleeve advancement pusher 172 and to provide a mechanism of advancement of the intestinal bypass sleeve through the duodenum (and the jejunum as applicable). Expandable anchor 179 and the intestinal bypass sleeve 180 are compressed and loaded onto the delivery catheter.

The distal outer sheath 170 may be made from a plastic polymer such as Pebax (polyether block amide), hytrel (polyester elastomer), nylon 12, nylon 11, nylon 6, nylon 6,6, polyethylene, polyurethane or other suitable polymer. The distal outer sheath 170 may have an inner lining made from a polymer with a low coefficient of friction such as PTFE. The distal outer sheath 170 may also have a metal re-enforcement in the wall thickness to improve the kink resistance or burst properties of the outer sheath. The metal re-enforcement may be comprised of a braided wire mesh or a coil in the wall thickness. The metal used for the braid may be stainless steel, Nitinol, MP35N, L605, Elgiloy or other suitable material. The distal outer sheath 170 may be from 1-2 inches long up to full length of the catheter.

The proximal outer sheath 182 may be made from a plastic polymer such as Pebax (polyether block amide), Hytrel (polyester elastomer), nylon 12, nylon 11, nylon 6, nylon 6,6, polyethylene, polyurethane or other suitable polymer. The proximal outer sheath 182 may have an inner lining made from a polymer with a low coefficient of friction such as PTFE. The proximal outer sheath 182 may also have a metal re-enforcement in the wall thickness to improve the kink resistance or burst properties of the outer sheath. The metal re-enforcement may be comprised of a braided wire mesh or a coil in the wall thickness. The metal used for the braid may be stainless steel, Nitinol, MP35N, L605, Elgiloy or other suitable material.

The proximal pusher catheter 171 may be made from a plastic polymer such as Pebax (polyether block amide), Peek, Hytrel (polyester elastomer), nylon 12, nylon 11, nylon 6, nylon 6,6, polyethylene, polyurethane or other suitable polymer. The proximal pusher catheter 171 may have an inner lining made from a polymer with a low coefficient of friction such as PTFE. The proximal pusher catheter 171 may also have a metal re-enforcement in the wall thickness to improve the kink resistance or burst properties of the outer sheath. The metal re-enforcement may be comprised of a braided wire mesh or a coil in the wall thickness. The metal used for the braid may be stainless steel, Nitinol, MP35N, L605, Elgiloy or other suitable material The sleeve advancement pusher 172 may be made from a plastic polymer such as Pebax (polyether block amide), Peek, Hytrel (polyester elastomer), nylon 12, nylon 11, nylon 6, nylon 6,6, polyethylene, polyurethane or other suitable polymer. The sleeve advancement pusher 172 may have an inner lining made from a polymer with a low coefficient of friction such as PTFE. The sleeve advancement pusher 172 may also have a metal re-enforcement in the wall thickness to improve the kink resistance or burst properties of the outer sheath. The metal re-enforcement may be comprised of a braided wire mesh or a coil in the wall thickness. The metal used for the braid may be stainless steel, Nitinol, MP35N, L605, Elgiloy or other suitable material. The sleeve advanced pusher 172 may have a hollow core to allow passage over a guidewire or it may be solid without an opening. The sleeve advanced pusher 172 may also be constructed of a simple tightly wound metal wire coil construction or it may be wound from multiple wires such as Hollow Helical Strand tube made be Fort Wayne Metals. The sleeve advancement pusher handle 175 may also be comprised of a solid tube of Peek, Nitinol or stainless steel. The solid tube may have a series of slots or a patterned on a portion of the tube length to increase the flexibility of the component as required.

The distal tip 176 may be molded from Pebax, polyurethane, Hytrel or other suitable elastomer. The distal tip 176 had an outer flange 181 that is soft and may rolled back and the intestinal bypass sleeve 180 inserted under it to secure the sleeve during transport to the distal duodenum (and the jejunum as applicable).

The delivery catheter handles may be molded or machined from metal or plastic. The outer sheath handle 173 is attached to the proximal outer sheath 182. The outer sheath handle 173 is used to hold or retract the distal outer sheath 170 and the proximal outer sheath 182 during the advancement of the delivery catheter into the human anatomy, and while deploying of the anchoring rings. The proximal pusher handle 174 is attached to the proximal pusher catheter 171. The outer sheath handle 173 is used to hold or push forward the proximal pusher catheter 171 and the implant pusher 178 during the advancement of the delivery catheter into the human anatomy, and while deploying of the anchoring rings.

An exemplary deployment sequence consists of the following: The delivery catheter of FIG. 10 is preloaded with the expandable anchor 179 and the intestinal bypass sleeve 180. The delivery catheter is advanced through the mouth 100, esophagus 101 and stomach 103 to the pylorus 106. The sleeve advancement pusher handle 175 is pushed distally while holding the rest of the catheter stationary. This pushes the sleeve advancement pusher handle 175, the distal tip 176 and the intestinal bypass sleeve 180 into the duodenum (and jejunum as applicable). The pusher handle 175 is further advanced until the intestinal bypass sleeve 180 reaches the ligament of treiz. At this point all the slack in the sleeve 180 is taken up and the sleeve pulls out from the distal tip 176 and is released from the distal tip 176.

FIG. 11 is a sectional view of the invention herein disclosed implanted into a pylorus 106, duodenal bulb 107 and duodenum 112. The expandable anchor 110 is covered with a membrane 186, 185 on both inside and outside surfaces of the anchor 110 to close the openings between the spring arm elements 187. An intestinal bypass sleeve 111 is attached to the expandable anchor 110. The membrane covering the expandable anchor may be made from a thin-walled polymer material such as silicone, polyurethane, polytetrafluoroethylene, fluorinated ethylene propylene, polyethylene, expanded polytetrafluoroethylene (ePTFE) or other suitable material. In exemplary embodiments, the wall thickness of the membrane covering the expandable anchor may be in the range of 0.001 inch to 0.030 inch thick. The membrane may be made by extrusion, dip coating from a liquid solution, powder coated from fine particles of polymer, or paste extruded and then stretched (e.g., as is typically done with ePTFE). The expandable anchor 110 membrane 185, 186 may also be cut from a flat sheet of material such as ePTFE and then bonded or sewn into a disk shape or spherical shaped structure and then attached the expandable anchor 110 frame work by sewing or gluing with a polymer such as FEP. The expandable anchor 110 has a recovery ring 188 attached to the proximal disk to provide for a location to grab the device for removal from the human body. Expandable anchor 110 has a central tube 194 bonded at location 195, but is free to telescope at location 196 as the anchor 110 is compressed in diameter and elongated in length to allow loading onto a delivery catheter. The central tube 194 may be made from a thin-walled metal material such as stainless steel, titanium or polymer material such as silicone, polyurethane, polytetrafluoroethylene, fluorinated ethylene propylene, polyethylene, expanded polytetrafluoroethylene (ePTFE) or other suitable material.

Figure 12:
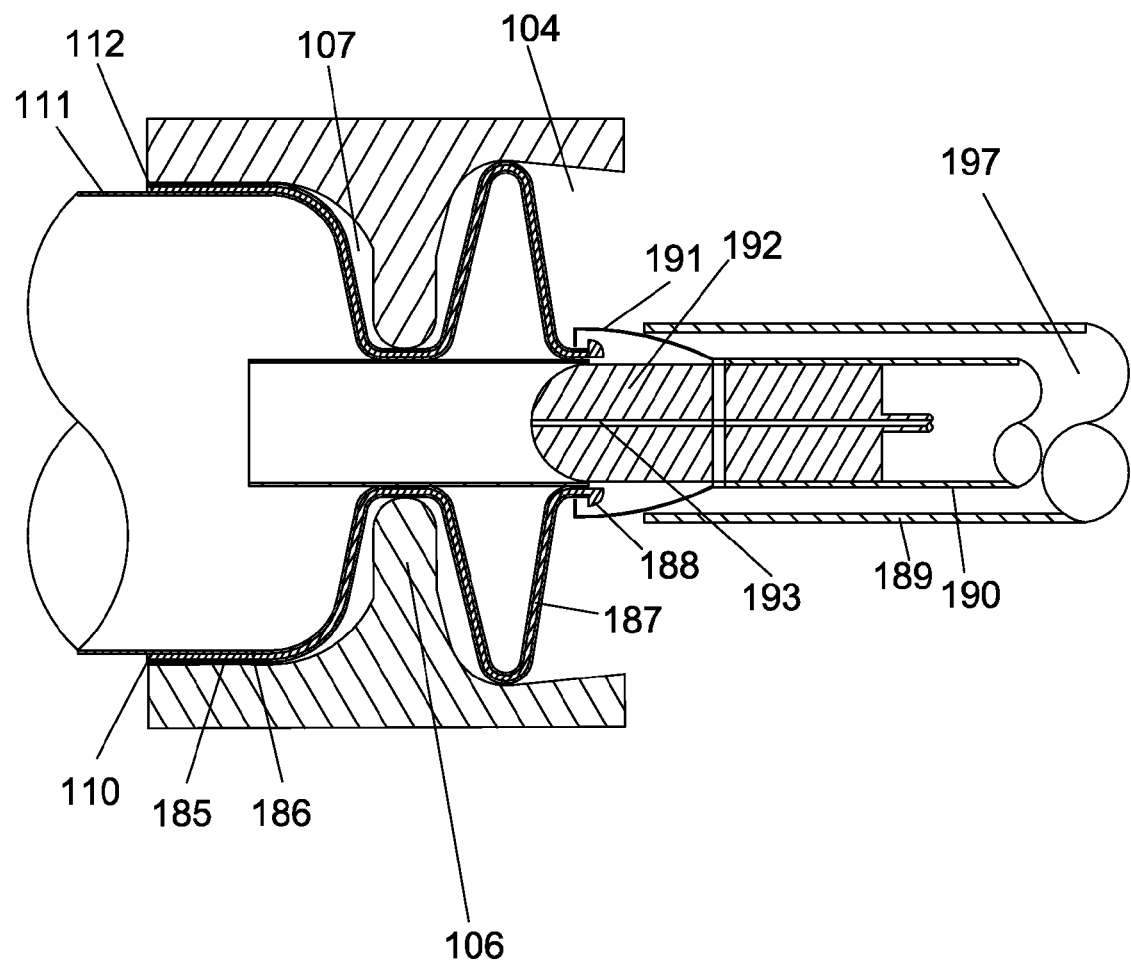
FIG. 12 is a sectional view of a recovery catheter for removing the expandable anchor and intestinal bypass sleeve from the human gastrointestinal tract.
Figure 13:
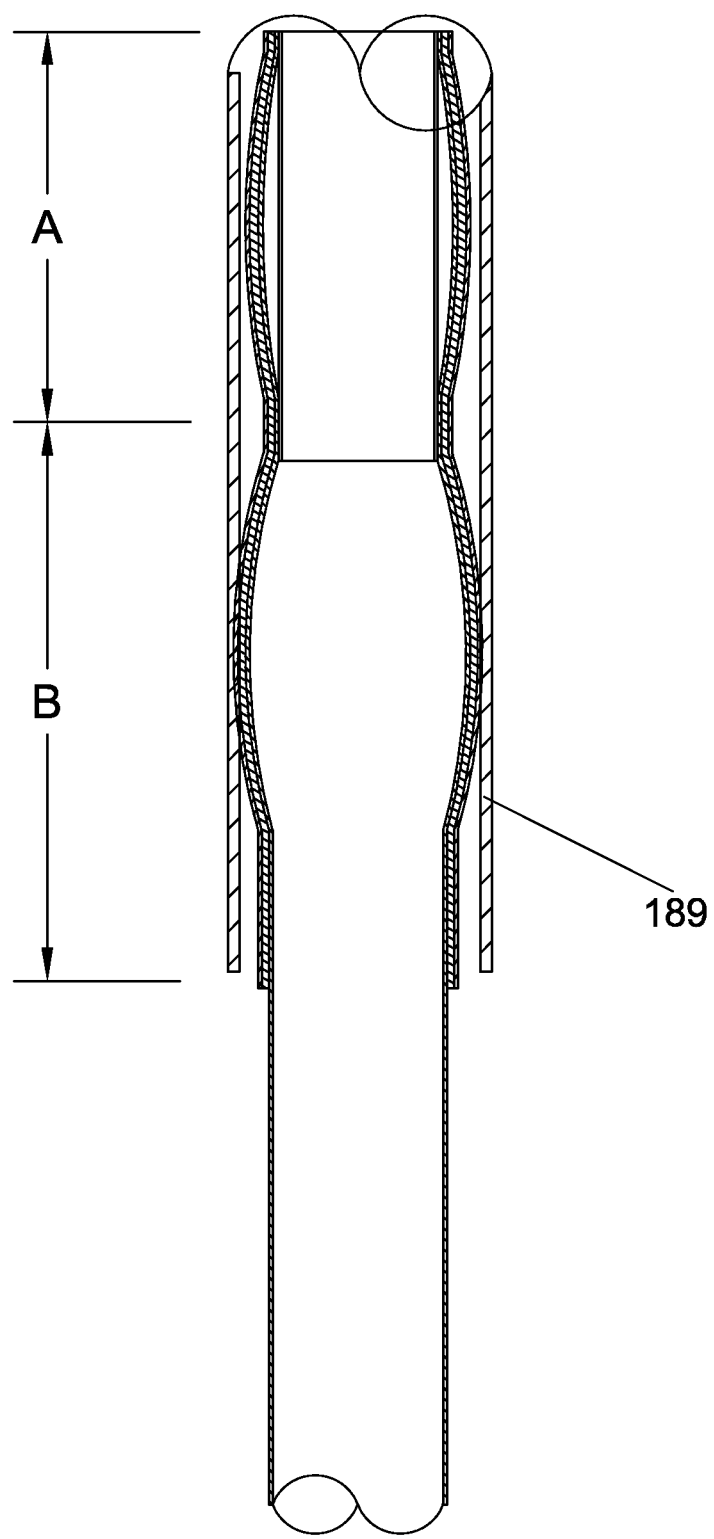
FIG. 13 is a sectional view of the expandable anchor in the collapsed state with the outer sheath of the recovery catheter covering and constraining the expandable anchor.

FIG. 12 is a sectional view of recovery catheter 197 for removing the expandable anchor 110 and intestinal bypass sleeve 111 from the human gastrointestinal tract. Recovery catheter has an outer sheath 189, an inner sheath 190, grasper forceps 191, central obturator 192, and a guidewire lumen 193. To remove the expandable anchor 110 and the intestinal bypass sleeve 111, the recovery catheter 197, with a guidewire inserted through the central obturator 192, is advanced through the mouth 100, esophagus 101, stomach 103, pyloric antrum 104 up to the pylorus 106. The obturator 192 is inserted into the central lumen of the recovery ring 188. The outer sheath 189 is pulled back to expose and allow the grasper forceps 191 to open. Grasper forceps 191 is pushed forward over the recovery ring 188 and the outer sheath 189 is the advanced to collapse grasper forceps 191. The central obturator 192 and grasper forceps 191 is then pulled into the outer sheath 189 by retraction of the inner sheath 190. The expandable anchor 110 is then fully collapsed and removed by retraction of the anchor 110 fully into the outer sheath 189. FIG. 13 is a sectional view of the expandable anchor 110 in the collapsed state within the outer sheath 189 of the recovery catheter covering and constraining the expandable anchor 110.

Figure 14:
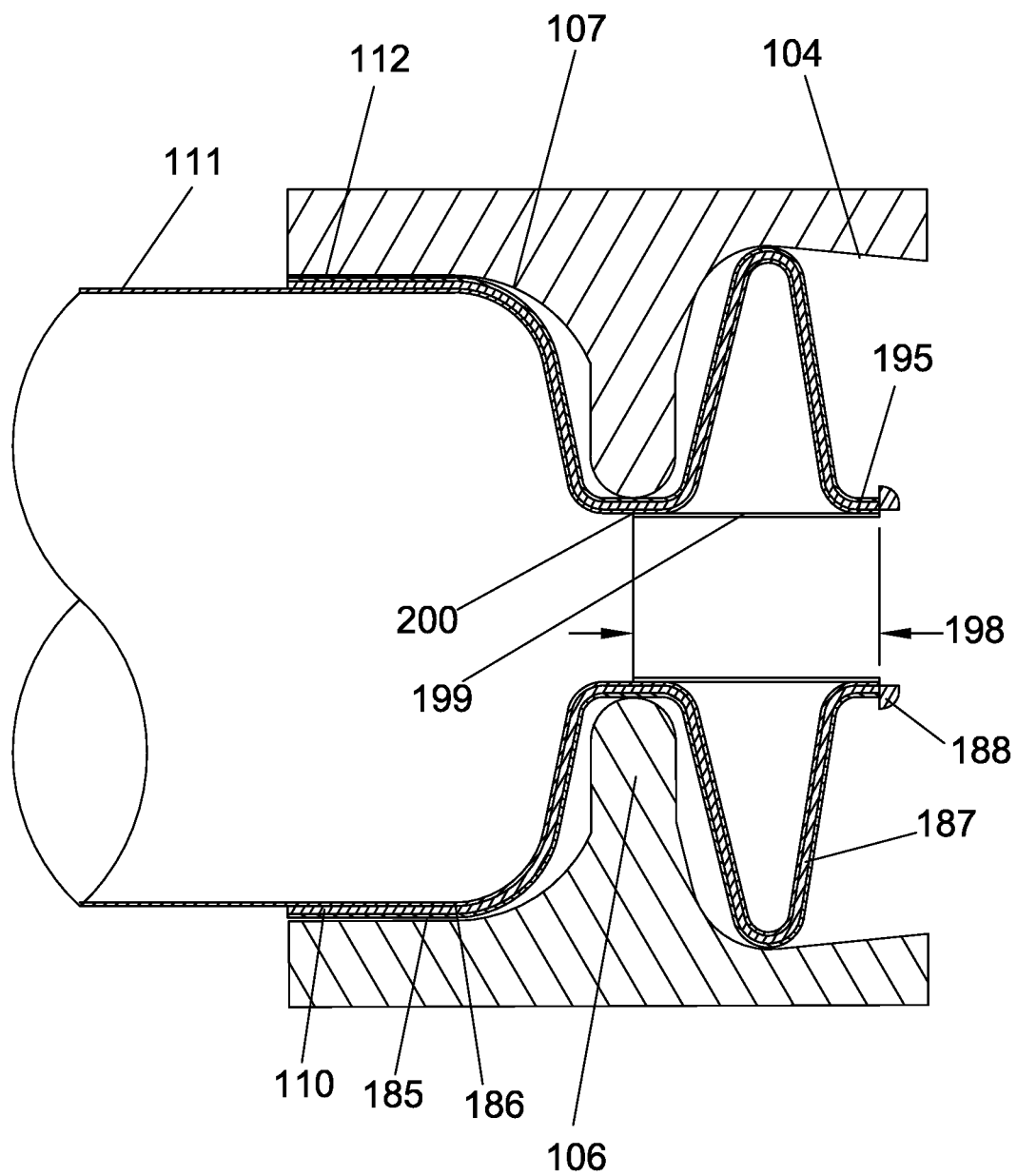
FIG. 14 is a sectional view of an alternative embodiment of an anchor and sleeve implanted into the pylorus and duodenal bulb and duodenum.

FIG. 14 is a sectional view of an alternative embodiment of the invention herein disclosed implanted into a pylorus 106, duodenal bulb 107 and duodenum 112. The expandable anchor 110 is covered with a membrane on both the inside 186 and outside 185 surfaces of the anchor 110 to close the openings in between the spring arm elements 187. An intestinal bypass sleeve 111 is attached to the expandable anchor 110. The membrane covering the expandable anchor may be made from a thin-walled polymer material such as silicone, polyurethane, polytetrafluoroethylene, fluorinated ethylene propylene, polyethylene, expanded polytetrafluoroethylene (ePTFE) or other suitable material. In some embodiments, the wall thickness of the membrane covering the expandable anchor 186 and 185 may be in the range of 0.001 inch to 0.030 inch thick. The membrane 186 and 185 may be made by extrusion, dip coating from a liquid solution. Powder coated from fine particles of polymer or paste extruded and then stretched as is the case with ePTFE. The expandable anchor 110 membrane 185, 186 may also be cut from a flat sheet of material such as ePTFE and then bonded or sewn into a disk-shaped or spherical-shaped structure and then attached to the expandable anchor 110 framework by sewing or gluing with a polymer such as FEP. The expandable anchor 110 has a recovery ring 188 attached to the proximal disk to provide for a location to grab the device for removal from the human body. Expandable anchor 110 has a central tube 199, which may be bonded at locations 195 and/or 200. The central tube 199 is comprised of an elastomeric material and can elongate in length as the anchor 110 is compressed in diameter and elongated in length to allow loading onto a delivery catheter. The central tube 199 may be made from a thin-walled polymer material such as silicone, polyurethane, polytetrafluoroethylene, fluorinated ethylene propylene, polyethylene, expanded polytetrafluoroethylene (ePTFE) or other suitable material.

Figure 15:
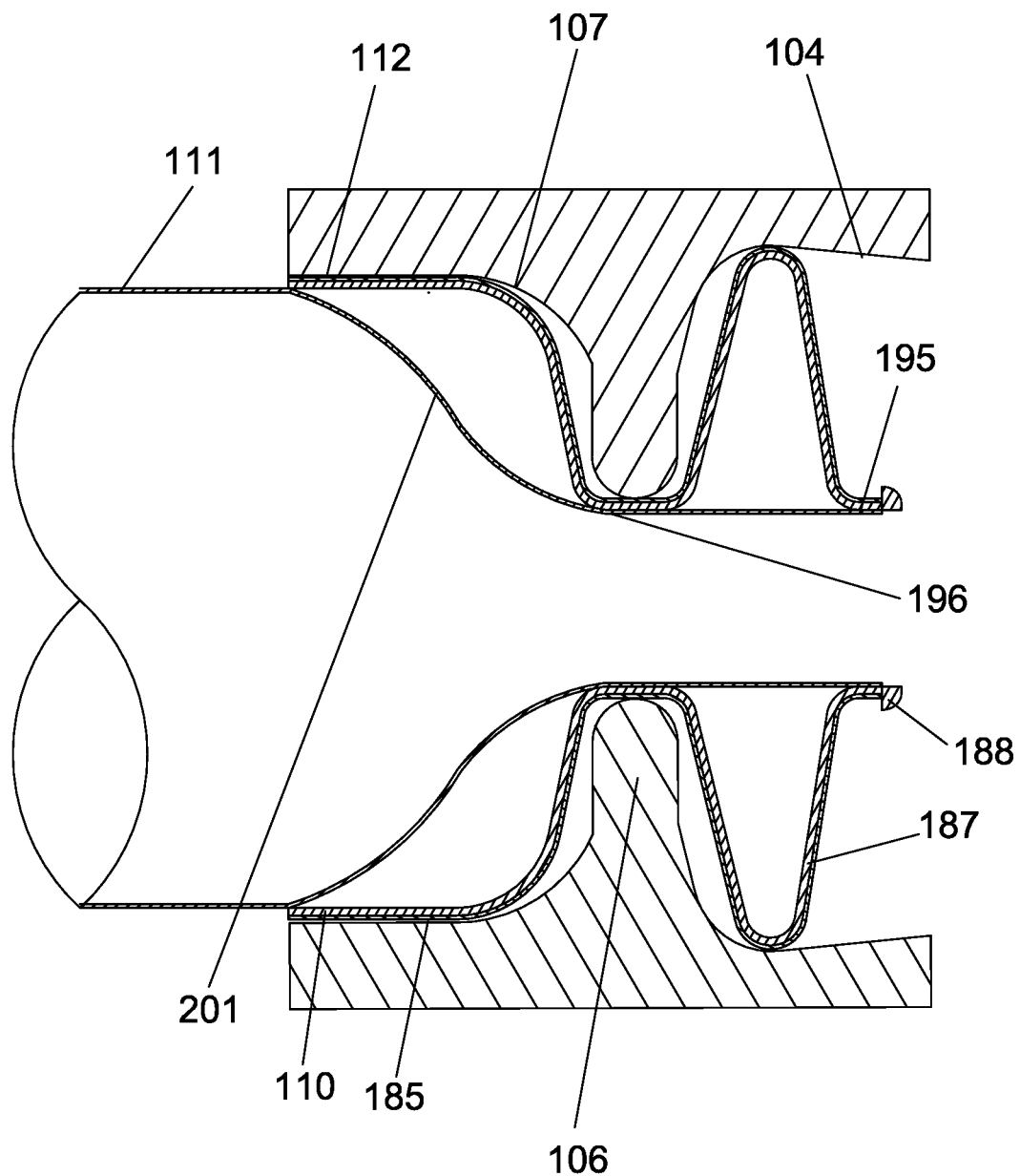
FIG. 15 is a sectional view of an alternative embodiment of an anchor and sleeve implanted into the pylorus and duodenal bulb and duodenum.

FIG. 15 is a sectional view of the invention herein disclosed implanted into a pylorus 106, duodenal bulb 107 and duodenum 112. The expandable anchor 110 is covered with a membrane on the outside 185 surface of the anchor 110 to close the openings in between the spring arm elements 187. An intestinal bypass sleeve 111 is tapered in diameter and attaches to the expandable anchor 110 at location 195. Intestinal bypass sleeve 111 is sized to fit the duodenum in the duodenal portion and is tapered 201 from the larger diameter to the smaller diameter at 196. Intestinal bypass sleeve 111 is not attached to the expandable anchor at 196, but is allowed to slide and telescope within the expandable anchor as it is compressed in diameter to load the anchor onto a delivery catheter. The membrane covering the expandable anchor 185 may be made from a thin-walled polymer material such as silicone, polyurethane, polytetrafluoroethylene, fluorinated ethylene propylene, polyethylene, expanded polytetrafluoroethylene (ePTFE) or other suitable material. In some embodiments, the wall thickness of the membrane covering the expandable anchor 185 may be in the range of 0.001 inch to 0.030 inch thick. The membrane 185 may be made by extrusion, dip coating from a liquid solution, powder coated from fine particles of polymer or paste extruded and then stretched as is the case with ePTFE. The expandable anchor 110 membrane 185 may also be cut from a flat sheet of material such as ePTFE and then bonded or sewn into a disk shape or spherical shaped structure and then attached to the expandable anchor 110 frame work by sewing or gluing with a polymer such as FEP. The expandable anchor 110 has a recovery ring 188 attached to the proximal disk to provide for a location to grab the device for removal from the human body.

Figure 16:
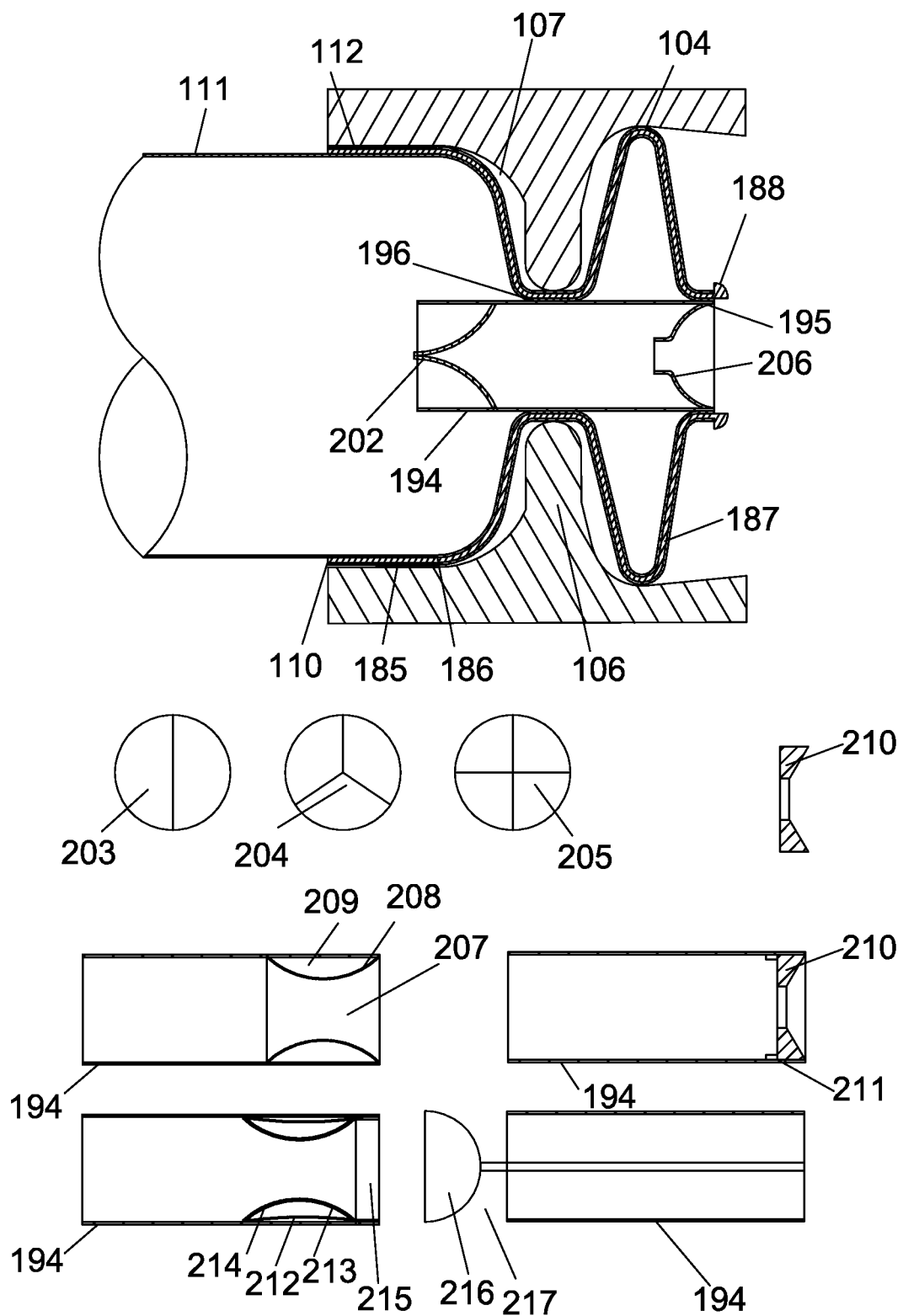
FIG. 16 is a sectional view of an alternative embodiment of the invention herein disclosed implanted into the pylorus and duodenal bulb and duodenum. The through lumen of the expandable anchor contains a duck bill type anti-reflux valve and a flow limiter.

FIG. 16 is a cross-sectional drawing of the invention herein disclosed implanted into a pylorus 106, duodenal bulb 107 and duodenum 112. The rings are sized large enough in diameter that there is a contact force between the ring diameter and the stomach pyloric antrum 104 and the duodenal bulb 107. The expandable anchor 110 is larger in diameter than the maximum opened diameter of the pylorus and therefore provides an anchoring means to hold the intestinal bypass sleeve 111. The intestinal bypass sleeve 111 can vary in length from 1-2 inches in length up to several feet. In some embodiments, the sleeve bypasses the length of the duodenum 112 up to the ligament of treitz 109. The intestinal bypass sleeve 111 can also be longer and bypass into the jejunum. The central tube 194 can be made from a rigid cylinder made from plastic material such as delrin, peek, high density polyethylene, polycarbonate or other suitable polymer. The central tube 194 may also be made from stainless steel, titanium or Nitinol. The fixed diameter of the central tube 194 of the device can be sized to provide for a full opening of the pylorus and not allow the pylorus to close normally. In various embodiments, the diameter of the central tube 194 ranges from as small as 3 mm in diameter up to as large as 14 mm in diameter. The central lumen of device has a one-way anti-reflux valve 202. The anti-reflux valve 202 allows for unobstructed flow in the direction from the stomach antrum 104 to the pylorus 106, but limits flow in the reverse direction. The anti-reflux valve 202 can be constructed of a duck bill design with two flexible leaflets 203, or may utilize other designs such as a tri leaflet valve 204 or quad leaflet valve 205. The anti-reflux valve may be constructed of silicone or polyurethane, polyethylene, ePTFE or other suitable polymer. In various embodiments, the anti-reflux valve functions to close an end of the bypass sleeve 111.

The central cylinder 194 may also be constructed to have a flow limiter 206. Flow limiter 206 is an orifice that can be added to limit the maximum flow rate of chyme through the central cylinder 202. Inflatable flow limiter 207 may also be added to the central cylinder 194 to provide for an adjustable means to change the orifice size. Cylindrical hollow balloon 208 on the inside of the central cylinder 194 can be inflated with air 209, saline or a cross-linkable polymer such as silicone to reduce the orifice size. Alternatively the central cylinder 194 may also designed to have an optional removable fixed orifice 210. Fixed orifice 210 may be inserted before the device is implanted in a human or it can be added or size changed at a later date in the future if it is so desirable. Fixed orifice 210 can be held into central cylinder 194 by a magnetic attraction means, snap fit or mechanical interlock feature. A mechanical stop 211 can limit how far the fixed orifice 210 inserts into the central cylinder 194. An alternative embodiment of a flow limiter may also include a compressible mechanical cage structure 213. The cage structure 213 has a thin tubular membrane 214 on the inside. The inside diameter of cage structure 213 can be reduced to 212 by axial compression of the length of the cage structure 213, by screwing in collar 215 into inside diameter of central cylinder 194. An additional alternative embodiment of a flow limiter can be configured to include an obstruction device 216 that is adjustable in position to change the gap 217 to effectively provide for an adjustable flow limiter. Adjustable flow limiter 216 or 208 may be driven by a motorized method and be adjusted remotely from outside of the patient at a later time by telemetry or magnetic induction.

Figure 18:
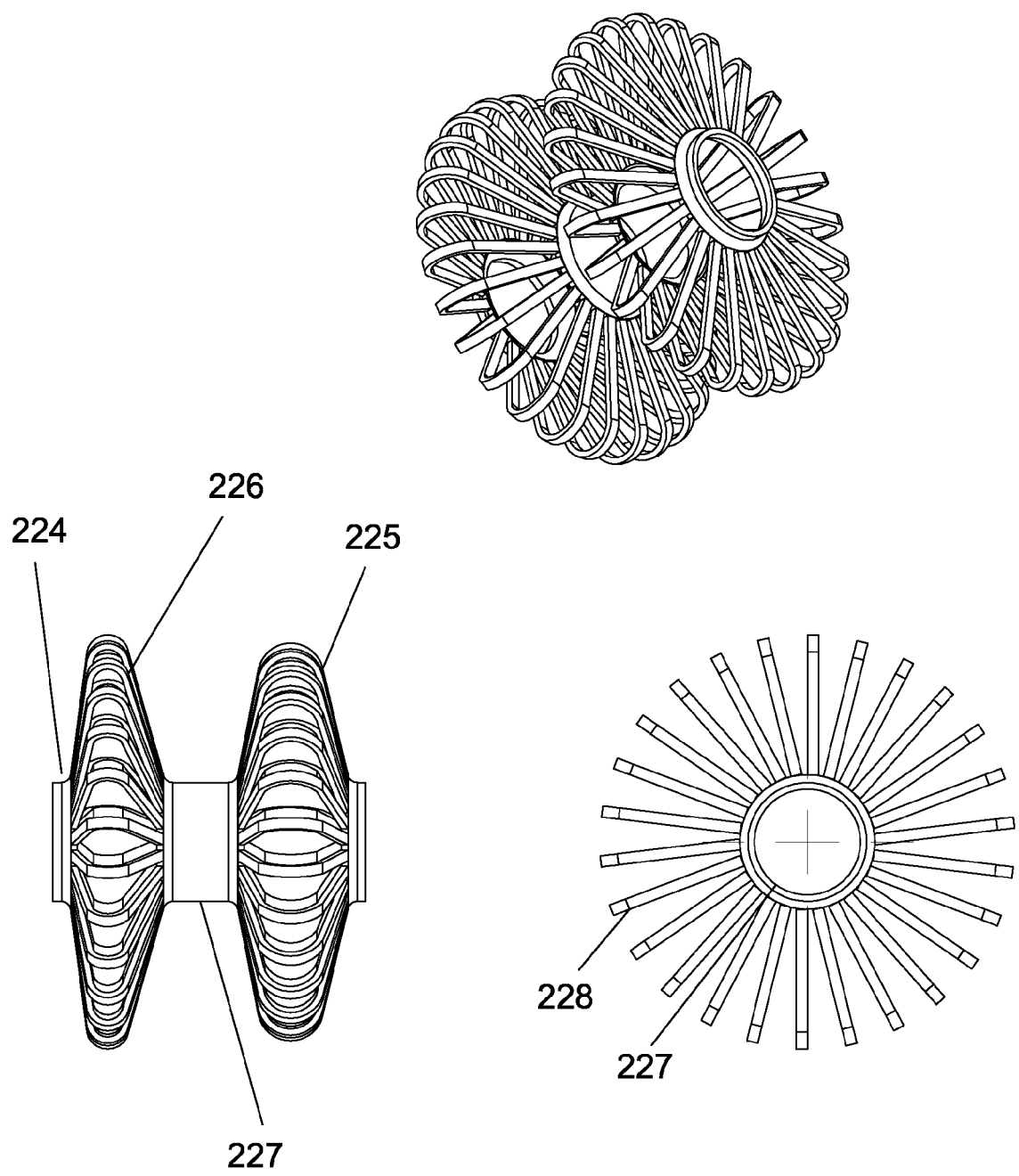
FIG. 18 shows an alternative embodiment of an expandable anchor.

FIG. 17 is an alternative embodiment of FIG. 16, wherein the anti-reflux valve is constructed of a ball 218 and cage 219 design. When the ball 218 is all the way towards the cage 219 the valve is all the way open and allows flow of chyme from the pyloric antrum 104 to duodenum 112. When the ball 218 is up against the valve seat 220 it is closed and the retrograde flow from the duodenum 112 to the stomach 103 should be minimized. The ball 218 and cage 219 may be constructed of metal or plastics. A bi-leaflet 221 valve may also be suitable for the reflux valve. The leaflets are in an open position 223 and a closed position 222. FIG. 18 is a drawing of an alternative embodiment of an expandable anchor 224. Expandable anchor 224 is comprised of a proximal expandable disk 225, a distal expandable disk 226, a central cylinder 227 and spring arms 228. The function and materials are similar to the anchor disclosed in FIG. 6. According to various embodiments, the spring arms of the expandable disks extend away from the longitudinal axis at an angle of between about 45 and about 135 degrees.

Figure 19:
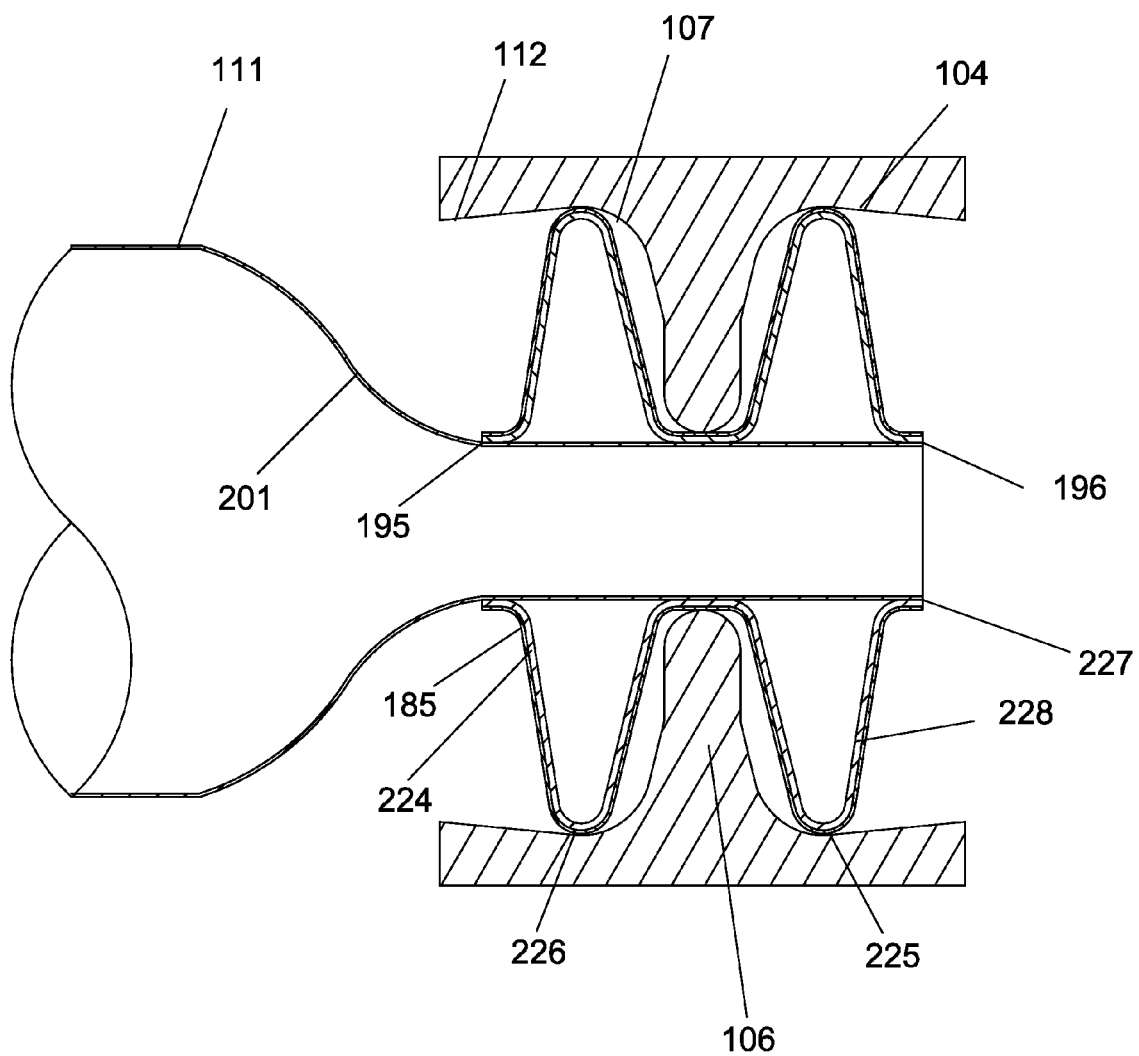
FIG. 19 is a partial cross-sectional drawing of the pyloric antrum, pylorus, duodenal bulb and duodenum. An alternative embodiment of an expandable anchor intestinal bypass sleeve is implanted into the pyloric antrum, pylorus, duodenal bulb and duodenum.

FIG. 19 is a cross-sectional drawing of expandable anchor disclosed in FIG. 18 and an intestinal bypass sleeve implanted into a pyloric antrum 104, pylorus 106 and duodenal bulb 107 and duodenum 112. As shown in FIG. 19, the disks 225 and 226 extend radially outward at an angle of between about 10 and about 30 degrees from perpendicular.

Figure 20:
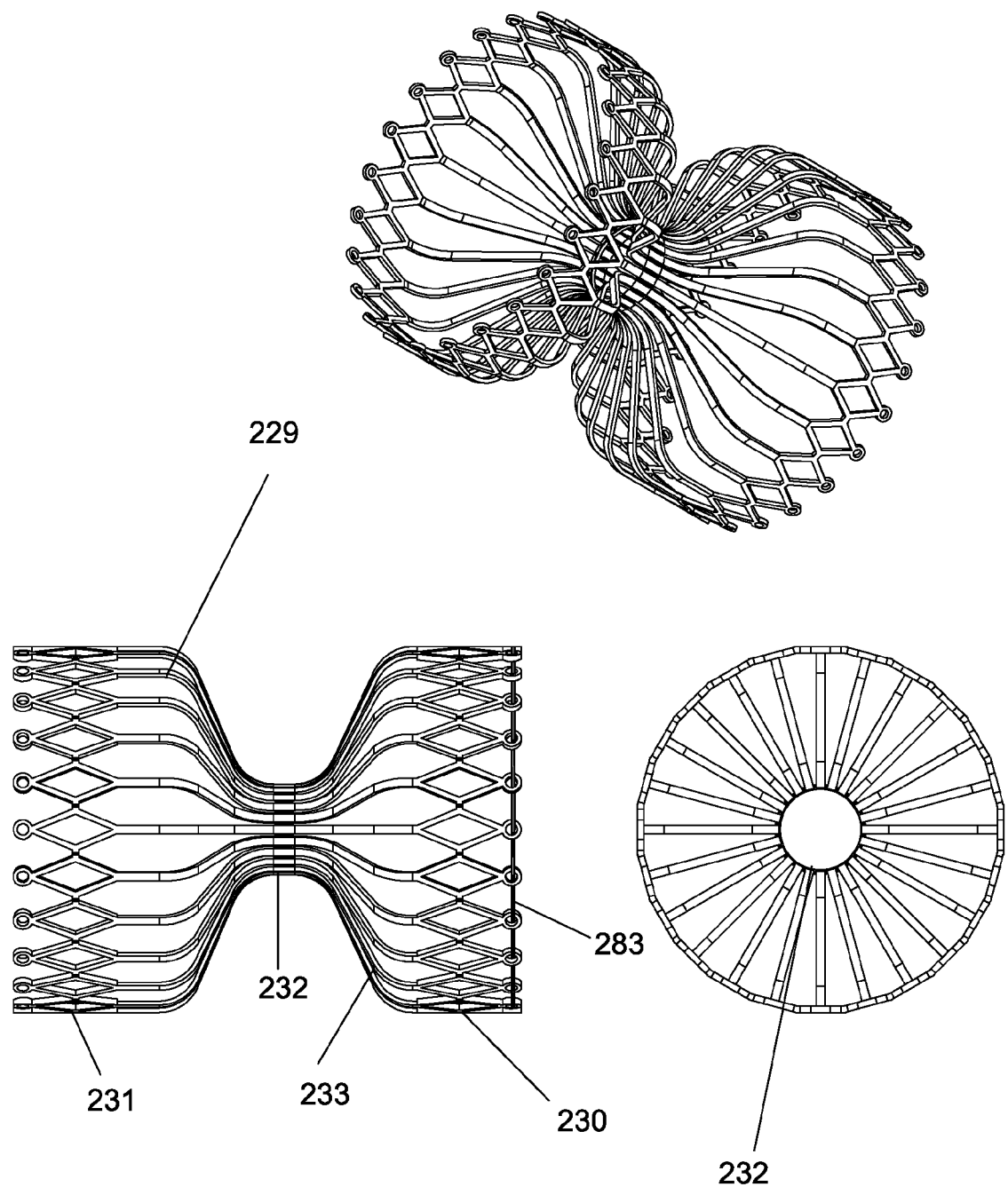
FIG. 20 shows an alternative embodiment of an expandable anchor.
Figure 21A:
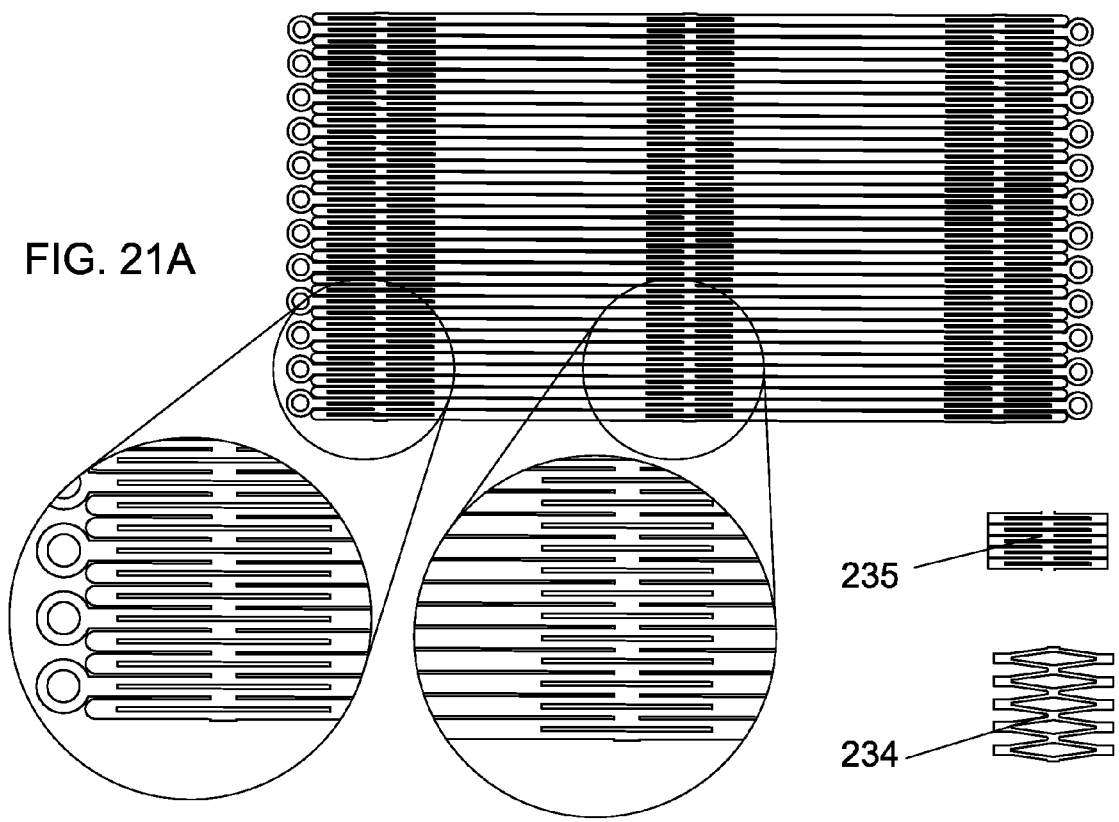
FIG. 21A is a drawing of a flat representation of the expandable anchor shown in FIG. 20.
Figure 21B:
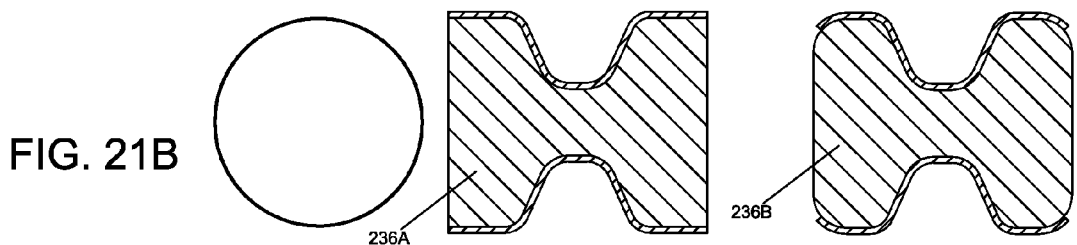
FIG. 21B is a drawing of a cylindrical mandrel for heat setting the expandable anchor to the hourglass shape as in FIG. 20.

FIG. 20 is a drawing of an alternative embodiment of an expandable anchor 229. Expandable anchor 229 is comprised of a proximal expandable cylinder 230, a distal expandable cylinder 231, a central cylinder 232 and spring arms 233. The function and materials are similar to the anchor disclosed in FIG. 6. According to various embodiments, the proximal cylinder 230 further includes a wire, suture, or drawstring 283. The drawstring 283 may be used to facilitate collapse and removal of the expandable anchor 229 from the patient. FIG. 21A is a drawing of a flat representation of the expandable anchor shown in FIG. 20. Cell geometry is shown in the expanded state 234 and in the compressed state 235. FIG. 21B shows embodiments of cylindrical mandrels 236A, 236B for heat setting the expandable anchor to the hour glass shape as in FIG. 20.

Figure 22:
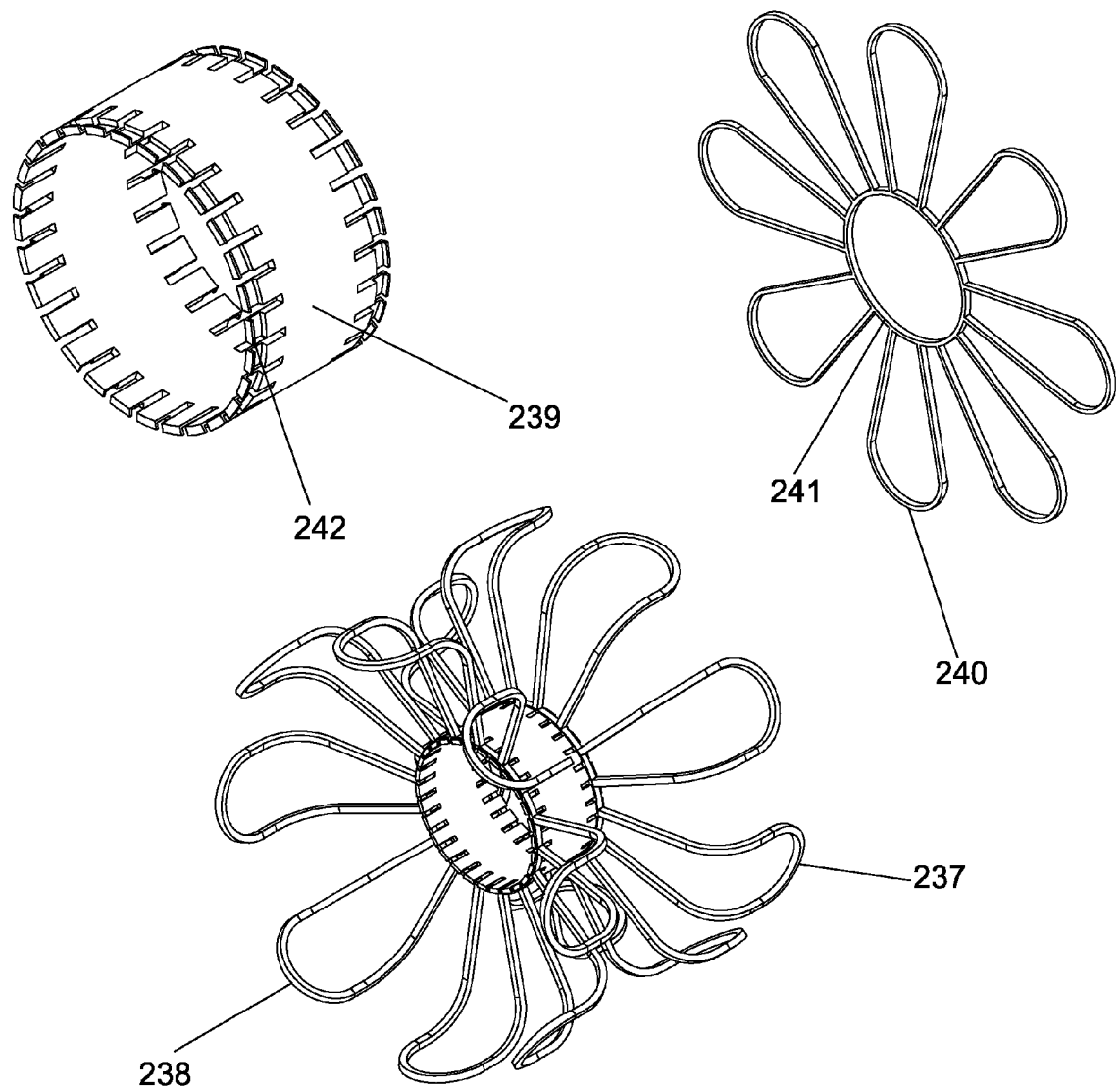
FIG. 22 shows an alternative embodiment of an expandable anchor.

FIG. 22 is a drawing of an alternative embodiment of an expandable anchor. Expandable anchor is comprised of a proximal disk 237, a distal disk 238, a central cylinder 239. The central cylinder 239 is laser cut or machined from Nitinol, titanium, stainless steel or other suitable metal. Alternatively central cylinder is molded from a plastic material previously disclosed in this application. According to various embodiments, the disks of 237 and 238 are laser cut from a flat sheet of Nitinol in a pattern as in 240 and then heat set into the final shape as in 237 and 238. Formed disk 237 and 238 may be snap fit onto annular groove 242 of central cylinder 239 by placing hole 241 over annular groove 242. Expandable anchor may be covered with a polymer covering as previously disclosed in this application. According to various embodiments, the disks 237, 238 extend outwardly substantially perpendicular to a longitudinal axis of the anchor.

Figure 23:
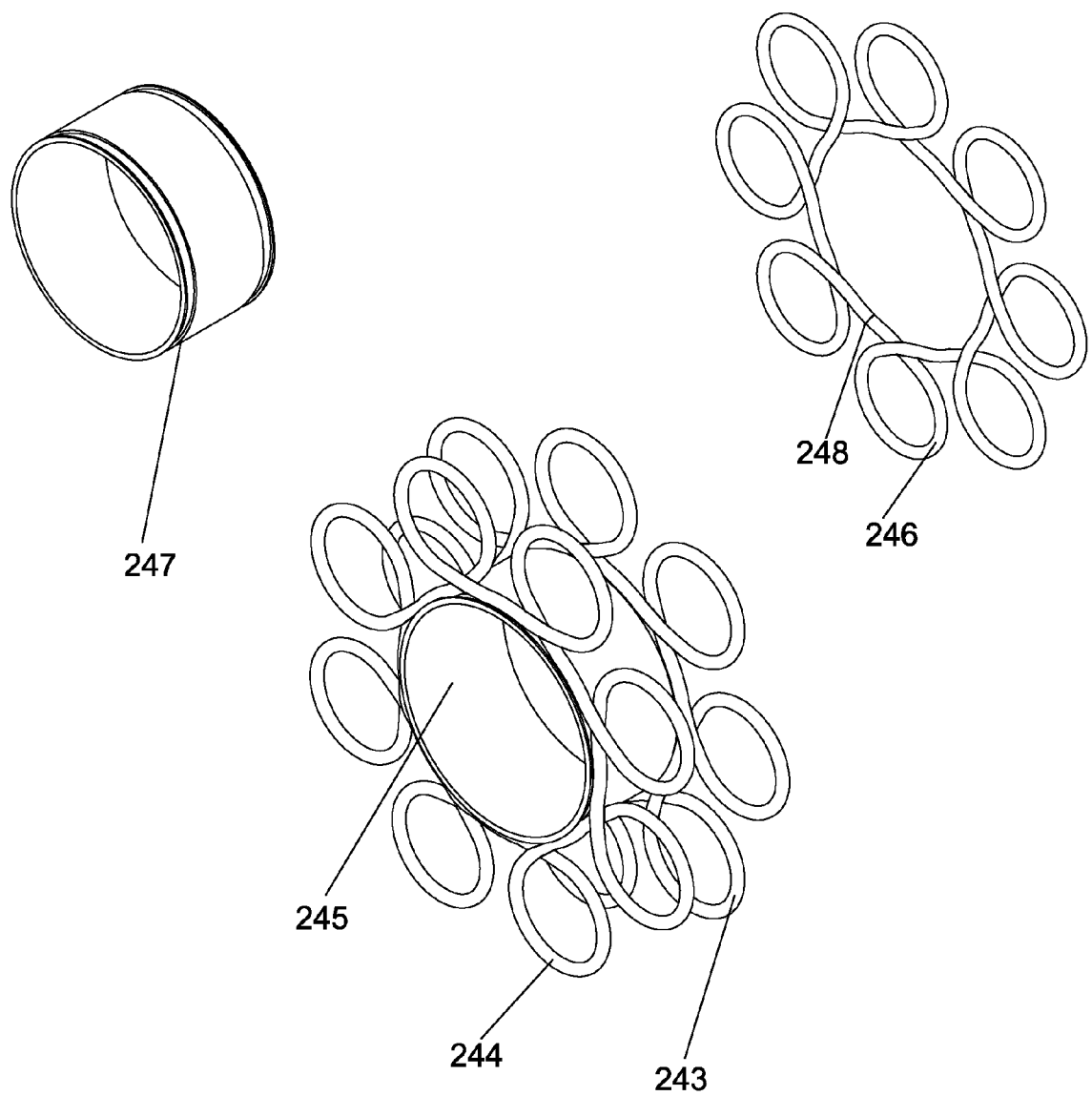
FIG. 23 shows an alternative embodiment of an expandable anchor.
Figure 24:
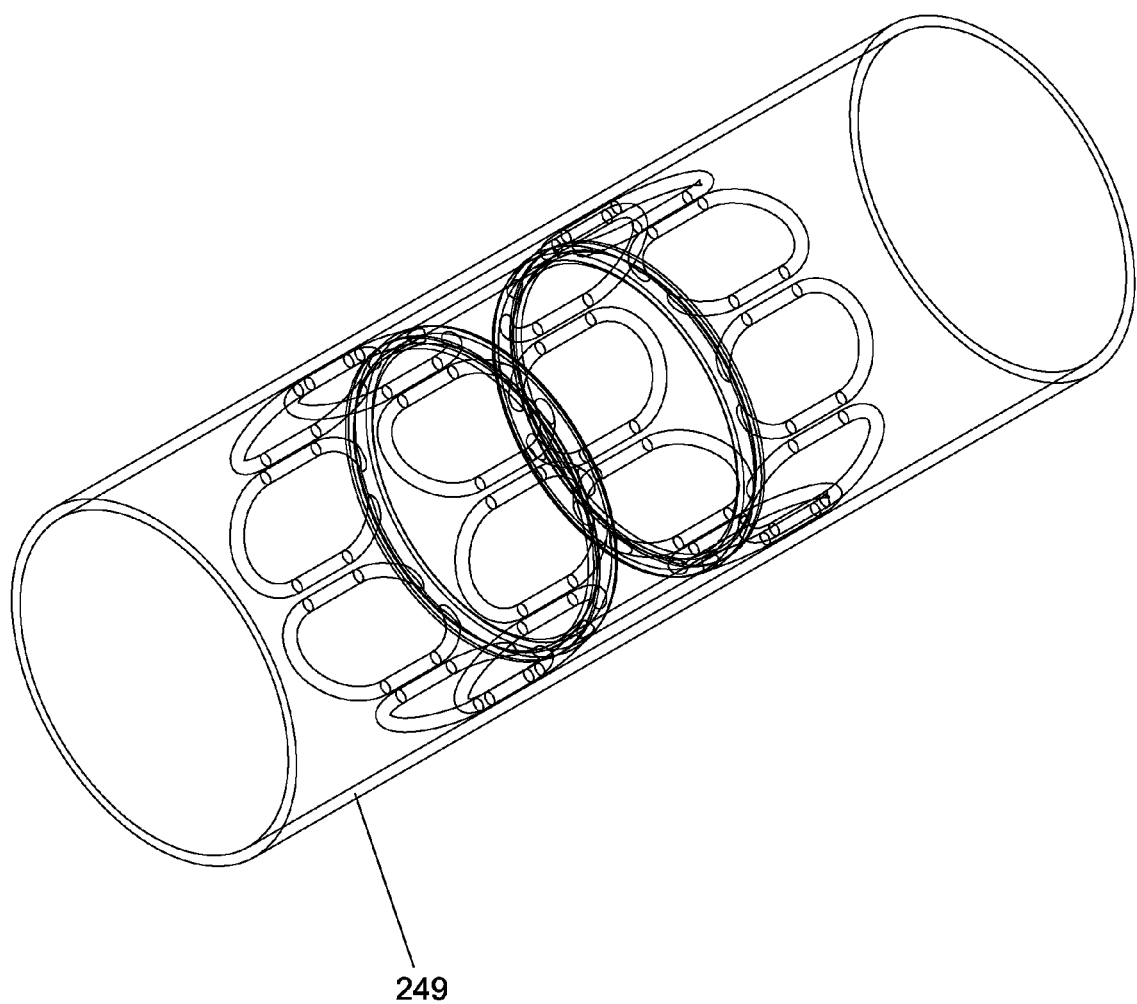
FIG. 24 is a drawing of expandable anchor of FIG. 23 in a compressed state, with a sheath constraining it on the outside diameter.

FIG. 23 is a drawing of an alternative embodiment of an expandable anchor. Expandable anchor is comprised of a proximal disk 243, a distal disk 244, a central cylinder 245. Central cylinder 245 is machined from Nitinol, titanium, stainless steel or other suitable metal. Alternatively central cylinder is molded from a plastic material previously disclosed in this application. Disk of 243 and 244 may be formed from Nitinol wire in a pattern as in 246. Formed disk 246 may be snap fit onto annular groove 247 of central cylinder 247 by placing hole 248 over annular groove 247. Expandable anchor may be covered with a polymer covering as previously disclosed in this application. FIG. 24 is a drawing of expandable anchor of FIG. 23 in a compressed state, with a sheath 249 constraining the anchor on the outside diameter.

Figure 25:
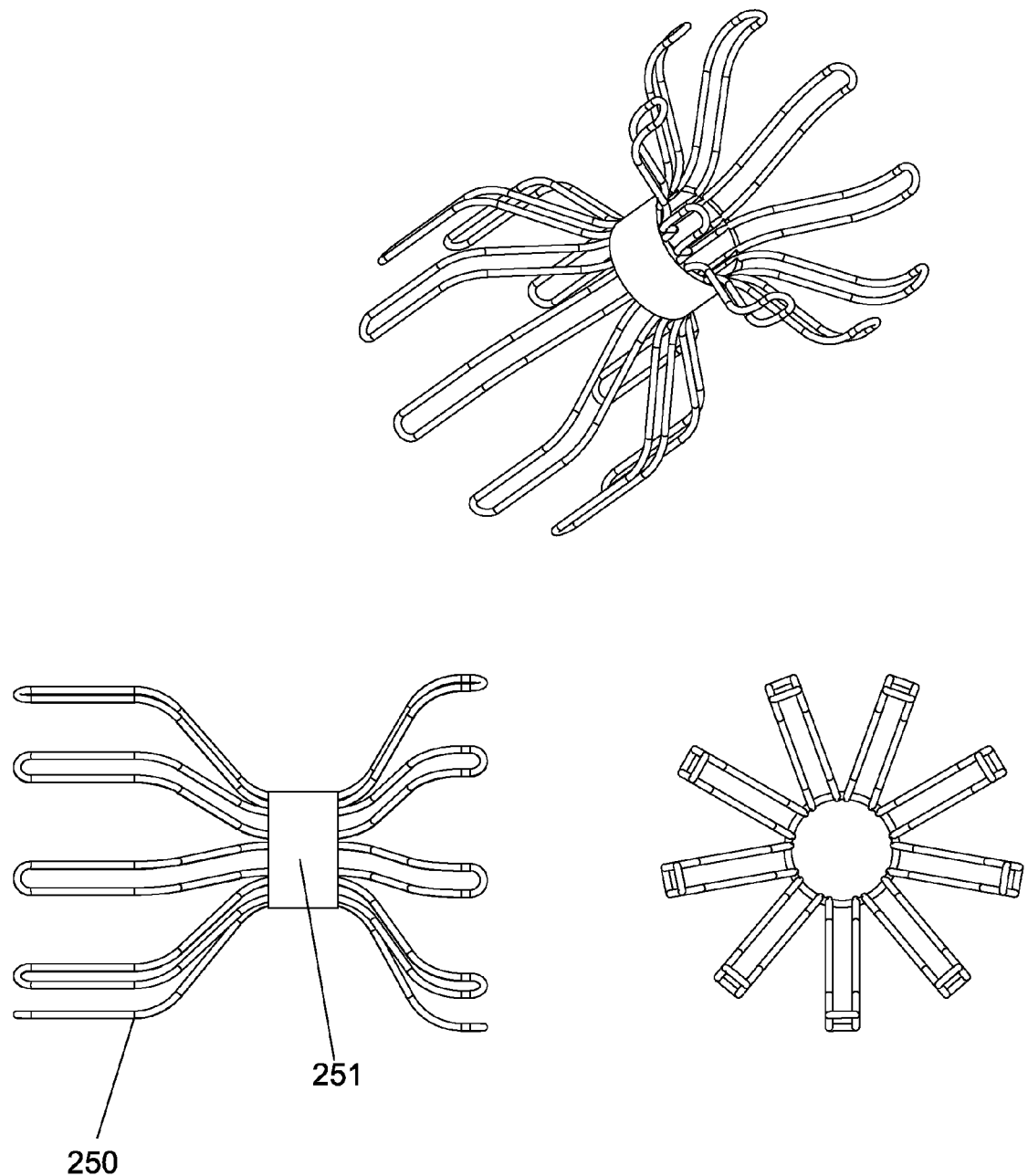
FIG. 25 shows an alternative embodiment of an expandable anchor formed from wire.

FIG. 25 is a drawing of an alternative embodiment of an expandable anchor formed from wire. Expandable anchor can be formed from a single Nitinol wire form 250. Central cylinder 251 can be attached to wire form 250 by laser welding or adhesive bonding. Wire may be made from Nitinol, stainless steel, Elgiloy, L605, MP35N titanium, niobium or other suitable metal. The wire can be made of a solid wire, stranded wire or braided. The outer diameter or inner core of the wire may be clad or plated with gold, tantalum, plantium, iridium or other suitable material. The wire may be co-drawn (e.g., drawn filled tube—Fort Wayne Metals) and have an outer core of a high strength material such as Nitinol, stainless steel, Elgiloy, L605, titanium, niobium and an inner core of a high radio-opacity material such as gold, tantalum, plantium, iridium. Alternatively, the wire is made from plastic monofilament.

Figure 26:
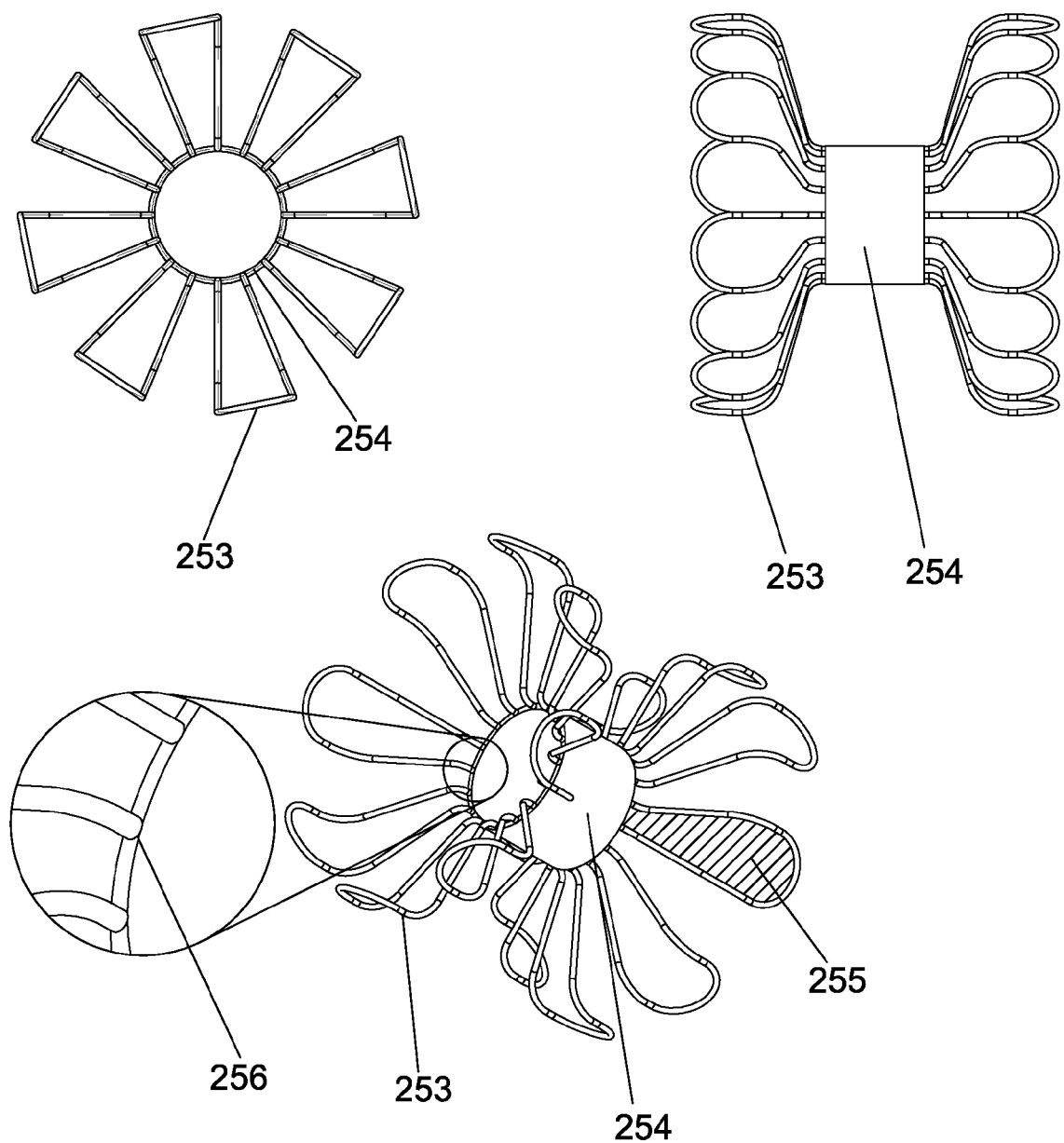
FIG. 26 shows an alternative embodiment of an expandable anchor formed from wire.

FIG. 26 is a drawing of an alternative embodiment of an expandable anchor made from wire. Expandable anchor can be made from a Nitinol wire form as in 253. Wire form 253 is attached to central cylinder 254 by inserting wire ends 256 into a receptacle in central cylinder 254. Wire ends of wire form 253, inserted into the central cylinder 254 may be attached to central cylinder by mechanical crimping or adhesive bonding or laser welding. Expandable anchor may be covered with ePTFE as previously disclosed to form an hour glass shaped cylinder or selective portions 255 can be covered like flower petals. The wire can be made of a solid wire, stranded wire or braided.

Figure 27:
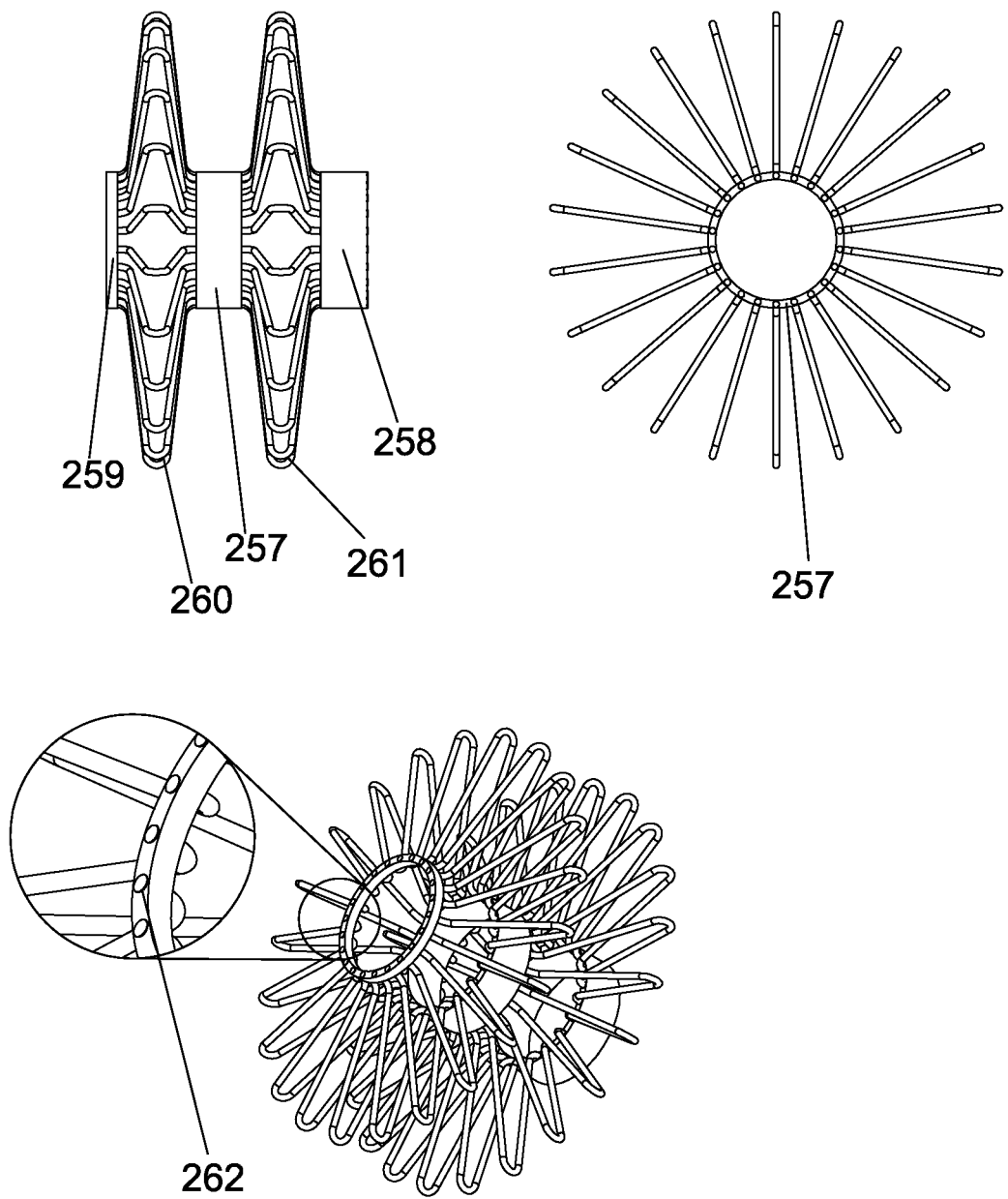
FIG. 27 shows an alternative embodiment of an expandable anchor formed from wire.

FIG. 27 is a drawing of an alternative embodiment of an expandable anchor formed from wire. Expandable anchor can be formed from Nitinol wire forms 260 and 261. Nitinol wire forms 260 and 261 are disk-shaped and are attached to central cylinder 257, proximal cylinder 258 and distal cylinder 259 by inserting wire ends into receptacles 262 in cylinders 257, 258 and 259. Wire ends of the wire form 260 and 261 are inserted into the central cylinder 257 and may be attached to central cylinder by mechanical crimping or adhesive bonding or laser welding. The wire can be made of a solid wire, stranded wire or braided.

Figure 28:
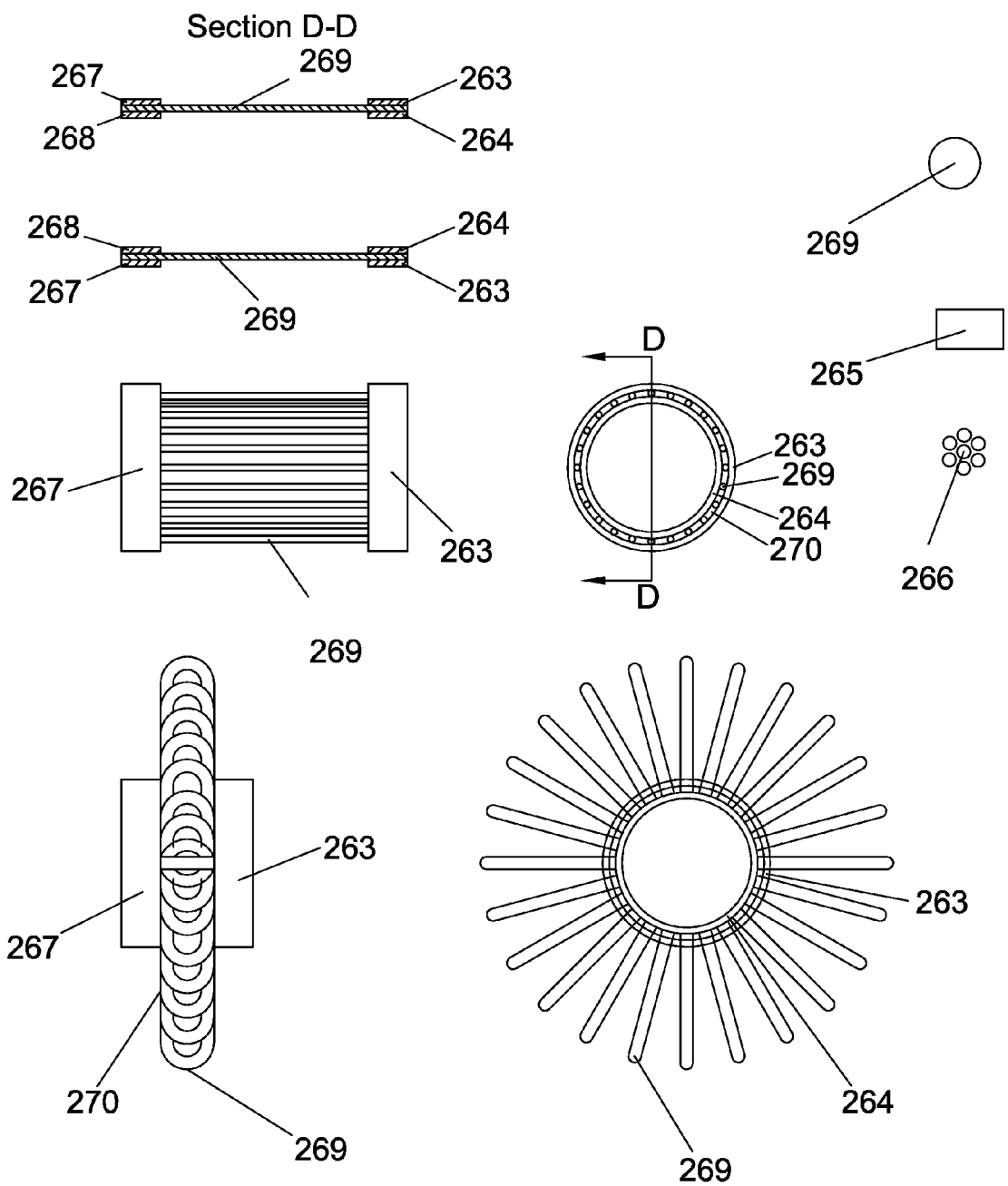
FIG. 28 shows an alternative embodiment of an expandable anchor formed from wire.

FIG. 28 is a drawing of an alternative embodiment of an expandable anchor. Expandable anchor is comprised of outer rings 263, 267, inner rings 264, 268 and wires 269. Rings and wire may be made from Nitinol, stainless steel, Elgiloy, L605, MP35N, titanium, niobium or other suitable material. Alternatively, the rings and wire may be made from plastics such as Nylon, FEP, PTFE, Delrin, PET, peek, high density polyethylene, polycarbonate or other suitable polymer. Outer ring 263 and inner ring 264 and wire 269 are bonded together by fusing of the materials together for example by laser or TIG welding. Entire annular space 270 between ring 264 and ring 263 can be melted and reflowed together to close up the annular space 270 and combine 263, 264 and 269 (and also 267, 268 and 269) into one solid mass at the outer ends of the ring. Individual wires 269 are not bonded except in the area near the outer ends of the rings. Alternatively, the rings 263, 264, 267, 268 and wires 269 are bonded together by spot welding or adhesive bonding. The wires may be in the form of round wires 269, flat wires 265, or stranded wires 266. After the rings and wires have been joined together the rings 263 and 267 can be compressed towards each other axially to reduce the axial spacing between the rings and cause the wires 269 to bend and cause the original cylinder shape to transform into a disk-shaped anchor 270. Alternatively the anchor can be shaped to form a spherical shape or a barrel shape. The diameter of the rings 263, 264, 267, 268 can range from 3 to 14 mm in diameter and the outer diameter of the disk 270 can range in the 12 to 50 mm diameter range in the expanded state and in the 3 to 14 mm diameter in the unexpanded state. The anchor can be actuated from the collapsed state to the actuated state by mechanical means or by the elastic properties of the wires 269 which can allow the anchor to self open to the disk-shaped state without mechanical actuation.

Figure 29:
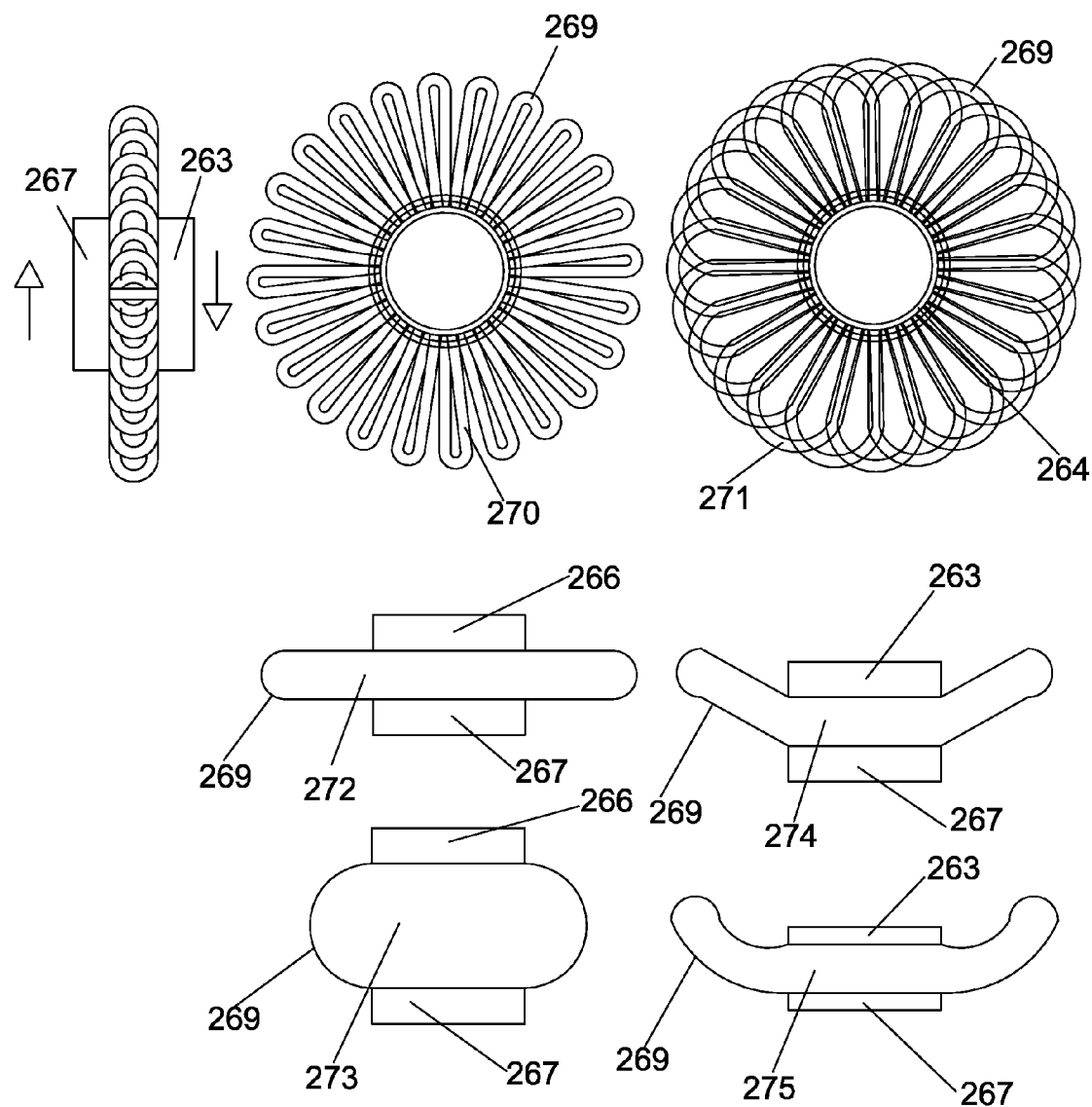
FIG. 29 shows an alternative embodiment of an expandable anchor.

FIG. 29 is a drawing of anchor previously disclosed in FIG. 28 in which the anchor is formed into alternative shapes. Ring 263 can be rotated in the opposite direction from ring 267 to form wires 269 to an alternative pattern in which the wires 269 are formed into patterns as in 270 or 271. Shape 272 is a disk-shaped anchor with a wire pattern of 270 or 271. Shape 274 is a concave shaped disk, wires 269 may be formed into the pattern of 270, 271 or as in FIG. 28. Shape 273 is a spherical shaped anchor. Shape 275 is an alternative shape to form the disk.

Figure 30:
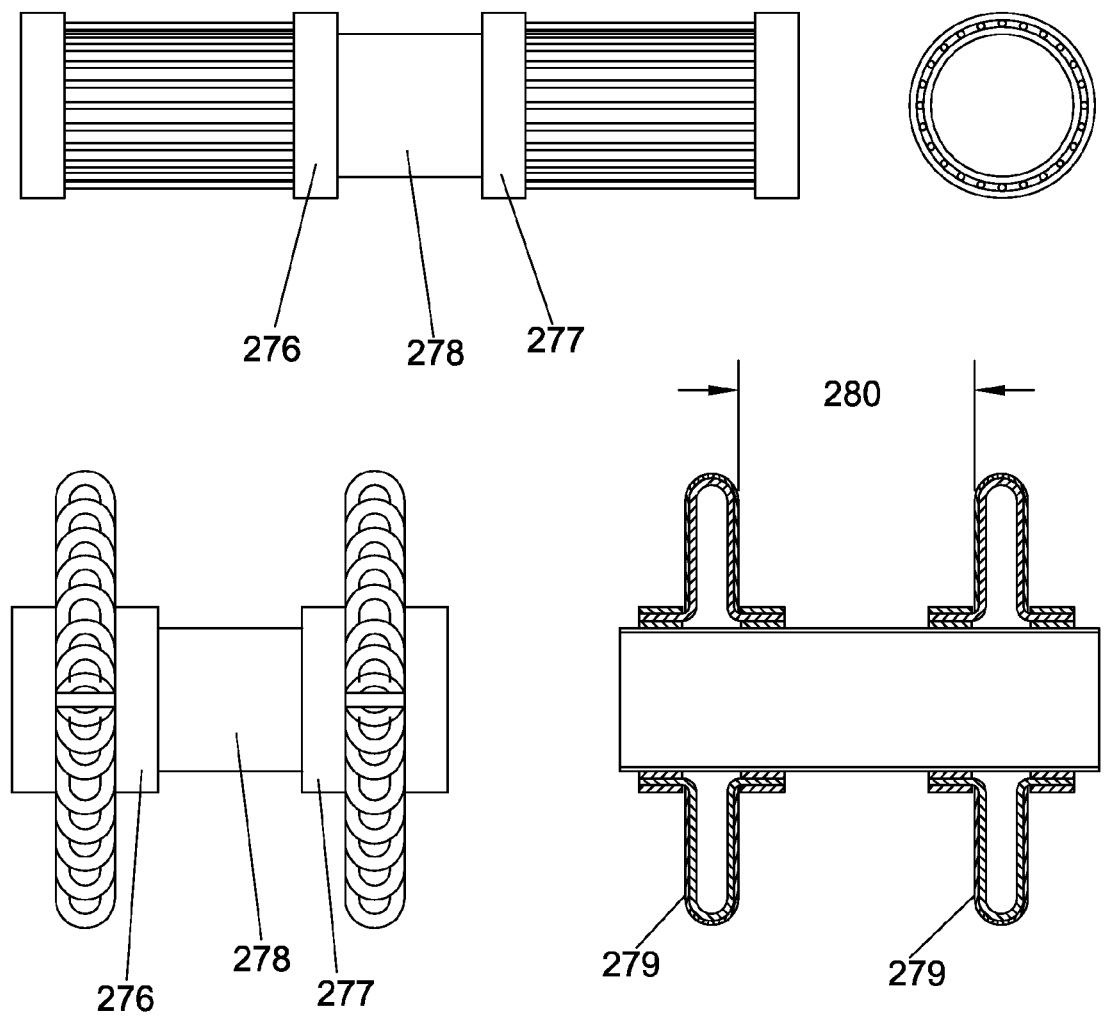
FIG. 30 shows an alternative embodiment of an expandable anchor.
Figure 31:
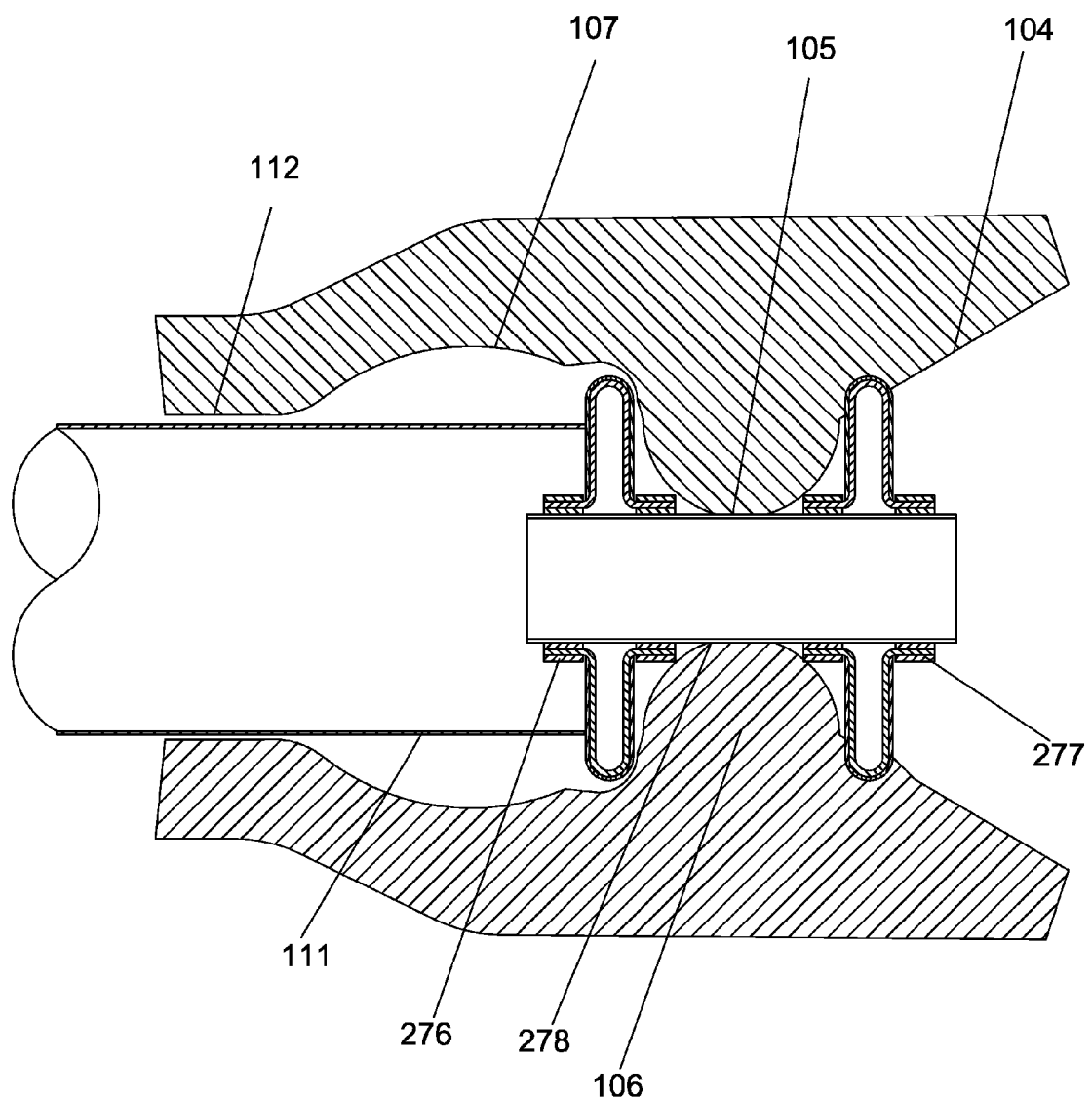
FIG. 31 is a cross-sectional view of the pyloric antrum, pylorus, duodenal bulb and the duodenum in the human body. An expandable anchor and intestinal bypass sleeve is implanted across the pylorus.

FIG. 30 is a drawing of an assembly of two of the expandable anchors previously disclosed in FIG. 28 and FIG. 29. Anchors 276 and 277 can be any of the alternatives from FIG. 28 and FIG. 29. The anchors are assembled onto a central cylinder 278. The spacing 280 between the two anchors can be adjusted to accommodate different pylorus widths. Expandable anchors can be covered with a polymer as previously disclosed in this application. FIG. 31 is a cross-sectional view of the pyloric antrum 104, pylorus 106, duodenal bulb 107 and the duodenum 112 in the human body. An expandable anchor as disclosed in FIG. 28, FIG. 29 and FIG. 30 and intestinal bypass sleeve 111 is implanted across the pylorus.

Figure 32:
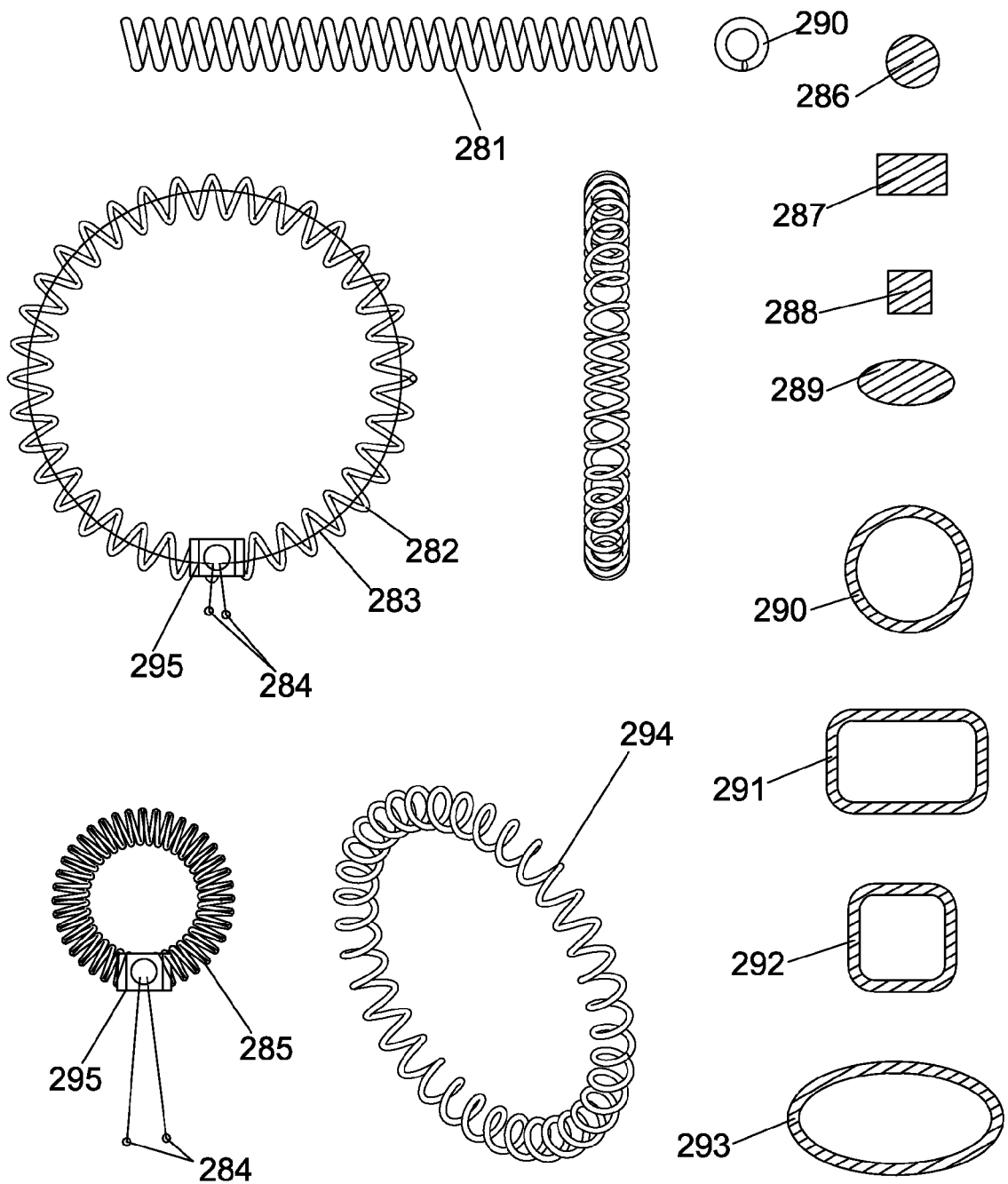
FIG. 32 shows an alternative embodiment of an expandable anchor formed in the shape of a toroidal-shaped coil.

FIG. 32 is a drawing of an alternative embodiment of an expandable anchor formed in the shape of a toroidal-shaped coil compression spring 282. The toroidal-shaped anchor may be first formed by winding a straight compression spring 281. The compression spring 281 may be made from round wire 286, rectangular wire 287, square wire 288 or elliptical wire 289. The compression spring 281 can be wound to have a round shape 290, rectangular shape 291, square shape 292, or an elliptical shape 293. The wire may be made from Nitinol, stainless steel, Elgiloy, L605, MP35N titanium, niobium or other suitable metal. The wire is, in various embodiments, made of a solid wire but can alternatively be made of stranded or braided wire. The outer diameter or inner core of the wire may be clad or plated with gold, tantalum, plantium, iridium or other suitable material. The wire may be co-drawn (e.g., drawn filled tube—Fort Wayne Metals) and have an outer core of a high strength material such as Nitinol, stainless steel, Elgiloy, L605, MP35N, titanium, niobium and an inner core of a high radio-opacity material such as gold, tantalum, plantium, iridium. Alternatively, the wire is made from a plastic monofilament such as peek, PET or delrin. Compression spring 281 is formed into a toroidal shape by bending spring ends towards each other and joining spring ends at connector 295. A perspective view of the torroidal spring is shown in 294. A drawstring 283 is contained within the center of the toroidal spring 282. The drawstring 283 is threaded through a hole in the connector 295. Drawstring 283 is terminated at spheres 284 that can be crimped onto the end of the drawstring 283. The spheres may be made of metal or plastic and may be attached to the drawstring 283 by crimping, welding, gluing, insert molding or other suitable means. The drawstring may be comprised of plastic or metal and may be made of a monofilament or braided cable material. When spheres 284 are withdrawn from connector 295, drawstring 283 is tensioned and the diameter of the toroidal spring is reduced to the smaller diameter as in 285.

Figure 33A:
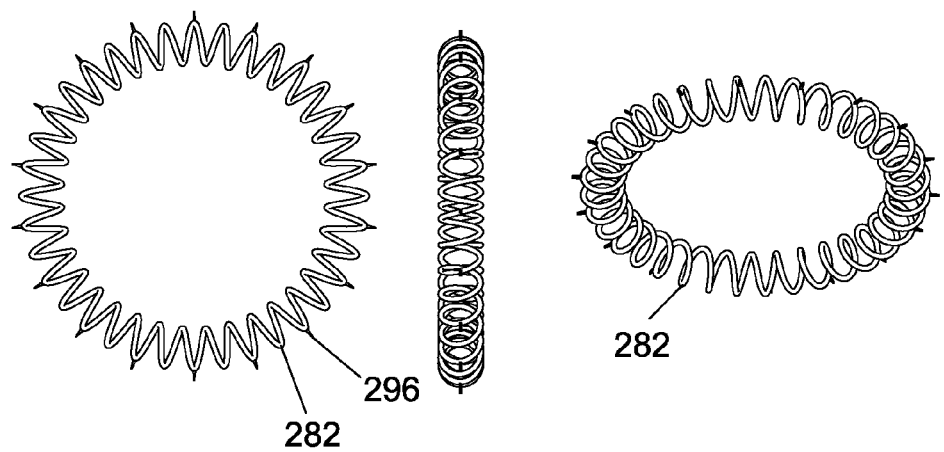
FIG. 33A is a drawing of an alternative embodiment of an expandable anchor formed in the shape of a toroidal-shaped coil. The coil may have small tissue penetrating anchors on the outer surface of the coil.
Figure 33B:
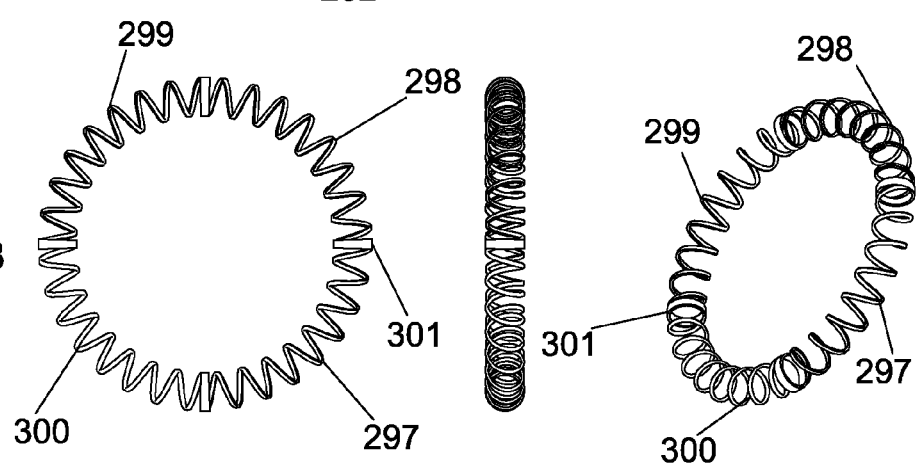
FIG. 33B is a drawing of an alternative embodiment of an expandable anchor formed in the shape of a toroidal-shaped coil. The direction of the winding of the coil is reversed to cancel out the helical twisting action of the spring.
Figure 33C:
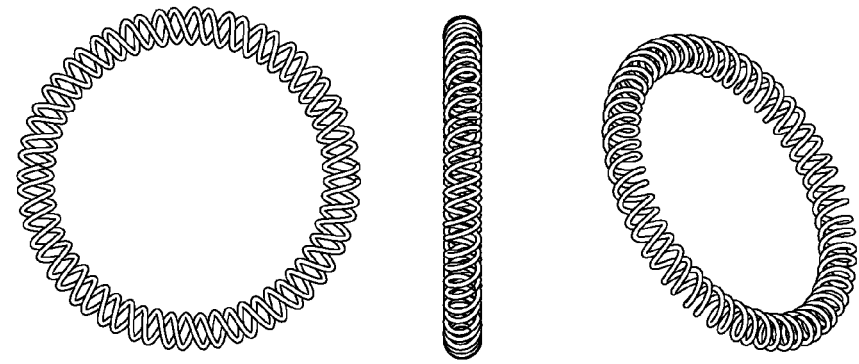
FIG. 33C is a drawing of an alternative embodiment of an expandable anchor formed in the shape of a toroidal-shaped coil as previously disclosed. The spring is wound to have double helices that are 180 degrees offset from each other.

FIG. 33A is a drawing of an alternative embodiment of an expandable anchor formed in the shape of a toroidal-shaped coil as previously disclosed in FIG. 32. The coil may have small tissue penetrating anchors 296 on the outer surface of the coil. Tissue penetrating anchor 296 may be made from, stainless steel, Elgiloy, L605, MP35N, titanium or niobium and may be crimped onto the wire or welded. Tissue penetrating anchors 296 may be an optional feature that can be added if the patient's anatomy does not have a pyloric ring that is adequate for anchoring. FIG. 33B is a drawing of an alternative embodiment of an expandable anchor formed in the shape of a toroidal-shaped coil as previously disclose in FIG. 32. The toroidal-shaped spring is formed of segments where the direction of the winding of the coil is reversed to cancel out the helical twisting action of the spring. The individual segments 297, 298, 299 and 300 can be connector at joiners 301. Alternatively the entire toroidal spring can be laser cut as one unitary piece by laser cutting the wound coil in the unformed shape as in 281 from a piece of round tubing. FIG. 33C is a drawing of an alternative embodiment of an expandable anchor formed in the shape of a toroidal-shaped coil as previously disclose in FIG. 32. The spring is wound to have double helices that are 180 degrees offset from each other.

Figure 34A:
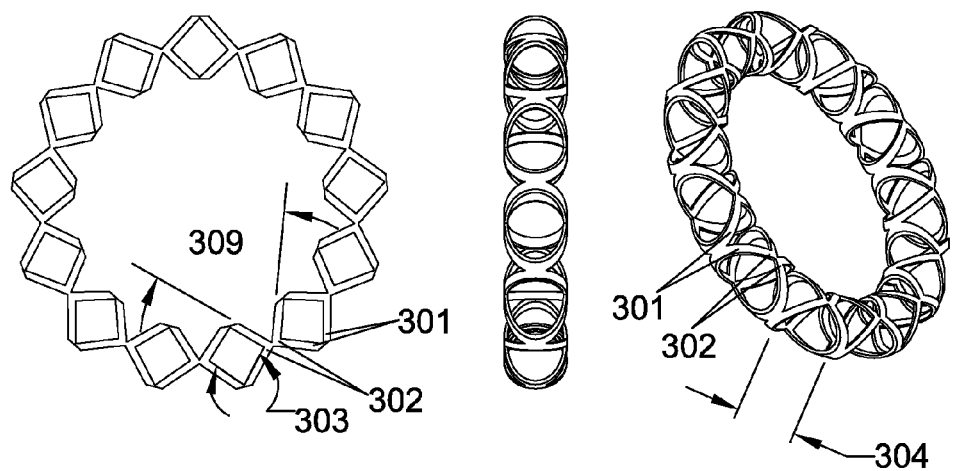
FIG. 34A is an alternative embodiment of a toroidal spring that is made from laser cutting a pattern into a round piece of Nitinol tubing. The Nitinol tubing is laser cut in the straight tubular shape and then the cut tube is then formed into the toroidal shape.
Figure 34B:
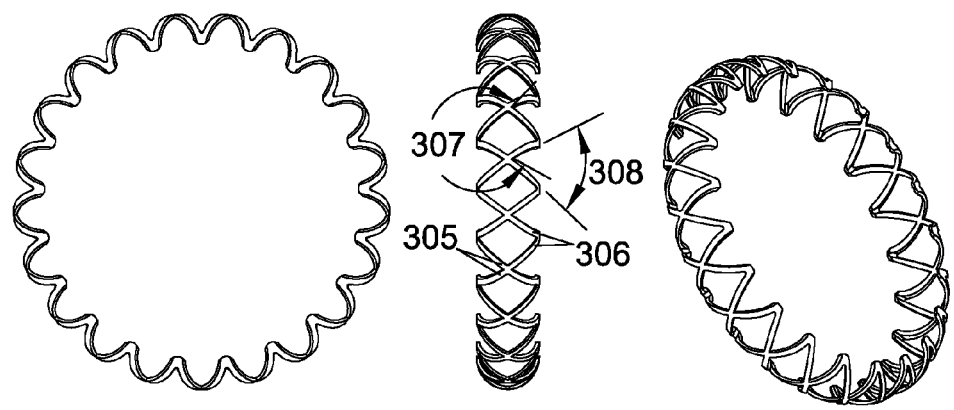
FIG. 34B is an alternative embodiment of a toroidal spring that is made from laser cutting a pattern into a round piece of Nitinol tubing. The Nitinol tubing is laser cut in the straight round tubular shape and then it is formed into the toroidal shape. Alternatively, the part may be cut from a flat sheet of Nitinol and then shape set into the final shape.

FIG. 34A is an alternative embodiment of a toroidal spring that is made from laser cutting a pattern into a round piece of Nitinol tubing. The Nitinol tubing is laser cut in the straight tubular shape and then the cut tube is then formed into the toroidal shape. Spring elements 301 and 302 elastically bend when the diameter of the toroidal spring is reduced. Bending of elements 301 and 302 reduces the included angles 303 and 309 and space 304 reduces to allow the diameter of toroidal spring to be compressed. FIG. 34B is an alternative embodiment of a toroidal spring that is made from laser cutting a pattern into a round piece of Nitinol tubing. The Nitinol tubing is laser cut in the straight round tubular shape and then it is formed into the toroidal shape. Alternatively the part may be cut from a flat sheet of Nitinol and then shape set into the final shape. Spring elements 306 and 305 elastically bend when the diameter of the toroidal spring is reduced. Bending of elements 306 and 305 reduces the included angles 307 and angle 308 to allow the diameter of the toroidal spring to be compressed.

Figure 35:
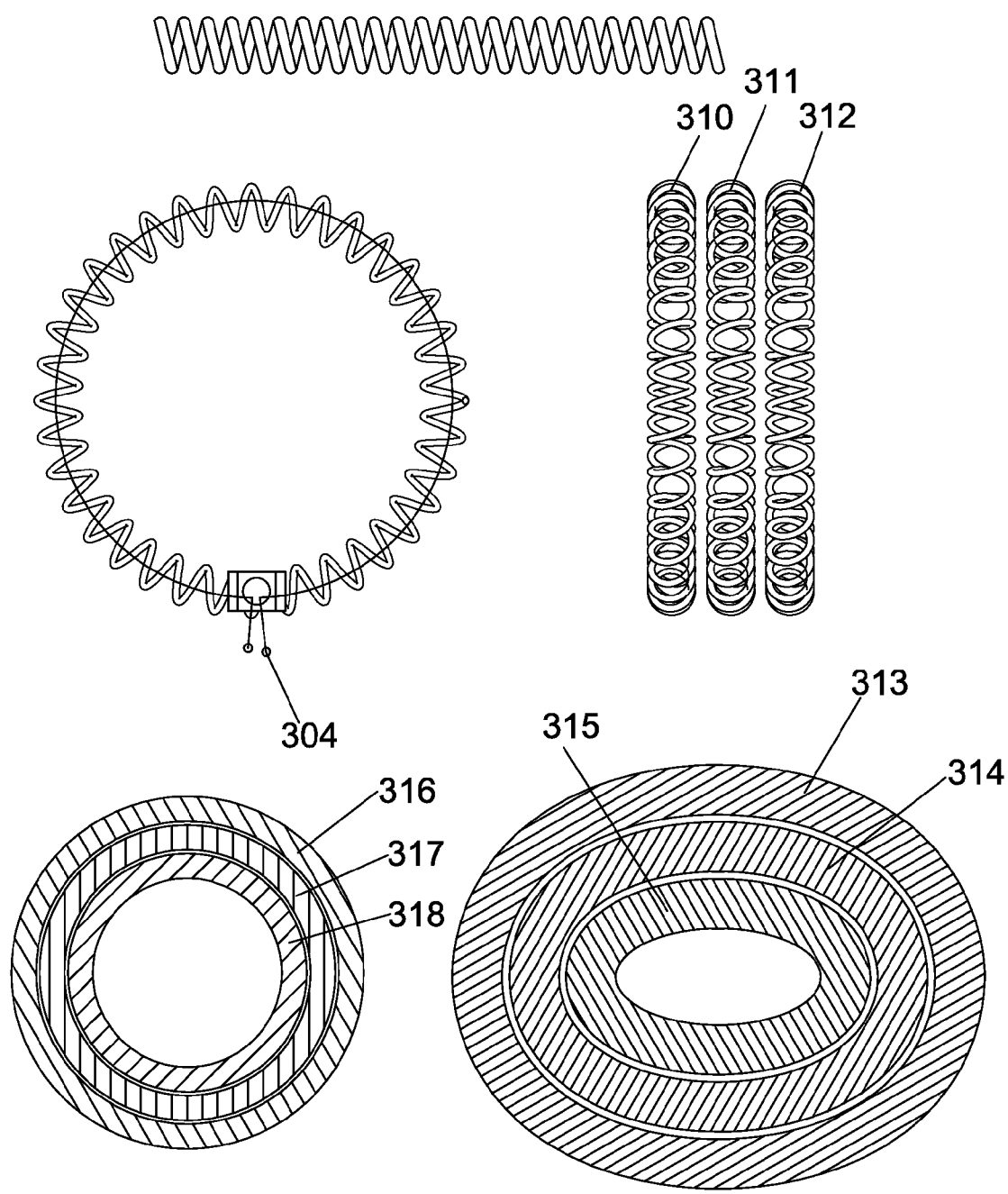
FIG. 35 is a drawing of an alternative embodiment of an expandable anchor. The drawing shows additional embodiments for the expandable anchors in FIG. 32, FIG. 33 and FIG. 34.

FIG. 35 is a drawing of an alternative embodiment of an expandable anchor as disclosed in FIG. 32 and FIG. 33. Toroidal-shaped springs 310, 311 and 312 are joined together side-by-side and integrated into an anchor together. In various embodiments, 1 to 3 springs will typically be used together, but in some configurations up to 100 springs may be joined side-by-side at some small spacing. Spring 316, 317 and 318 are assembled in a coaxial arrangement (one spring coaxial within the center of another) to provide for a combined spring with increased compression resistance. The direction of the spring winding for the three coaxial springs may be alternated. Springs 313, 314 and 315 are also coaxial springs that are wound in an elliptical shape.

Figure 36:
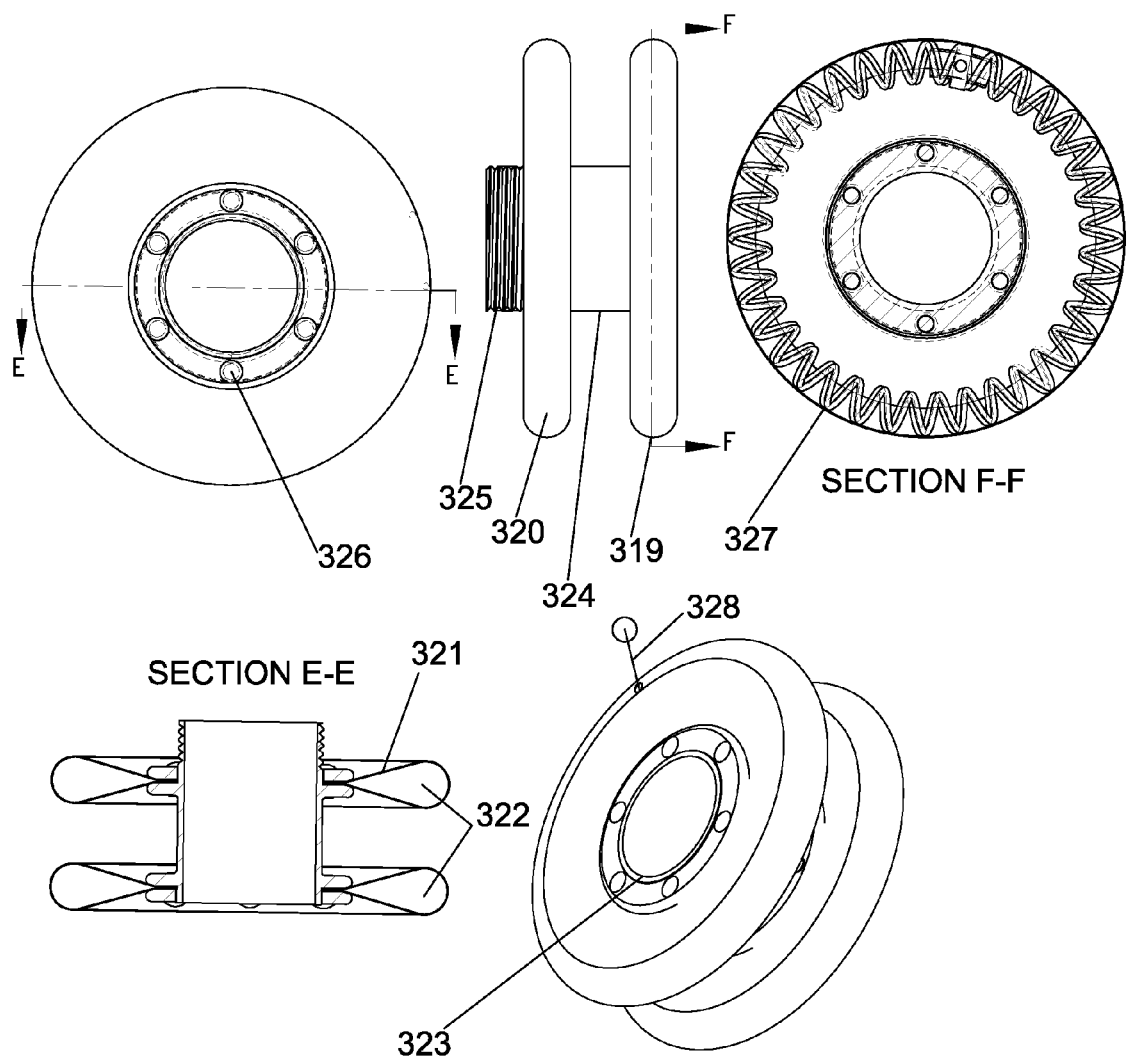
FIG. 36 is an assembly drawing with the expandable anchors in FIG. 32, FIG. 33, FIG. 34

FIG. 36 is an assembly drawing of an expandable anchor assembly. Expandable anchor assembly comprises two toroidal springs 327 as previously disclosed which are placed into pockets 322 to form disks 319 and 320, central cylinder 324 is located in between disks 319 and 320. Pockets 322 are formed from a polymer membrane 321 from materials previously disclosed in this application. Polymer membrane 321 is attached to central cylinder at pins 326. Outflow opening 325 provides for a location to attach the intestinal bypass sleeve 111. Inflow opening 323 is positioned towards the pyloric antrum 104. Drawstring 328 can be withdrawn from the toroidal spring assembly to compress and retrieve the device.

Figure 37:
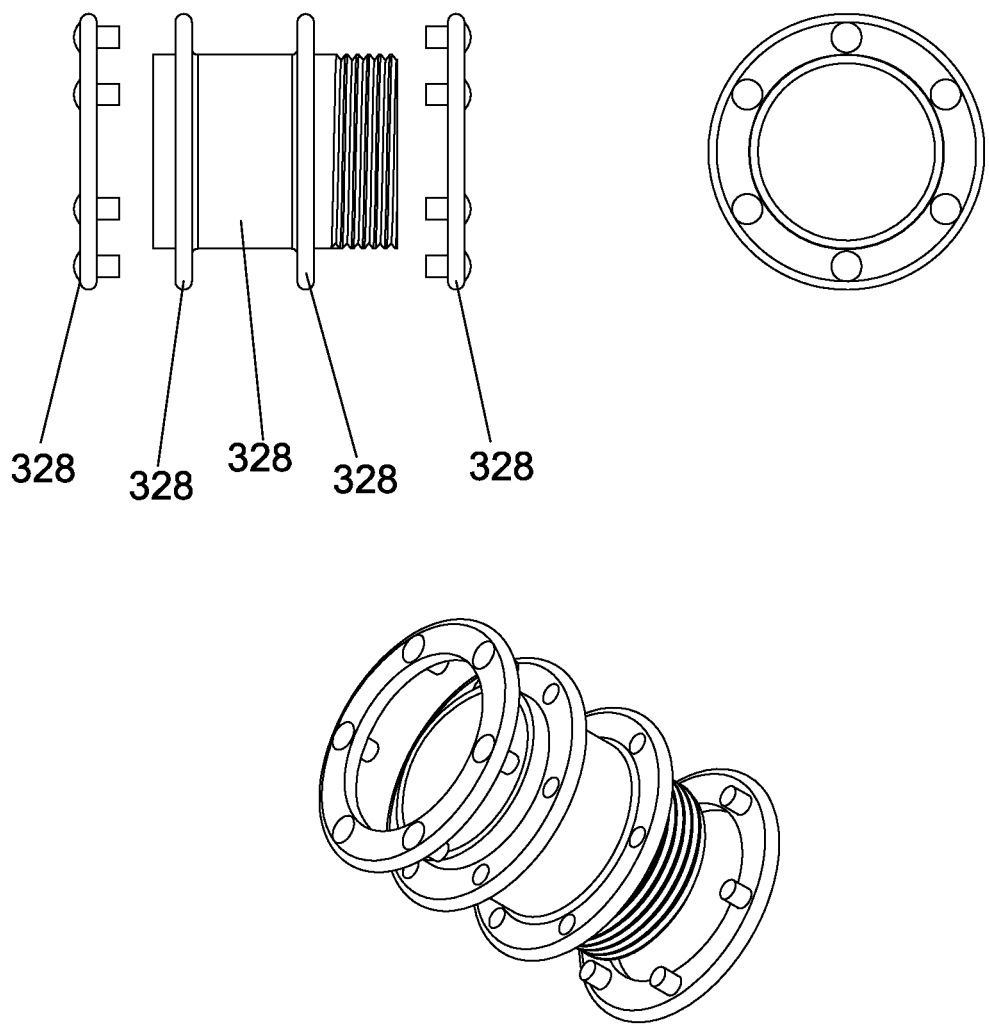
FIG. 37 is a drawing showing an assembly drawing of a fixed diameter cylinder for the central pyloric portion of the invention herein disclosed.

FIG. 37 is an assembly drawing of a fixed diameter cylinder for the central pyloric portion of the invention herein disclosed. The central cylinder 324 is ridge and provides a means to attach the polymer membrane to the central cylinder at disks 329 and 330. Securement rings 331 and 332 penetrate through holes in the polymer membrane and into holes in the central cylinder. Securement rings 331 and 332 can be fastened to the disks 329 and 330 by diameter interference of the pins with the holes, by welding, gluing or mechanical fasteners.

Figure 38:
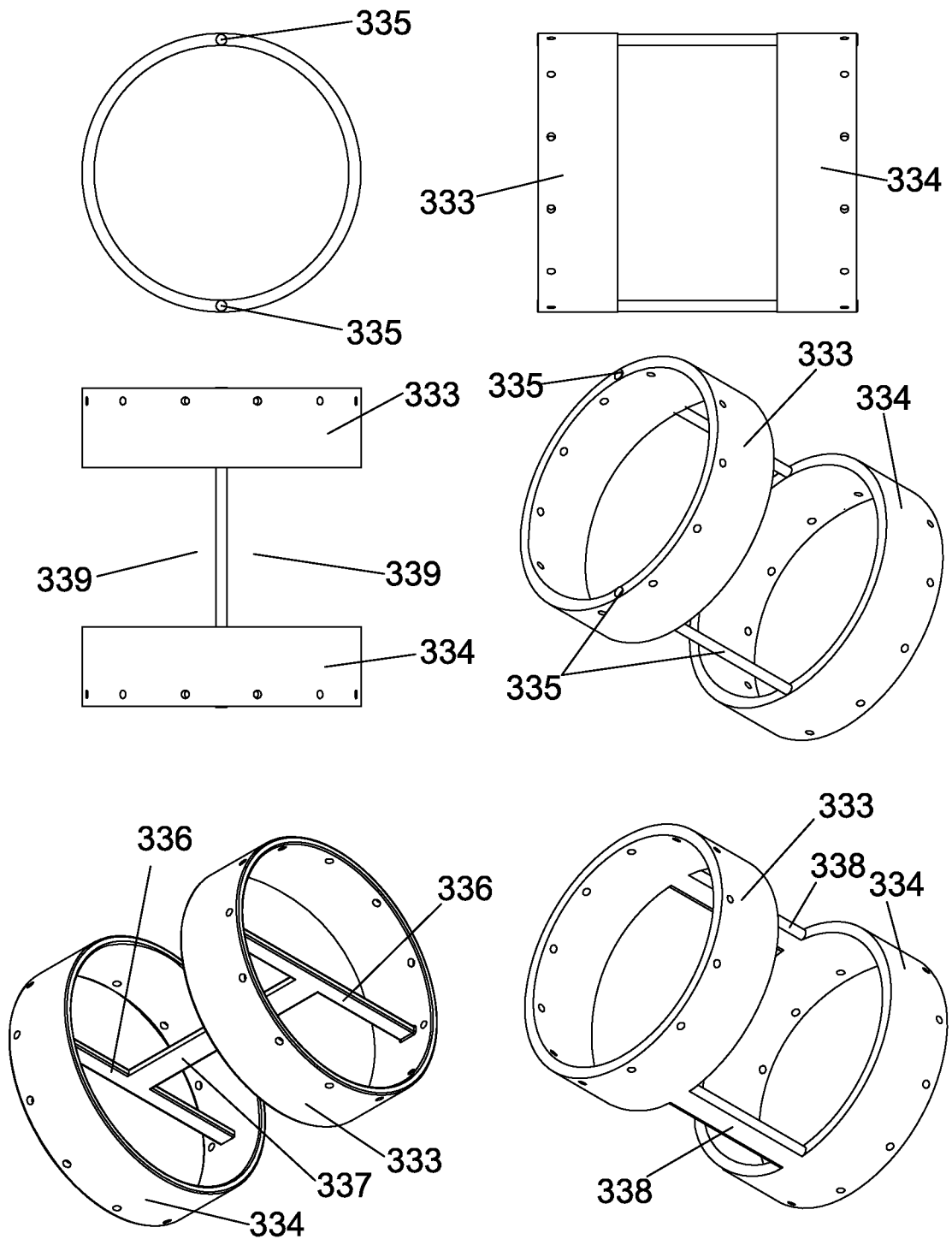
FIG. 38 is drawing showing of a central pyloric portion of the invention herein disclosed in which the mid portion allows for opening and closing of the pylorus, while there is a first and a second ring which are fixed rigidly together. The expandable anchors in the pyloric antrum and the duodenal bulb are tethered to the first and second rings.

FIG. 38 is drawing of a central cylinder pyloric portion for use with any of the anchor embodiments herein disclosed in which the mid-portion allows for normal opening and closing of the pylorus. There is a first ring 333 and a second ring 334 which are fixed rigidly together by connector links 335, 338 or 337. The connector links cross through the pyloric aperture 105 while not obstructing the pyloric aperture 105 or limiting opening or closing of the pylorus. In various embodiments, a thin polymeric membrane will be used over both rings 333, 334 and will span the space between the two rings as disclosed in FIG. 39. The pylorus 106 can close by entering into the space 339 in between rings 333 and 334 to open and close. Rigid linking of rings 333 and 334 provides for a rigid structure to anchor expandable anchors to and helps to keep expandable anchor (disks) oriented in the proper orientation without canting within the pyloric antrum or duodenal bulb. The rigid linking also does not allow rotational movement between the two rings 333 and 334 and still allows for normal opening and closing of the pylorus, Rotational movement between 333 and 334 may cause the pyloric polymer membrane 340 portion to close. The expandable anchors in the pyloric antrum and the duodenal bulb are tethered to the first ring 333 and second ring 334 by a polymer membrane.

Figure 39:
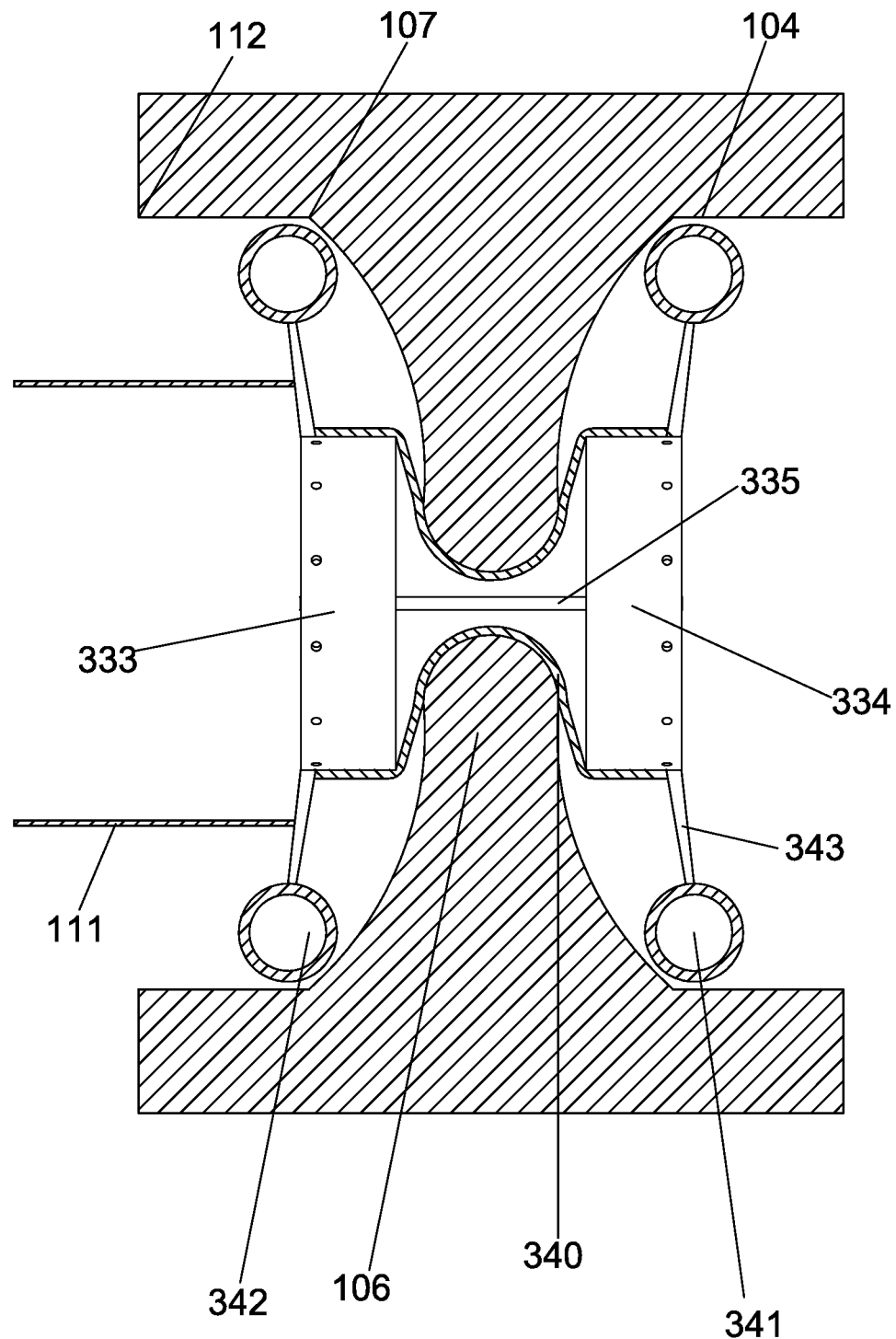
FIG. 39 is a sectional view of the invention herein disclosed implanted into the pyloric antrum, pylorus and duodenal bulb and duodenum. The anchoring device is comprised of two disk-shaped expandable anchors that are connected to a central cylinder which has a thin-walled compliant membrane over the central portion to allow opening and closing of the pyloric aperture.

FIG. 39 is a sectional view of the invention herein disclosed implanted into the pyloric antrum 104, pylorus 106 and duodenal bulb 107 and duodenum 112. The anchoring device is comprised of two disk-shaped expandable anchors 341 and 342 that are connected to a central cylinder which has a thin-walled compliant membrane 340 over the central portion to allow opening and closing of the pyloric aperture. Central cylinder has rings 333 and 334 which are linked by a connector link 335. Compliant membrane 340 is free to open and close with the movement of the pylorus 106. Expandable anchors 341 and 342 are tethered to rings 333 and 334 by a polymer membrane 343.

Figure 40:
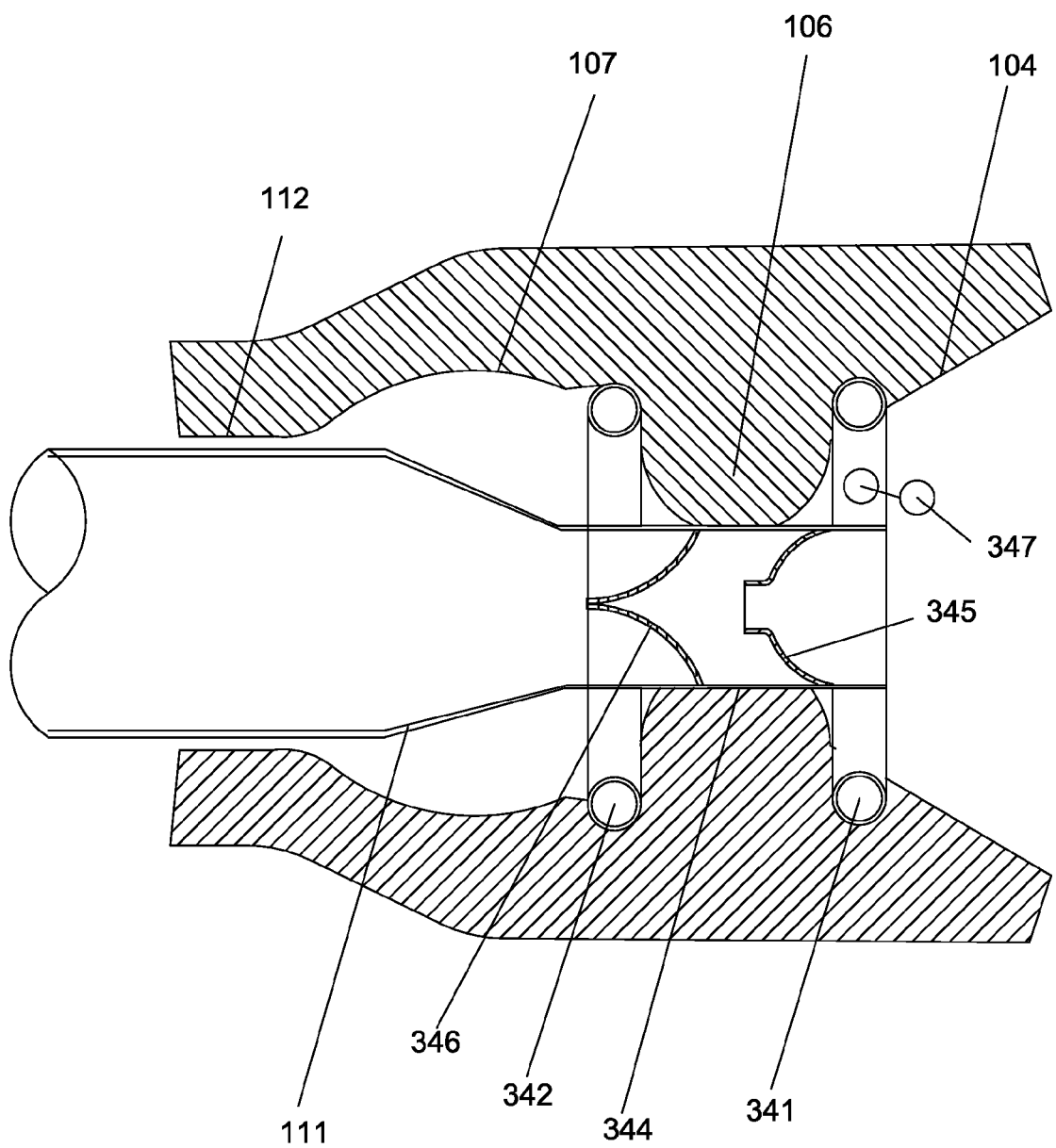
FIG. 40 is a sectional view of the invention herein disclosed implanted into the pyloric antrum, pylorus and duodenal bulb and duodenum. The anchoring device is comprised of two disk-shaped expandable anchors that are connected to a central cylinder. The lumen of the anchoring device has a one-way anti-reflux valve and a flow limiter.

FIG. 40 is a sectional view of the invention herein disclosed implanted into the pyloric antrum 104, pylorus 106, duodenal bulb 107 and duodenum 112. The anchoring device is comprised of two disk-shaped expandable anchors 341, 342 as previously disclosed in this application that are connected to a rigid central cylinder 344. The lumen of the anchoring device has a one way anti-reflux valve 346 and a flow limiter 345. Drawstring 347 can be tensioned to collapse the diameter of the expandable anchors for removal and for loading the device onto a delivery catheter.

Figure 41:
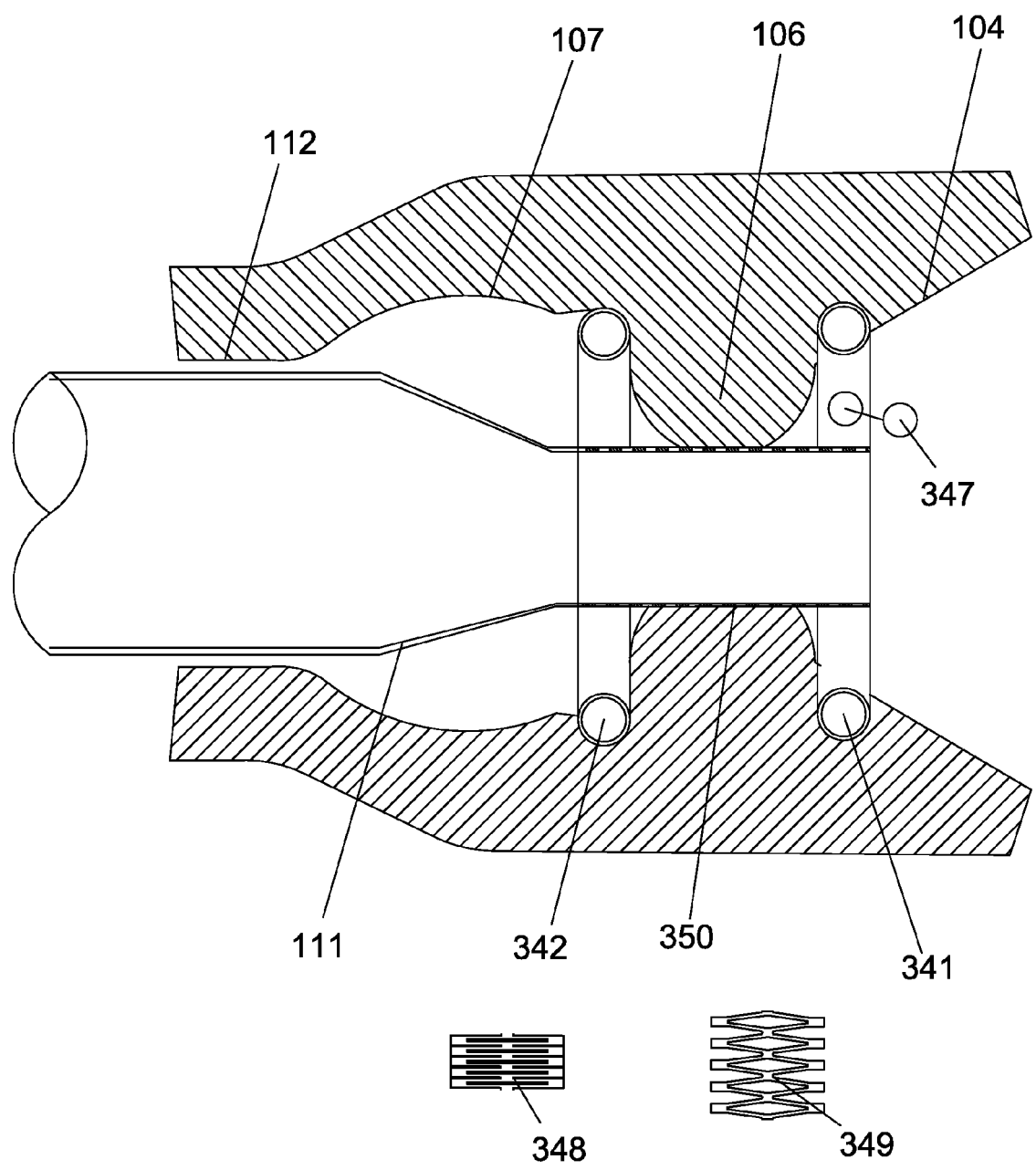
FIG. 41 is a sectional view of the invention herein disclosed implanted into the pyloric antrum, pylorus and duodenal bulb and duodenum. The anchoring device is comprised of two disk-shaped expandable anchors that are connected to a central cylinder. The diameter of the central cylinder is elastic and the diameter can be compressed to allow a reduced diameter of the anchor to allow the anchor to be loaded onto a smaller diameter catheter than with a fixed diameter central cylinder.

FIG. 41 is a sectional view of the invention herein disclosed implanted into the pyloric antrum 104, pylorus 106, duodenal bulb 107 and duodenum 112. The anchoring device is comprised of two disk-shaped expandable anchors 341, 342 as previously disclosed in this application that are connected to a central cylinder 350. The tube of central cylinder is elastically compressible in diameter so that the diameter can be compressed from the first state 349 to reduced diameter state 348. This will provide for a smaller profile on the delivery catheter. In some configurations, the central cylinder can be soft enough to allow pylorus movement to compress the central cylinder and close the central cylinder opening when the pylorus closes. Drawstring 347 can be tensioned to collapse the diameter of the expandable anchors for removal and for loading the device onto a delivery catheter.

Figure 42:
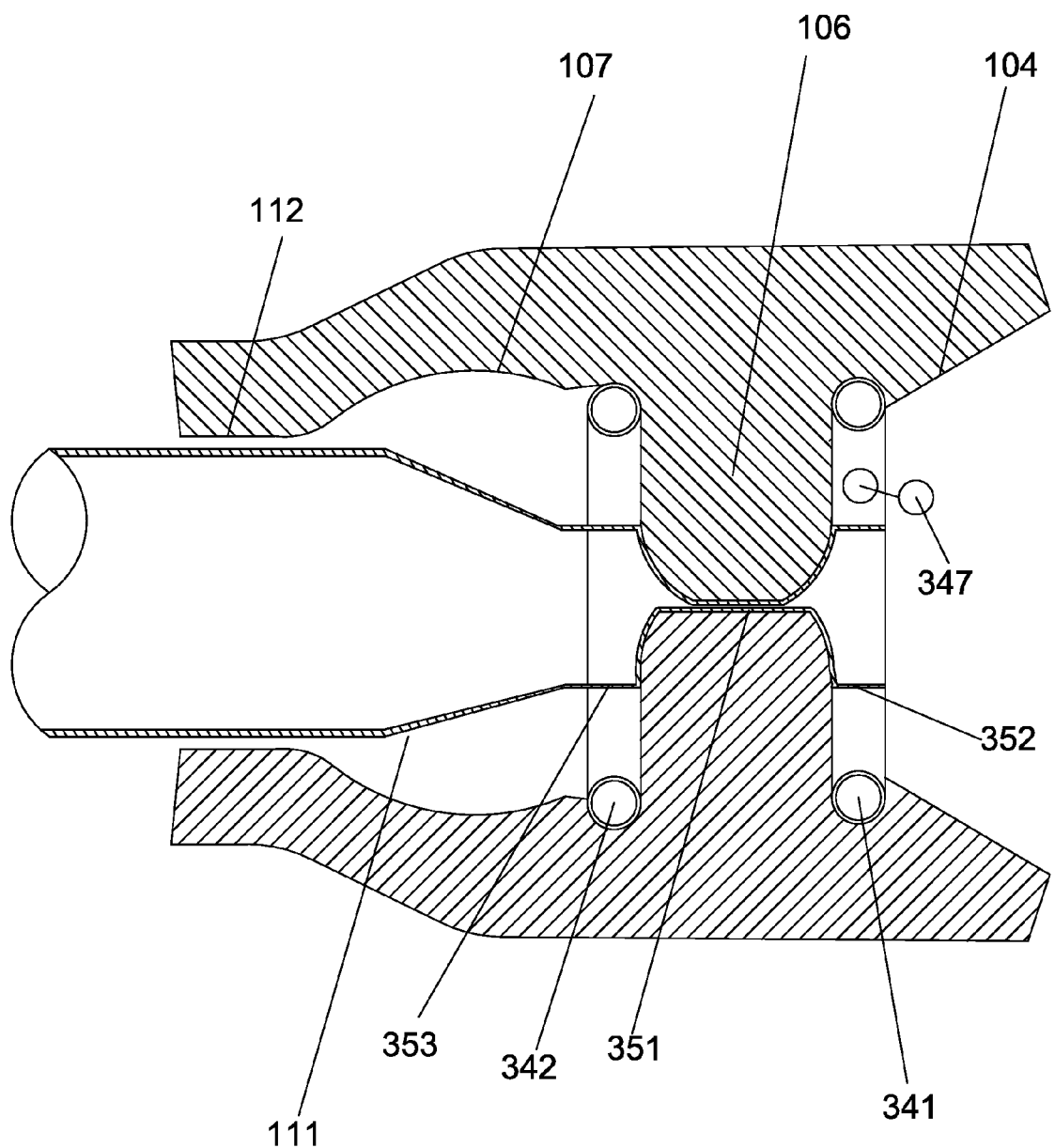
FIG. 42 is a sectional view of the invention herein disclosed implanted into the pyloric antrum, pylorus and duodenal bulb and duodenum. The anchoring device is comprised of two disk-shaped expandable anchors that are connected by a thin-walled tubular membrane. The thin-walled tubular membrane allows normal pylorus opening and closing.

FIG. 42 is a sectional view of the invention herein disclosed implanted into the pyloric antrum 104, pylorus 106, duodenal bulb 107 and duodenum 112. The anchoring device is comprised of two disk-shaped expandable anchors 341, 342 as previously disclosed in this application that are connected to rings 352 and 353. The rings 353, 353 are not rigidly connected to each other. Thin-walled central membrane 351 is connected to the two rings 352 and 353. Central membrane can open and close with the pylorus. Drawstring 347 can be tensioned to collapse the diameter of the expandable anchors for removal and for loading the device onto a delivery catheter.

Figure 43:
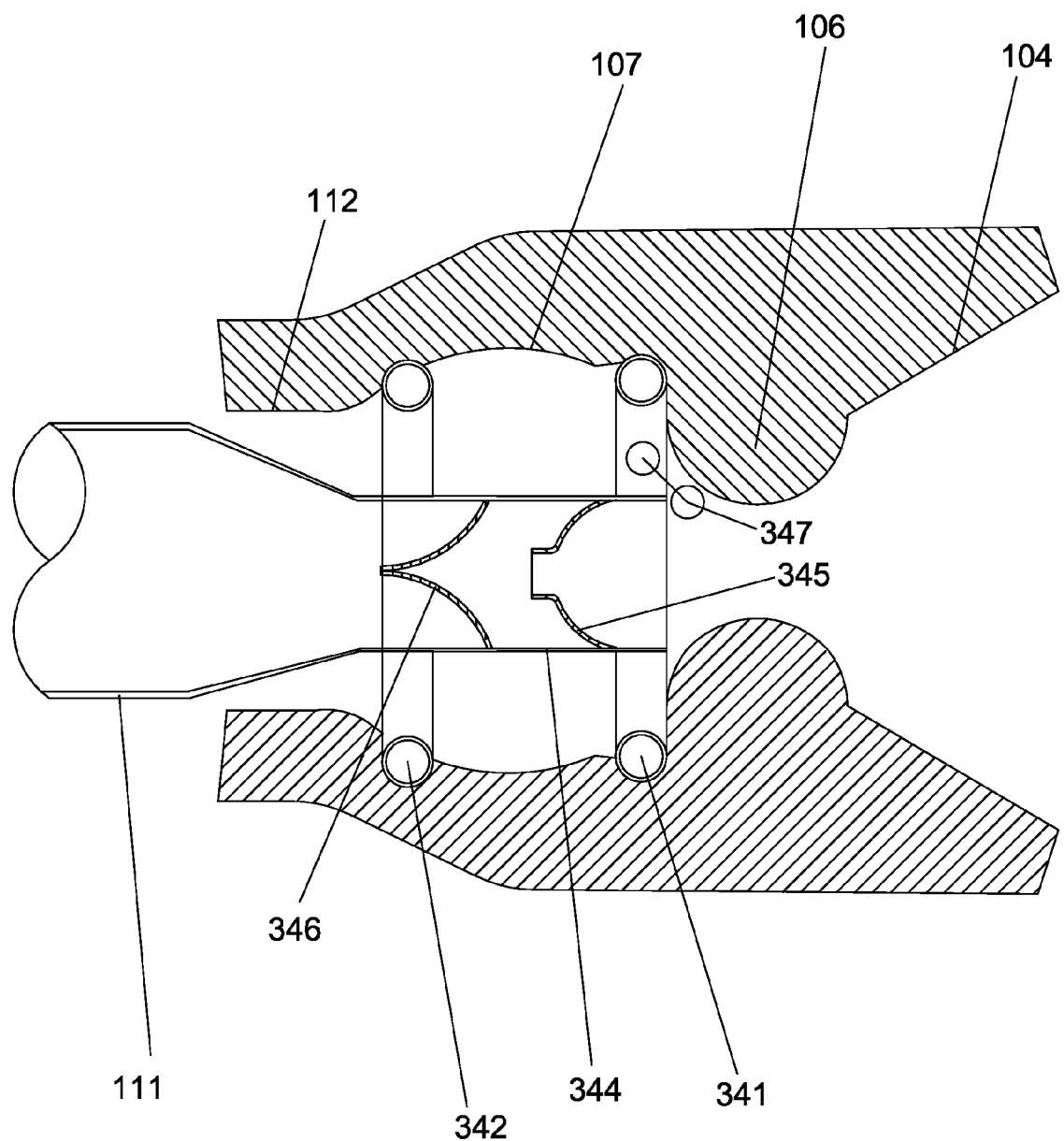
FIG. 43 is a sectional view of the invention herein disclosed implanted into the duodenal bulb and duodenum. The anchoring device is comprised of two disk-shaped expandable anchors that are connected to a central cylinder. The lumen of the anchoring device has an optional one-way anti-reflux valve and an optional flow limiter. The anti-reflux valve and flow-limiter can be used together in combination or separately on the device.

FIG. 43 is a sectional view of the invention herein disclosed implanted into the duodenal bulb 107 and duodenum 112. The anchoring device is comprised of two disk-shaped expandable anchors 341, 342 as previously disclosed in this application that are connected to a rigid central cylinder 344. The lumen of the anchoring device has a one way anti-reflux valve 346 and a flow limiter 345. Drawstring 347 can be tensioned to collapse the diameter of the expandable anchors for removal and for loading the device onto a delivery catheter.

Figure 44:
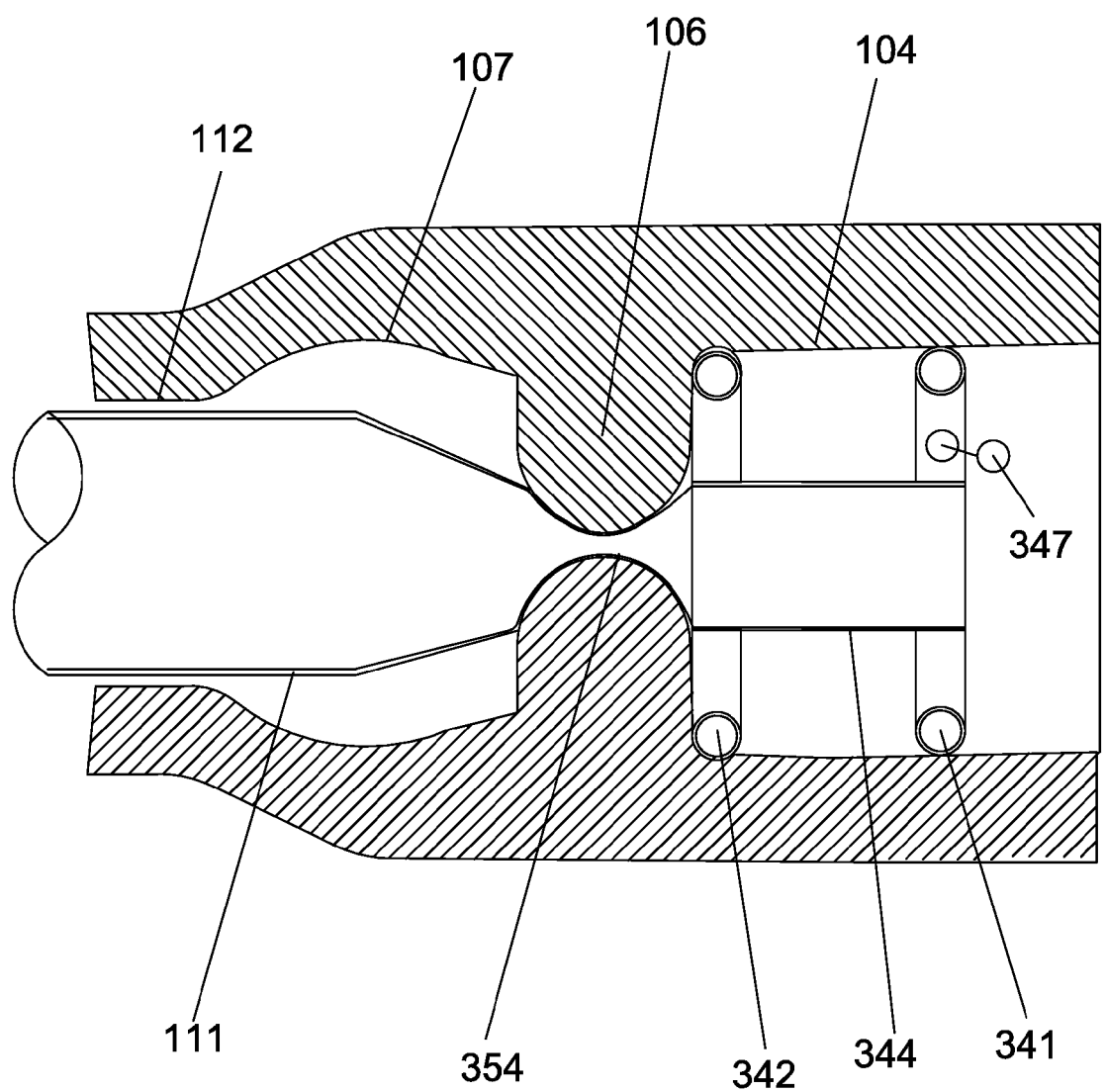
FIG. 44 is a sectional view of the invention herein disclosed. The anchoring device is comprised of two disk-shaped expandable anchors that are connected to a central cylinder. The anchoring device is implanted into the pyloric antrum and the intestinal bypass sleeve is implanted from the pyloric antrum to the duodenum.

FIG. 44 is a sectional view of the invention herein disclosed implanted into the pyloric antrum 104, pylorus 106, duodenal bulb 107 and duodenum 112. The anchoring device is comprised of two disk-shaped expandable anchors 341, 342 as previously disclosed in this application that are connected to a rigid central cylinder 344. Drawstring 347 can be tensioned to collapse the diameter of the expandable anchors for removal and for loading the device onto a delivery catheter. Intestinal bypass sleeve 111 crosses the pylorus 106 and can be compressed shut at 354 by the pylorus 106.

Figure 45A:
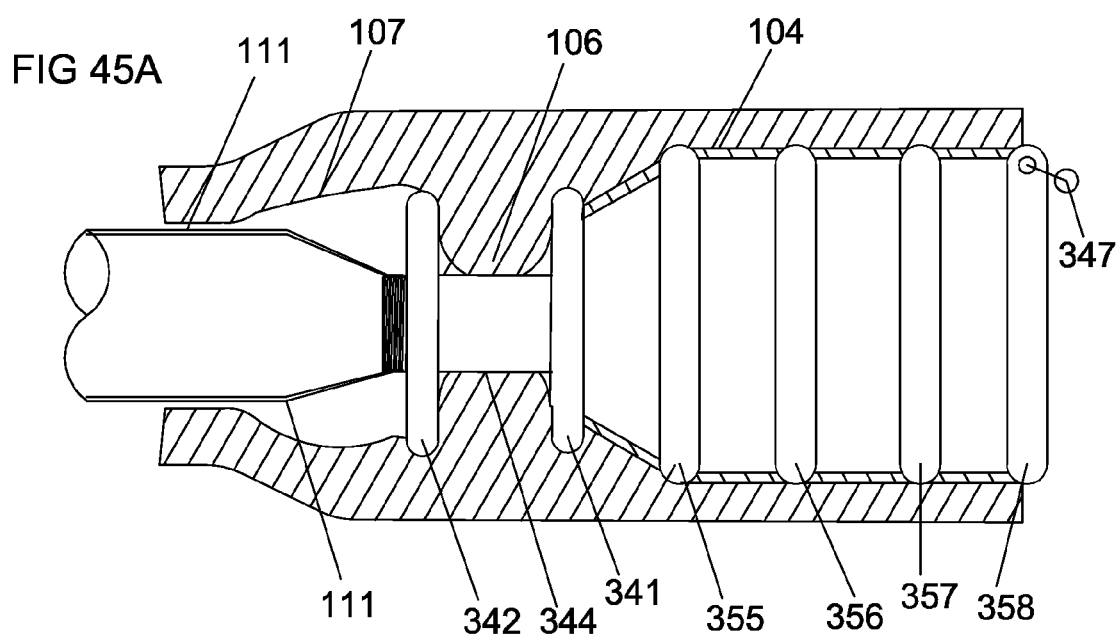
FIG. 45A is a sectional view of the invention herein disclosed. The anchoring device is comprised of two disk-shaped expandable anchors that are connected to a central cylinder. Four additional expandable anchors are attached to the thin-walled sleeve and are implanted into the pyloric antrum.

FIG. 45A is a sectional view of the invention herein disclosed implanted into the pyloric antrum 104, pylorus 106, duodenal bulb 107 and duodenum 112. The anchoring device is comprised of two disk-shaped expandable anchors 341, 342 as previously disclosed in this application that are connected to a rigid central cylinder 344. Additional expandable anchors 355, 356, 357 and 358 are extended into the pyloric antrum 104.

Figure 45B:
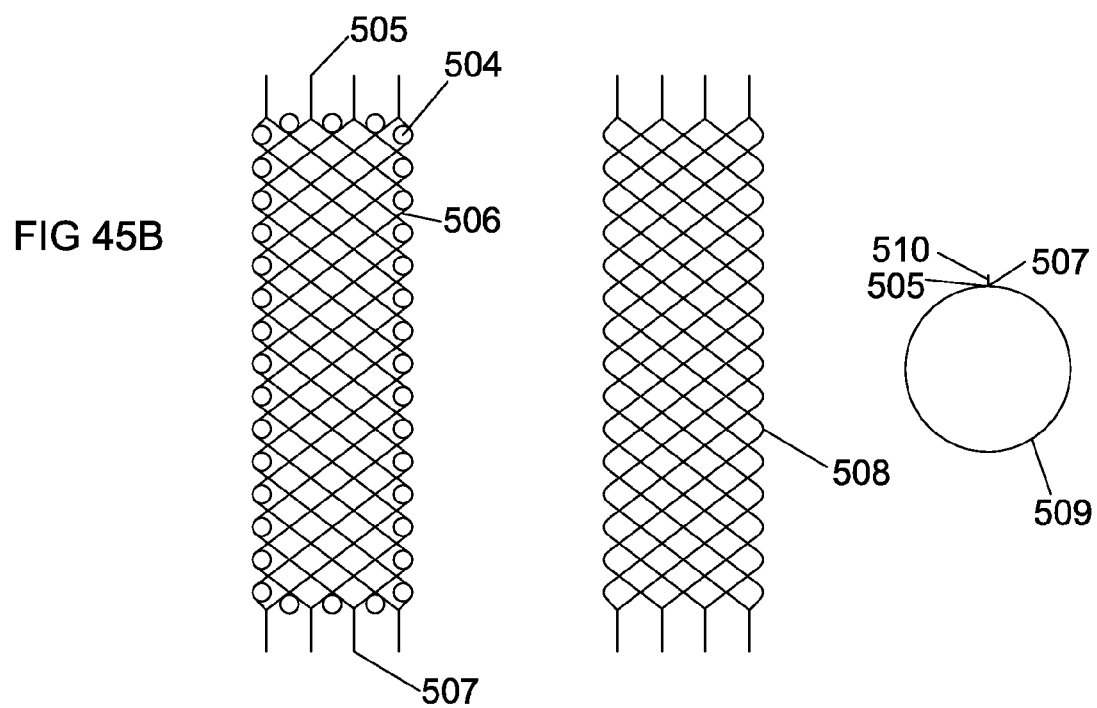
FIG. 45B is a drawing of a flat braided wire form that may be used as an expandable anchor.

FIG. 45B is a drawing of a flat braided expandable anchor made from Nitinol wire. A series of dowels pins 504 is press fit into an aluminum plate in a determined pattern. Eight wires 506 are braided into a flat braid by wrapping the wires around the dowel pins 504 and then braiding one wire over, one wire under. Four wires are braided in each diagonal direction. Wires are doubled up at end locations 505 and 507. After the braiding pattern is complete, the wires and the plate are heat set in a salt bath at 500 degrees centigrade for 10 minutes and then water quenched to room temperature. Heat set wire flat braid 508 is then removed from the forming fixture and the wires retain the heat set shape mandrel from the fixture. Flat braid 508 is then wrapped around a round mandrel to form a cylinder shaped braid 509. The wire ends 505 and 507 at the end of the flat braid are joined at 510.

Figure 46:
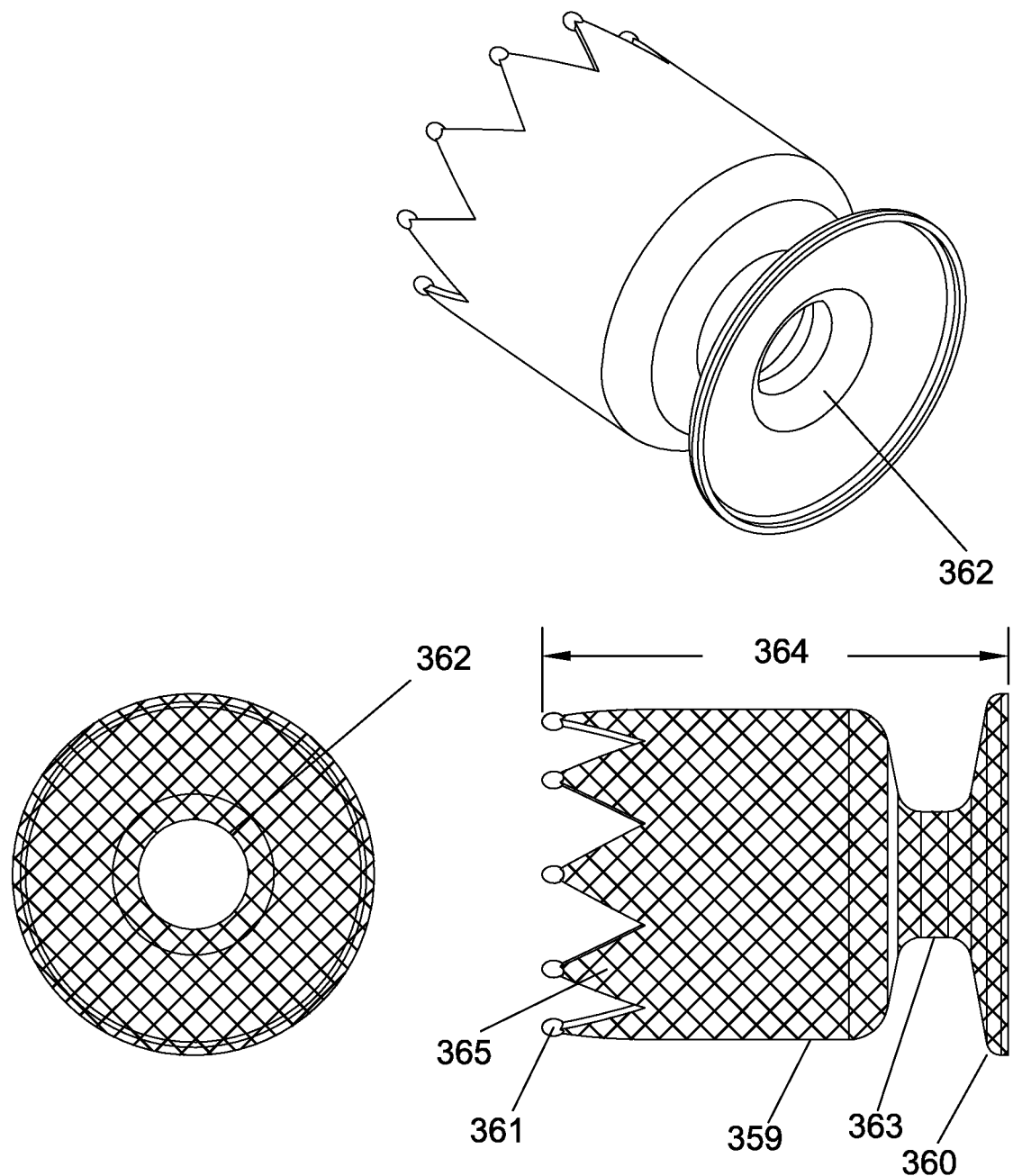
FIG. 46 is a drawing of an alternative embodiment of the invention herein disclosed. The expandable anchor is comprised of a hollow tubular braided structure of wire. The wire form has been shaped to conform to the shape of the pylorus and the duodenal bulb.

FIG. 46 is a drawing of an alternative embodiment of the invention herein disclosed. The expandable anchor is comprised of a hollow tubular braided structure of wire. The tubular braid can be braided in the diameter range from 10 mm in diameter up to about 70 mm in diameter. The wire diameter can range from 0.001 inch to 0.014 inch. In exemplary embodiments, the number of wire ends in the braid is 96 ends, but it can range from as few as 4 ends up to 256 ends. The wire can be made from a metal such as Nitinol, MP35N, L605, Elgiloy, stainless steel or from a plastic such as Pet, Peek or Delrin or other suitable material. The tubular wire braid is formed into a shape with a disk 360, a central cylinder portion 363, cylindrical portion 359. Wire ends are gathered into bunches 361 and welded together or a sleeve is crimped onto wires to keep the braided ends from fraying and unraveling. Alternatively, the structure could be made from a braid using a single wire end. Central cylinder 363 has a through lumen 362 that allows chyme to flow from the stomach to the duodenum. The central cylinder 363 can be rigid to hold the pylorus 106 open or it may be compliant to allow the opening and closure of through lumen 362 with the pylorus.

The length of the device is typically about 50 mm but can range from about 10 mm to 100 mm. The diameter of the cylindrical portion 359 is typically about 25 mm in diameter, but can range from 10 mm to 75 mm. The diameter of the central cylinder portion is typically about 10 mm in diameter but can range from 2 mm up to 25 mm in diameter. The length of the central cylinder 363 is approximately that of the width of the pylorus, but the central cylinder 363 can be slightly longer to provide a gap between central cylinder and pylorus or slightly shorter to provide for a compressive force to be applied to the pylorus. The expandable anchor is compressible in diameter and the diameter can be reduced to about 5 to 10 mm in diameter typically to allow the anchor to be loaded into a catheter. The expandable anchor can be covered on the outside and/or inside side with a polymer membrane covering. The membrane 365 covering the expandable anchor may be made from a thin-walled polymer material such as silicone, polyurethane, polytetrafluoroethylene, fluorinated ethylene propylene, polyethylene, expanded poly tetrafluoroethylene (ePTFE) or other suitable material. In some embodiments, the wall thickness of the membrane covering the expandable anchor may be in the range of 0.001 inch to 0.030 inch thick. The membrane 365 may be made by extrusion, dip coating from a liquid solution, powder coated from fine particles of polymer or paste extruded and then stretched as is the case with ePTFE. The expandable anchor membrane 365 may also be cut from a flat sheet of material such as ePTFE and then bonded or sewn into a disk shape or spherical shaped structure and then attached to the expandable anchor by sewing or gluing with a polymer such as FEP.

Figure 47:
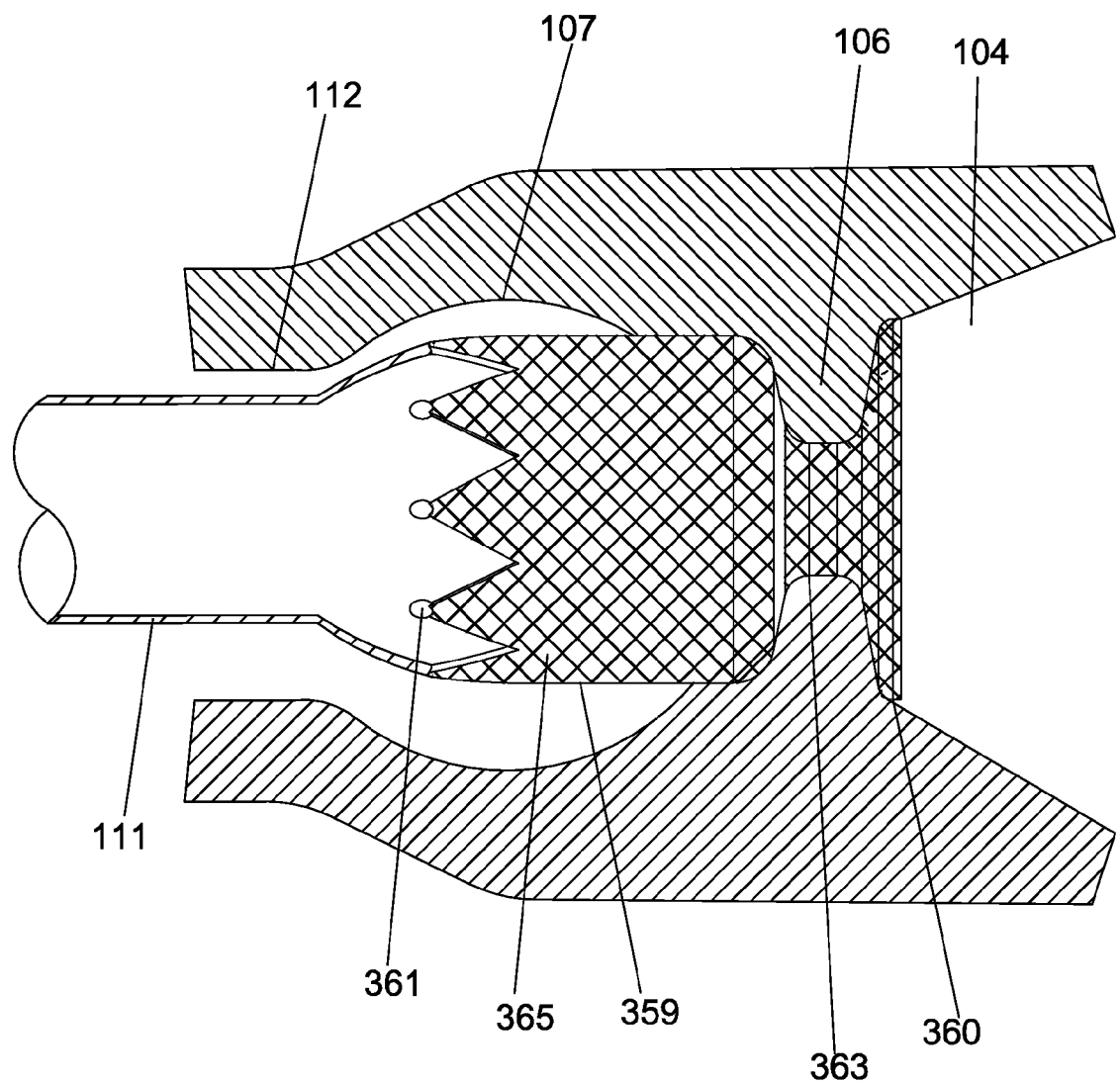
FIG. 47 is a drawing of an alternative embodiment of the invention herein disclosed. The expandable anchor is comprised of hollow tubular braided structure of wire. The wire form has been shaped to conform to the shape of the pylorus and the duodenal bulb. The expandable anchor and the intestinal bypass sleeve have been implanted into a human pylorus and duodenal bulb.

FIG. 47 is a sectional view of the invention herein disclosed in FIG. 46 implanted into the pyloric antrum 104, pylorus 106, duodenal bulb 107 and duodenum 112. An intestinal bypass sleeve 111 is attached to the anchor.

Figure 48:
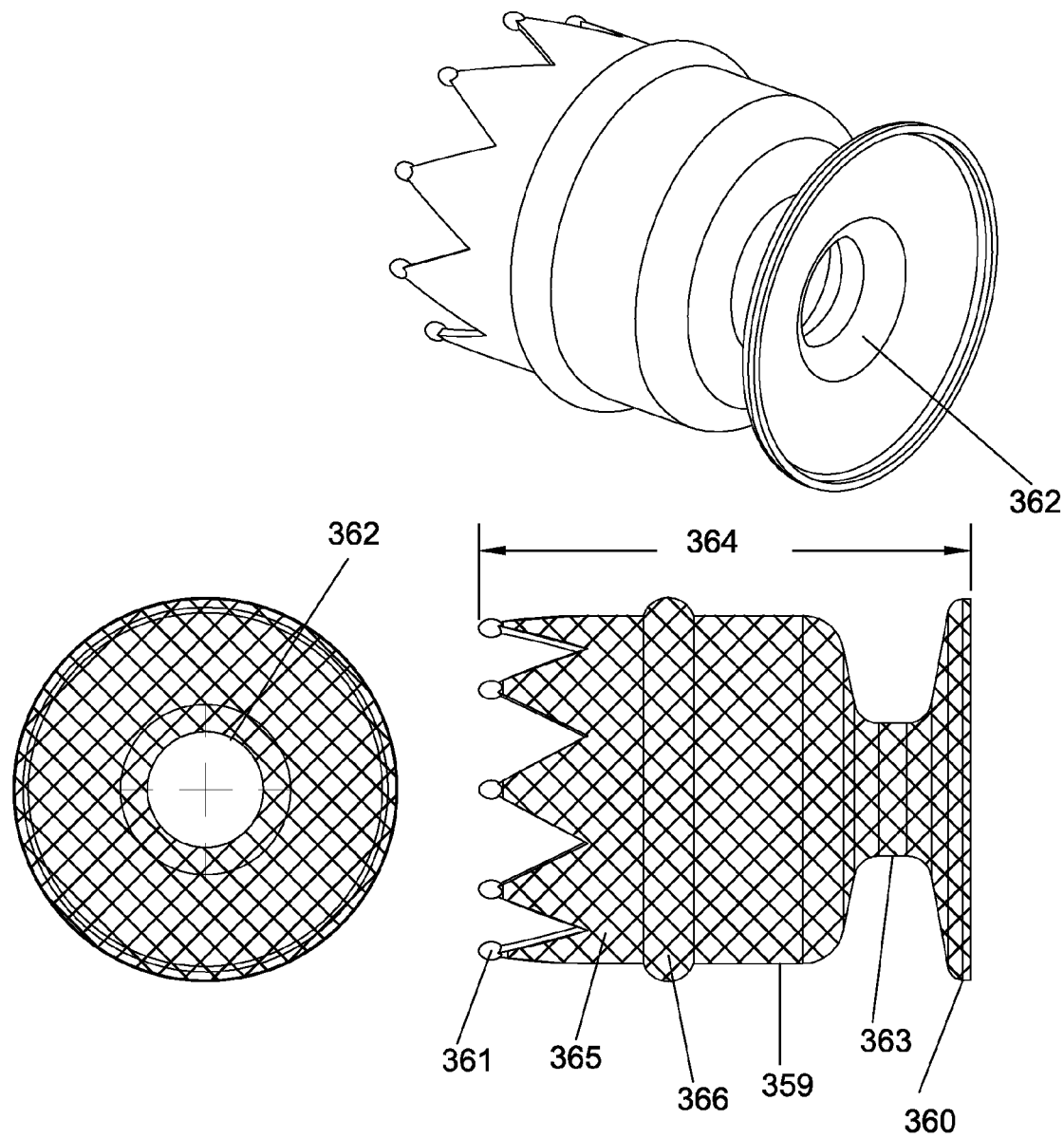
FIG. 48 is a drawing of an alternative embodiment of the invention herein disclosed. The expandable anchor is comprised of a hollow tubular braided structure of wire. The wire form has been shaped to conform to the shape of the pylorus and the duodenal bulb. The expandable anchor has an annular groove formed in wall the duodenal bulb portion of the expandable anchor. The annular groove is sized to provide for a modular connection means between an expandable anchor and intestinal bypass sleeve.
Figure 49:
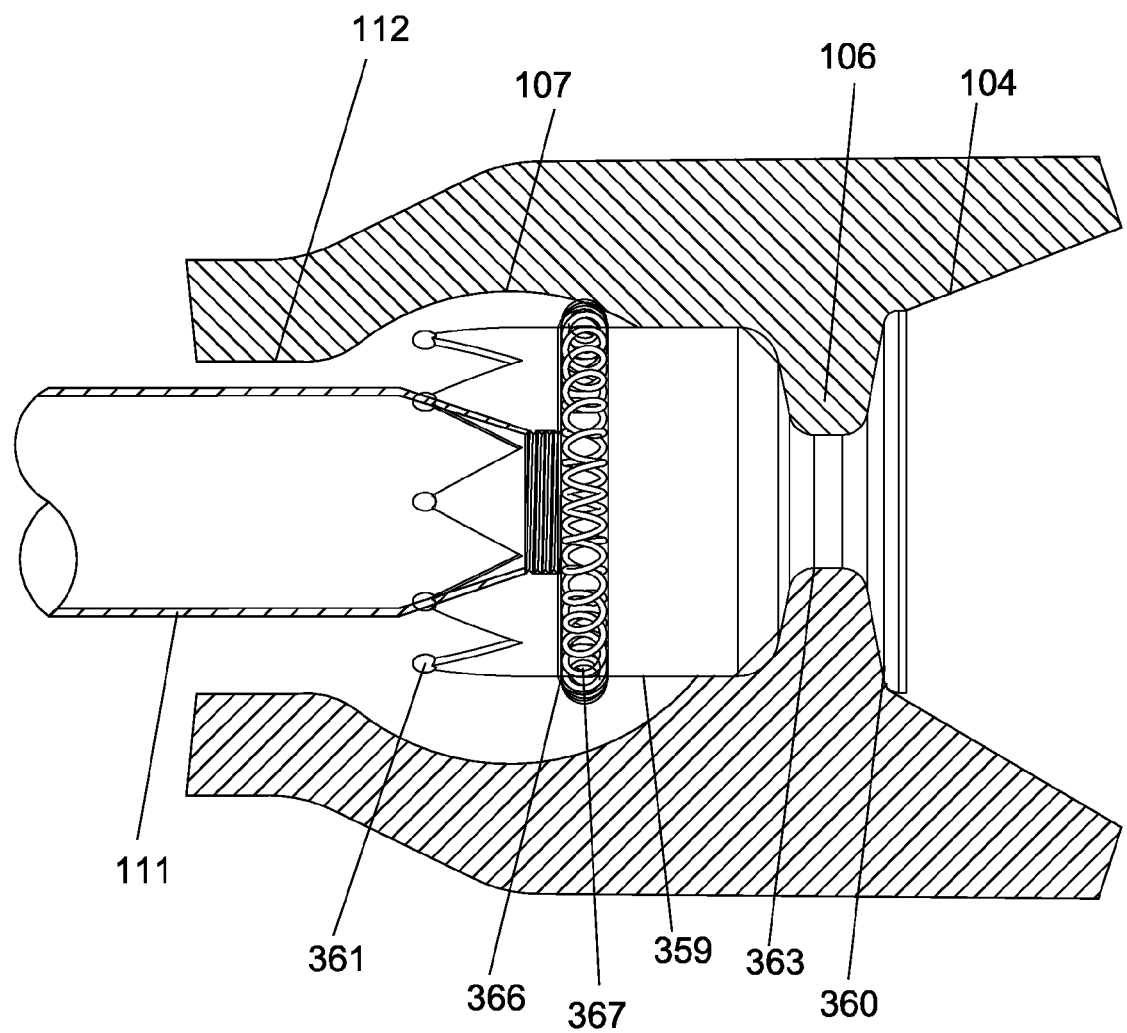
FIG. 49 is a drawing of an alternative embodiment of the invention herein disclosed implanted into a pyloric antrum, pylorus, duodenal bulb, and duodenum. The expandable anchor is comprised of a hollow tubular braided structure of wire. The wire form has been shaped to conform to the shape of the pylorus and the duodenal bulb. The expandable anchor has an annular grove formed in wall the duodenal bulb portion of the expandable anchor. The annular groove is sized to provide for a modular connection means between an expandable anchor and intestinal bypass sleeve. An intestinal bypass sleeve with an expandable anchor attached to the end of the sleeve is attached to the annular groove in the anchor in the pylorus.

FIG. 48 is a drawing of an alternative embodiment of the invention herein disclosed in FIG. 46. The expandable anchor is comprised of a hollow tubular braided structure of wire. The wire form has been shaped to conform to the shape of the pylorus and the duodenal bulb. The expandable anchor has an annular grove 366 formed in the wall of the duodenal bulb portion of the expandable anchor. The annular groove 366 is sized to provide for a modular connection means between an expandable anchor and intestinal bypass sleeve 111. FIG. 49 is a sectional view of the invention herein disclosed in FIG. 48 implanted into the pyloric antrum 104, pylorus 106, duodenal bulb 107 and duodenum 112. An intestinal bypass sleeve 111 is attached to the anchor at annular groove 366 and anchored with a second expandable anchor 367.

Figure 50:
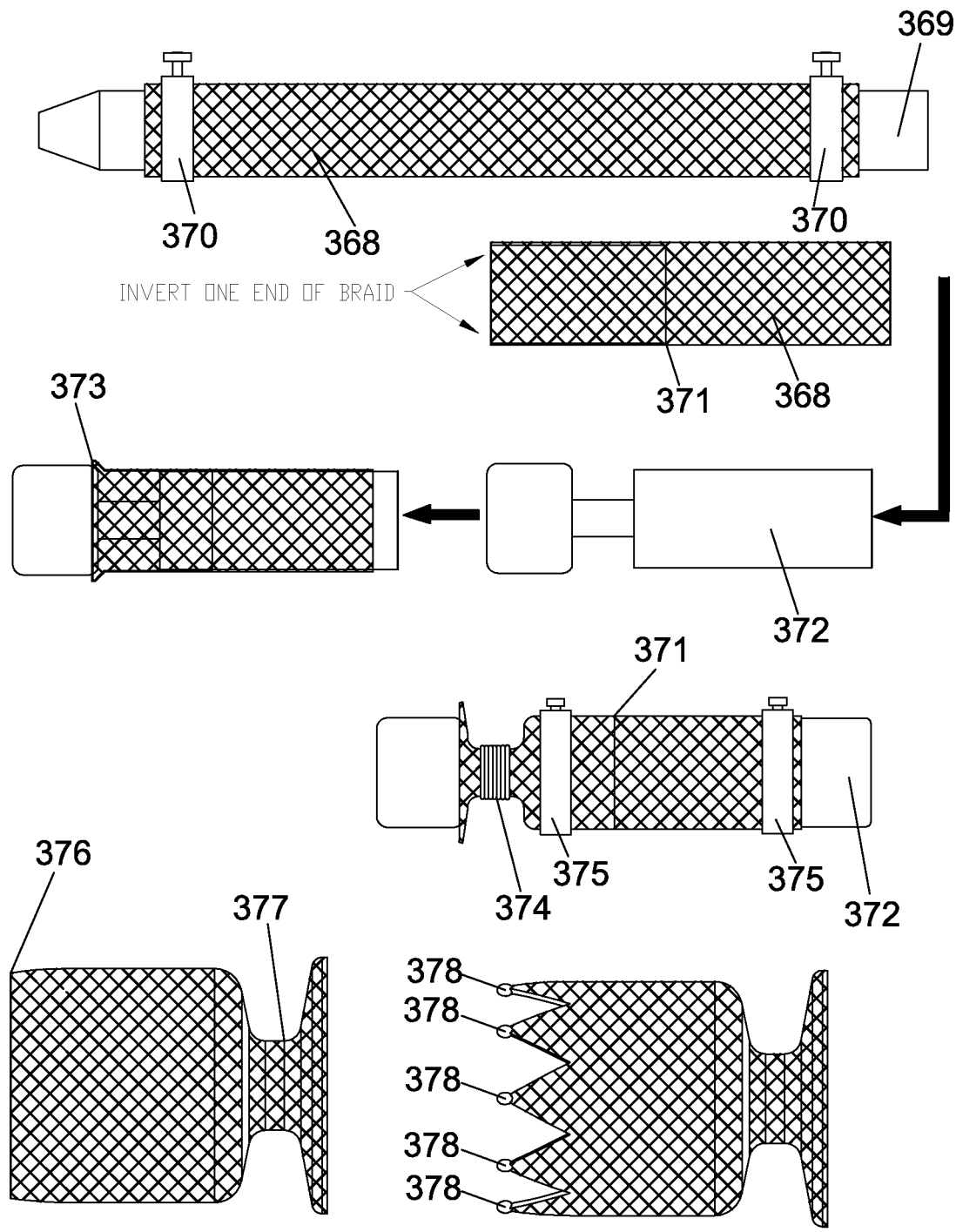
FIG. 50 is a drawing showing the process steps for the manufacturing of the expandable anchor as in FIG. 46, FIG. 47 and FIG. 48.

FIG. 50 is a drawing showing the process steps for the manufacturing of the expandable anchor as in FIG. 46, FIG. 47 and FIG. 48. Braided Nitinol wire tube 368 is placed onto mandrel 369, one clamp 370 is tightened and then the braid is smoothed and longitudinally tightened on the mandrel 369. The second clamp 370 is then tightened to secure braid 368 onto mandrel. Braid 368, secured on mandrel 369 is then heat set in a salt bath for 5 minutes at a temperature of 500 degrees centigrade. The mandrel and braid is then removed from the salt bath and rapidly cooled by immersing braid and mandrel into a room temperature water bath. Clamps 370 are then removed from the braid 368 and mandrel 369 and the braid 368 is removed from the mandrel. One end of heat set braid 368 is then inverted through the lumen of 368 to point 371 to form a layer of double braid from the left end to point 371. Braid is then placed onto mandrel 372 and the left end of braid 372 is lined up to point 373. End of overlapped braid is located at 371. Braid is then secured to the mandrel 372 at location 374 by a wire clamp and at locations 375 by two additional clamps. A secondary heat set is then performed on mandrel 372 and braid in a salt bath for 5 minutes at a temperature of 500 degrees centigrade. The mandrel and braid is then removed from the salt bath and rapidly cooled by immersing braid and mandrel into a room temperature water bath. Clamps 374, 375 are then removed from the braid and the braid is removed from the mandrel 372. The braid now has permanently taken on the shape of the mandrel 372 and has the narrow central cylinder 377 shape. The braid length is trimmed at 376. All the ends of wires in the braid from both layers are at the end of braid at location 376. Wire ends are gathered and secured at location 378

Figure 51:
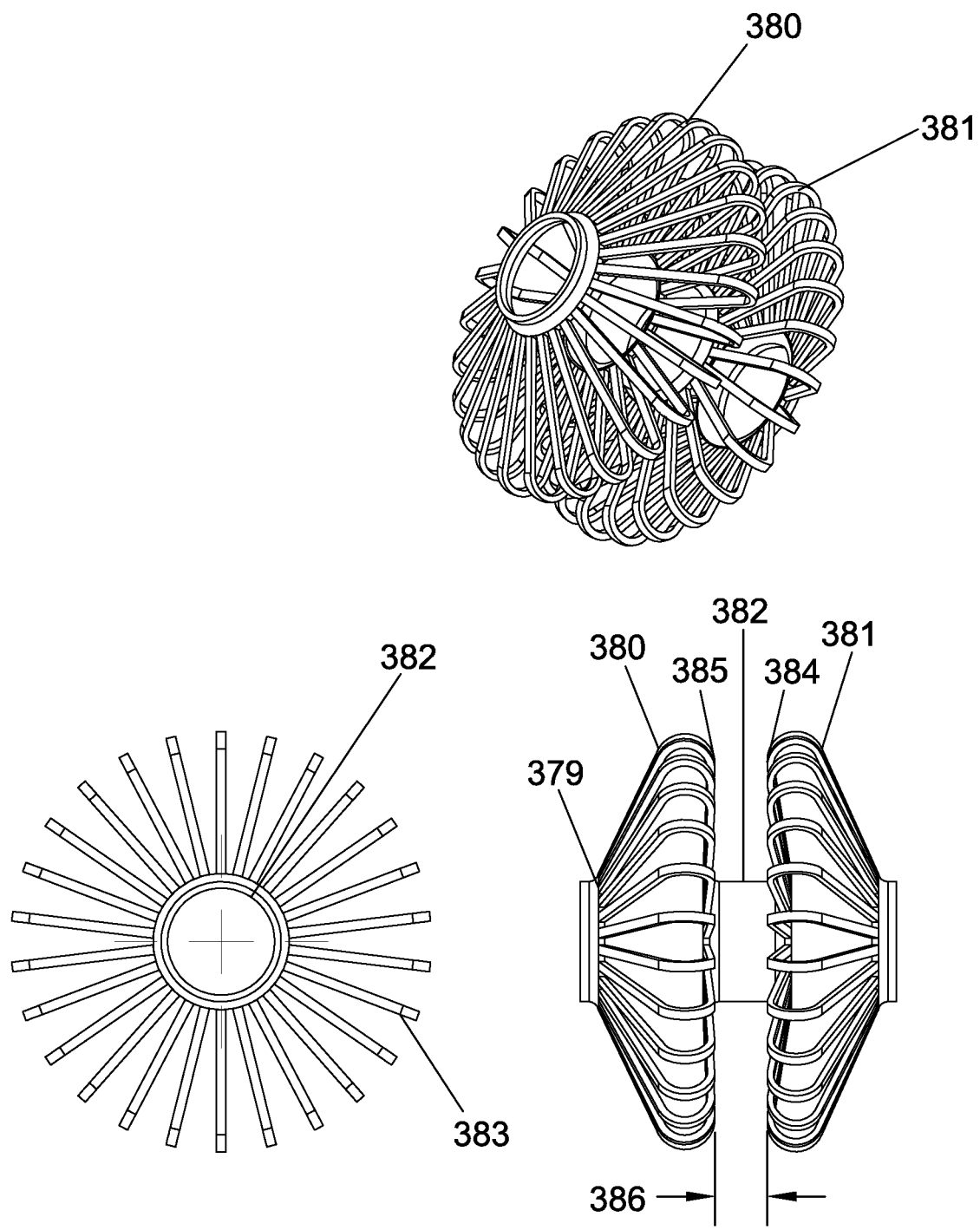
FIG. 51 is drawing of an alternative embodiment of the expandable anchor herein disclosed.
Figure 52A:
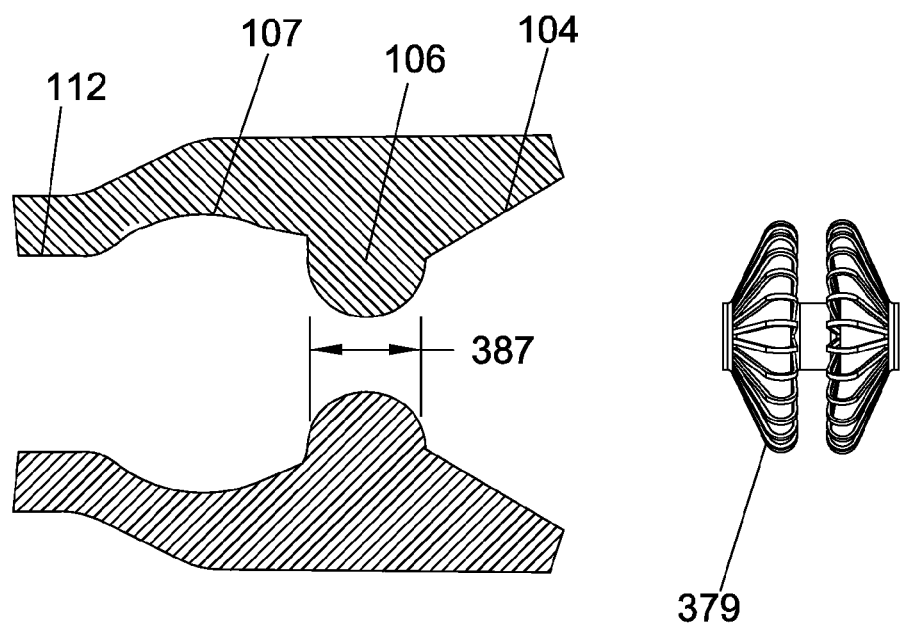
FIG. 52A is a drawing of a pyloric antrum, pylorus, duodenal bulb and duodenum and of the expandable anchor of FIG. 52.
Figure 52B:
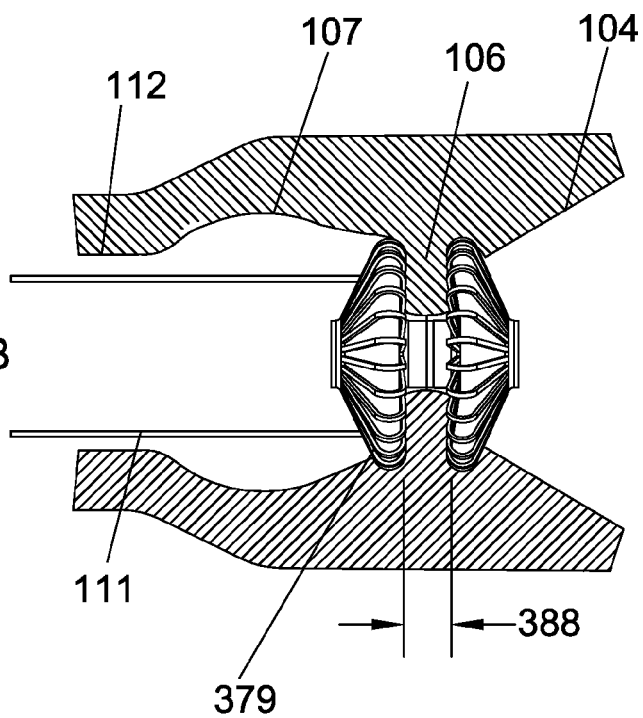
FIG. 52B is a drawing of a pylorus and of the expandable anchor of FIG. 52 implanted into it.

FIG. 51 is a drawing of an alternative embodiment of an expandable anchor 379. Expandable anchor 379 is comprised of a proximal expandable disk 381, a distal expandable disk 380, a central cylinder 382 and spring arms 383. The function and materials are similar to the anchor disclosed in FIG. 18. Spring arms 384 and 385 are formed inwards to form to concave shaped disk surfaces toward the central cylinder 382. Gap 386 between disks 380 and 381 can be elastically opened and closed by bending spring arms 384 and 385. FIG. 52A is a drawing of a pyloric antrum 104, pylorus 106, duodenal bulb 107 and duodenum 112 and of the expandable anchor 379 of FIG. 52. The pylorus width is shown by reference 387. FIG. 52B is a drawing of a pyloric antrum 104, pylorus 106, duodenal bulb 107 and duodenum 112 and of the expandable anchor 379 of FIG. 52 implanted into it. The pyloric width 387 is greater than anchor width or gap 386. The pyloric width 387 has been reduced to a narrower width 388 due to clamping action of the anchor 379.

Figure 53:
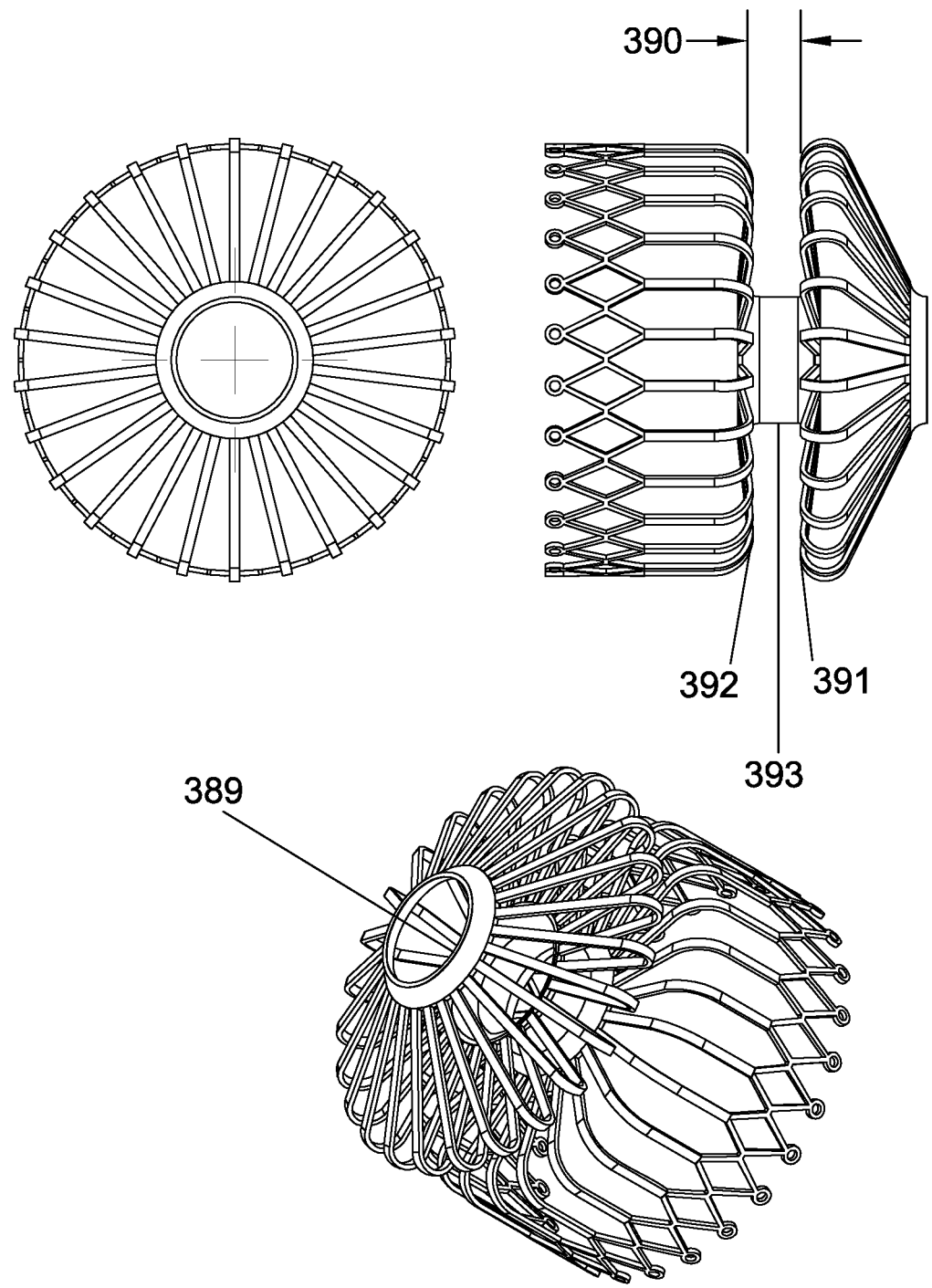
FIG. 53 is drawing of an alternative embodiment of the expandable anchor herein disclosed.

FIG. 53 is a drawing of an alternative embodiment of an expandable anchor 389. The function and materials are similar to the anchor disclosed in FIG. 6. Spring arms 392 and 391 are formed inwards to form to concave shaped disk surfaces toward the central cylinder 393. Gap 390 between arms 392 and 391 can be elastically opened and closed by bending spring arms 392 and 391. Expandable anchor 389 can clamp on the pylorus in a similar manner as disclosed in FIG. 52b.

Figure 54:
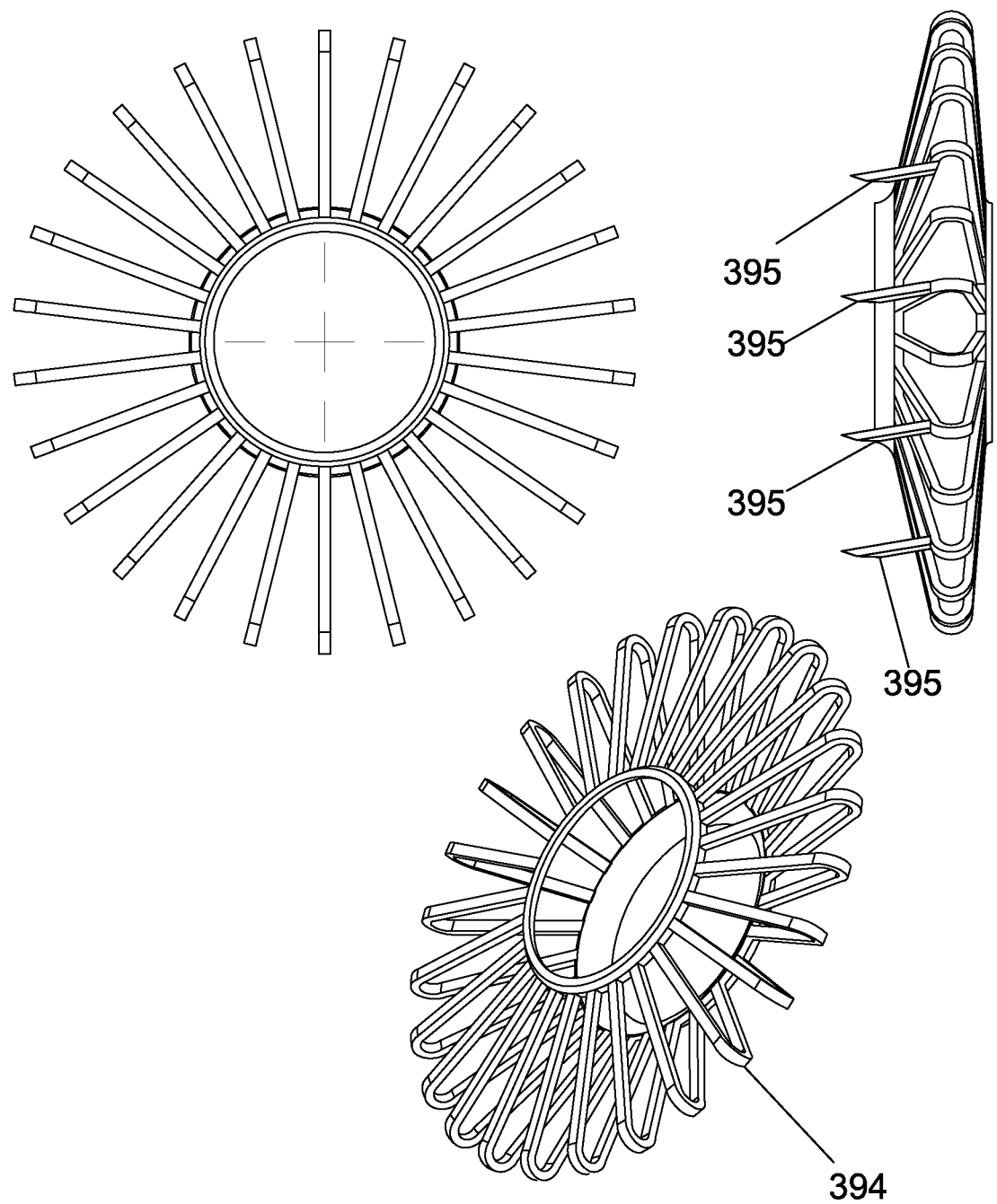
FIG. 54 is a drawing of an alternative embodiment of an expandable anchor that has optional barbs to provide for an additional securing means to the pylorus.
Figure 55:
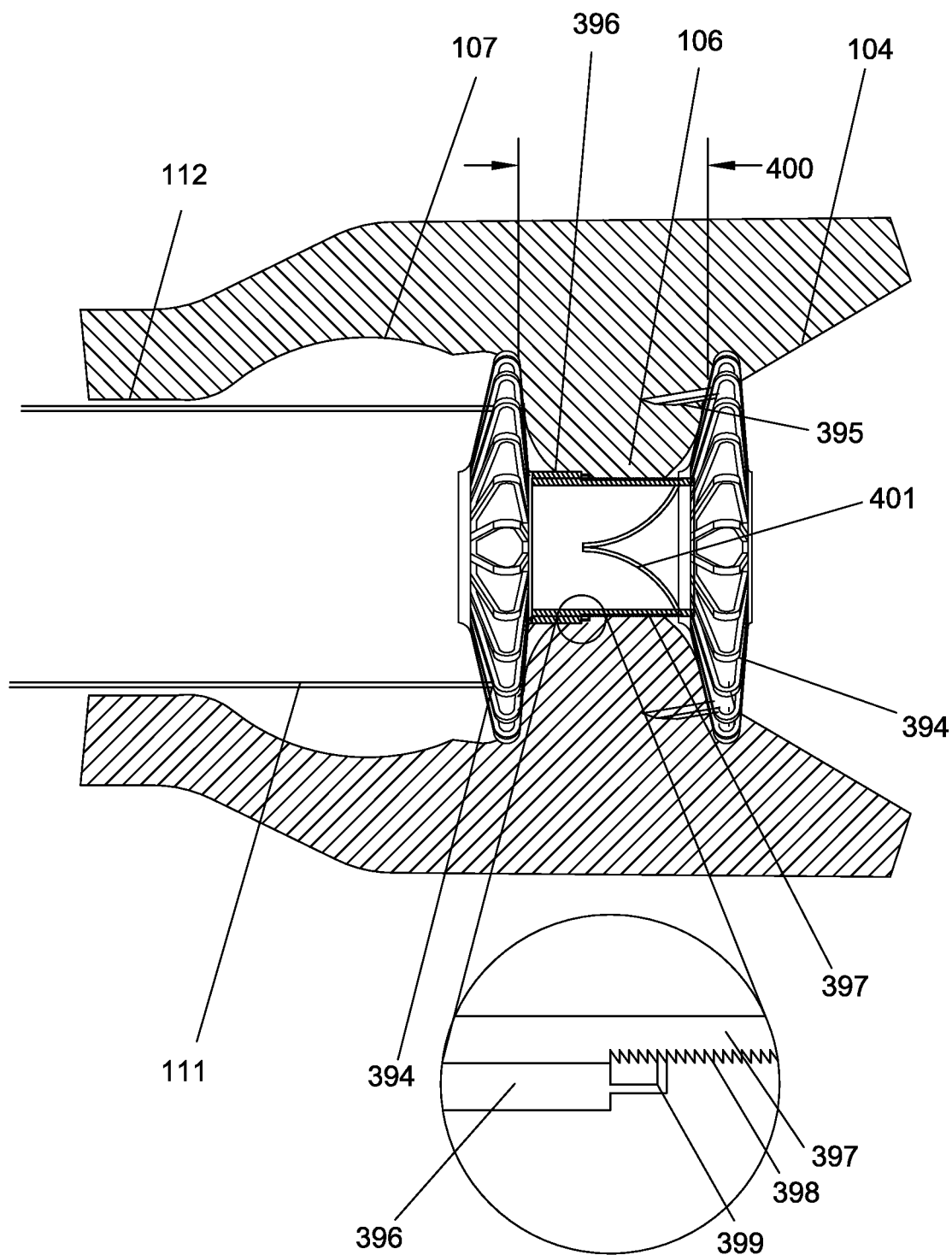
FIG. 55 is a sectional view of the invention herein disclosed implanted into the pyloric antrum, pylorus and duodenal bulb and duodenum. The anchoring device is comprised of two disk-shaped expandable anchors that are connected to a central cylinder. The diameter of the central cylinder is fixed, but it may also be designed to allow it to be reduced in diameter during loading of the device onto a catheter. The length of the central cylinder is adjusted to allow the spacing between the two disks to be variable in spacing.

FIG. 54 is a drawing of an alternative embodiment of a single disk of expandable anchor 394 that has optional barbs 395 to provide for an additional securing means to the pylorus. FIG. 55 is a sectional view of the invention herein disclosed implanted into the pyloric antrum 104, pylorus 106, duodenal bulb 107 and duodenum 112. The anchoring device is comprised of two disk-shaped expandable anchors 394 that are connected to a central cylinder 396 and 397. The central cylinder of the device 396 and 397 in between the two anchor rings 394 can be made from plastic material such as Delrin, peek, high density polyethylene, polycarbonate or other suitable polymer. The central cylinder portion 396, 397 may also be made from stainless steel, titanium or Nitinol. The fixed diameter of the pyloric portion pieces 396 and 397 of the device can be sized to provide for a full opening of the pylorus and not allow the pylorus to close normally. The length of the pyloric portion of the device 400 can be adjusted by sliding the outer cylinder 396 over inner cylinder 397 by sliding on the ratcheting mechanism. This will change the spacing between the anchor rings 394 and will allow the device to be adjusted for ring spacing in-situ. It may be desirable to change the ring spacing to accommodate differences in the pylorus 106 dimensions from patient to patient. It may also be desirable to change the length 400 of the central cylinder portion to allow the anchor ring 394 spacing to be adjusted to allow the expandable anchor to put a clamping force on to the pylorus in a longitudinal direction. The mechanism used for 398 and 399 could also be a screw thread arrangement such as a male thread on 398 and a female thread on 399. In various embodiments, the inside diameter of the central cylinder 396 and 397 ranges from as small as 2 mm in diameter up to as large as 14 mm in diameter. The central lumen of device has a one-way anti-reflux valve 401. The anti-reflux valve 401 allows for unobstructed flow in the direction of the stomach antrum 104 to the duodenal bulb 107, but limits flow in the reverse direction. The anti-reflux valve 401 can be constructed of a duck bill design with two flexible leaflets, or may utilize other designs such as a tri-leaflet valve or quad-leaflet valve. The anti reflux valve may be constructed of silicone, polyurethane, polyethylene, ePTFE or other suitable polymer. The diameter of the central cylinder is fixed, but it may also be designed to allow it to be reduced in diameter during loading of the device onto a catheter.

Figure 56:
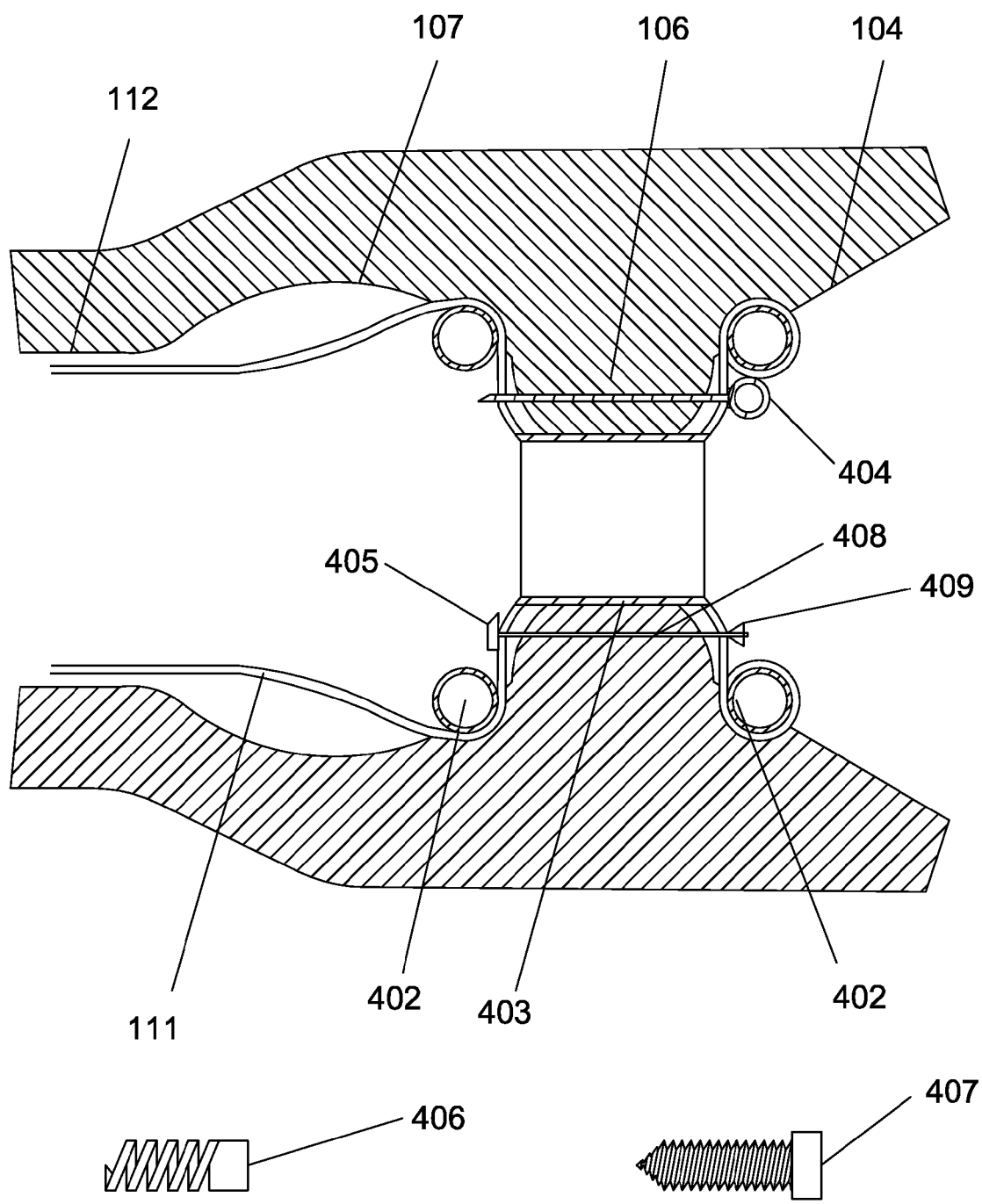
FIG. 56 is a sectional view of the invention herein disclosed implanted into the pyloric antrum, pylorus and duodenal bulb and duodenum. The anchoring device is comprised of two toroidal-shaped expandable anchors that are connected to a central cylinder. The diameter of the central cylinder is fixed, but it may also be elastic to allow it to be reduced in diameter during loading of the device onto a catheter. An optional needle, suture, T-bar, hollow helical anchor or screw type anchor is inserted into and or through the tissue of the pylorus, pyloric antrum or duodenum to provide additional anchoring and securement of the intestinal bypass sleeve anchoring device to the pylorus anatomy. Additional anchoring means may include a T-Bar and suture.

FIG. 56 is a sectional view of the invention herein disclosed implanted into the pyloric antrum 104, pylorus 106 and duodenal bulb 107 and duodenum 112. The anchoring device is comprised of two toroidal-shaped expandable anchors 402 that are connected to a central cylinder 403. The diameter of the central cylinder 403 is fixed, but it may also be elastic to allow it to be reduced in diameter during loading of the device onto a catheter. An optional needle 404, suture, T-bar 405, hollow helical anchor 406 or screw type anchor 407 is inserted into and/or through the tissue of the pylorus 106, pyloric antrum 104 or duodenum 107 to provide additional anchoring and securement of the intestinal bypass sleeve 111 anchoring device to the pylorus anatomy 106. The T-Bar 405 is anchored by a tensioning member 408 and cincher 409.

Figure 57:
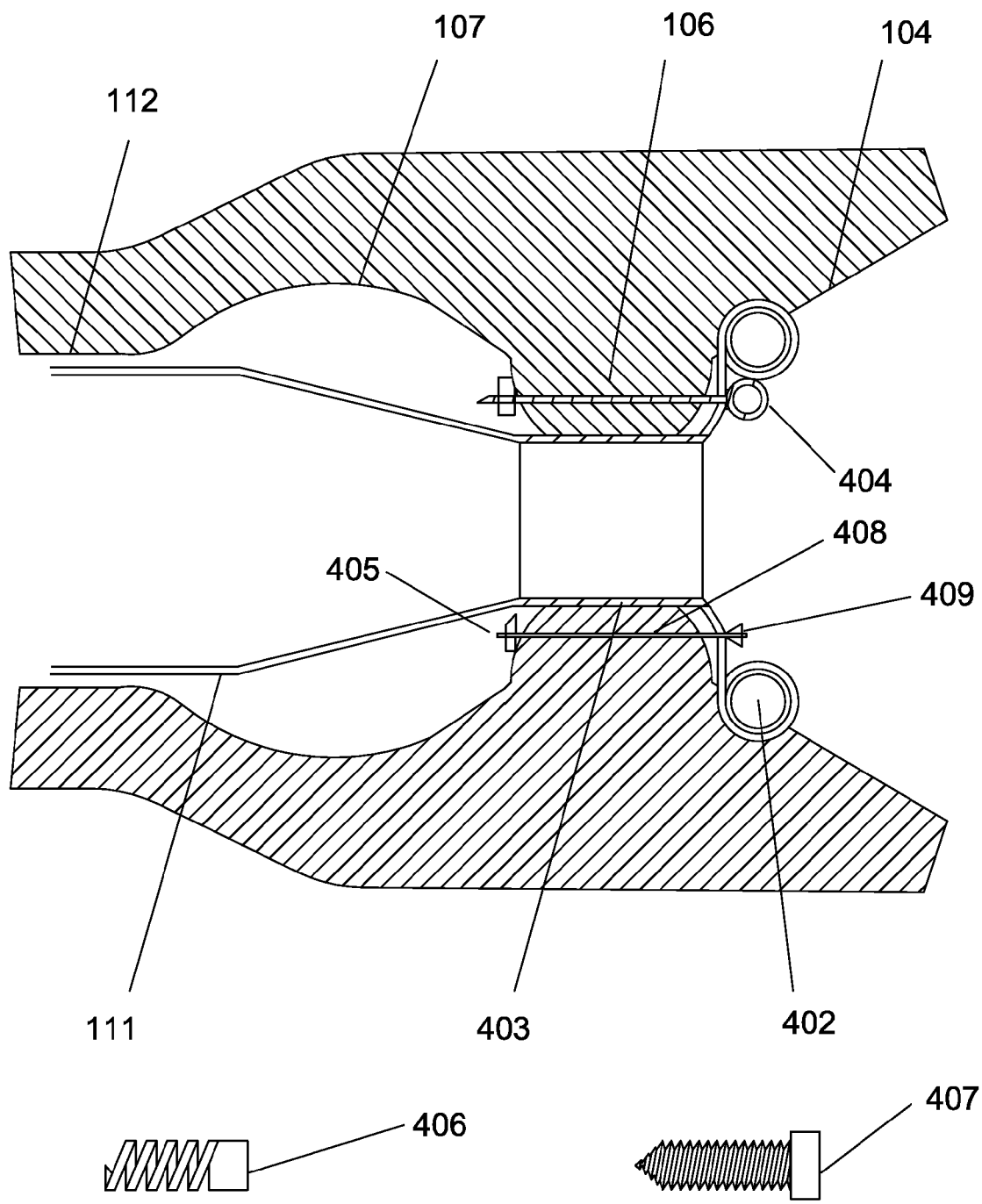
FIG. 57 is a sectional view of the invention herein disclosed implanted into a pylorus, duodenal bulb and duodenum. An expandable ring is sized large enough in diameter to engage the wall of the stomach pyloric antrum. The central portion of the device is constructed of a ridged fixed diameter cylinder, or alternatively a compressible cylinder or a thin-walled sleeve. An optional needle, suture, T-bar, hollow helical anchor or screw-type anchor is inserted into and or through the tissue of the pylorus, pyloric antrum or duodenum to provide additional anchoring and securement of the intestinal bypass sleeve anchoring device to pylorus anatomy or other suitable location.

FIG. 57 is a sectional view of the invention herein disclosed implanted into the pyloric antrum 104, pylorus 106, duodenal bulb 107 and duodenum 112. An expandable ring 402 is sized large enough in diameter to engage the wall of the pyloric antrum 104. The central portion of the device is constructed of a ridged fixed diameter central cylinder 403, or alternatively a compressible cylinder or a thin-walled sleeve. An optional needle 404, suture, T-bar, hollow helical anchor 406 or screw type anchor 407 is inserted into and or through the tissue of the pylorus 106, pyloric antrum 104 or duodenum 112 to provide additional anchoring and securement of the intestinal bypass sleeve 111 and anchoring device to pylorus anatomy 106 or other suitable location. The T-Bar 405 is anchored by a tensioning member 408 and cincher 409.

Figure 58:
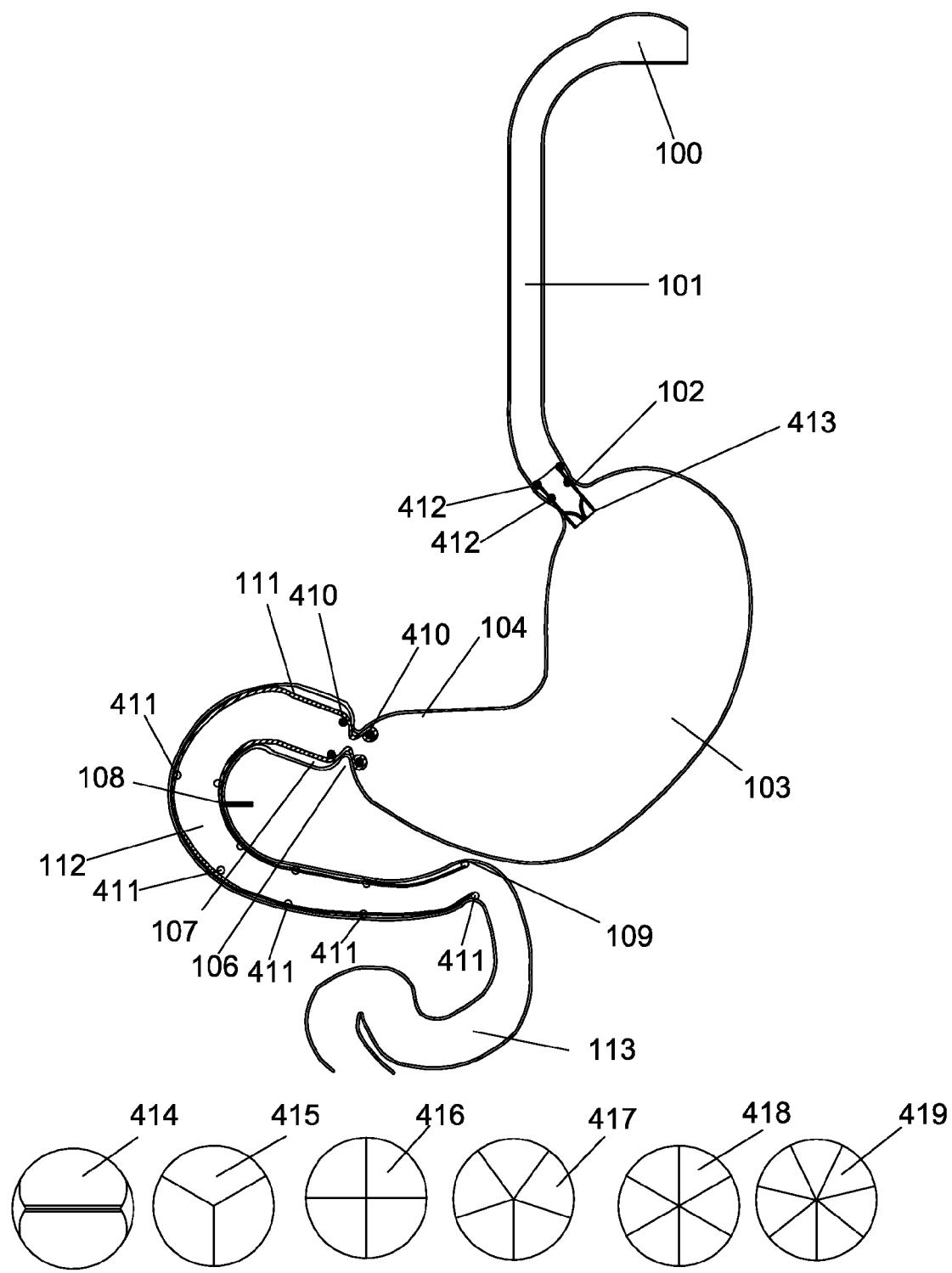
FIG. 58 is a cross-sectional view of a portion of the digestive tract in a human body. An intestinal bypass sleeve is implanted in the duodenum from the pylorus to the ligament of treitz. The sleeve is held in place at the pylorus by an expandable anchor that anchors on the pylorus optional secondary expandable anchors anchor the sleeve at additional locations in the duodenum and jejunum. An expandable anchor with an anti-reflux valve is implanted at the gastroesophageal (GE) junction to help resolve gastroesophageal reflux disease (GERD).

FIG. 58 is a cross-sectional view of a portion of the digestive tract in a human body. An intestinal bypass sleeve 111 is implanted in the duodenum 112 from the pylorus 106 to the ligament of treitz 109. The sleeve is held in place at the pylorus 106 by expandable anchors 410 that anchor on the pylorus 106 optional secondary expandable anchors 411 anchor the intestinal bypass sleeve 111 at additional locations in the duodenum 112 and jejunum 113. An expandable anchor 412 with an anti-reflux valve is implanted at the gastro esophageal (GE) junction 102 to help resolve gastroesophageal reflux disease (GERD). Reference numbers 414, 415, 416, 417, 418 and 419 denote valve designs that have from two to seven flaps in the valve and may be used for the anti-reflux device 413.

Figure 59A:
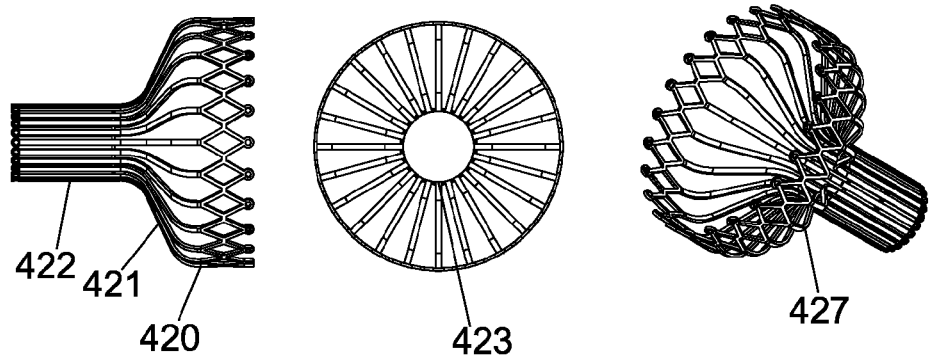
FIG. 59A is a drawing of an alternative embodiment of an expandable anchor.
Figure 59B:
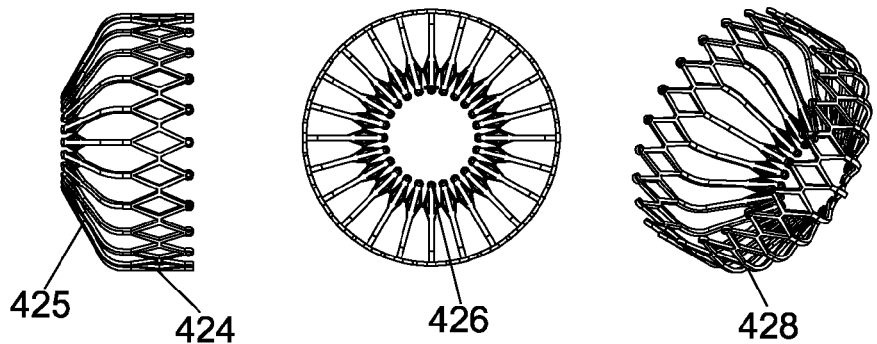
FIG. 59B is a drawing of an alternative embodiment of an expandable anchor.
Figure 59C:
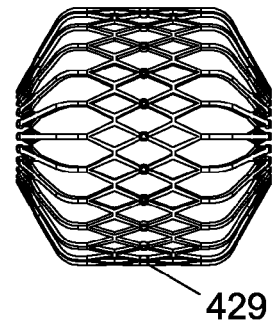
FIG. 59C is a drawing of an alternative embodiment of an expandable anchor.
Figure 60:
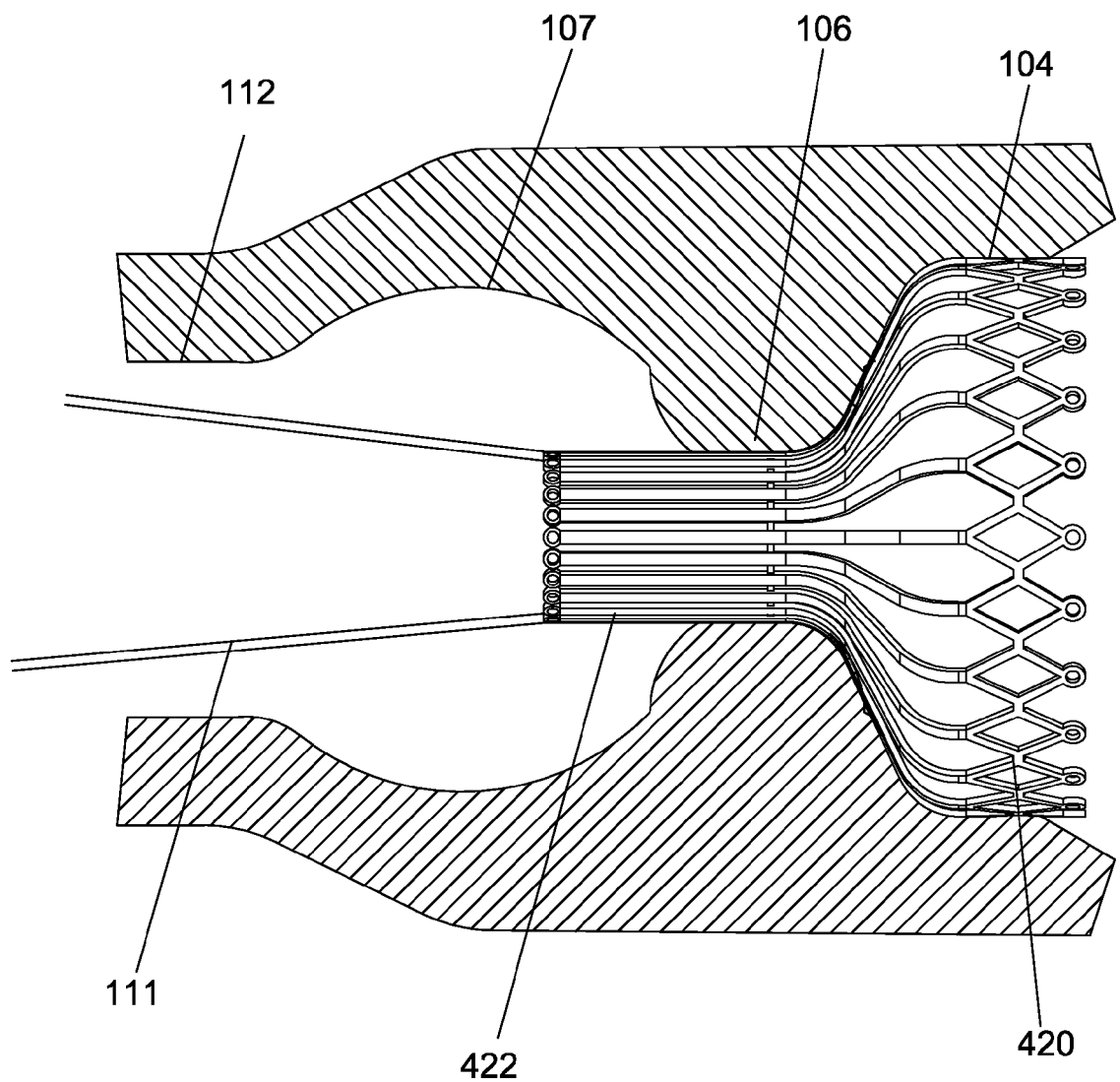
FIG. 60 is a drawing of FIG. 59A implanted into a pylorus. Alternatively FIG. 59A, FIG. 59B and FIG. 59C could also be implanted into the pyloric antrum, duodenal bulb or duodenum or GE junction.

FIG. 59A is a drawing of an alternative embodiment of an expandable anchor. Expandable anchor has a cylindrical portion 420, spring arms 421, a central cylinder portion 422, through lumen 423 and an isometric view of the expandable anchor 427. Expandable anchor is laser cut from Nitinol tubing and heat set to final shape on a mandrel with processing steps as previously disclosed in this application. Large diameter cylindrical portion 420 has a diameter in the range from 10 to 70 mm. FIG. 59B is a drawing of an alternative embodiment of an expandable anchor. Expandable anchor has a cylindrical portion 424, spring arms 425, through lumen 426 and an isometric view of the expandable anchor 428. Expandable anchor is laser cut from Nitinol tubing and heat set to final shape on a mandrel with processing steps as previously disclosed in this application. Large diameter cylindrical portion 424, according to various embodiments, has a diameter in the range from 10 to 70 mm. FIG. 59C is a drawing of an alternative embodiment of an expandable anchor. Expandable anchor 429 is a double-sided version of anchor as in FIG. 59C. FIG. 60 is a drawing of FIG. 59A and an intestinal bypass sleeve 111 implanted into a pyloric antrum 104, pylorus 106 duodenal bulb 107 and duodenum 112. Alternatively, FIG. 59B and FIG. 59C could also be implanted into the pyloric antrum 104, duodenal bulb 107, duodenum 112 or GE junction 102.

FIG. 61A is a drawing of an intestinal bypass sleeve with a diameter transition from a larger diameter to a smaller diameter. Intestinal bypass sleeve is comprised of three sections: a first tube 430, a second tube 432, and a transitional piece 431. Intestinal bypass sleeve is made from a polymer material such as ePTFE, PTFE, FEP, polyurethane, silicone, polyethylene, cross-linked polyethylene, high density polyethylene, polypropylene or other suitable material. The intestinal bypass sleeve may be dip coated in one-piece with all three components 430, 431, and 432 made into a seamless one-piece unitary structure. Alternatively 430, 431 and 432 can be made as separate components and they can be joined by adhesive bonding (such as with silicone adhesive) or FEP hot melt adhesive, or they can be sewn together at seams 434, 435, 436 using suture such polyester, Nylon, polypropylene, PTFE or ePTFE. Intestinal bypass sleeve may range in diameter from 3 to 80 mm. Intestinal bypass sleeve may have a wall thickness in the range of 0.001 inch to 0.060 inch thick.

Intestinal bypass sleeve may be made porous or nonporous. Sleeve may have surface coatings to close up pores of porous membrane. Such as a surface coating of silicone, polyurethane, FEP applied to porous substrate to render it non-permeable. ePTFE is inherently hydrophobic and has some resistance to water penetration, but it may be desirable to have a higher water entry pressure or make ePTFE impermeable. Intestinal bypass sleeve may have a lubricious (or sticky) hydrophilic coating or a hydrogel added to the inner or outer surface to reduce the friction of the surface or to make it easier for food to pass through the liner or to decrease the outer surface coefficient of friction or make the sleeve stay in place better in the intestines. Intestinal bypass sleeve or expandable anchor may be used for drug delivery, delivery of peptides or other therapeutics by incorporating a drug or peptide into the polymer wall thickness of the intestinal bypass sleeve. The drug or peptide may be added directly to the surface of the intestinal liner without a polymer or covalently bonded to the polymer surface.

The drug or peptide may be eluted from a surface coating on the sleeve or anchor which incorporates the drug into the coating. Polymers that may be used as a coating to elute a drug include silicone, polyurethane, Polyvinyl Alcohol, Ethylene vinyl acetate, Styrene acrylonitrile, Styrene-Butadiene, Pebax or other suitable polymer. Absorbable polymers that may be used for drug delivery include, Polyglycolic acid (PGA), Polylactide (PLA), Poly(ε-caprolactone), Poly(dioxanone) Poly(lactide-co-glycolide) or other suitable polymer. Other suitable coatings for increased biocompatibility or drug release may include human amnion, collagen Type I, II, III, IV, V, VI—Bovine, porcine, or ovine. The coating on the intestinal bypass sleeve can also take the form of a liquid that can be used to release the drug or peptide include, Vitamin D, A, C, B, E, olive oil, polyethylene glycol, vegetable oils, essential fatty acids, alpha-linolenic acid, lauric acid, linoleic acid, gamma-linolenic acid, palmitoleic acid or other suitable liquids. The drug may serve to increase satiety, to interrupt the secretion of secondary hormones or digestive enzymes, release antibacterial agents to reduce infection, to increase the fibrotic reaction of the intestinal tract, to decrease the fibrotic reaction of the intestinal tract, to target changes in the cellular composition such as decreasing the number of receptor cells in the duodenum.

Intestinal bypass sleeve can release cholecystokinin, gastrin, secretin, gastric inhibitory peptide, motilin, glucagon like peptide 1, bile, insulin, pancreatic enzymes, ghrelin, penicillin, amoxicillin, ampicillin, carbenicillin, cloxacillin, dicloxacillin, nafcillin, oxacillin, penicillin g, penicillin V, Piperacillin, Ticarcillin Aminoglycosides, Amikacin, Gentamicin, Kanamycin, Neomycin, NEO-RX, Netilmicin, Streptomycin, Tobramycin, Carbapenems, Ertapenem, Doripenem, DORIBAX, Emipenem-cilastatin, Meropenem, Cefadroxil, Cefazolin, Cephalexin rapymicin, taxol, vitamin A, vitamin C, vitamin D, vitamin B, vitamin E, fatty acids, oils, vegetable oils, aspirin, somastatin, motilin, trypsinogen, chymotrypsinogen, elastase, carboxypeptidase, pancreatic lipase, amylase, enteroglucagon, gastric inhibitory polypeptide, Vasoactive intestinal peptide, PYY, Peptide Tyrosine Tyrosine, Leptin, Pancreatic polypeptide.

FIG. 61B is a drawing of an alternative embodiment of an intestinal bypass sleeve. First tube 437 a V-shaped notch 438 is cut into the top and bottom surfaces of tube. V-shaped notch 438 is closed by sewing or adhesive bonding to reduce the tube diameter 439. Intestinal bypass sleeve is made from ePTFE tubing or other polymers as previously disclosed in FIG. 61A.

Figure 62A:
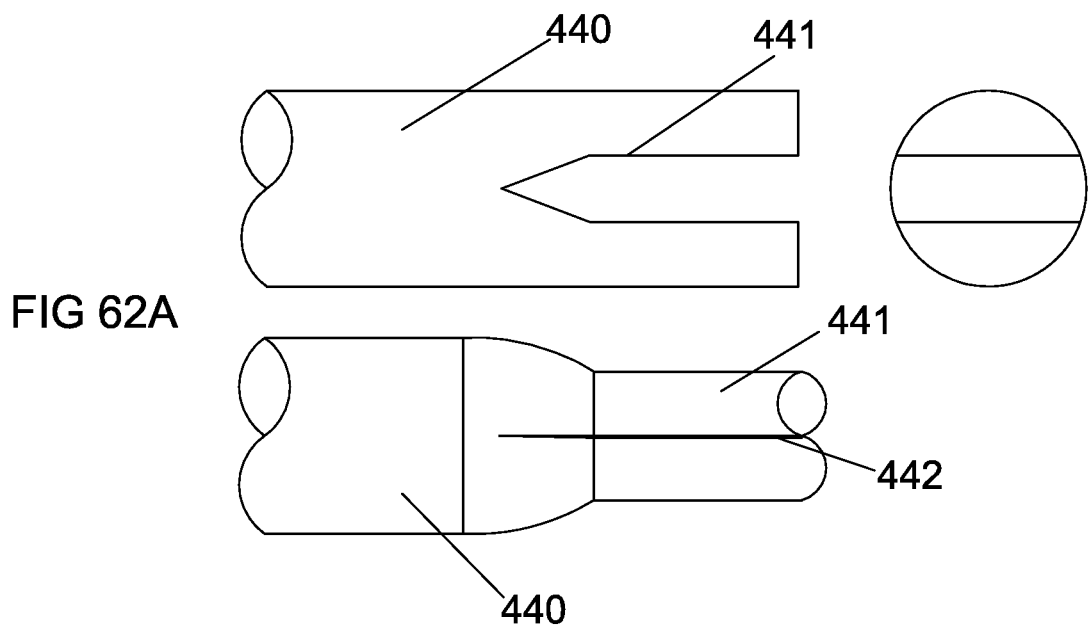
FIG. 62A is a drawing of an alternative embodiment of an intestinal bypass sleeve.
Figure 62B:
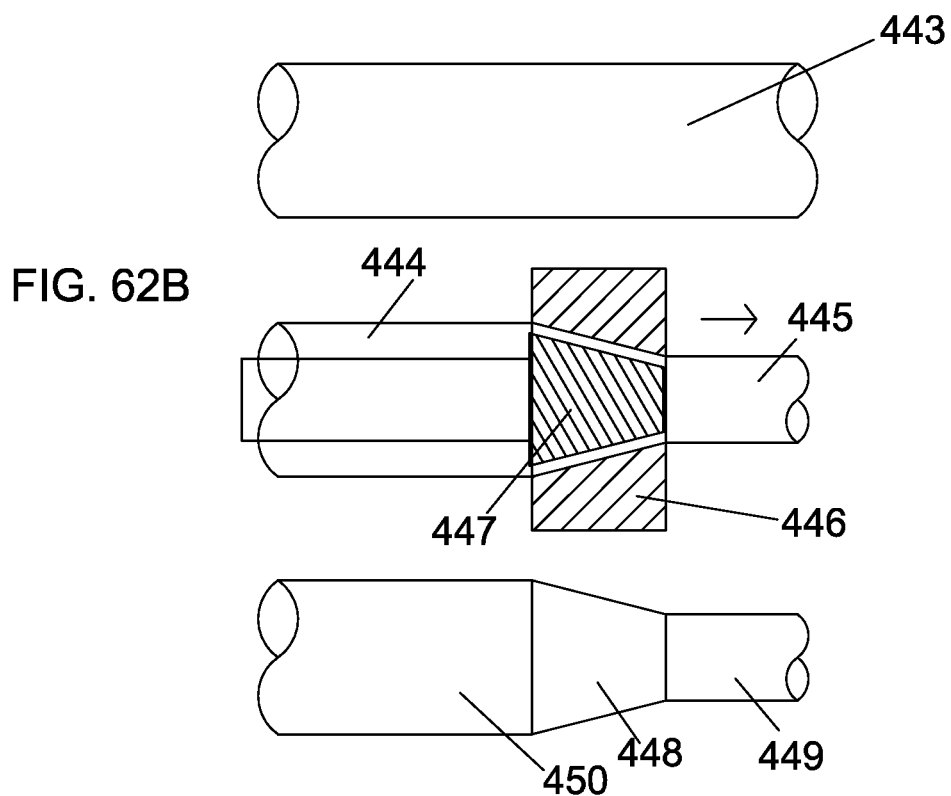
FIG. 62B is a drawing of an alternative embodiment of an intestinal bypass sleeve.

FIG. 62A is a drawing of an alternative embodiment of an intestinal bypass sleeve. Intestinal bypass sleeve starts out as a round tube 440. Slot 441 is cut into sleeve 440 at the top and bottom surfaces. Slot in sleeve 441 is closed by sewing or adhesive bonding at seam 442. Final tube is an open end tube with a diameter change from the original larger diameter in 440 to the smaller diameter at 441. FIG. 62B is a drawing of an alternative embodiment of an intestinal bypass sleeve. Intestinal bypass sleeve starts out as a round tube 443 of ePTFE. Tube diameter is reduced from 444 to 445 by drawing (pulling) the tube 444 through a reducing die 446. An optional floating plug 447 can be placed inside of tube during diameter reduction. The final tube is seamless and has a large diameter section 450, a tapered section 448, and small diameter section 449.

FIG. 63A is a drawing of an alternative embodiment of an intestinal bypass sleeve. Intestinal bypass sleeve starts out as a round tube 451 of ePTFE. Tube diameter is increased from 451 to 454 by pulling the tube 451 over a mandrel 452. Tube 451 moves in direction 453 while mandrel 452 is stationery. The final tube is seamless and has a large diameter section 454, a tapered section 455, and small diameter section 456. An optional final tube configuration has a large diameter section 457 and a tapered section 458. FIG. 63B is a drawing of an alternative embodiment of an intestinal bypass sleeve. Intestinal bypass sleeve is made by rolling up a thin wall sheet of ePTFE around a mandrel and laminating the ePTFE sheet into a tapered tube configuration and sintering or bonding with an adhesive such as FEP. Final tube may have a large diameter section 459 a transition section 460 and a small diameter section 461. Final wall thickness can be formed by 1 to 20 layers 462.

Figure 64A:
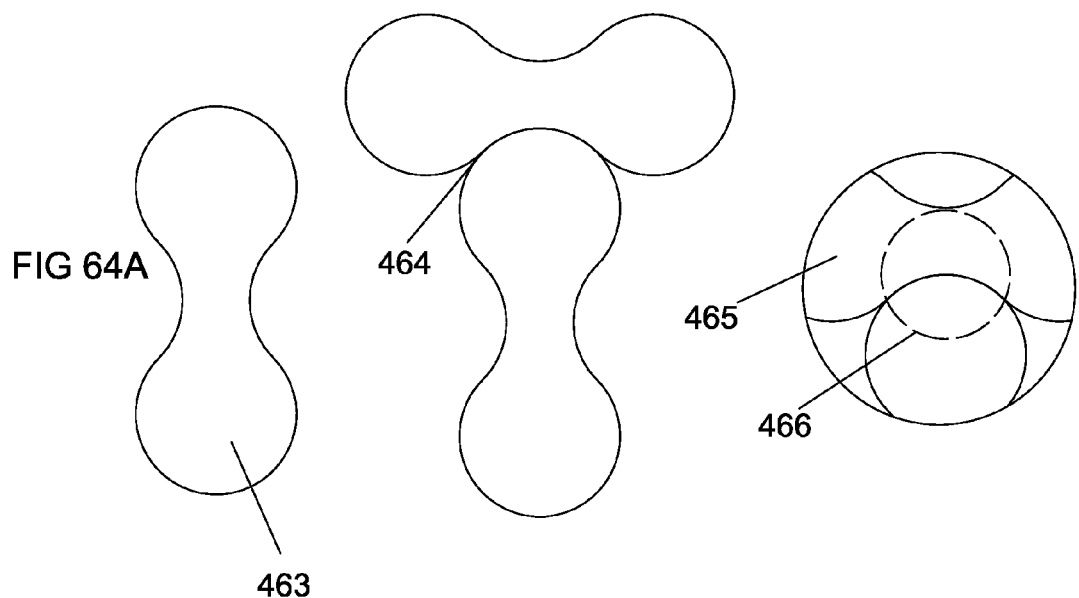
FIG. 64A is drawing of a hemispherical-shaped covering for an expandable anchor that is assembled from a sheet of polymer material into a spherical shape.
Figure 64B:
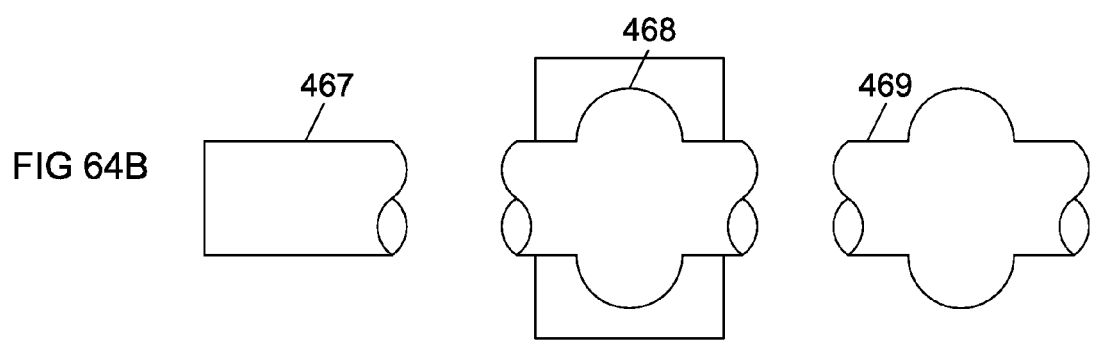
FIG. 64B is a drawing of hemispherical-shaped covering for an expandable anchor that is made by radial stretching a tube perform into a spherical shape by blow-molding or mechanical stretching.
Figure 64C:
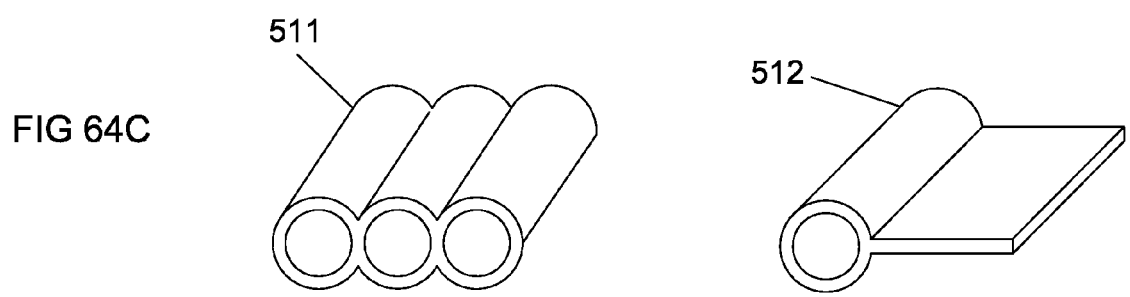

FIG. 64A is drawing of a hemispherical shaped covering for an expandable anchor that is assembled from sheet material into a spherical shape. Figure "8" shape 463 is cut from a sheet of ePTFE sheet. Two shapes of 463 are joined together by sewing or adhesive bonding to produce final spherical shape 465. Spherical shape 465 may have a hole 466 cut through one or both sides to provide for a through hole to allow attachment to an expandable anchor. FIG. 64B is a drawing of hemispherical shaped covering for an expandable anchor that is made by radial stretching a tube preform into a spherical shape by blow-molding or mechanical stretching. Starting shape is a tube of ePTFE 467 is tube 467. Tube 467 is placed into mold 468 and an internal pressure or force is applied to stretch and radially orient the tube 467 to shape of inside of mold 468. Pressure is released from tube 467 and stretched tube is removed from inside of mold 468. Final shape of tube after removing from mold 468 is 469. In FIG. 64C, reference number 511 is a drawing of a multi-lumen tubing that can be used for an expandable anchor to hold parallel toroidal springs as shown in FIG. 35, item 310, 311, 312. Reference number 512 is a tubing extrusion with a pre-attached flange to be used with an anchor as shown in FIG. 39 and FIG. 65C.

FIG. 65A is drawing of a hemispherical or disk-shaped covering for an expandable anchor that is assembled from sheet material into a spherical or disk shape. Shape 466 is cut from a sheet of ePTFE. Multiple sections of 466 are joined together into a sphere or disk shape by sewing or joining the seams by adhesive bonding. An optional throughhole 472 can be cut through the sphere or disk shape to allow the sphere or disk-shaped membrane to be attached to the expandable anchor. FIG. 65B is a drawing of a disk-shaped covering for an expandable anchor that is assembled from sheet material into a disk shape. Shape 473 is cut from a sheet of ePTFE. The two items of 473 are placed back-to-back. The outer rims of the two pieces of 473 are joined together by adhesive bonding with a hot melt of FEP or other suitable adhesive or sewing with suture. The two disks 473 that have been joined together at the outer rim are now inverted or turned inside out to move the seam to the inside of the disks 475. FIG. 65C is a drawing of a hemispherical or disk-shaped covering for an expandable anchor that is assembled from a tube and sheet material into a disk shape. Outer shape toroidal tube 476 is cut from a straight piece of ePTFE tube and formed into a toroid by sewing the tube ends together at 477. In various embodiments, an expandable anchor as in FIG. 32 is inserted inside the tube 476 before the two ends of the tube are joined at 477. Toroidal tube 476 is sewn to flat round disk 479 of ePTFE sheet at 478.

Figure 66:
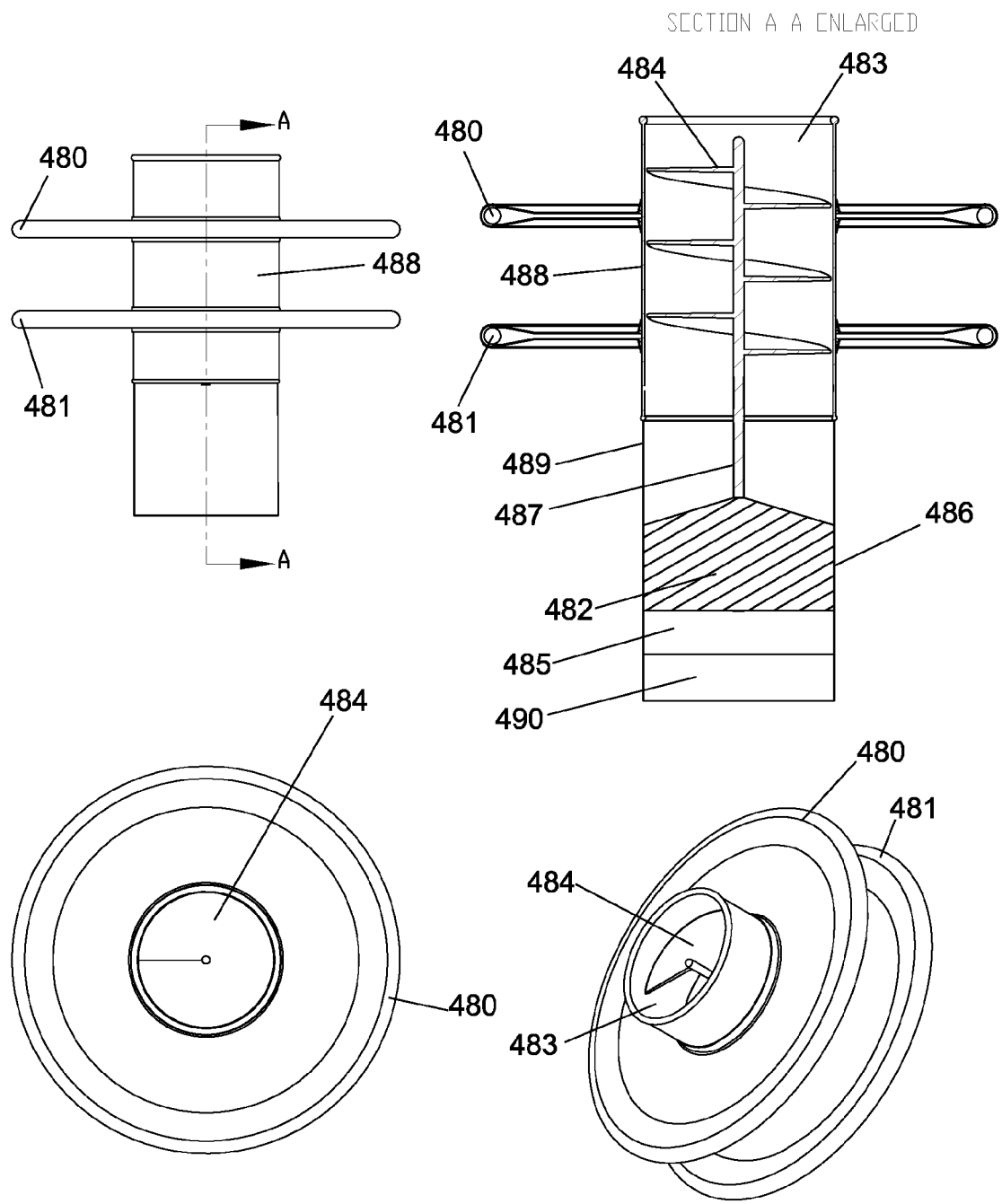
FIG. 66 is a drawing of an expandable anchor that has an Archimedes screw-type pump and motor integrated into the central cylinder or thru lumen of the device. The Archimedes screw is used to control the flow rate of chyme and/or to pump chyme from the stomach into the duodenum.

FIG. 66 is a drawing of an expandable anchor with toroidal-shaped anchors 480 and 481, expandable anchor has an Archimedes type screw pump 484, drive motor 482, battery 485, recharging antennae 486 integrated into the central cylinder 488 or through a lumen of the device. The Archimedes screw pump can be used as a means to help treat gastroparesis by actively pumping chyme from the stomach to the small intestine (e.g., the duodenum). The entire assembly may be placed into the stomach and intestine using an endoscope and delivering the device through the patient's mouth and stomach to the pylorus. Alternatively some portions of the device may be surgically placed and may not reside entirely within the digestive tract. The pump can also be used in diabetic patients to more precisely control the flow rate of chyme from the stomach to the small intestine. A more constant and controllable flow of chyme will allow the diabetic individual to be able to more accurately control their blood sugar levels. The pump will allow the flow rate of chyme from the stomach to the small intestine to be varied and controlled by the patient.

The Archimedes screw 484 is used to control the flow rate of chyme and/or to pump chyme from the pyloric antrum 104 into the duodenum 112. Battery 485 powers drive motor 482, drive motor 482 turns drive shaft 487 and in turn the Archimedes screw 484 is rotated and chyme enters input side of Archimedes screw 483 and is pumped through to the output port of pump 489. Output port of pump may incorporate a duck bill type anti reflex valve to prevent retrograde flow of chyme. The expandable anchor may be used with or without an intestinal bypass sleeve. The battery 485 can be remotely charged by inductive charging via the induction coil or antenna 486. The control of the motor operation, start stop and rotational speed and direction is control by controller 490. Controller 490 can be remotely controlled and programmed by telemetry. Controller can communicate with a controller via telemetry on the outside of the patients to change the flow rate of chyme. The Archimedes screw may also be driven magnetically by external magnets (outside the patient) and internal magnets on Archimedes screw pump.

The flow rate of chyme can be modified depending on the blood glucose levels of the patient. Blood glucose levels can be continuously monitored by a glucose sensor and the insulin infusion rates and chyme flow rates can be controlled by the motor 482 controlling the Archimedes screw 484 speed. Currently diabetic patients monitor blood glucose levels and then based on their insulin levels inject themselves with insulin either with a syringe or with an infusion pump. Gastric emptying rates vary depending upon the composition of the food eaten. Sugars pass quickly from the stomach into the small intestine and protein and fats move from the stomach into the small intestine more slowly. Blood sugar control can be difficult to manage if the flow rate of chyme from the stomach to the small intestine is unpredictable and in the case of patients with gastroparesis the chyme flow rate can be very slow to zero. The invention herein disclosed will allow for a tighter glucose level control by allowing more precise control of the flow rate of chyme into small intestine and modulating the flow rate of chyme base on blood glucose levels and insulin infusion rate.

Figure 67:
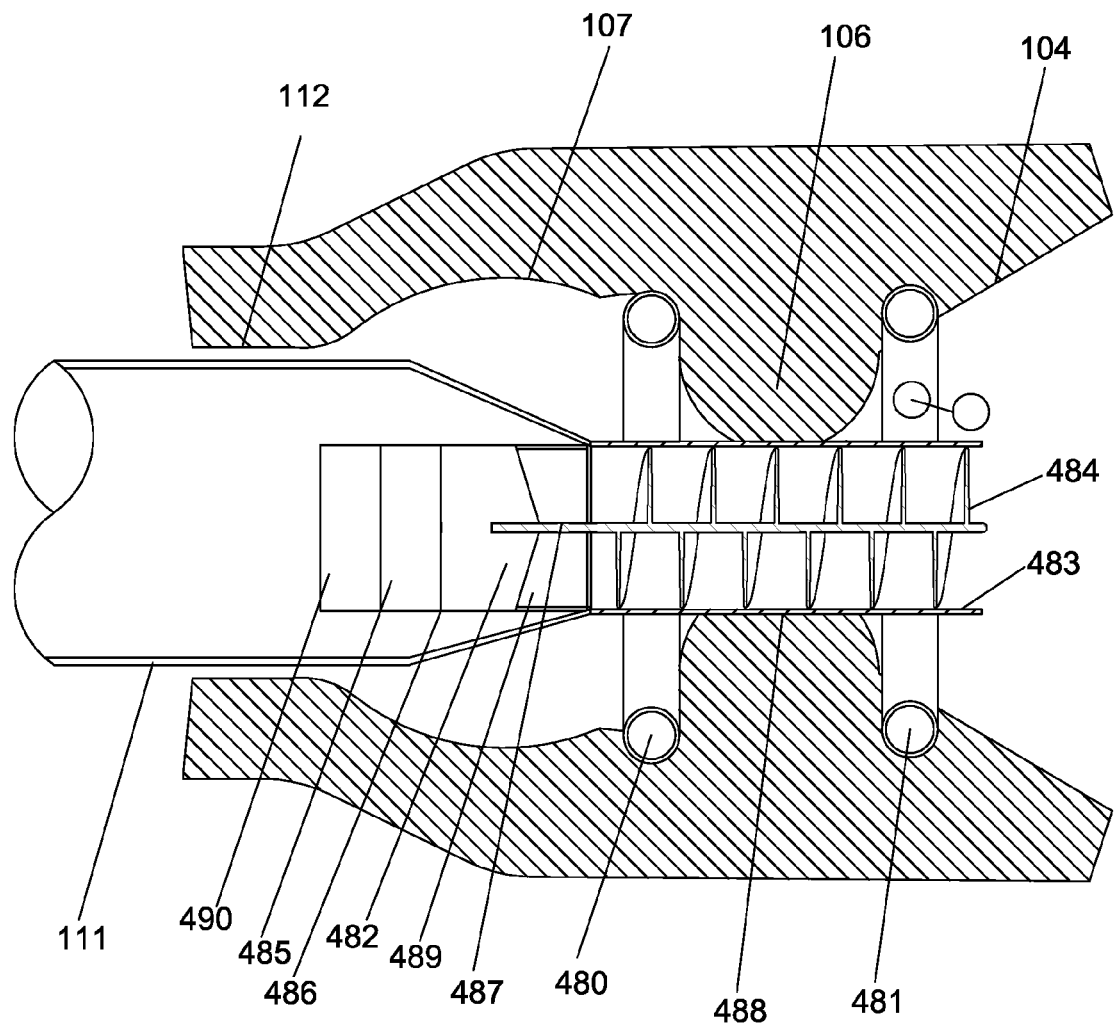
FIG. 67 is a sectional drawing of a part of the anatomy, a pyloric antrum, pylorus, duodenal bulb, and duodenum. The expandable anchor of FIG. 66 is implanted into the pyloric antrum, pylorus, duodenal bulb and duodenum.

FIG. 67 is a sectional drawing of a part of the gastrointestinal anatomy, a pyloric antrum 104, pylorus 106, duodenal bulb 107 and duodenum 112. The expandable anchor of FIG. 66 is implanted into the pyloric antrum 104, pylorus 106, duodenal bulb 107 and duodenum 112.

Figure 68:
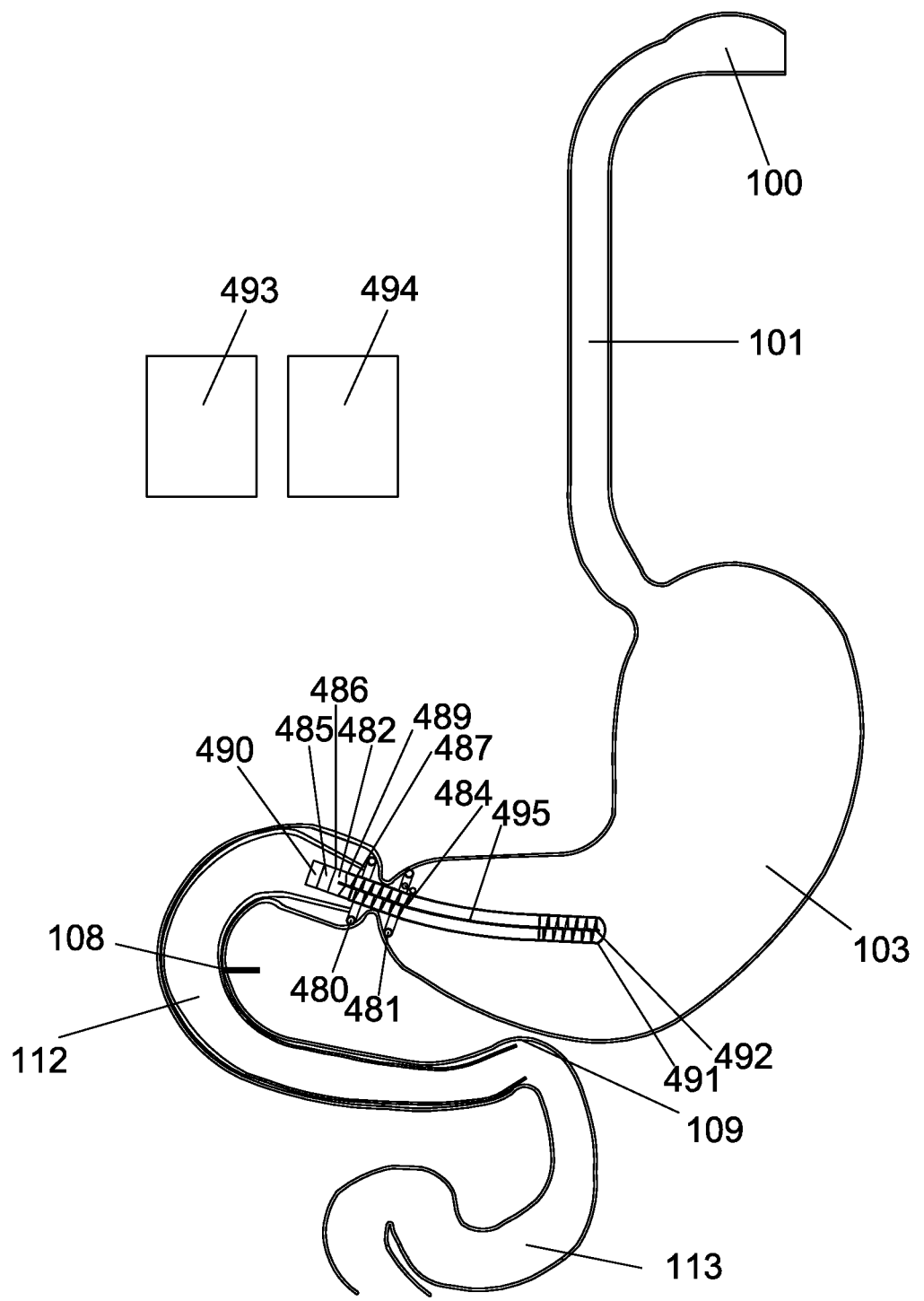
FIG. 68 is a cross-sectional drawing of a portion of the digestive tract in a human body. The expandable anchor of FIG. 66 is implanted into the pyloric antrum, pylorus, duodenal bulb and duodenum. A secondary Archimedes screw-type pump is attached to the first pump by means of a flexible drive shaft and is housed in a hollow flexible cannula that is attached to the expandable anchor.

FIG. 68 is a cross-sectional drawing of a portion of the digestive tract in a human body. The expandable anchor of FIG. 66 is implanted into the pyloric antrum 104, pylorus 106, duodenal bulb 107 and duodenum 112. A secondary Archimedes screw type pump 492 is attached to the first pump by means of a flexible drive shaft 495 and is housed in a hollow flexible cannula 491 that is attached to the expandable anchor. An optional intestinal bypass sleeve 111 is attached to the expandable anchor. A blood glucose monitor sensor and an insulin infusion drug pump can monitor and adjust the flow rate of chyme from the stomach to the small intestine by adjusting the speed of the motor driving the Archimedes screw pump.

Figure 69A:
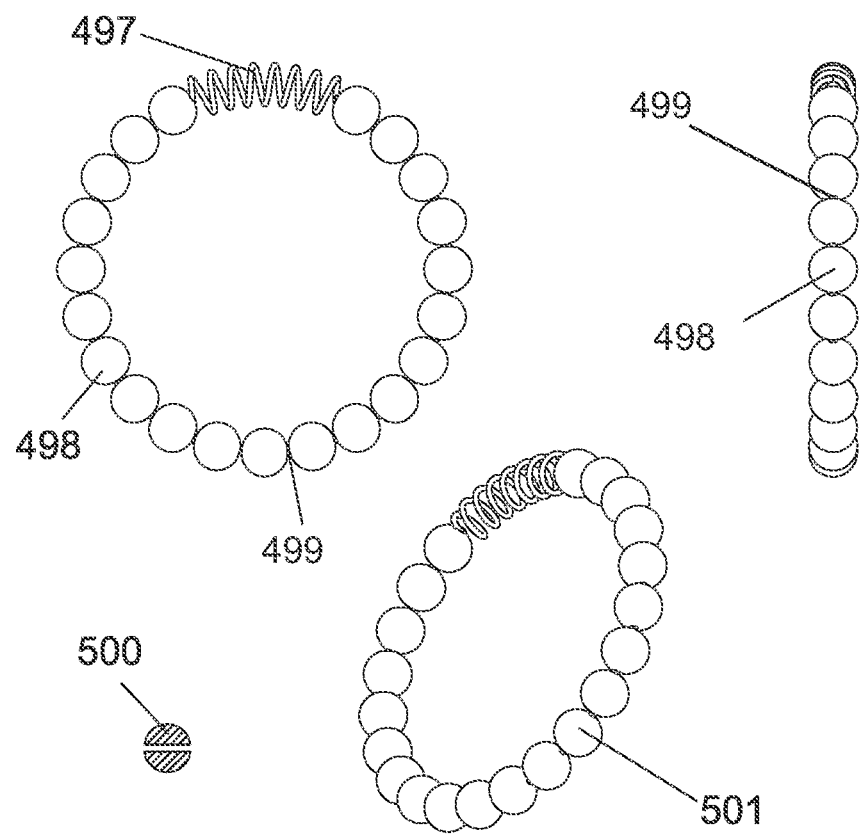
FIG. 69A is a drawing an alternative embodiment of an expandable anchor.

FIG. 69A is an alternative embodiment of an expandable anchor. Expandable anchor is comprised of a ring of beads 498 with a through hole drilled through the bead 500. Beads 498 are threaded onto a tensioning cable 499. Tension on tensioning cable 499 is maintained by spring 497. Ring of beads 498 can be deformed into noncircular shape for loading the expandable anchor onto a catheter. The tensioning cable elastically recovers ring shape of beads 498 due to tension exerted by spring on cable. The ring of beads can repeatedly undergo deformation to a non ring shape to a ring shape.

Figure 69B:
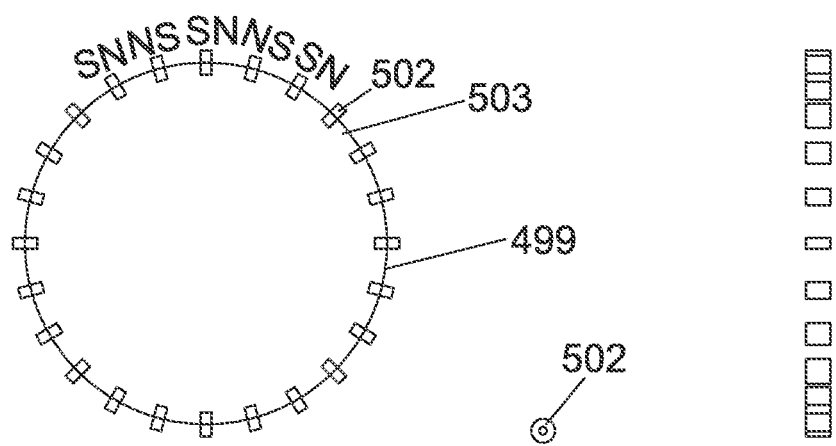
FIG. 69B is a drawing of an alternative embodiment of an expandable anchor.

FIG. 69B is an alternative embodiment of an expandable anchor. Expandable anchor is comprised of ring of magnets 502 with a through hole drilled through the magnets 500. Magnets 498 are threaded onto a cable 499. Magnets 502 are loaded onto a tensioning cable 503 with the magnetic poles alternating in polarity. Ring of magnets maintain separation by magnetic levitation or magnetic repulsion. Magnets 502 can be deformed into noncircular shape for loading the expandable anchor onto a catheter. The cable and ring of magnets recovers the original ring shape of magnets 502 due to the force exerted by magnets on each other and the cable. The ring of magnets can repeatedly undergo deformation from a non ring shape to a ring shape.

Figure 70A:
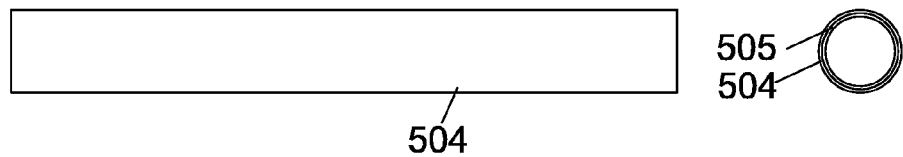
FIG. 70A is drawing of a piece of ePTFE tubing with an inner tube of silicone or latex inserted through the inside diameter of the ePTFE. The ePTFE tube in the final form can be use for covering an expandable anchor used to anchor an intestinal bypass sleeve. The covering for the expandable anchor and the intestinal bypass sleeve can be formed into one single unitary piece in some embodiments.
Figure 70B:
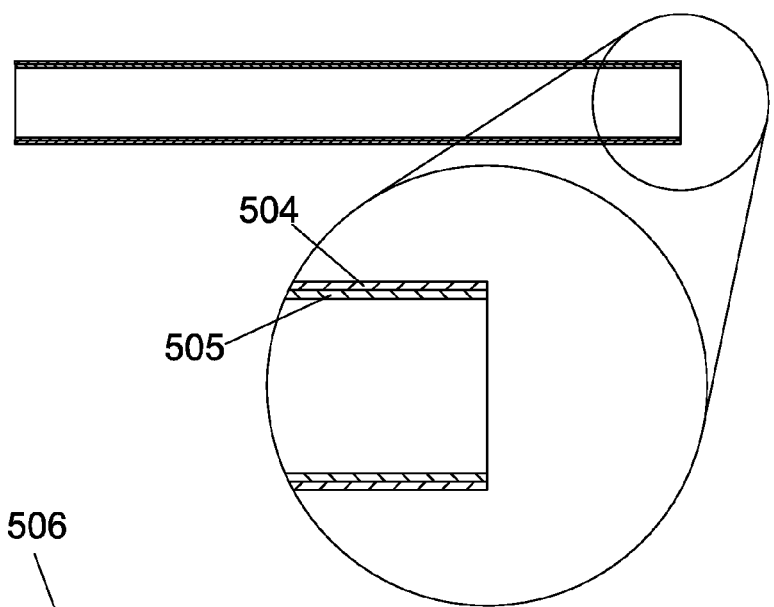
FIG. 70B is a longitudinal cross-section drawing of the ePTFE tube and silicone tube shown in FIG. 70A.
Figure 70C:
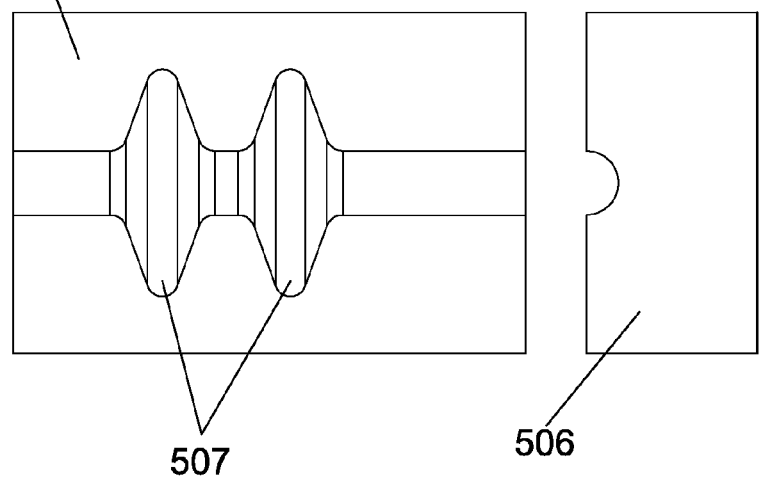
FIG. 70C is a drawing of a mold cavity the ePTFE tube from FIG. 70A and FIG. 70B will be radially stretched and inflated into the shape of the mold cavity. The radial expansion of the tube of ePTFE is like what was previously disclosed in FIG. 64B.

FIG. 70A is a drawing of a piece of ePTFE tubing 504 with a tube 505 of silicone or latex inserted through the inside diameter of the ePTFE tube 504. The ePTFE tube 504 in the final radially expanded shape can be used for covering an expandable anchor used to anchor an intestinal bypass sleeve. The ePTFE covering for the expandable anchor and the intestinal bypass sleeve can be formed into a single unitary tube in some embodiments disclosed. The ePTFE starting tube 504 can be made in a uni-axial or a bi-axial orientation. In some embodiments, the final shape is made by radially expanding the ePTFE tube 504 into the final shape, alternatively the final shape can also be accomplished by wrapping of thin films of ePTFE sheet into the final shape on a mandrel and then laminating them together by sintering the ePTFE layers together with heat or by fusing the ePTFE layers together by using a material such as FEP as a hot melt adhesive. The starting ePTFE tube 504 can range in size from 3 mm to 12 mm with a wall thickness in the range of 0.003 inch to 0.060 inch. The final expanded diameter of the ePTFE tube can range from the original tube diameter up to 7 times diameter increase from the original tube diameter. The ePTFE tube is plastically deformed during the radial expansion and the diameter largely remains at the new diameter with some diameter lost, 1 to 20 percent due to recoil. The final diameter of the radially stretched ePTFE tube can range from 3 mm to as large as 70 mm. FIG. 70B is a longitudinal cross-section drawing of the ePTFE tube 504 and silicone tube 505 shown in FIG. 70A. FIG. 70C is a drawing of a forming mold 506. The forming mold 506 can be made from plastic or metal such as aluminum or stainless steel. The ePTFE tube and silicone tube, FIGS. 70A and 70B will be radially stretched and inflated into the shape of inside of the forming mold 506. The radial expansion of the tube of ePTFE was previously disclosed in FIG. 64B. Two disk-shaped apertures 507 are machined into inside of the forming mold 506.

Figure 71A:
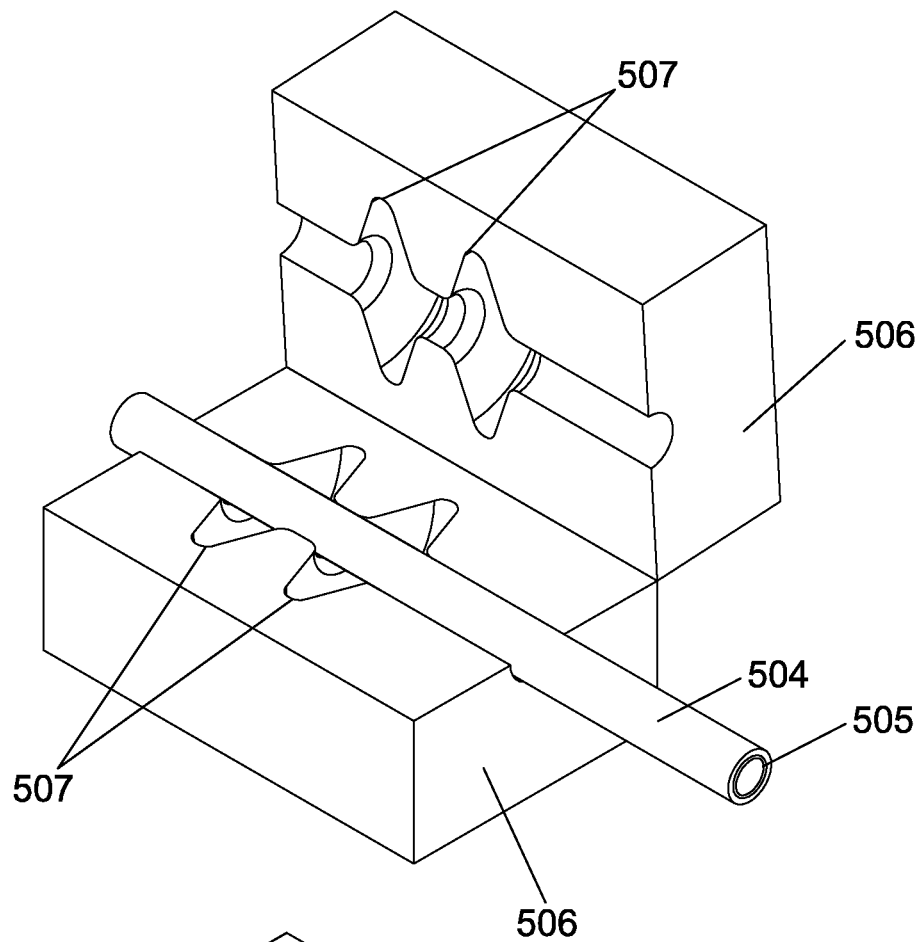
FIG. 71A is a drawing of a two mold cavities of FIG. 70C that are used together to provide an enclosed cavity to limit the expansion of the ePTFE during the blow-molding radial stretching process.
Figure 71B:
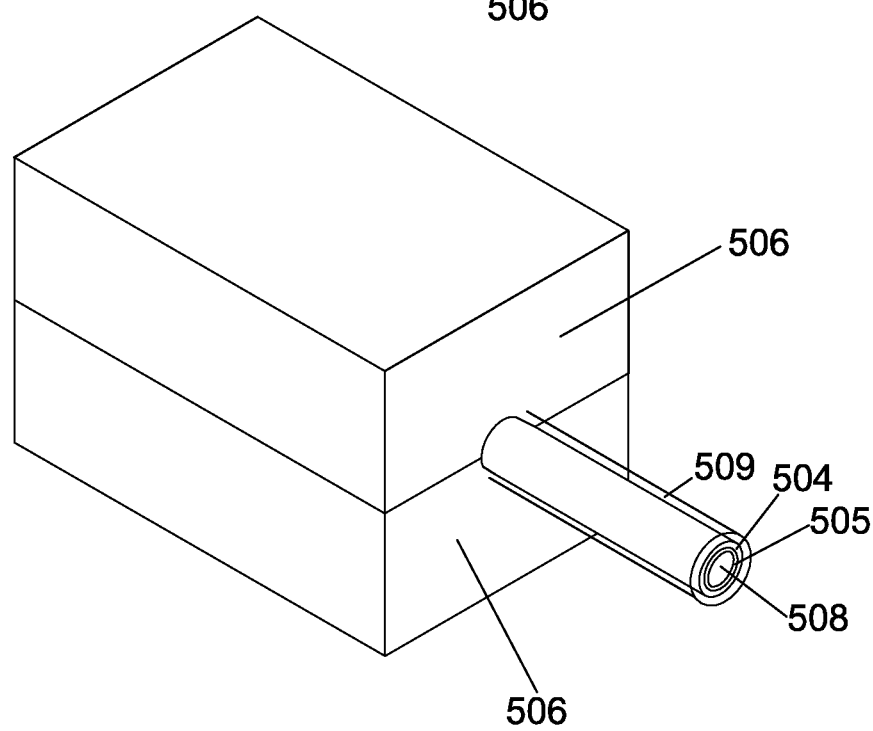
FIG. 71B is a drawing of the two mold cavities assembled one cavity half on top of the other. The ePTFE tube and latex tubing are inserted through the central bore between the two mold halves.

FIG. 71A is a drawing of two forming molds 506 of FIG. 70C that are used to provide an enclosed cavity to limit the expansion of the ePTFE tube 504 during the blow-molding (radial stretching process). Forming molds 506 have disk shape apertures 507 machined into them. The ePTFE tube 504 with an inner tube of silicone 505 is place into the forming mold 506. FIG. 71B is a drawing of the forming molds 506 assembled one mold half on top of the other. The ePTFE tube 504 and silicone tube 505 are inserted through the central bore between the two forming mold halves 506. Central lumen of silicone tube 508 is open and provides for a pathway to introduce pressurized air or liquid into the lumen of silicone tube. Rigid tube 509 surrounds ePTFE tube 504 and silicone tube 505. The mold 506, ePTFE tube 504, silicone tube 505 can by heated to an elevated temperature (e.g., a temperature of between about 30-150 degrees Celsius) to increase the ultimate elongation of the ePTFE tube 504 and the silicone tube 505. The inside of the silicone tube 508 is pressurized with air or liquid to radially expand the ePTFE tube 504 into the shape of the central bore and apertures 507. A pressure in the range of 80 psi to 160 psi is typically used to expand the ePTFE tube 504 and the silicone tube 505.

Figure 72A:
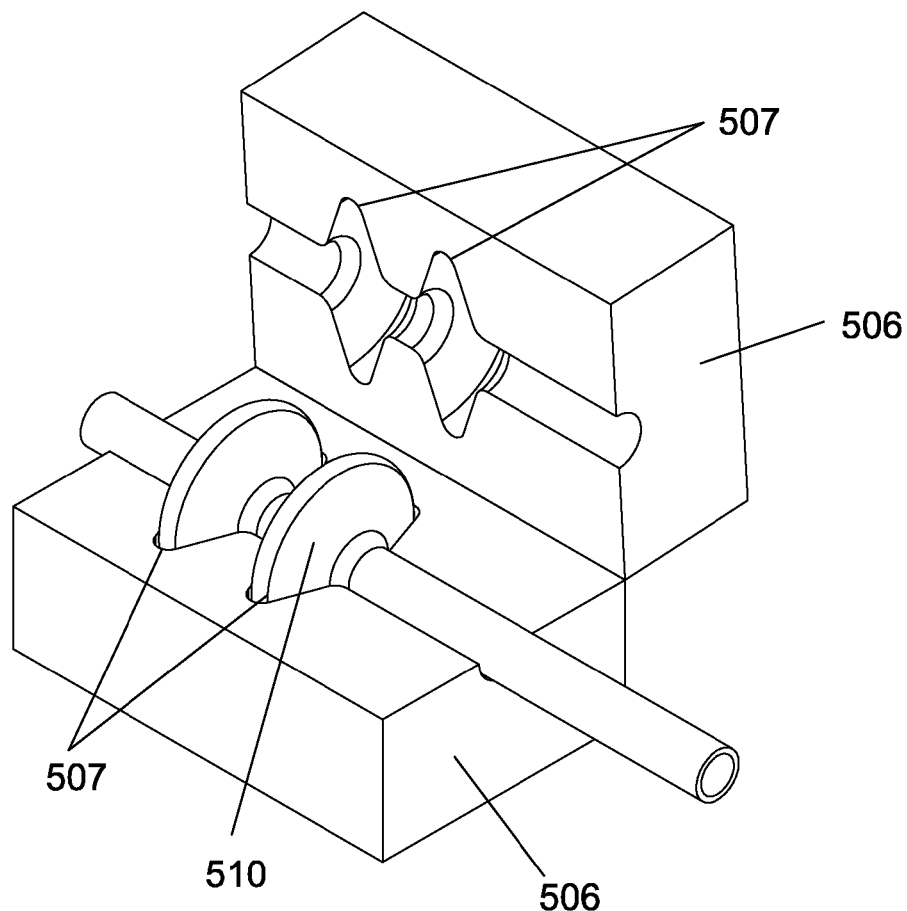
FIG. 72A is a drawing of the two mold halves opened after the ePTFE tube has been blow-molded to the shape of the mold cavities.
Figure 72B:
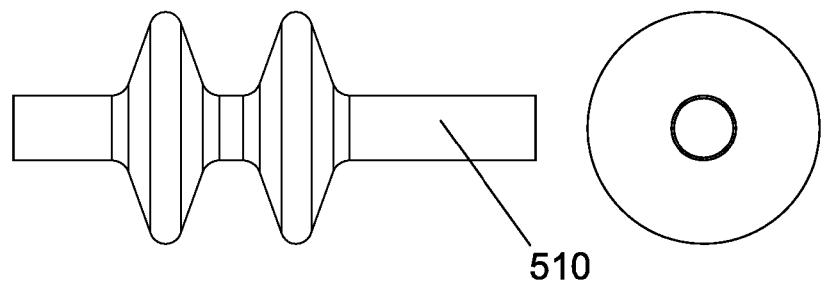
FIG. 72B is a drawing of the ePTFE tube removed from the mold cavity after the blow-molding/radial stretching process is complete.
Figure 72C:
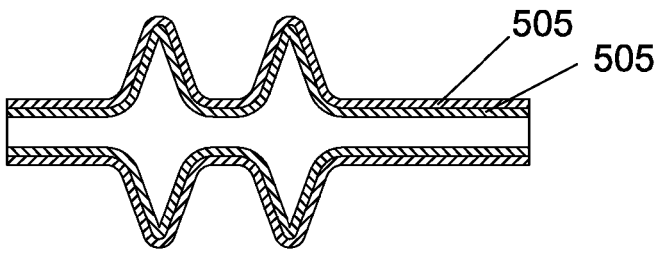
FIG. 72C is a drawing of the cross-section of the ePTFE tube and silicone tube inflated, while the two tubes are still in the mold of FIG. 71B, after the pressure is released.

FIG. 72A is a drawing of the two forming molds 506 opened after the ePTFE tube has been blow molded to the shape of the disk-shaped apertures 507. The ePTFE tube is now permanently formed into the new final shape 510. FIG. 72B is a drawing of the formed ePTFE tube 510 removed from the mold cavity after the blow-molding/radial stretching process is complete. The ePTFE tube 510 is now permanently formed into the new final hour glass shape. FIG. 72C is a drawing of the cross-section of the ePTFE tube 504 and silicone tube 505 inflated while the two tubes are still in the mold of 71B. After the pressure is released the silicone tube 505 elastically returns to its original starting diameter and the ePTFE tube 504 partially recoil in diameter but loses only about 10 to 20 percent of the inflated diameter.

Figure 73:
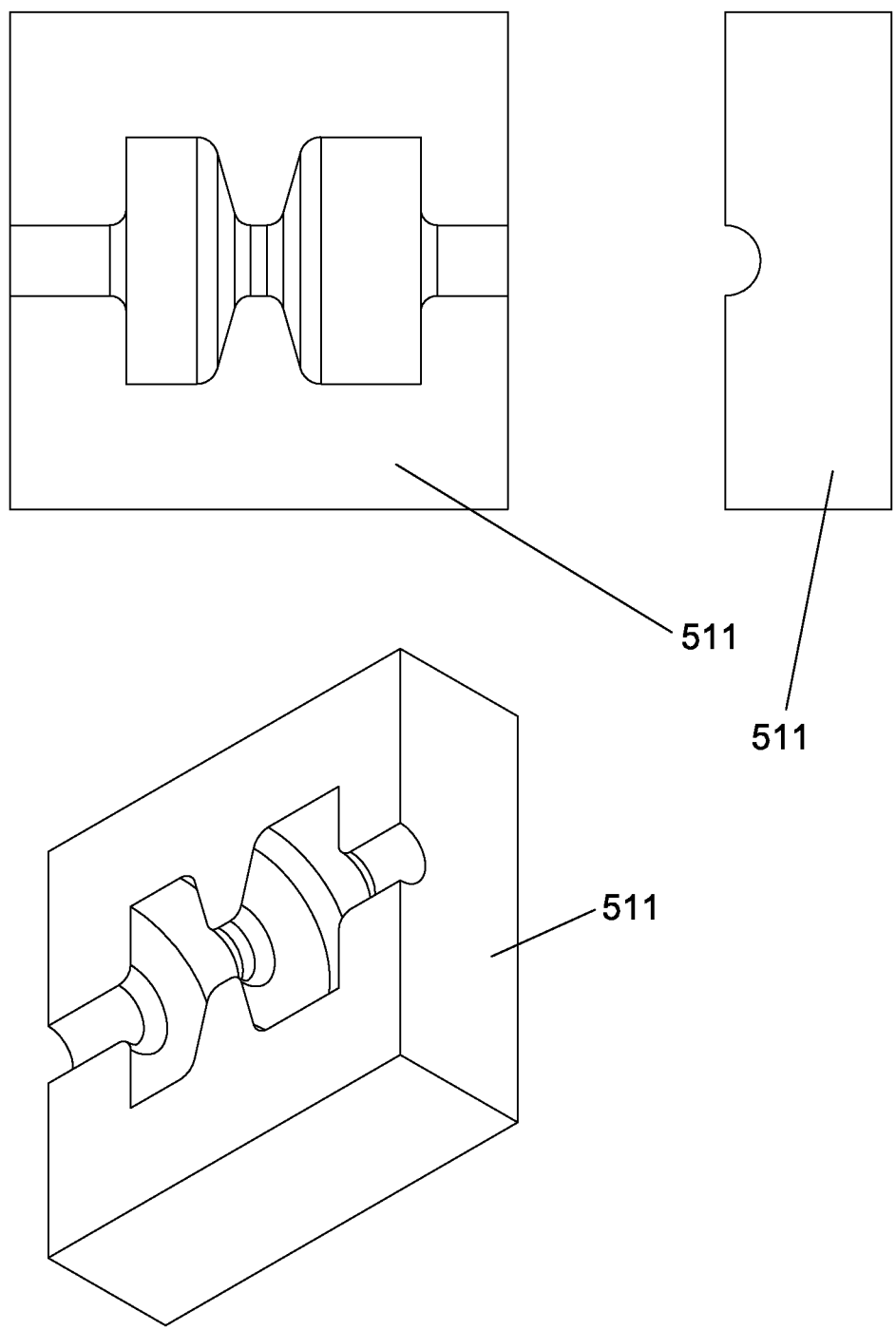
FIG. 73 is a drawing of an alternate embodiment for a shape for the mold cavity for blow-molding the ePTFE tube.
Figure 74:
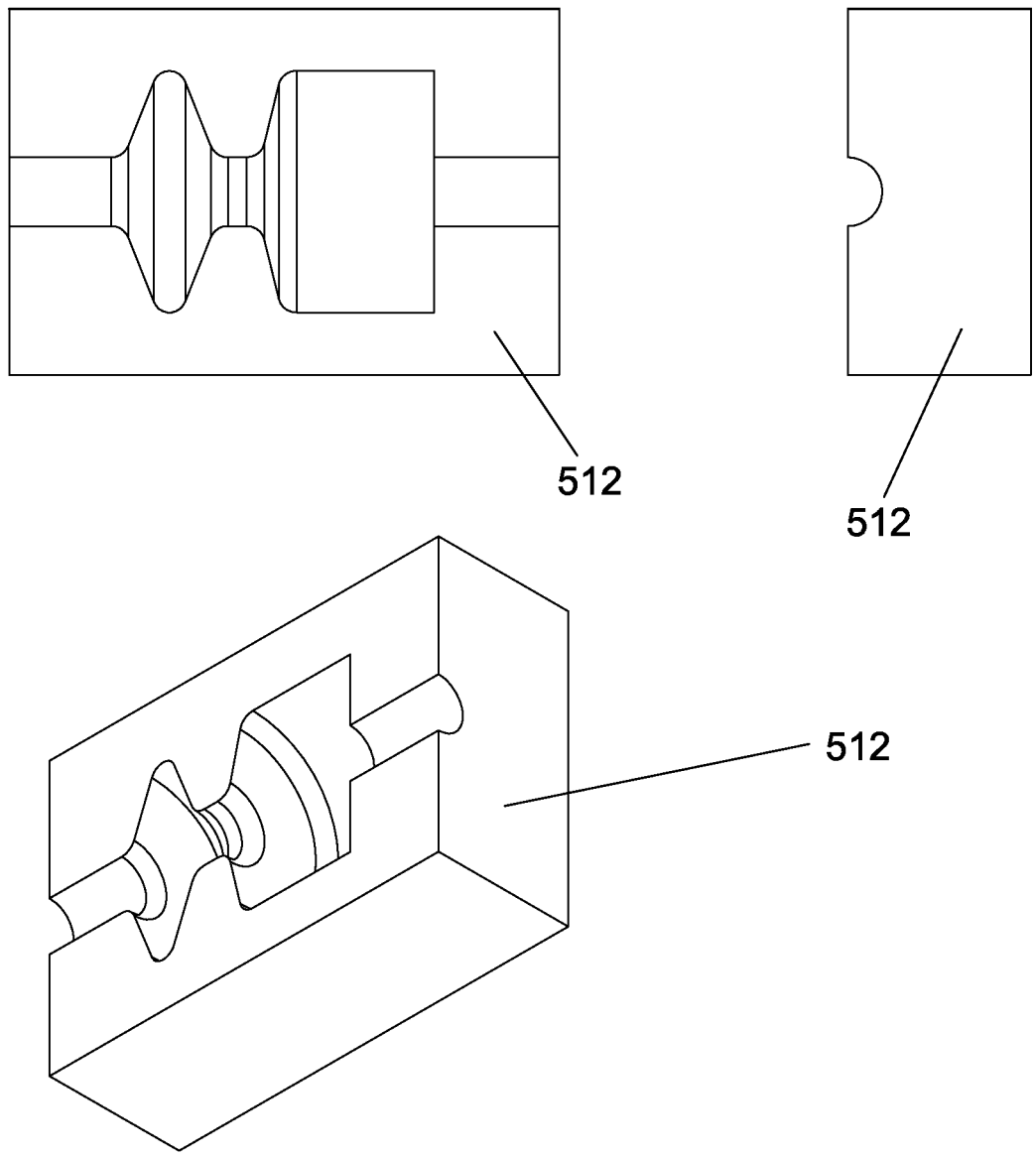
FIG. 74 is a drawing of an alternate embodiment of a shape for the mold cavity for blow-molding the ePTFE tube.
Figure 75:
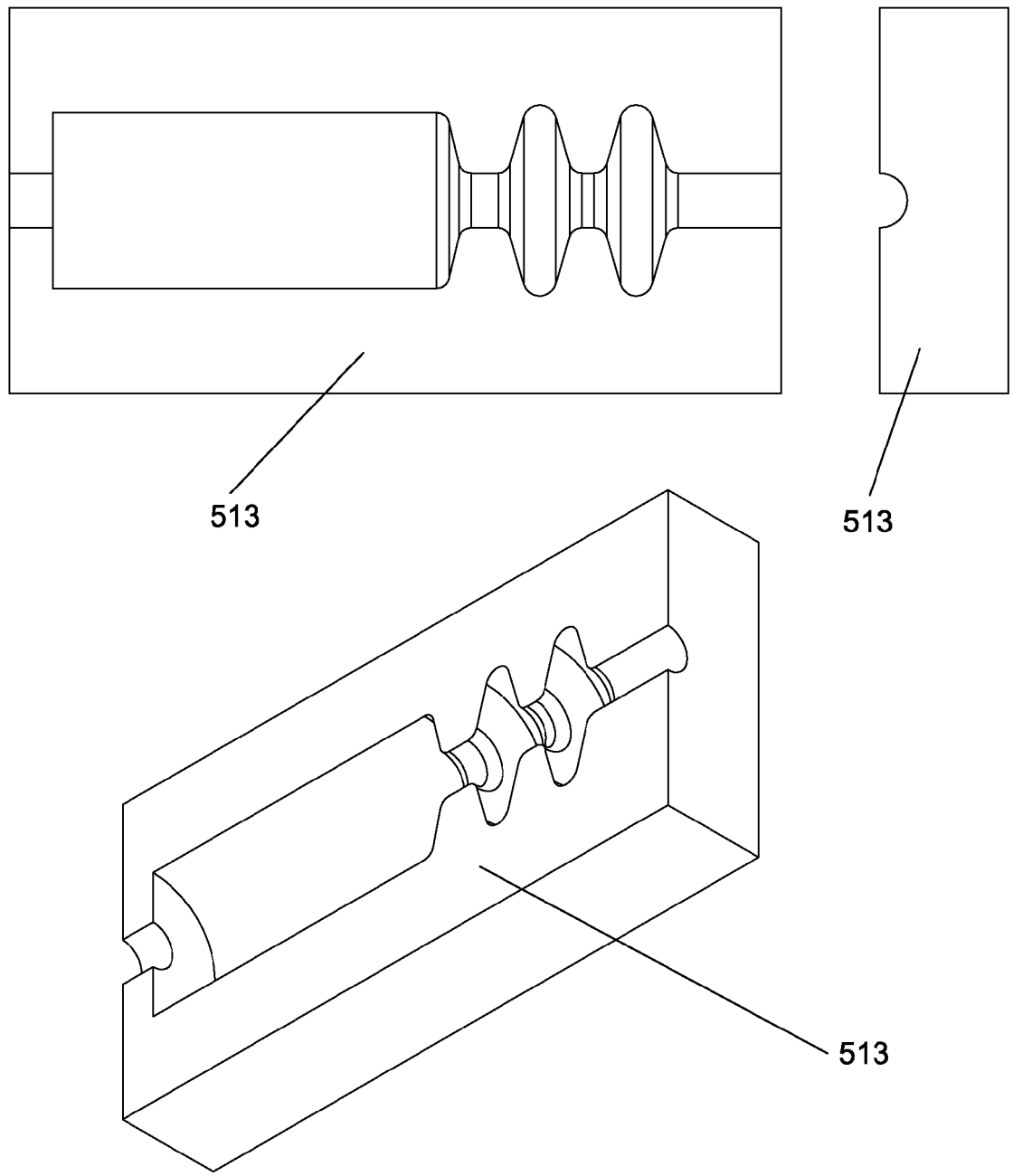
FIG. 75 is a drawing of an alternate embodiment of a shape for the mold cavity for blow-molding the ePTFE tube.
Figure 76:
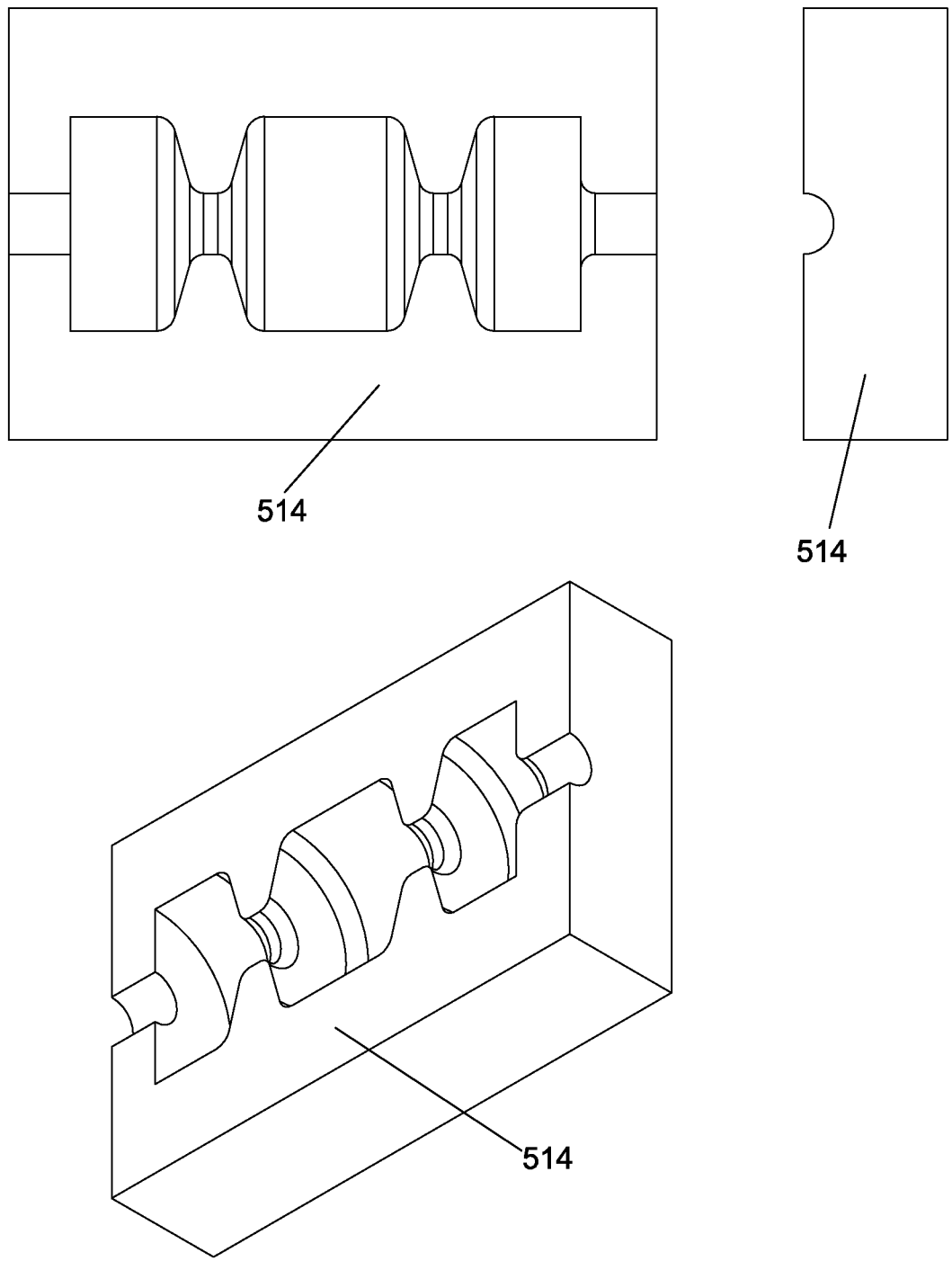
FIG. 76 is a drawing of an alternate embodiment of a shape for the mold cavity for blow-molding the ePTFE tube.

FIG. 73 is a drawing of an alternate embodiment for a shape for the internal cavity for the forming mold 511 for blow-molding the ePTFE tube. FIG. 74 is a drawing of an alternate embodiment for a shape for the internal cavity for the forming mold 512 for blow-molding the ePTFE tube. FIG. 75 is a drawing of an alternate embodiment for a shape for the internal cavity for the forming mold 513 for blow-molding the ePTFE tube. FIG. 76 is a drawing of an alternate embodiment for a shape for the internal cavity for the forming mold 514 for blow-molding the ePTFE tube.

FIG. 77A is a drawing of the shape of the ePTFE tube formed into a double disk shape after blow-molding/radial stretching of the original cylindrical tube of ePTFE. The ends of the radially expanded ePTFE tube shape may be trimmed in length to accomplish the desired final shape. FIG. 77B is a drawing of the shape of the ePTFE tube formed into a double disk shape after blow-molding/radial stretching of the original cylindrical tube of ePTFE. The ends of the radially expanded ePTFE tube shape may be trimmed in length to accomplish the desired final shape. FIG. 77C is a drawing of the shape of the ePTFE tube formed into a double cup shape after blow-molding/radial stretching of the original cylindrical tube of ePTFE. The ends of the radially expanded ePTFE tube shape may be trimmed in length to accomplish the desired final shape. FIG. 77D is a drawing of the shape of the ePTFE tube formed into a disk and cup shape after blow-molding/radial stretching of the original cylindrical tube of ePTFE. The ends of the radially expanded ePTFE tube shape may be trimmed in length to accomplish the desired final shape. FIG. 77E is a drawing of the shape of the ePTFE tube formed into a double spherical shape after blow-molding/radial stretching of the original cylindrical tube of ePTFE. The ends of the radially expanded ePTFE tube shape may be trimmed in length to accomplish the desired final shape.

FIG. 78A is a drawing of the final formed shape of the ePTFE tube after blow-molding/radial stretching of the original cylindrical tube of ePTFE. The anchor covering portion 515 of the sleeve and the intestinal bypass 516 sleeve are formed integrally into one sleeve. The length 517 of the intestinal bypass sleeve 516 may range from a few inches up to 4 feet or more. The sleeve may include an optional bulbous shape 518 for the duodenal bulb. The intestinal bypass sleeve length 517 can range from a few inches to 4 feet or more. FIG. 78B is a drawing of the final formed shape of the ePTFE tube after blow-molding/radial stretching of the original cylindrical tube of ePTFE. The anchor covering portion 515 of the sleeve and the intestinal bypass sleeve 516 are formed integrally into one sleeve. The small diameter end of the tube 519 is started to be inverted inside to pull it inside to form an interior tube layer for the expandable anchor. FIG. 78C is a drawing of the final formed shape of the ePTFE tube after blow-molding/radial stretching of the original cylindrical tube of ePTFE. The anchor covering portion of the sleeve 515 and the intestinal bypass sleeve 516 are formed integrally into one sleeve. The small diameter end of the tube is fully inverted inside forming an interior layer 521 for the expandable anchor. Two pockets 520 are formed with the sleeve, an expandable anchor as previously disclosed in this patent application may be placed within the pockets.

Figures 79A, 79B, 79C:
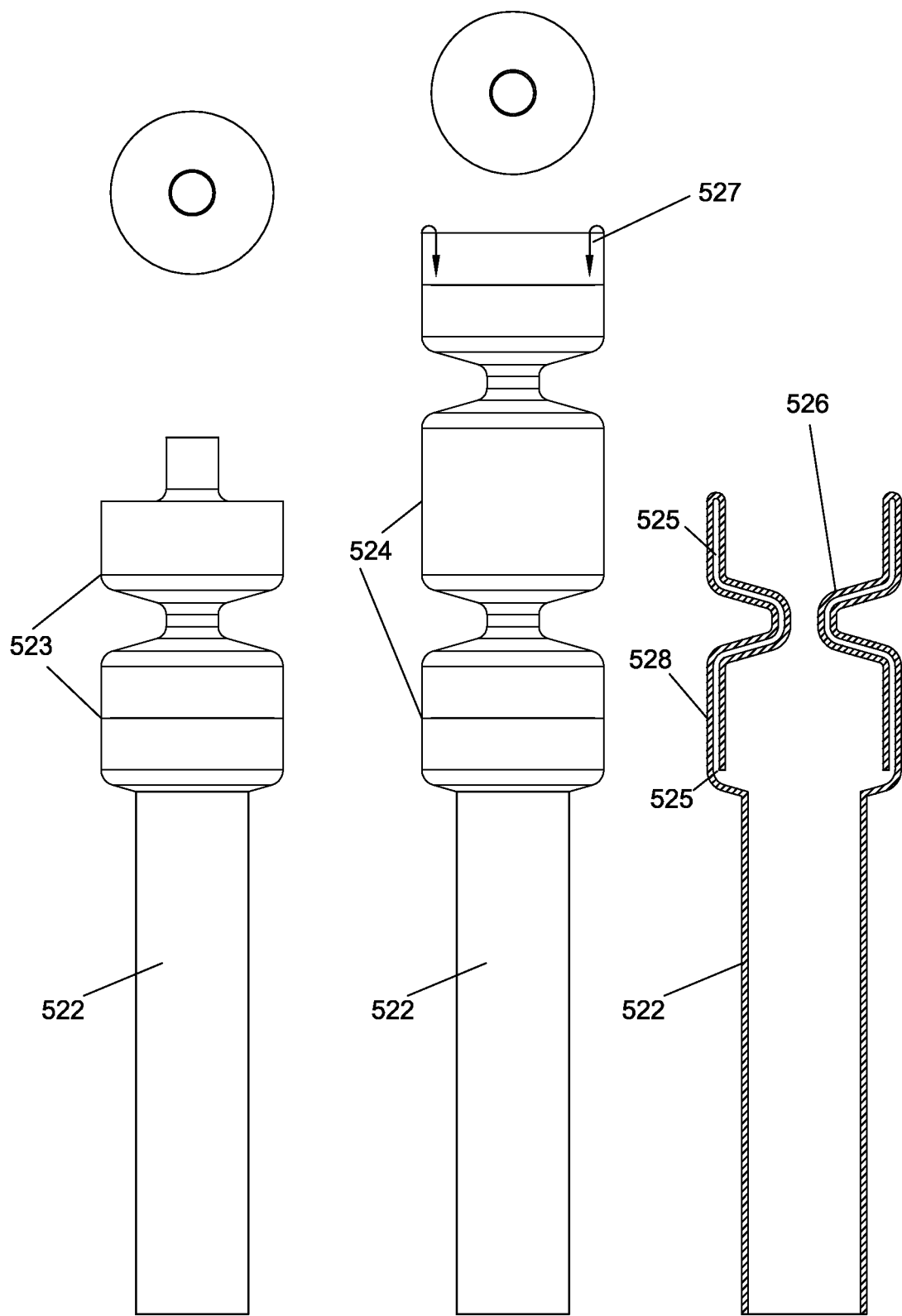
FIG. 79A is a drawing of an alternative embodiment of the final formed shape of the ePTFE tube after blow-molding/radial stretching of the original cylindrical tube of ePTFE. The anchor covering portion of the sleeve and the intestinal bypass sleeve are formed integrally into one sleeve.
FIG. 79B is a drawing of an alternative embodiment of the final formed shape of the ePTFE tube after blow-molding/radial stretching of the original cylindrical tube of ePTFE. The anchor covering portion of the sleeve and the intestinal bypass sleeve are formed integrally into one sleeve. The small diameter end of the tube is started to be inverted inside to pull it inside to form an interior tube layer for the expandable anchor.
FIG. 79C is a drawing of an alternative embodiment of the final formed shape of the ePTFE tube after blow-molding/radial stretching of the original cylindrical tube of ePTFE. The anchor covering portion of the sleeve and the intestinal bypass sleeve are formed integrally into one sleeve. The small diameter end of the tube is fully inverted inside forming an interior layer for the expandable anchor.

FIG. 79A is a drawing of an alternative embodiment of the final formed shape of the ePTFE tube after blow-molding/radial stretching of the original cylindrical tube of ePTFE. The anchor covering portion of the sleeve 523 and the intestinal bypass sleeve 522 are formed integrally into one sleeve. FIG. 79B is a drawing of an alternative embodiment of the final formed shape of the ePTFE tube after blow-molding/radial stretching of the original cylindrical tube of ePTFE. The anchor covering portion of the sleeve 524 and the intestinal bypass sleeve 522 are formed integrally into one sleeve. The end of the tube 527 is started to be inverted inside to pull it inside to form an interior tube layer for the expandable anchor. FIG. 79C is a drawing of an alternative embodiment of the final formed shape of the ePTFE tube after blow-molding/radial stretching of the original cylindrical tube of ePTFE. The anchor covering portion of the sleeve 528 and the intestinal bypass sleeve 522 are formed integrally into one sleeve. The end of the tube 527 is fully inverted inside forming an interior layer 526 for the expandable anchor which can be located in pockets 525.

Figures 80A, 80B:
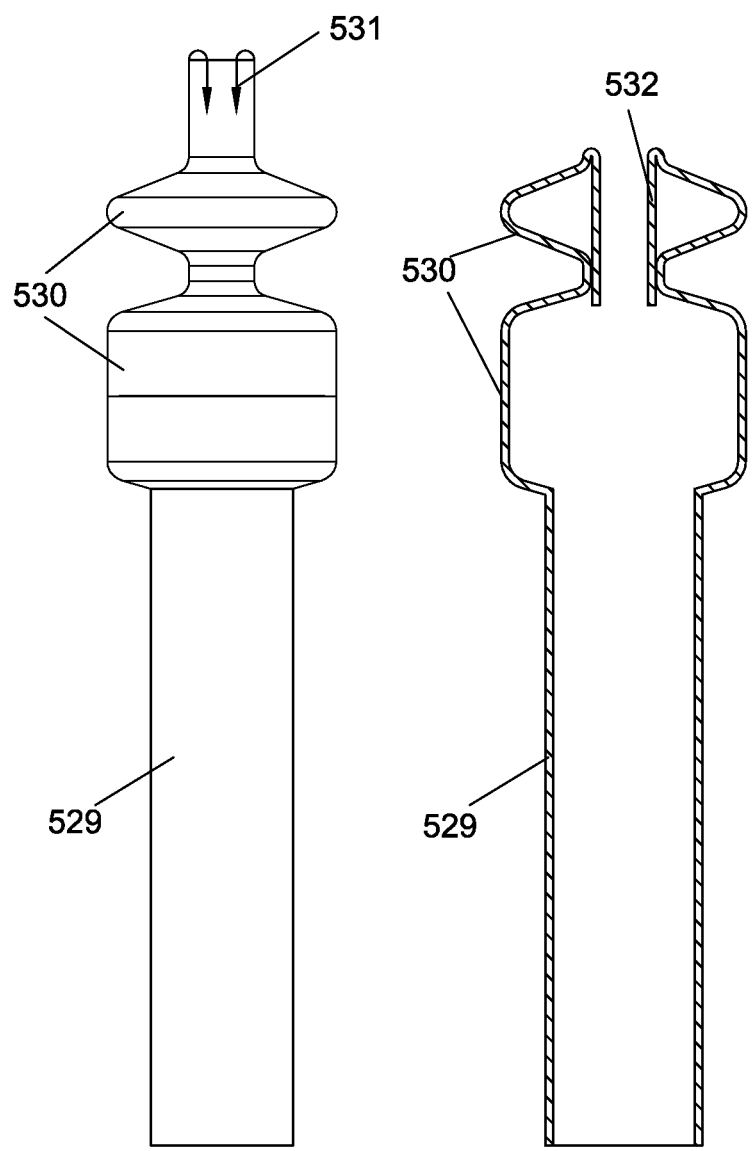
FIG. 80A is a drawing of an alternative embodiment of the final formed shape of the ePTFE tube after blow-molding/radial stretching of the original cylindrical tube of ePTFE. The anchor covering portion of the sleeve and the intestinal bypass sleeve are formed integrally into one sleeve.
FIG. 80B is a drawing of an alternative embodiment of the final formed shape of the ePTFE tube after blow-molding/radial stretching of the original cylindrical tube of ePTFE. The anchor covering portion of the sleeve and the intestinal bypass sleeve are formed integrally into one sleeve. The small-diameter end of the tube is started to be inverted inside to pull it inside to form an interior tube layer for the expandable anchor.

FIG. 80A is a drawing of an alternative embodiment of the final formed shape of the ePTFE tube after blow-molding/radial stretching of the original cylindrical tube of ePTFE. The anchor covering portion of the sleeve 530 and the intestinal bypass sleeve 529 are formed integrally into one sleeve. The end of the tube 531 is started to be inverted inside to pull it inside to form an interior tube layer for the expandable anchor. FIG. 80B is a drawing of an alternative embodiment of the final formed shape of the ePTFE tube after blow-molding/radial stretching of the original cylindrical tube of ePTFE. The anchor covering portion of the sleeve 530 and the intestinal bypass sleeve 529 are formed integrally into one sleeve. The small diameter end of the tube is fully inverted inside to pull it inside to form an interior tube layer 532 for an expandable anchor as previously disclosed.

FIG. 81A is a drawing of an alternative embodiment of the final formed shape of the ePTFE tube after blow-molding/radial stretching of the original cylindrical tube of ePTFE. The anchor covering portion of the sleeve 534 and the intestinal bypass sleeve 533 are formed integrally into one sleeve. FIG. 81B is a drawing of an alternative embodiment of the final formed shape of the ePTFE tube after blow-molding/radial stretching of the original cylindrical tube of ePTFE. The anchor covering portion of the sleeve 535 and the intestinal bypass sleeve 533 are formed integrally into one sleeve. The end of the tube 537 is started to be inverted inside to pull it inside to form an interior tube layer for the expandable anchor. FIG. 81C is a drawing of an alternative embodiment of the final formed shape of the ePTFE tube after blow-molding/radial stretching of the original cylindrical tube of ePTFE. The anchor covering portion of the sleeve 538 and the intestinal bypass sleeve 533 are formed integrally into one sleeve. The end of the tube is fully inverted inside forming an interior layer 536 for the expandable anchor. The end of the tube is fully inverted inside to pull it inside to form an interior tube layer 532 for an expandable anchor as previously disclosed. An expandable anchor may be place in between the layers at 539.

Figures 82A, 82B, 82C:
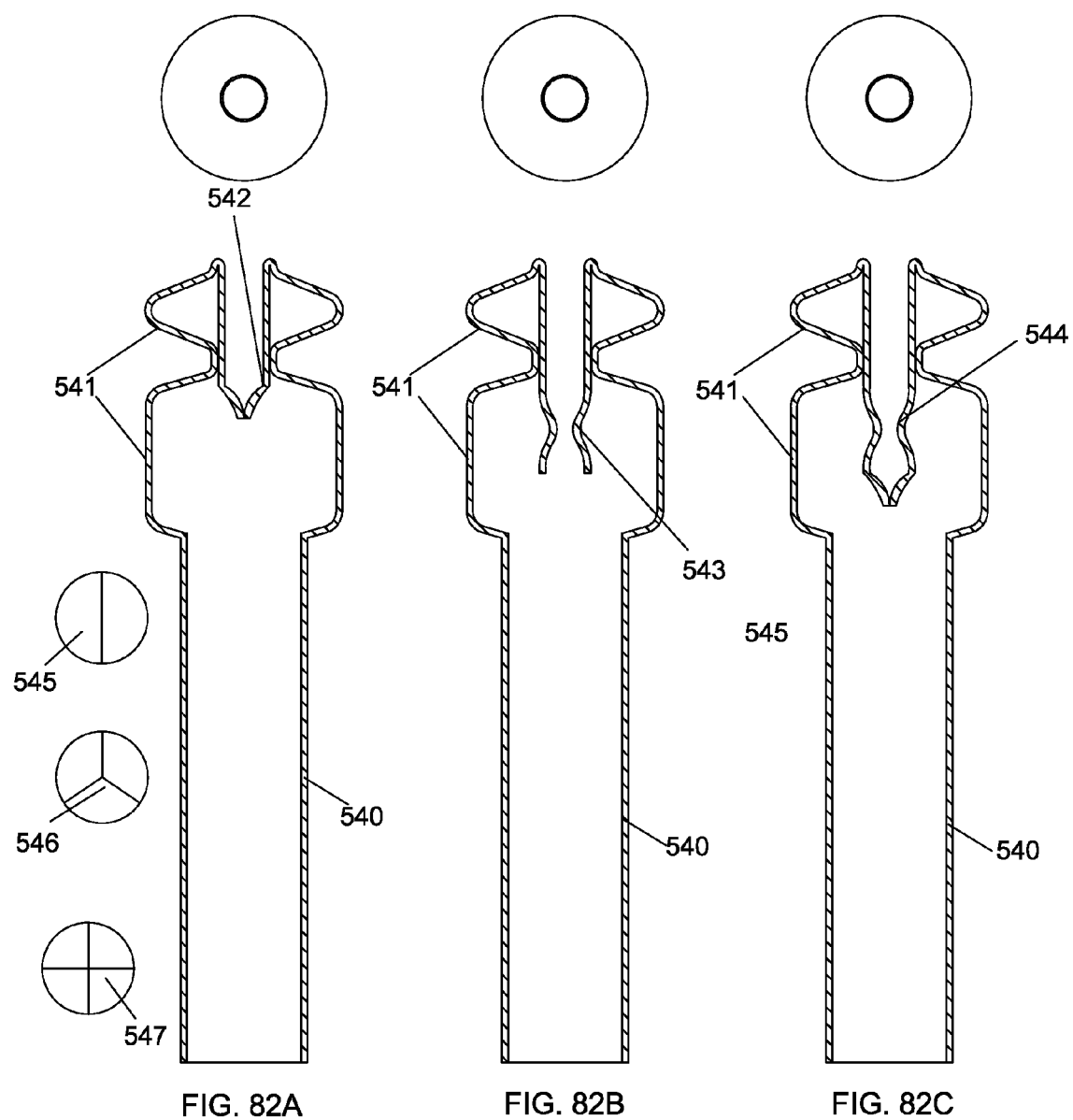
FIG. 82A is a drawing of an alternative embodiment of the final formed shape of the ePTFE tube after blow-molding/radial stretching of the original cylindrical tube of ePTFE. The anchor covering portion of the sleeve and the intestinal bypass sleeve are formed integrally into one sleeve. The small diameter end of the tube is inverted inside to pull it inside to form an interior tube layer for the expandable anchor. The interior tube is formed into the shape of anti-reflux valve.
FIG. 82B is a drawing of an alternative embodiment of the final formed shape of the ePTFE tube after blow-molding/radial stretching of the original cylindrical tube of ePTFE. The anchor covering portion of the sleeve and the intestinal bypass sleeve are formed integrally into one sleeve. The small diameter end of the tube is inverted inside to pull it inside to form an interior tube layer for the expandable anchor. The interior tube is formed into the shape of a restrictive stoma.

FIG. 82A is a drawing of an alternative embodiment of the final formed shape of the ePTFE tube after blow-molding/radial stretching of the original cylindrical tube of ePTFE. The anchor covering portion of the sleeve 541 and the intestinal bypass sleeve 540 are formed integrally into one sleeve. The small diameter end of the tube is inverted inside to pull it inside to form an interior tube layer for the expandable anchor. The interior tube is formed into the shape of anti-reflux valve 542. The anti reflux valve 542 may be formed of two leaflets 545, three leaflets 546, or four leaflets 547. FIG. 82B is a drawing of an alternative embodiment of the final formed shape of the ePTFE tube after blow-molding/radial stretching of the original cylindrical tube of ePTFE. The anchor covering portion of the sleeve 541 and the intestinal bypass sleeve 540 are formed integrally into one sleeve. The small diameter end of the tube is inverted inside to pull it inside to form an interior tube layer for the expandable anchor. The interior tube is formed into the shape of a restrictive stoma 543. FIG. 82C is a drawing of an alternative embodiment of the final formed shape of the ePTFE tube after blow-molding/radial stretching of the original cylindrical tube of ePTFE. The anchor covering portion of the sleeve and the intestinal bypass sleeve are formed integrally into one sleeve. The small diameter end of the tube is inverted inside to pull it inside to form an interior tube layer for the expandable anchor. The interior tube is formed into the shape of a restrictive stoma and then an anti-reflux valve in series 544.

Figures 83A, 83B:
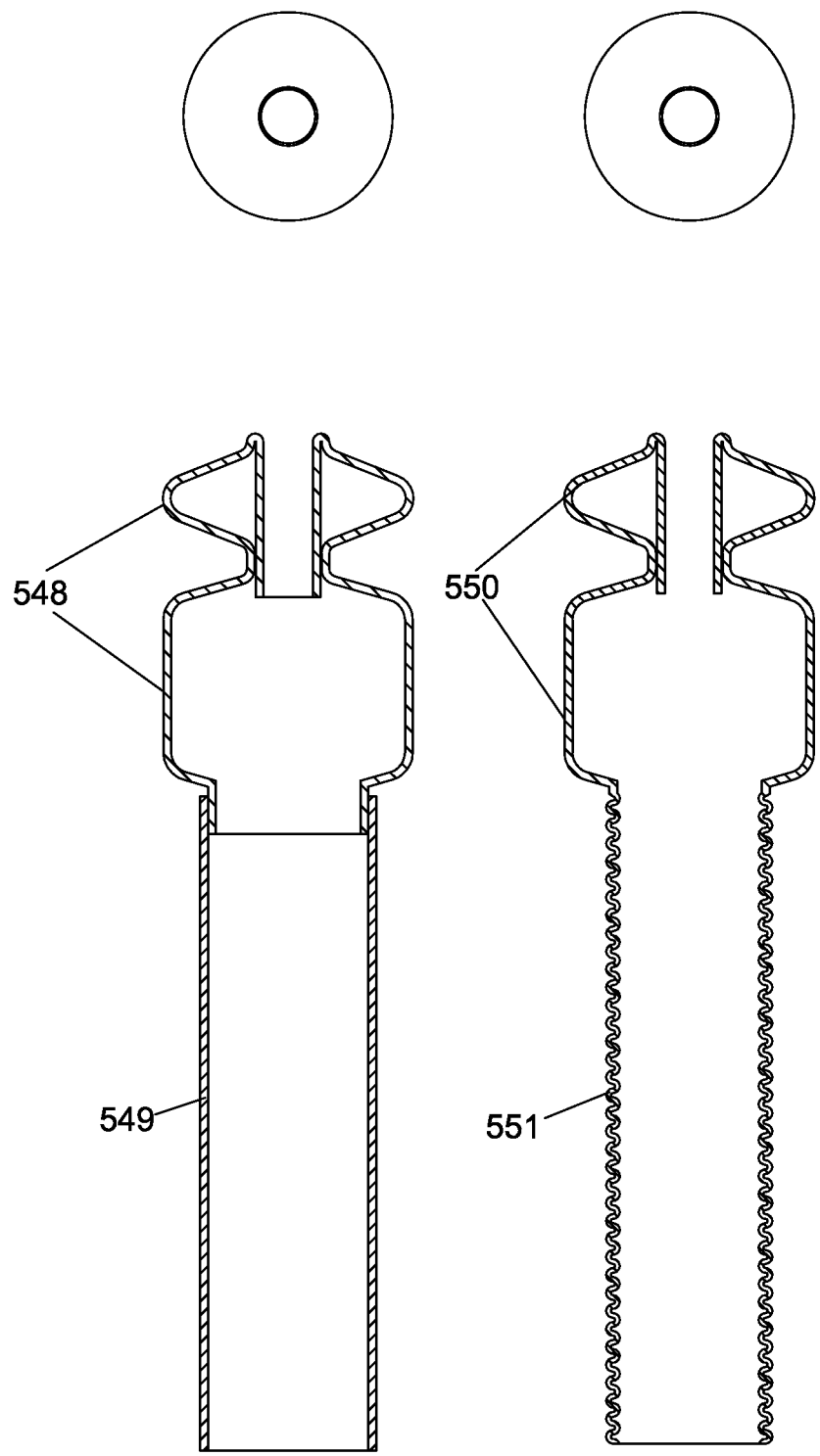
FIG. 83A is a drawing of an alternative embodiment of the final formed shape of the ePTFE tube after blow-molding/radial stretching of the original cylindrical tube of ePTFE. The anchor covering portion of the sleeve and the intestinal bypass sleeve are formed integrally into one sleeve. The small-diameter end of the tube is inverted inside to pull it inside to form an interior tube layer for the expandable anchor. The interior tube is formed into the shape of a restrictive stoma and then an anti-reflux valve in series.
FIG. 83B is a drawing of an alternative embodiment of the final formed shape of the ePTFE tube after blow-molding/radial stretching of the original cylindrical tube of ePTFE. The anchor covering portion of the sleeve and the intestinal bypass sleeve are formed integrally into one sleeve. The small-diameter end of the tube is inverted inside to pull it inside to form an interior tube layer for the expandable anchor. The intestinal bypass sleeve has annular rings or corrugations molded into it to allow for the sleeve to bend easier without kinking and to provide for more longitudinal elasticity.

FIG. 83A is a drawing of an alternative embodiment of the final formed shape of the ePTFE tube after blow-molding/radial stretching of the original cylindrical tube of ePTFE. The anchor covering portion of the sleeve 548 and the intestinal bypass sleeve 549 are formed separately and bonded together. Intestinal bypass sleeve 549 may be formed from FEP or other suitable polymer. FIG. 83B is a drawing of an alternative embodiment of the final formed shape of the ePTFE tube after blow-molding/radial stretching of the original cylindrical tube of ePTFE. The anchor covering portion of the sleeve 550 and the intestinal bypass 551 sleeve are formed integrally into one sleeve. The small diameter end of the tube is inverted inside to pull it inside to form an interior tube layer for the expandable anchor. The intestinal bypass sleeve 551 has annular rings or corrugations formed into it to allow for the sleeve to bend easier without kinking and to provide for more longitudinal elasticity.

Figure 84:
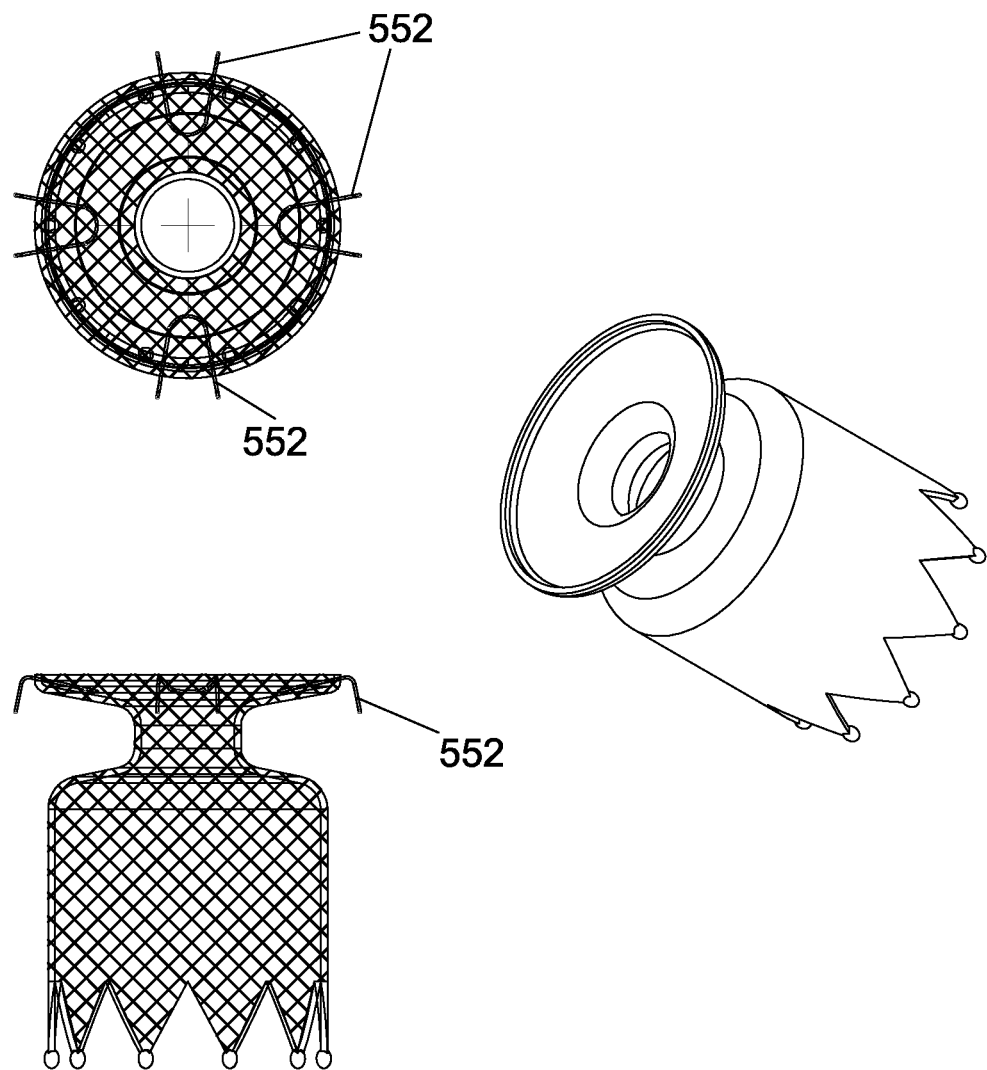
FIG. 84 is a drawing of an alternative embodiment of the embodiment shown in FIG. 46. The expandable anchor is comprised of a hollow tubular braided structure of wire. The wire form has been shaped to conform to the shape of the pylorus and the duodenal bulb. Optional barbs and/or hooks provide for additional tissue penetration and anchoring.
Figure 85:
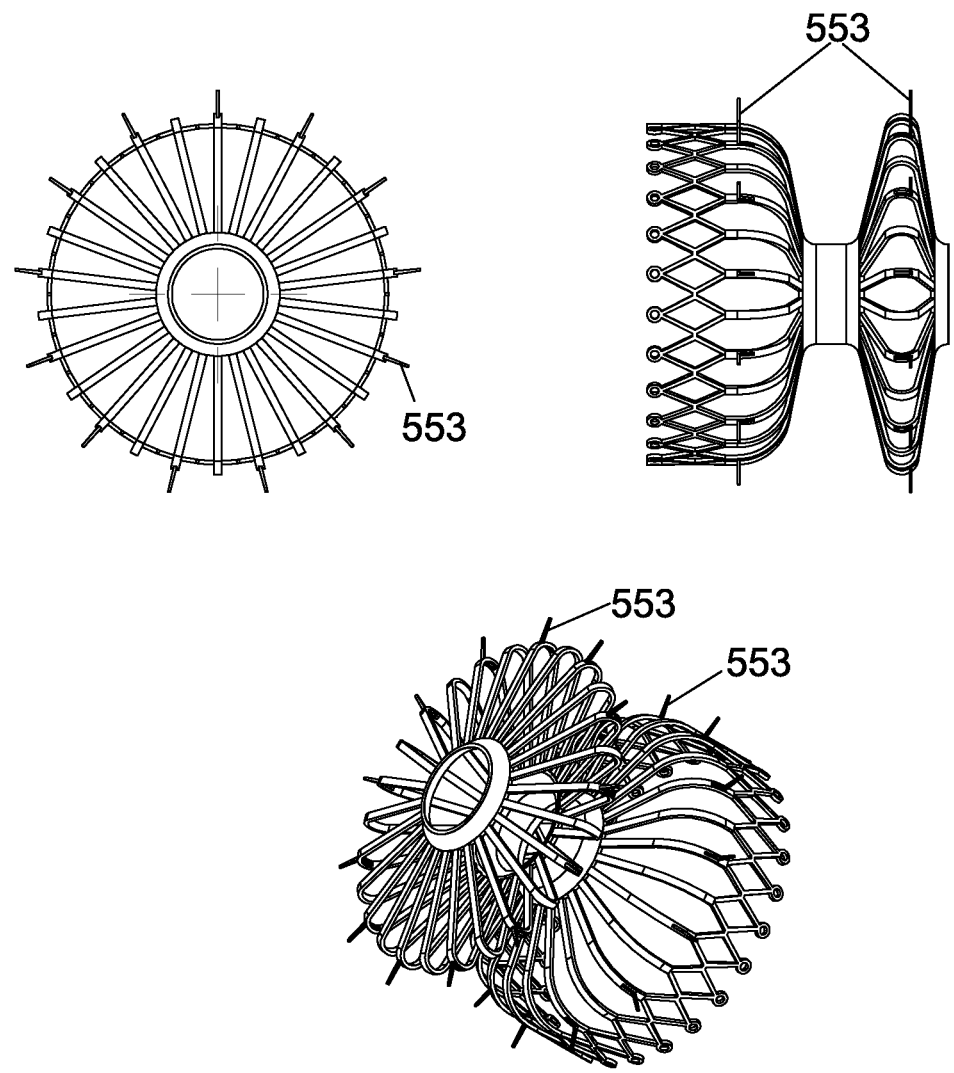

FIG. 84 is a drawing of an alternative embodiment of the invention previously disclosed in FIG. 46. The expandable anchor is comprised of a hollow tubular braided structure of wire. The wire form has been heat set or shaped to conform to the shape of the pylorus and the duodenal bulb. Optional barbs and/or hooks 552 that have been incorporated into the anchor to provide for additional tissue penetration and additional anchoring. FIG. 85 is a drawing of an expandable anchor. The expandable anchor incorporates optional barbs and/or hooks 553 have been incorporated into the anchor to provide for tissue penetration and additional anchoring. The barbs are outwardly oriented to engage the tissue of the pyloric antrum, pylorus and/or duodenal bulb. In various embodiments, the barbs extend outwardly in a direction generally perpendicular to the longitudinal axis. According to other embodiments, the barbs extend at an angle with respect to the longitudinal axis of anywhere between about 0 and about 90 degrees. The lengths of the barbs may range from less than 1 mm up to several mm in length. The barbs may be constructed from Nitinol, titanium, Elgiloy, MP35N, stainless steel, platinum, platinum iridium, plastics or other suitable materials. The design and construction of the expandable anchor is similar to what was previously disclosed in FIG. 6.

Figure 86:
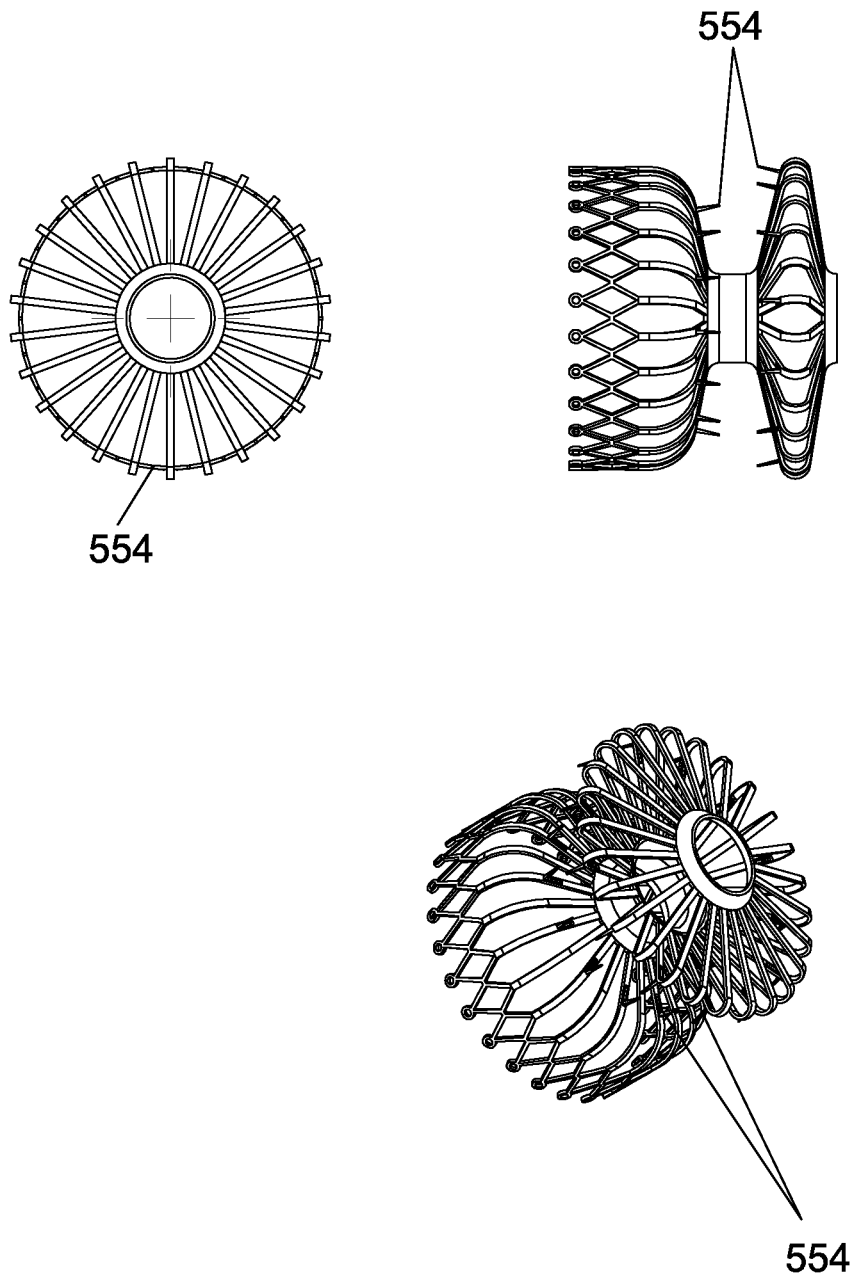
Figure 87:
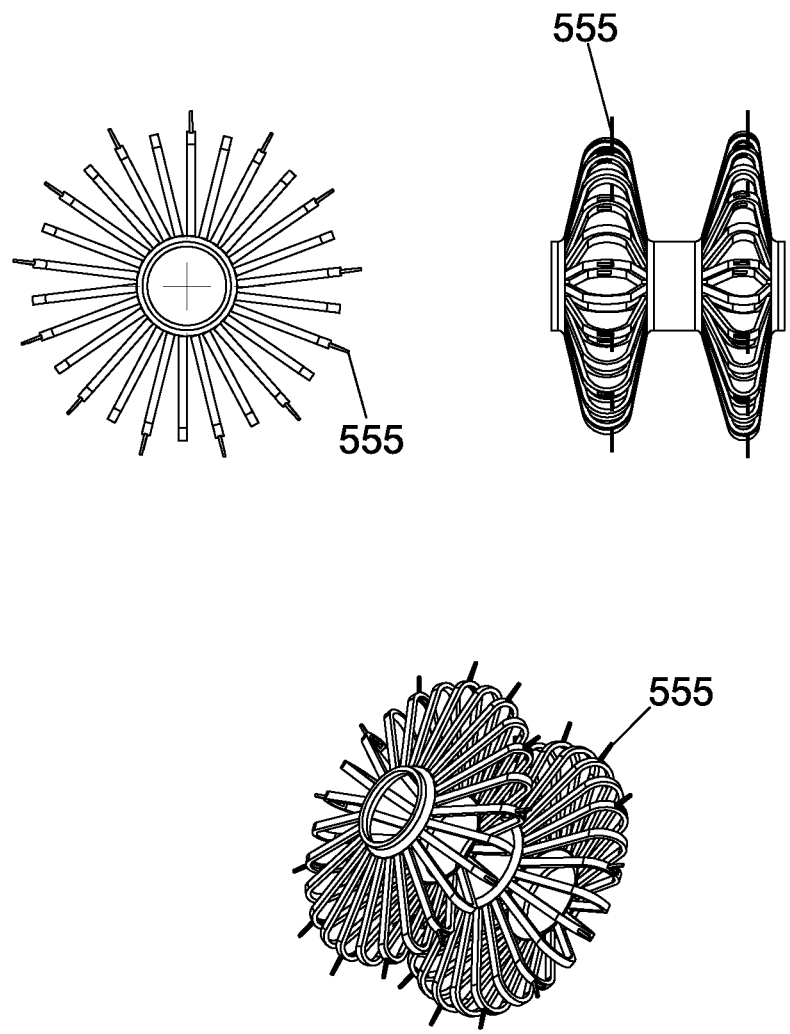
Figure 88:
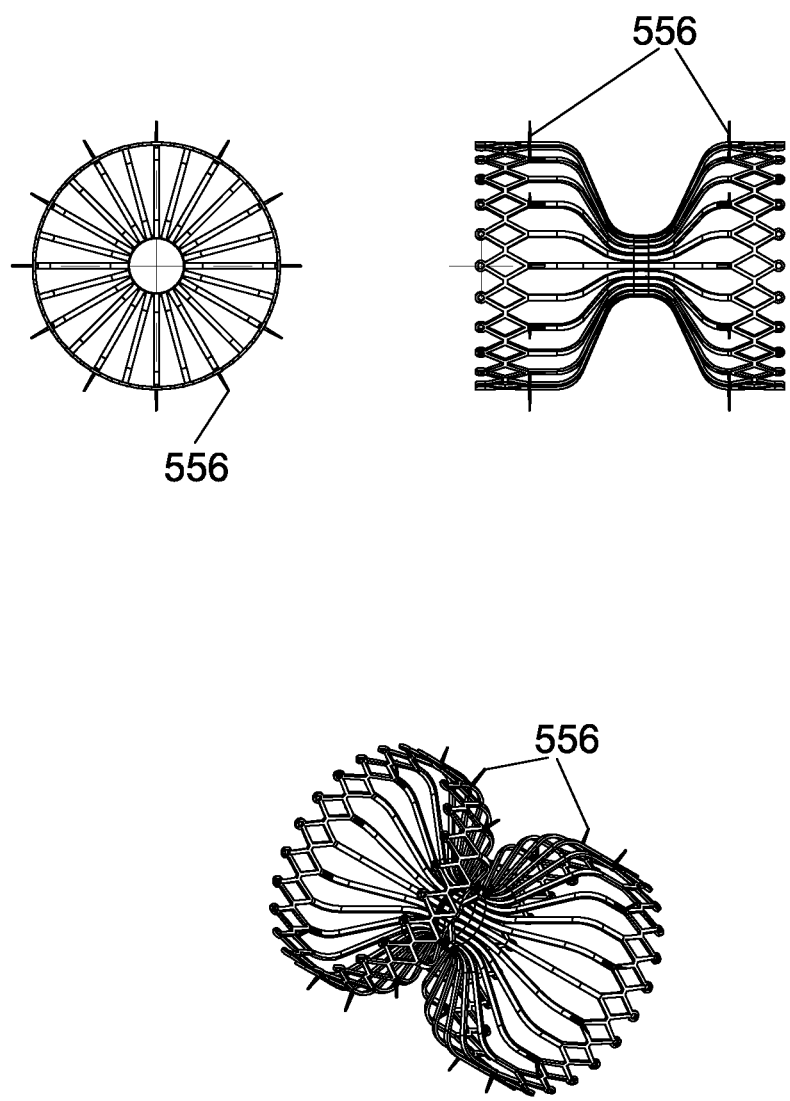
Figure 89:
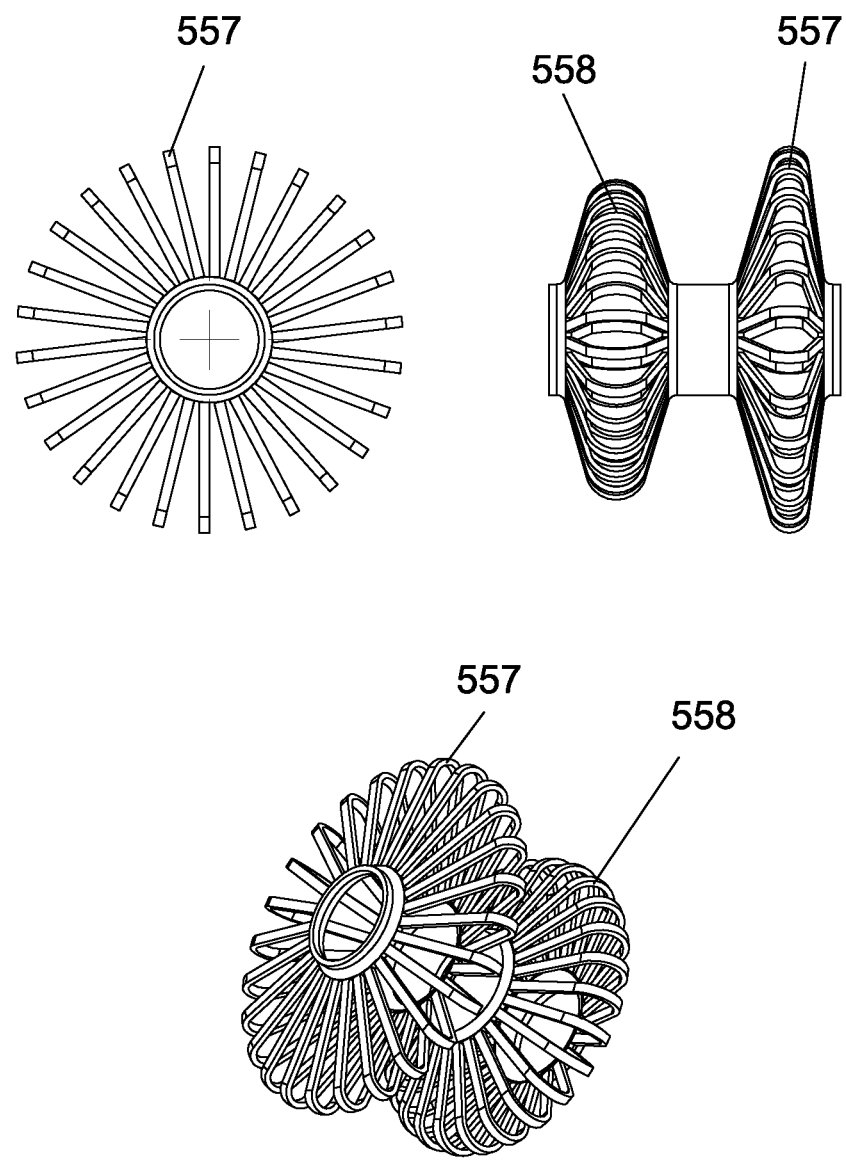

FIG. 86 is a drawing of an expandable anchor. The expandable anchor incorporates optional barbs and/or hooks 554 that have been incorporated into the anchor to provide for tissue penetration and additional anchoring. The design and construction of the expandable anchor is similar to what was previously disclosed in FIG. 6. FIG. 87 is a drawing of an expandable anchor. The expandable anchor incorporates optional barbs and/or hooks 555 that have been incorporated into the anchor to provide for tissue penetration and additional anchoring. The design and construction of the expandable anchor is similar to what was previously disclosed in FIG. 18. FIG. 88 is a drawing of an expandable anchor. The expandable anchor incorporates optional barbs and/or hooks 556 that have been incorporated into the anchor to provide for tissue penetration and additional anchoring. In various embodiments, the barbs extend outwardly in a direction generally perpendicular to the longitudinal axis. According to other embodiments, the barbs extend at an angle with respect to the longitudinal axis of anywhere between about 0 and about 90 degrees. The design and construction of the expandable anchor is similar to what was previously disclosed in FIG. 20. FIG. 89 is a drawing of an expandable anchor in which the expandable anchor's antral disk 557 is larger in diameter than the duodenal bulb disk 558. The design and construction of the expandable anchor is similar to what was previously disclosed in FIG. 18.

Figure 90:
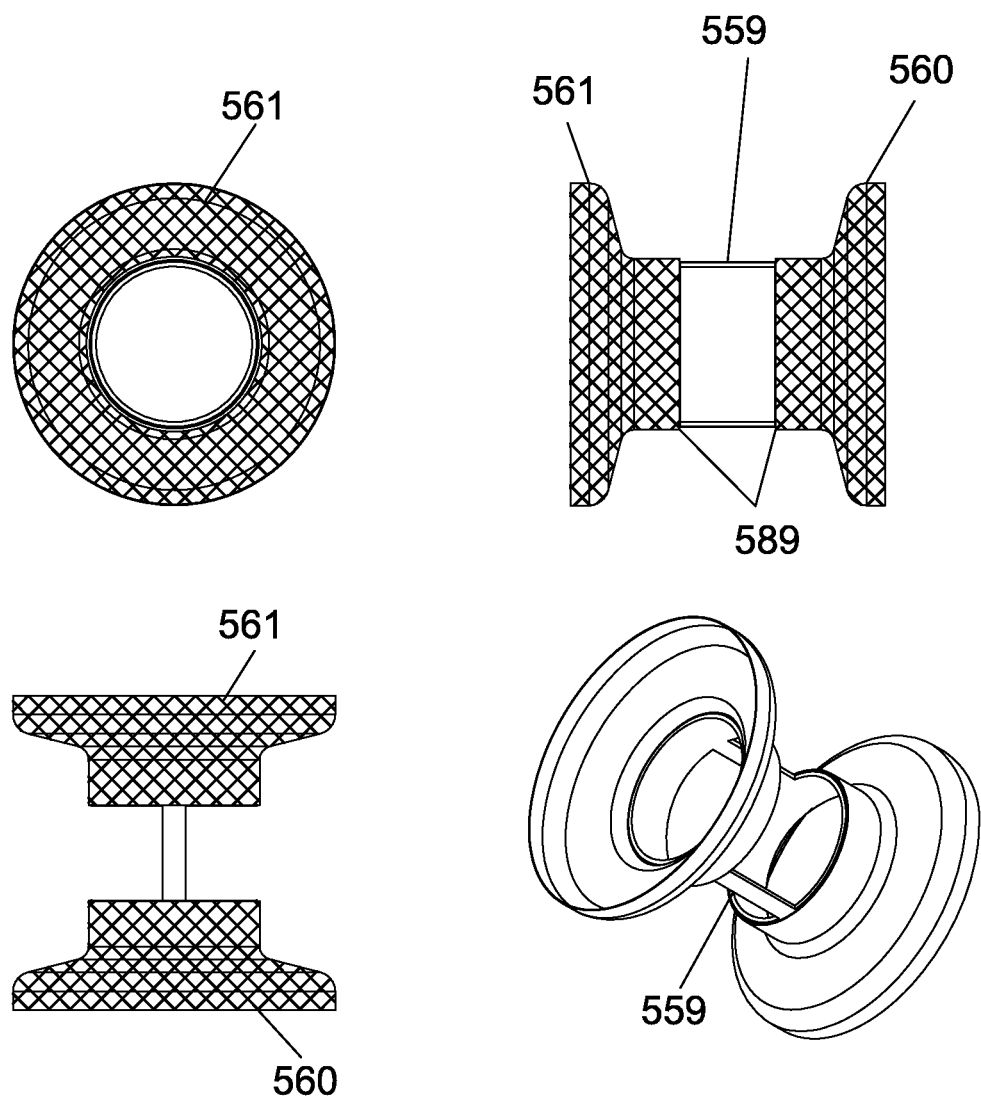

FIG. 90 is a drawing of an expandable anchor. The expandable anchor has a central cylinder 559 as previously disclosed in FIG. 38. The expandable anchor has an antral disk 560 comprised of Nitinol wire in a braided form and a duodenal disk 561 comprised of Nitinol wire in a braided form. The Nitinol braid can be comprised of a single layer of braid or it may be double back on itself and the cut wire ends of the braid may be attached to the central cylinder at location 589. The Nitinol wire braid may be shape set or formed into the desired shape by the means previously disclosed in this application.

Figure 91:
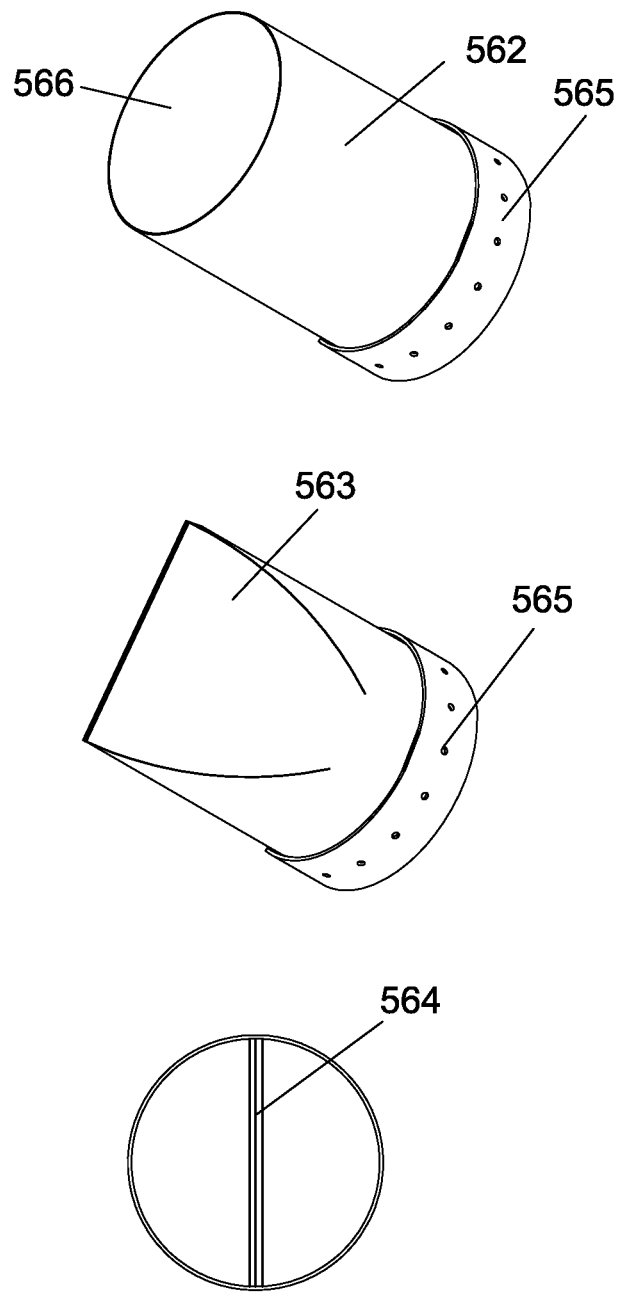

FIG. 91 is a drawing of an anti-reflux valve for an expandable anchor. The anti-reflux valve 562 can be located within the central cylinder as previously disclosed as item 346 in FIG. 40. The anti-reflux valve 562 may be made from a thin-walled tube of polymer such as ePTFE, PTFE, FEP, silicone, polyurethane, polyethylene or other suitable polymer. The polymer may be designed with the proper thickness and mechanical properties to allow the valve to self seal or close when retrograde flow is exerted on the valve. The anti-reflux valve may be bonded to the central cylinder 565. Anti-reflux valve is in an open position 566 when chyme flows from the stomach to the duodenum and in a closed position 563 and 564 when chyme flows in a retrograde direction from the duodenum to the stomach. The anti-reflux valve can allow chyme to flow from the stomach to the duodenum without being restricted, but it can also limit or prevent retrograde flow from the duodenum to the antrum. Retrograde flow from the duodenum to the pylorus can be undesirable and cause eversion of the intestinal bypass sleeve and allow the sleeve to evert through the expandable anchor into the stomach. The anti-reflux valve 562 can be designed to evert and allow retrograde flows at very high pressures such as during vomiting. The inside diameter of the anti-reflux valve in the open state can range from 4 mm to 18 mm in diameter.

Figure 92:
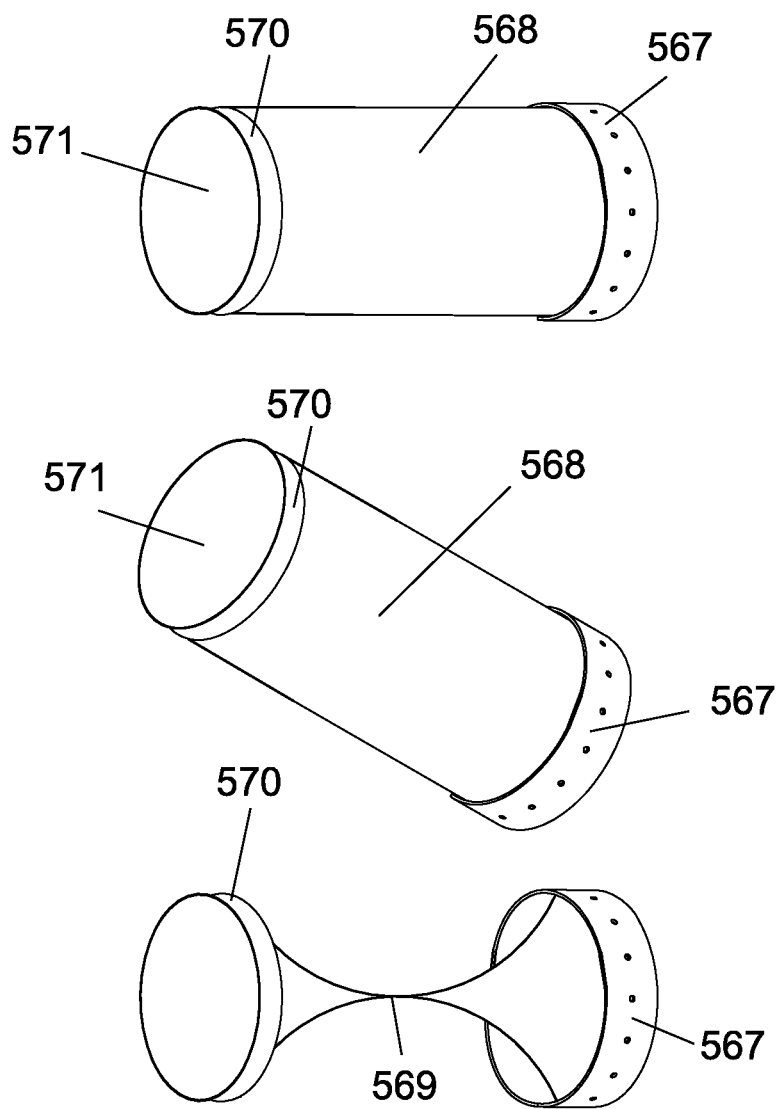

FIG. 92 is a drawing of an anti-reflux valve for an expandable anchor. The anti-reflux valve 568 can be located within the central cylinder as previously disclosed as item 346 in FIG. 40. The anti-reflux valve 568 may be made from a thin-walled tube of polymer such as ePTFE, PTFE, FEP, silicone, polyurethane, polyethylene or other suitable polymer. The anti-reflux valve may be bonded to the central cylinder 567. Anti-reflux valve 568 can have a rigid ring 571 bonded onto the end of the tube to prevent the anti-reflux valve 568 from being everted through the central cylinder at high pressures. Anti-reflux valve is in an open position 571 when chyme flows from the stomach to the duodenum and in a closed position 569 when chyme flows in a retrograde direction from the duodenum to the stomach. The anti-reflux valve can allow chyme to flow from the stomach to the duodenum without being restricted, but it can also limit or prevent retrograde flow from the duodenum to the antrum. Retrograde flow from the duodenum to the pylorus can be undesirable and cause eversion of the intestinal bypass sleeve and allow the sleeve to evert through the expandable anchor into the stomach.

FIG. 93 is a drawing alternative embodiment of an anti-reflux valve for an expandable anchor. The anti-reflux valve 573 can be located within the central cylinder as previously disclosed as item 346 in FIG. 40. The anti-reflux valve 573 may be made from a thin-walled tube of polymer such as ePTFE, PTFE, FEP, silicone, polyurethane, polyethylene or other suitable polymer. The tube can be constructed of one extrusion of tubing or it may be made from three individual sections or leaflets joined to form the circumference of the valve. The anti-reflux valve 573 may be bonded to the central cylinder 572. The polymer tube for the anti-reflux valve 573 can be attached to the metal flexing post 577. The anti-reflux valve has three flexing posts 577 at a spacing of about 120 degrees around the circumference of the valve. The polymer tube can be attached to the flexing posts by sewing, gluing or other mechanical means. The flexing posts 577 can be made from metals such as Titanium, Nitinol, stainless steel, elgiloy, MP35N, or plastics such as PEEK or delrin or other suitable material. The flexing posts 577 allows the valve to open at low pressures, but holds the valve leaflets so that they do not evert back into the lumen of the central cylinder 572. Anti-reflux valve is in an open position 574 when chyme flows from the stomach to the duodenum and in a partially closed position 575 and fully closed position 576 when chyme flows in a retrograde direction from the duodenum to the stomach. The anti-reflux valve 573 can allow chyme to flow from the stomach to the duodenum without being restricted, but it can also limit or prevent retrograde flow from the duodenum to the antrum. The inside diameter of the anti-reflux valve in the open state can range from 4 mm to 18 mm in diameter.

Figure 94:
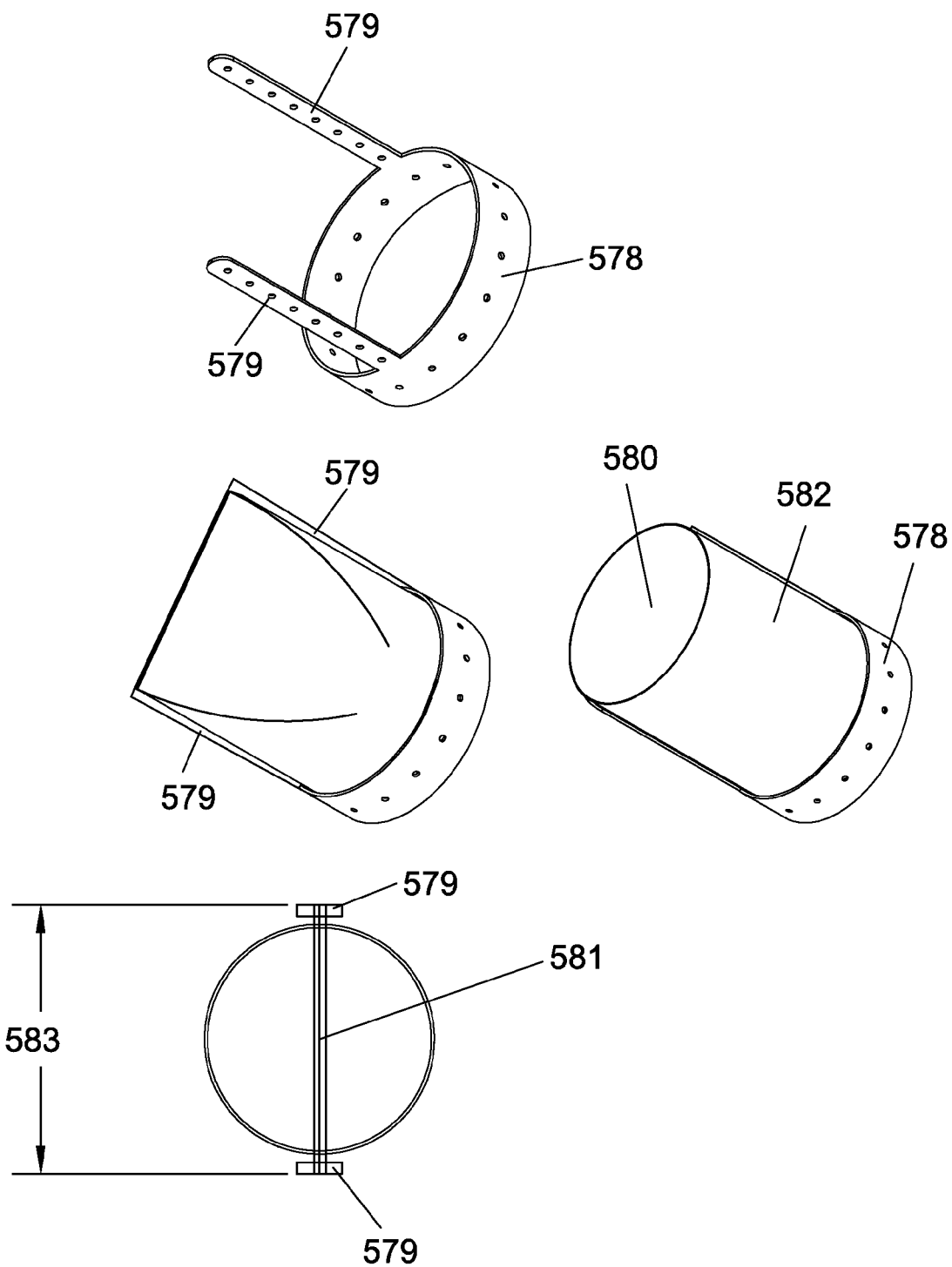

FIG. 94 is a drawing of an alternative embodiment of an anti-reflux valve for an expandable anchor. The anti-reflux valve 582 can be located within the central cylinder as previously disclosed as item 346 in FIG. 40. The anti-reflux valve 582 can be made from a thin-walled tube of polymer such as ePTFE, PTFE, FEP, silicone, polyurethane, polyethylene or other suitable polymer. The tube can be constructed of one extrusion of tubing or it may be made from two individual sections or leaflets joined to form the circumference of the valve. The anti-reflux valve 582 may be bonded to the central cylinder 578. The polymer tube for the anti-reflux valve 582 can be attached to the metal flexing posts 579. The anti-reflux valve has two flexing posts 579 at a spacing of about 180 degrees around the circumference of the valve. The polymer tube can be attached to the flexing posts by sewing, gluing or other mechanical means. The flexing posts 579 can be made from metals such as Titanium, Nitinol, stainless steel, elgiloy, MP35N, or plastics such as PEEK or delrin or other suitable material. The space 583 between the flexing posts can be adjusted to increase the pretension on the leaflets and affect the opening pressure of the anti-reflux valve. If the post spacing 583 is increased the leaflets will be under greater tension and the valve opening pressure will be increased. The flexing posts 579 can be designed to allow the valve to open at low pressures, but the posts still hold the valve leaflets so that the leaflets do not evert back into the lumen of the central cylinder 578. Anti-reflux valve is in an open position 580 when chyme flows from the stomach to the duodenum and in closed position 581 when chyme flows in a retrograde direction from the duodenum to the stomach. The opening pressure of the anti-reflux valve can be designed to be close to zero if little to no flow resistance is desired to the flow of chime from the stomach to the duodenum. To induce additional weight loss in a patient or if a dumping syndrome occurs it may be desirable to have the anti-reflux valve that has a moderate flow resistance in an anti-grade flow direction. The post stiffness or post spacing 583 can be adjusted to customize the desired flow resistance in the antegrade direction while still maintaining the anti-reflux properties of the valve. Thus the anti-reflux valve 582 can be designed to accomplish multiple different functions: provide for an anti-reflux function, valve opens at low pressures in an antegrade flow direction, or valve opens at a higher pressure in the antegrade flow direction. Previous prior art flow limiters consisted of orifice type valves. This provides for a flow limiter that can open easily to a larger diameter to allow large food particles to pass through the valve without the stretching of a polymer orifice and still provide the desired flow resistance. Thus this design provides for a flow limiter without the inherent risk of having the orifice become obstructed with large particles of chyme. The inside diameter of the anti-reflux valve in the open state can range from 4 mm to 18 mm in diameter.

Figure 95:
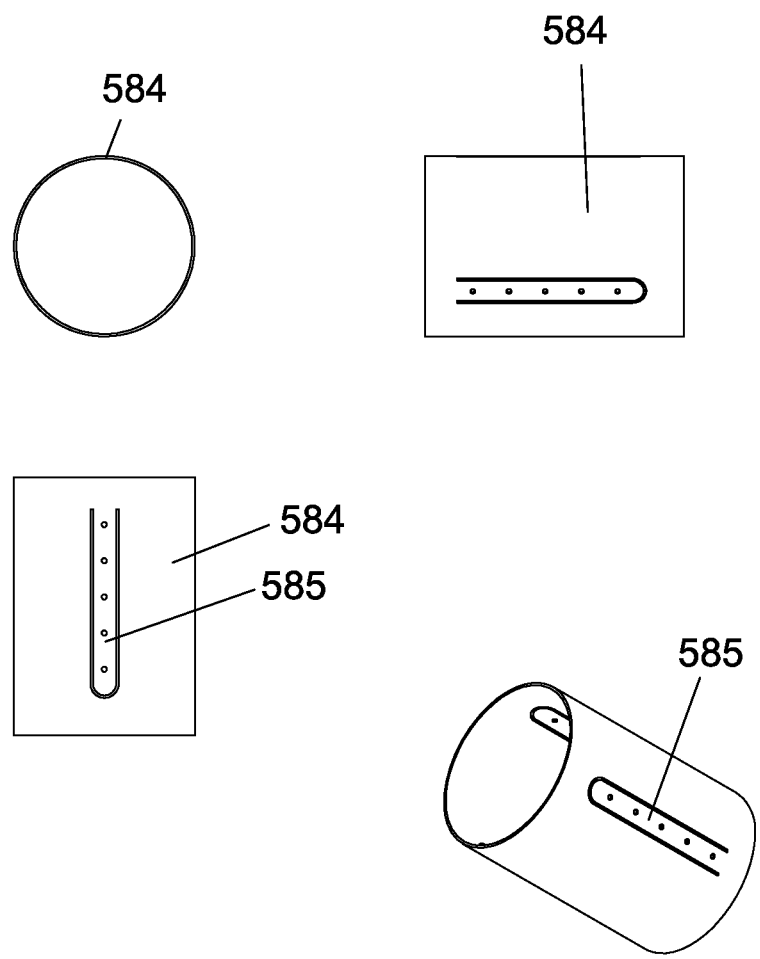
Figure 96:
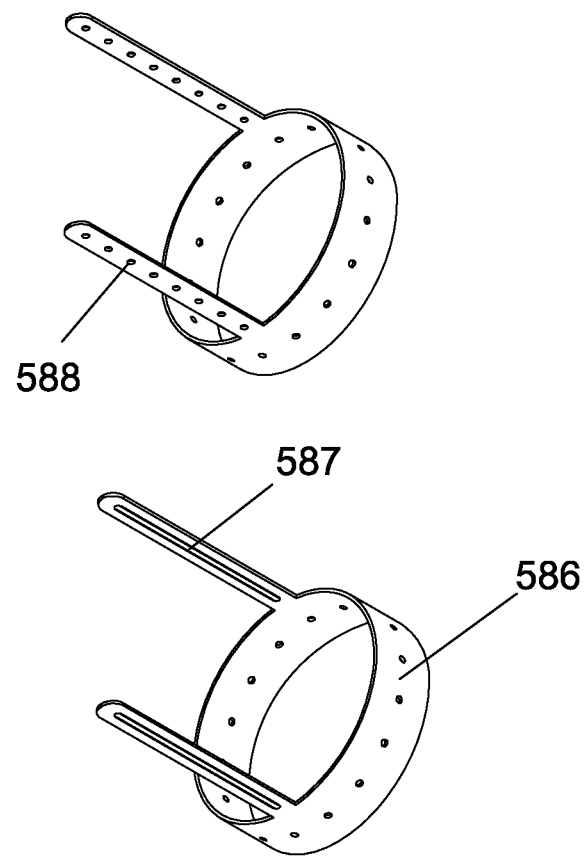

FIG. 95 is a drawing of an alternative embodiment of an anti-reflux valve frame with flexing posts. The frame is constructed so the flexing posts 585 are integrated into the wall of the central cylinder 584. FIG. 96 is a drawing of an alternative embodiment of an anti-reflux valve frame with flexing posts. The flexing posts can be designed to have holes in the posts 588 or a slot 587 to provide for a means to mechanically attach the leaflets to the flexing posts.

We claim:

1. A gastrointestinal device for implanting within a pylorus, a duodenal bulb, and a duodenum of a patient's gastrointestinal tract, the device configured to have an expanded configuration and a contracted configuration, the device comprising:
    an expandable structure including a proximal portion having a first diameter in the expanded configuration that is configured for engaging a first wall of the pylorus at a first location adjacent the pyloric antrum and having a coil compression spring, and a distal portion having a second diameter in the expanded configuration that is configured for engaging a second wall of the pylorus at a second location adjacent the duodenal bulb and having a coil compression spring, the proximal and distal portions coupled by a central cylinder portion having a third diameter in the expanded configuration that is less than the first diameter and less than the second diameter but equal to or larger than a maximum diameter of the pylorus such that the central cylinder portion does not restrict flow through the pylorus and has a length greater than a width of the pylorus, wherein the coil compression springs of the proximal and the distal portions extend radially outward to the first and second diameters, respectively, and extend circumferentially around the central cylinder;
    a membrane coupled to and covering at least a portion of one of the proximal portion and the distal portion of the expandable structure; and
    an intestinal bypass sleeve coupled to at least one of the proximal and distal portions of the expandable structure and having a length sufficient to extend at least partially into the duodenum;
    wherein, in the expanded configuration, the proximal portion has a diameter larger than a maximum opening diameter of the pylorus and wherein, in the expanded configuration, the distal portion has a diameter larger than a maximum opening diameter of the pylorus, and further wherein the proximal and distal portions are spaced apart at discrete locations along the central cylinder.

2. The gastrointestinal device of claim 1 wherein at least one of the proximal portion and the distal portion of the expandable structure is a disk-shaped element.

3. The gastrointestinal device of claim 1 wherein at least one of the coil compression springs of the proximal portion and the distal portion of the expandable structure has a shape selected from one or more of the following: a toroidal-shaped element, a spherical-shaped element, and a cylindrical-shaped element.

4. The gastrointestinal device of claim 1 wherein the central cylinder portion has an anti-reflux valve adapted for preventing reflux of the duodenal contents back into the stomach.

5. The gastrointestinal device of claim 1 further including a supplemental securement mechanism for securing the device to the pylorus or the stomach, the supplemental securement mechanism including one or more of the following: a suture, a T-bar, a hook, a barb and a screw-type anchor.

6. The gastrointestinal device of claim 1 wherein the intestinal bypass sleeve has a length sufficient to extend at least partially into a jejunum of the patient's gastrointestinal tract.

7. A gastrointestinal device for treatment of gastroparesis, the device configured to have an expanded configuration and a contracted configuration, the device comprising:
- an expandable structure including a proximal portion having a first diameter in the expanded configuration that is configured for engaging a first wall of the pylorus at a first location adjacent the pyloric antrum and having a coil compression spring, and a distal portion having a second diameter in the expanded configuration that is configured for engaging a second wall of the pylorus at a second location adjacent the duodenal bulb and having a coil compression spring, the proximal and distal portions coupled by a central cylinder having a third diameter in the expanded configuration that is less than the first diameter and less than the second diameter but equal to or larger than a maximum diameter of the pylorus such that the central cylinder portion does not restrict flow through the pylorus, wherein the coil compression springs of the proximal and the distal portions extend radially outward to the first and second diameters, respectively, and extend circumferentially around the central cylinder;
- a membrane coupled to and covering at least a portion of one of the proximal portion and the distal portion of the expandable structure; and
- a pump device adapted for coupling at least partially within the central cylinder portion, the pump device adapted to pump chyme from a stomach, through the pylorus, to a duodenum;
- wherein, in the expanded configuration, the proximal portion has a diameter larger than a maximum opening diameter of the pylorus and wherein, in the expanded configuration, the distal portion has a diameter larger than a maximum opening diameter of the pylorus, and further wherein the proximal and distal portions are spaced apart at discrete locations along the central cylinder.

8. The gastrointestinal device of claim 7 wherein at least one of the proximal portion and the distal portion of the expandable structure is a disk-shaped element.

9. The gastrointestinal device of claim 7 wherein at least one of the coil compression springs has a shape selected from one or more of the following: a toroidal-shaped element, a spherical-shaped element, and a cylindrical-shaped element.

10. The gastrointestinal device of claim 7 wherein the central cylinder portion has an anti-reflux valve adapted for preventing reflux of the duodenal contents back into the stomach.

11. The gastrointestinal device of claim 7 further including a supplemental securement mechanism for securing the device to the pylorus or the stomach, the supplemental securement mechanism including one or more of the following: a suture, a T-bar, a hook, a barb and a screw-type anchor.

12. The gastrointestinal device of claim 7 further comprising an intestinal bypass sleeve coupled to at least one of the proximal and distal portions of the expandable structure and having a length sufficient to extend at least partially into the jejunum.

13. A gastrointestinal device for implanting within a pylorus, a duodenal bulb, and a duodenum of a patient's gastrointestinal tract, the device configured to have an expanded configuration and a contracted configuration, the device comprising:
- an expandable structure including a proximal portion having a first diameter in the expanded configuration that is configured for engaging a first wall of the pylorus at a first location adjacent the pyloric antrum and having a coil compression spring, and a distal portion having a second diameter in the expanded configuration that is configured for engaging a second wall of the pylorus at a second location adjacent the duodenal bulb and having a coil compression spring, the proximal and distal portions coupled by a central cylinder portion having a third diameter in the expanded configuration that is less than the first diameter and less than the second diameter but equal to or larger than a maximum diameter of the pylorus such that the central cylinder portion does not restrict flow through the pylorus and having a length less than a width of the pylorus so as to enable the expandable structure to exert a compressive force on the pylorus, wherein the coil compression springs of the proximal and the distal portions extend radially outward to the first and second diameters, respectively, and extend circumferentially around the central cylinder;
- an intestinal bypass sleeve coupled to at least one of the proximal and distal portions of the expandable structure and having a length sufficient to extend at least partially into the duodenum; and
- an anti-reflux valve coupled to the central cylinder and adapted to close one end of the bypass sleeve;
- wherein, in the expanded configuration, the proximal portion has a diameter larger than a maximum opening diameter of the pylorus and wherein, in the expanded configuration, the distal portion has a diameter larger than a maximum opening diameter of the pylorus, and further wherein the proximal and distal portions are spaced apart at discrete locations along the central cylinder.

14. The gastrointestinal device of claim 12 wherein at least one of the proximal portion and the distal portion of the expandable structure is a disk-shaped element.

15. The gastrointestinal device of claim 12 wherein at least one of the coil compression springs has a shape selected from one or more of the following: a toroidal-shaped element, a spherical-shaped element, and a cylindrical-shaped element.

16. The gastrointestinal device of claim 12 wherein the central cylinder portion has an anti-reflux valve adapted for preventing reflux of the duodenal contents back into the stomach.

17. The gastrointestinal device of claim 12 further including a supplemental securement mechanism for securing the device to the pylorus or the stomach, the supplemental securement mechanism including one or more of the following: a suture, a T-bar, a hook, a barb and a screw-type anchor.

* * * * *